US009770471B2

(12) United States Patent
Eggan et al.

(10) Patent No.: US 9,770,471 B2
(45) Date of Patent: Sep. 26, 2017

(54) CONVERSION OF SOMATIC CELLS INTO FUNCTIONAL SPINAL MOTOR NEURONS, AND METHODS AND USES THEREOF

(75) Inventors: Kevin Carl Eggan, Boston, MA (US); Clifford J. Woolf, Newton, MA (US); Brian J. Wainger, Brookline, MA (US); Justin K. Ichida, Los Angeles, CA (US); Esther Yesde Son, Palo Alto, CA (US)

(73) Assignees: PRESIDENT AND FELLOWS OF HARVARD COLLEGE, Cambridge, MA (US); CHILDREN'S MEDICAL CENTER CORPORATION, Boston, MA (US)

(*) Notice: Subject to any disclaimer, the term of this patent is extended or adjusted under 35 U.S.C. 154(b) by 430 days.

(21) Appl. No.: 14/238,682

(22) PCT Filed: Aug. 17, 2012

(86) PCT No.: PCT/US2012/051264
§ 371 (c)(1),
(2), (4) Date: Sep. 29, 2014

(87) PCT Pub. No.: WO2013/025963
PCT Pub. Date: Feb. 21, 2013

(65) Prior Publication Data

US 2015/0023927 A1 Jan. 22, 2015

Related U.S. Application Data

(60) Provisional application No. 61/524,599, filed on Aug. 17, 2011.

(51) Int. Cl.
*A61K 35/30* (2015.01)
*C12N 5/0793* (2010.01)
*A61K 48/00* (2006.01)

(52) U.S. Cl.
CPC ............ *A61K 35/30* (2013.01); *C12N 5/0619* (2013.01); *A61K 48/00* (2013.01); *C12N 2501/60* (2013.01); *C12N 2506/13* (2013.01); *C12N 2506/1307* (2013.01); *C12N 2510/00* (2013.01)

(58) Field of Classification Search
CPC ...... A61K 35/30; A61K 48/00; C12N 5/0619; C12N 2510/00; C12N 2506/1307; C12N 2501/60
See application file for complete search history.

(56) References Cited

U.S. PATENT DOCUMENTS

2008/0206865 A1 8/2008 Zhang et al.
2008/0305086 A1 12/2008 Poole
2009/0117085 A1 5/2009 Deshpande et al.
2009/0286857 A1 11/2009 O'Riordan et al.
2011/0091927 A1 4/2011 Reubinoff et al.
2013/0022583 A1* 1/2013 Wernig ................ C12N 5/0619 424/93.7

FOREIGN PATENT DOCUMENTS

WO 2010042669 A2 4/2010

OTHER PUBLICATIONS

Karumbayaram et al. Directed differentiation of human induced pluripotent stem cells generates active motor neurons. Stem Cells. Apr. 2009 ; 27(4): 806-811.*
Thaler et al.LIM Factor Lhx3 Contributes to the Specification of Motor Neuron and Interneuron Identity through Cell-Type-Specific Protein-Protein Interactions. Cell, vol. 110, 237-249, Jul. 26, 2002.*
Pfaff et al.Requirement for LIM Homeobox Gene Isl1 in Motor Neuron Generation Reveals a Motor Neuron-Dependent Step in Interneuron Differentiation. Cell, vol. 84, 309-320, Jan. 26, 1996.*
Wiedenmann et al. Synaptophysin: A marker protein for neuroendocrine cells and neoplasms. Proc. Natl. Acad. Sci. USA vol. 83, pp. 3500-3504, May 1986.*
Radde-Gallwitz et al. Expression of Islet1 Marks the Sensory and Neuronal Lineages in the Mammalian Inner Ear. J Comp Neurol. Sep. 27, 2004; 477(4): 412-421.*
Yasuhara et al. Primary sensory neurons containing choline acetyltransferase of the peripheral type in the rat trigeminal ganglion and their relation to neuropeptides-, calbindin- and nitric oxide synthase-containing cells. Brain Research 1141 (2007) 92-98.*
Abe et al., "Establishment of conditional reporter mouse lines at ROSA26 locus for live cell imaging" Genesis, 49(7):579-90 (2011).
Alessandri-Haber et al., "Specific distribution of sodium channels in axons of rat embryo spinal motoneurones", J Physiol, 518(Pt 1):203-14 (1999).
Burns et al., "Nestin-CreER mice reveal DNA synthesis by nonapoptotic neurons following cerebral ischemia hypoxia", Cereb Cortex, 17(11):2585-92 (2007).
Caiazzo et al., "Direct generation of functional dopaminergic neurons from mouse and human fibroblasts", Nature, 176(7359):224-7 (2011).

(Continued)

*Primary Examiner* — Taeyoon Kim
(74) *Attorney, Agent, or Firm* — Nixon Peabody LLP

(57) ABSTRACT

The present invention provides methods of transdifferentiation of somatic cells, for example, directly converting a somatic cell of a first cell type, e.g., a fibroblast into a somatic cell of a second cell type, are described herein. In particular, the present invention generally relates to methods for converting a somatic cell, e.g., a fibroblast into a motor neuron, e.g., an induced motor neuron (iMN) with characteristics of a typical motor neuron. The present invention also relates to an isolated population comprising induced motor neurons (iMNs), compositions and their use in the treatment of motor neuron diseases such as ALS and SMA. In particular, the present invention relates to direct conversion of a somatic cell to an induced motor neuron (iMN) having motor neuron characteristics by increasing the protein expression of at least three motor-neuron inducing (MN-inducing) factors selected from Lhx3, Ascl1, Brn2, Myt1l, Isl1, Hb9, Ngn2 or NeuroD1 in a somatic cell, e.g., a fibroblast to convert the fibroblast to an induced motor neuron (iMN) which exhibits at least two characteristics of an endogenous motor neuron.

8 Claims, 26 Drawing Sheets

(56) References Cited

OTHER PUBLICATIONS

Cui et al., "Divergence between motoneurons: gene expression profiling provides a molecular characterization of functionally discrete somatic and autonomic motoneurons", Physiol Genomics, 24(3):276-89 (2006). Dahm et al., "The regulation of intramuscular nerve branching during normal development and following activity blockade", Dev Biol, 130(2):621-44 (1988).
Digiorgio et al., "Human embryonic stem cell-derived motor neurons are sensitive to the toxic effect of glial cells carrying an ALS-causing mutation", Cell Stem Cell, 3(6):637-48 (2008).
Digiorgio et al., "Non-cell autonomous effect of glia on motor neurons in an embryonic stem cell-based ALS model", Nat Neurosci, 10(5):608-14 (2007).
Frederiksen et al., "Proliferation and differentiation of rat neuroepithelial precursor cells in vivo", J Neurosci, 8(4):1144-51 (1988).
Ichida et al., "A small-molecule inhibitor of tgf-Beta signaling replaces sox2 in reprogramming by inducing nanog", Cell Stem Cell, 5(5):491-503 (2009).
Ieda et al., "Direct reprogramming of fibroblasts into functional cardiomyocytes by defined factors", Cell, 142(3)375-86 (2010).
Jessell, "Neuronal specification in the spinal cord: inductive signals and transcriptional codes", Nat Rev Genet, 1(1):20-9 (2000).
Lee et al., "Olig2 and Ngn2 function in opposition to modulate gene expression in motor neuron progenitor cells", 19(2):282-94 (2005).
Lupa et al., "Progressive restriction of synaptic vesicle protein to the nerve terminal during development of the Neuromuscular junction", J Neurosci, 9(11):3937-45 (1989).
Messam et al., "Analysis of the temporal expression of nestin in human fetal brain derived neuronal and glial progenitor cells", Brain Res Dev Brain Res, 134(1-2):87-92 (2002).
Miles et al., "Functional properties of motoneurons derived from mouse embryonic stem cells", J Neurosci, 24(36):7848-58 (2004).
Nagai et al., "Astrocytes expressing ALS-linked mutated SOD1 release factors selectively toxic to motor neurons", Nat Neurosci, 10(5):615-22 (2007).
Peljto et al., "Programming embryonic stem cells to neuronal subtypes", Curr Opin Neurobiol, 21(1):43-51 (2011).
Peljto et al., "Functional diversity of ESC-derived motor neuron subtypes revealed through intraspinal transplantation", Cell Stem Cell, 7(3):355-66 (2010).
Pfisterer et al., "Direct conversion of human fibroblasts to dopaminergic neurons", Proc Natl Acad Sci U S A, 108(25):10343-8 (2011).
Puia et al., "Neurosteroids act on recombinant human GABAA receptors", Neuron, 4(5):759-65 (1990).
Soundararajan et al., "Easy and rapid differentiation of embryonic stem cells into functional motoneurons using sonic hedgehog-producing cells", Stem Cells, 25(7):1697-706 (2007).
Soundararajan et al., "Guidance of postural motoneurons requires MAPK/ERK signaling downstream of fibroblast growth factor receptor 1", J Neurosci, 30(19):6595-606 (2010).
Soundararajan et al., "Motoneurons derived from embryonic stem cells express transcription factors and develop phenotypes characteristic of medial motor column neurons", J Neurosci, 26(12):3256-68 (2006).
Szabo et al., "Direct conversion of human fibroblasts to multilineage blood progenitors", Nature, 468(7323):521-6 (2010).
Takahashi et al., "Induction of pluripotent stem cells from mouse embryonic and adult fibroblast cultures by defined factors", Cell, 126(4):663-76 (2006).
Pang et al., Nature, 476(7359):220-223 (2011). "Induction of Human Neuronal Cells by Defined Transcription Factors."
Vierbuchen et al., Nature, 463(7284):1035-1041 (2010). "Direct Conversion of Fibroblasts to Functional Neurons by Defined Factors."
Wichterle et al., Cell, 110(3):385-397 (2002). "Directed Differentiation of Embryonic Stem Cells into Motor Neurons."

* cited by examiner

SEQUENCE LISTING

```
<160> NUMBER OF SEQ ID NOS: 47

<210> SEQ ID NO 1
<211> LENGTH: 402
<212> TYPE: PRT
<213> ORGANISM: Homo sapiens

<400> SEQUENCE: 1

Met Glu Ala Arg Gly Glu Leu Gly Pro Ala Arg Glu Ser Ala Gly Gly
1               5                   10                  15

Asp Leu Leu Leu Ala Leu Leu Ala Arg Arg Ala Asp Leu Arg Arg Glu
            20                  25                  30

Ile Pro Leu Cys Ala Gly Cys Asp Gln His Ile Leu Asp Arg Phe Ile
        35                  40                  45

Leu Lys Ala Leu Asp Arg His Trp His Ser Lys Cys Leu Lys Cys Ser
    50                  55                  60

Asp Cys His Thr Pro Leu Ala Glu Arg Cys Phe Ser Arg Gly Glu Ser
65                  70                  75                  80

Val Tyr Cys Lys Asp Asp Phe Phe Lys Arg Phe Gly Thr Lys Cys Ala
                85                  90                  95

Ala Cys Gln Leu Gly Ile Pro Pro Thr Gln Val Val Arg Arg Ala Gln
            100                 105                 110

Asp Phe Val Tyr His Leu His Cys Phe Ala Cys Val Val Cys Lys Arg
        115                 120                 125

Gln Leu Ala Thr Gly Asp Glu Phe Tyr Leu Met Glu Asp Ser Arg Leu
    130                 135                 140

Val Cys Lys Ala Asp Tyr Glu Thr Ala Lys Gln Arg Glu Ala Glu Ala
145                 150                 155                 160

Thr Ala Lys Arg Pro Arg Thr Thr Ile Thr Ala Lys Gln Leu Glu Thr
                165                 170                 175

Leu Lys Ser Ala Tyr Asn Thr Ser Pro Lys Pro Ala Arg His Val Arg
            180                 185                 190

Glu Gln Leu Ser Ser Glu Thr Gly Leu Asp Met Arg Val Val Gln Val
        195                 200                 205
```

```
Trp Phe Gln Asn Arg Arg Ala Lys Glu Lys Arg Leu Lys Lys Asp Ala
    210                 215                 220

Gly Arg Gln Arg Trp Gly Gln Tyr Phe Arg Asn Met Lys Arg Ser Arg
225                 230                 235                 240

Gly Gly Ser Lys Ser Asp Lys Asp Ser Val Gln Glu Gly Gln Asp Ser
                245                 250                 255

Asp Ala Glu Val Ser Phe Pro Asp Glu Pro Ser Leu Ala Glu Met Gly
            260                 265                 270

Pro Ala Asn Gly Leu Tyr Gly Ser Leu Gly Glu Pro Thr Gln Ala Leu
        275                 280                 285

Gly Arg Pro Ser Gly Ala Leu Gly Asn Phe Ser Leu Glu His Gly Gly
    290                 295                 300

Leu Ala Gly Pro Glu Gln Tyr Arg Glu Leu Arg Pro Gly Ser Pro Tyr
305                 310                 315                 320

Gly Val Pro Pro Ser Pro Ala Ala Pro Gln Ser Leu Pro Gly Pro Gln
                325                 330                 335

Pro Leu Leu Ser Ser Leu Val Tyr Pro Asp Thr Ser Leu Gly Leu Val
            340                 345                 350

Pro Ser Gly Ala Pro Gly Gly Pro Pro Pro Met Arg Val Leu Ala Gly
        355                 360                 365

Asn Gly Pro Ser Ser Asp Leu Ser Thr Gly Ser Ser Gly Gly Tyr Pro
    370                 375                 380

Asp Phe Pro Ala Ser Pro Ala Ser Trp Leu Asp Glu Val Asp His Ala
385                 390                 395                 400

Gln Phe


<210> SEQ ID NO 2
<211> LENGTH: 402
<212> TYPE: PRT
<213> ORGANISM: Mus musculus

<400> SEQUENCE: 2

Met Glu Ala Arg Gly Glu Leu Asp Pro Ser Arg Glu Ser Ala Gly Gly
1               5                   10                  15

Asp Leu Leu Leu Ala Leu Leu Ala Arg Arg Ala Asp Leu Arg Arg Glu
            20                  25                  30

Ile Pro Met Cys Ala Gly Cys Asp Gln His Ile Leu Asp Arg Phe Ile
        35                  40                  45

Leu Lys Ala Leu Asp Arg His Trp His Ser Lys Cys Leu Lys Cys Ser
    50                  55                  60

Asp Cys His Val Pro Leu Ala Glu Arg Cys Phe Ser Arg Gly Glu Ser
65                  70                  75                  80

Val Tyr Cys Lys Asp Asp Phe Phe Lys Arg Phe Gly Thr Lys Cys Ala
                85                  90                  95

Ala Cys Gln Leu Gly Ile Pro Pro Thr Gln Val Val Arg Arg Ala Gln
            100                 105                 110

Asp Phe Val Tyr His Leu His Cys Phe Ala Cys Val Val Cys Lys Arg
        115                 120                 125

Gln Leu Ala Thr Gly Asp Glu Phe Tyr Leu Met Glu Asp Ser Arg Leu
    130                 135                 140

Val Cys Lys Ala Asp Tyr Glu Thr Ala Lys Gln Arg Glu Ala Glu Ala
145                 150                 155                 160

Thr Ala Lys Arg Pro Arg Thr Thr Ile Thr Ala Lys Gln Leu Glu Thr
                165                 170                 175
```

Leu Lys Ser Ala Tyr Asn Thr Ser Pro Lys Pro Ala Arg His Val Arg
180 185 190

Glu Gln Leu Ser Ser Glu Thr Gly Leu Asp Met Arg Val Val Gln Val
195 200 205

Trp Phe Gln Asn Arg Arg Ala Lys Glu Lys Arg Leu Lys Lys Asp Ala
210 215 220

Gly Arg Gln Arg Trp Gly Gln Tyr Phe Arg Asn Met Lys Arg Ser Arg
225 230 235 240

Gly Ser Ser Lys Ser Asp Lys Asp Ser Ile Gln Glu Gly Gln Asp Ser
245 250 255

Asp Ala Glu Val Ser Phe Thr Asp Glu Pro Ser Met Ala Asp Met Gly
260 265 270

Pro Ala Asn Gly Leu Tyr Ser Ser Leu Gly Glu Pro Ala Pro Ala Leu
275 280 285

Gly Arg Pro Val Gly Gly Leu Gly Ser Phe Thr Leu Asp His Gly Gly
290 295 300

Leu Thr Gly Pro Glu Gln Tyr Arg Glu Leu Arg Pro Gly Ser Pro Tyr
305 310 315 320

Gly Ile Pro Pro Ser Pro Ala Ala Pro Gln Ser Leu Pro Gly Pro Gln
325 330 335

Pro Leu Leu Ser Ser Leu Val Tyr Pro Asp Thr Asn Leu Ser Leu Val
340 345 350

Pro Ser Gly Pro Pro Gly Gly Pro Pro Pro Met Arg Val Leu Ala Gly
355 360 365

Asn Gly Pro Ser Ser Asp Leu Ser Thr Glu Ser Ser Ser Gly Tyr Pro
370 375 380

Asp Phe Pro Ala Ser Pro Ala Ser Trp Leu Asp Glu Val Asp His Ala
385 390 395 400

Gln Phe

<210> SEQ ID NO 3
<211> LENGTH: 236
<212> TYPE: PRT
<213> ORGANISM: Homo sapiens

<400> SEQUENCE: 3

Met Glu Ser Ser Ala Lys Met Glu Ser Gly Gly Ala Gly Gln Gln Pro
1 5 10 15

Gln Pro Gln Pro Gln Gln Pro Phe Leu Pro Pro Ala Ala Cys Phe Phe
20 25 30

Ala Thr Ala Ala Ala Ala Ala Ala Ala Ala Ala Ala Ala Ala Ala Gln
35 40 45

Ser Ala Gln Gln Gln Gln Gln Gln Gln Gln Gln Gln Gln Gln Ala Pro
50 55 60

Gln Leu Arg Pro Ala Ala Asp Gly Gln Pro Ser Gly Gly Gly His Lys
65 70 75 80

Ser Ala Pro Lys Gln Val Lys Arg Gln Arg Ser Ser Ser Pro Glu Leu
85 90 95

Met Arg Cys Lys Arg Arg Leu Asn Phe Ser Gly Phe Gly Tyr Ser Leu
100 105 110

Pro Gln Gln Gln Pro Ala Ala Val Ala Arg Arg Asn Glu Arg Glu Arg
115 120 125

Asn Arg Val Lys Leu Val Asn Leu Gly Phe Ala Thr Leu Arg Glu His
130 135 140

-continued

Val Pro Asn Gly Ala Ala Asn Lys Lys Met Ser Lys Val Glu Thr Leu
145 150 155 160

Arg Ser Ala Val Glu Tyr Ile Arg Ala Leu Gln Gln Leu Leu Asp Glu
165 170 175

His Asp Ala Val Ser Ala Ala Phe Gln Ala Gly Val Leu Ser Pro Thr
180 185 190

Ile Ser Pro Asn Tyr Ser Asn Asp Leu Asn Ser Met Ala Gly Ser Pro
195 200 205

Val Ser Ser Tyr Ser Ser Asp Glu Gly Ser Tyr Asp Pro Leu Ser Pro
210 215 220

Glu Glu Gln Glu Leu Leu Asp Phe Thr Asn Trp Phe
225 230 235

<210> SEQ ID NO 4
<211> LENGTH: 231
<212> TYPE: PRT
<213> ORGANISM: Mus musculus

<400> SEQUENCE: 4

Met Glu Ser Ser Gly Lys Met Glu Ser Gly Ala Gly Gln Gln Pro Gln
1 5 10 15

Pro Pro Gln Pro Phe Leu Pro Pro Ala Ala Cys Phe Phe Ala Thr Ala
20 25 30

Ala Ala Ala Ala Ala Ala Ala Ala Ala Ala Ala Gln Ser Ala Gln Gln
35 40 45

Gln Gln Pro Gln Ala Pro Pro Gln Gln Ala Pro Gln Leu Ser Pro Val
50 55 60

Ala Asp Ser Gln Pro Ser Gly Gly Gly His Lys Ser Ala Ala Lys Gln
65 70 75 80

Val Lys Arg Gln Arg Ser Ser Ser Pro Glu Leu Met Arg Cys Lys Arg
85 90 95

Arg Leu Asn Phe Ser Gly Phe Gly Tyr Ser Leu Pro Gln Gln Gln Pro
100 105 110

Ala Ala Val Ala Arg Arg Asn Glu Arg Glu Arg Asn Arg Val Lys Leu
115 120 125

Val Asn Leu Gly Phe Ala Thr Leu Arg Glu His Val Pro Asn Gly Ala
130 135 140

Ala Asn Lys Lys Met Ser Lys Val Glu Thr Leu Arg Ser Ala Val Glu
145 150 155 160

Tyr Ile Arg Ala Leu Gln Gln Leu Leu Asp Glu His Asp Ala Val Ser
165 170 175

Ala Ala Phe Gln Ala Gly Val Leu Ser Pro Thr Ile Ser Pro Asn Tyr
180 185 190

Ser Asn Asp Leu Asn Ser Met Ala Gly Ser Pro Val Ser Ser Tyr Ser
195 200 205

Ser Asp Glu Gly Ser Tyr Asp Pro Leu Ser Pro Glu Glu Gln Glu Leu
210 215 220

Leu Asp Phe Thr Asn Trp Phe
225 230

<210> SEQ ID NO 5
<211> LENGTH: 443
<212> TYPE: PRT
<213> ORGANISM: Homo sapiens

<400> SEQUENCE: 5

-continued

```
Met Ala Thr Ala Ala Ser Asn His Tyr Ser Leu Leu Thr Ser Ser Ala
1               5                   10                  15

Ser Ile Val His Ala Glu Pro Pro Gly Gly Met Gln Gln Gly Ala Gly
            20                  25                  30

Gly Tyr Arg Glu Ala Gln Ser Leu Val Gln Gly Asp Tyr Gly Ala Leu
        35                  40                  45

Gln Ser Asn Gly His Pro Leu Ser His Ala His Gln Trp Ile Thr Ala
    50                  55                  60

Leu Ser His Gly Gly Gly Gly Gly Gly Gly Gly Gly Gly Gly Gly Gly
65                  70                  75                  80

Gly Gly Gly Gly Gly Gly Gly Gly Asp Gly Ser Pro Trp Ser Thr Ser
                85                  90                  95

Pro Leu Gly Gln Pro Asp Ile Lys Pro Ser Val Val Val Gln Gln Gly
            100                 105                 110

Gly Arg Gly Asp Glu Leu His Gly Pro Gly Ala Leu Gln Gln Gln His
        115                 120                 125

Gln Gln Gln Gln Gln Gln Gln Gln Gln Gln Gln Gln Gln Gln Gln Gln
    130                 135                 140

Gln Gln Gln Gln Gln Arg Pro Pro His Leu Val His His Ala Ala Asn
145                 150                 155                 160

His His Pro Gly Pro Gly Ala Trp Arg Ser Ala Ala Ala Ala Ala His
                165                 170                 175

Leu Pro Pro Ser Met Gly Ala Ser Asn Gly Gly Leu Leu Tyr Ser Gln
            180                 185                 190

Pro Ser Phe Thr Val Asn Gly Met Leu Gly Ala Gly Gly Gln Pro Ala
        195                 200                 205

Gly Leu His His His Gly Leu Arg Asp Ala His Asp Glu Pro His His
    210                 215                 220

Ala Asp His His Pro His Pro His Ser His Pro His Gln Gln Pro Pro
225                 230                 235                 240

Pro Pro Pro Pro Pro Gln Gly Pro Pro Gly His Pro Gly Ala His His
                245                 250                 255

Asp Pro His Ser Asp Glu Asp Thr Pro Thr Ser Asp Asp Leu Glu Gln
            260                 265                 270

Phe Ala Lys Gln Phe Lys Gln Arg Arg Ile Lys Leu Gly Phe Thr Gln
        275                 280                 285

Ala Asp Val Gly Leu Ala Leu Gly Thr Leu Tyr Gly Asn Val Phe Ser
    290                 295                 300

Gln Thr Thr Ile Cys Arg Phe Glu Ala Leu Gln Leu Ser Phe Lys Asn
305                 310                 315                 320

Met Cys Lys Leu Lys Pro Leu Leu Asn Lys Trp Leu Glu Glu Ala Asp
                325                 330                 335

Ser Ser Ser Gly Ser Pro Thr Ser Ile Asp Lys Ile Ala Ala Gln Gly
            340                 345                 350

Arg Lys Arg Lys Lys Arg Thr Ser Ile Glu Val Ser Val Lys Gly Ala
        355                 360                 365

Leu Glu Ser His Phe Leu Lys Cys Pro Lys Pro Ser Ala Gln Glu Ile
    370                 375                 380

Thr Ser Leu Ala Asp Ser Leu Gln Leu Glu Lys Glu Val Val Arg Val
385                 390                 395                 400

Trp Phe Cys Asn Arg Arg Gln Lys Glu Lys Arg Met Thr Pro Pro Gly
                405                 410                 415

Gly Thr Leu Pro Gly Ala Glu Asp Val Tyr Gly Gly Ser Arg Asp Thr
```

420 425 430

Pro Pro His His Gly Val Gln Thr Pro Val Gln
435 440

<210> SEQ ID NO 6
<211> LENGTH: 445
<212> TYPE: PRT
<213> ORGANISM: Mus musculus

<400> SEQUENCE: 6

Met Ala Thr Ala Ala Ser Asn His Tyr Ser Leu Leu Thr Ser Ser Ala
1 5 10 15

Ser Ile Val His Ala Glu Pro Pro Gly Gly Met Gln Gln Gly Ala Gly
20 25 30

Gly Tyr Arg Glu Ala Gln Ser Leu Val Gln Gly Asp Tyr Gly Ala Leu
35 40 45

Gln Ser Asn Gly His Pro Leu Ser His Ala His Gln Trp Ile Thr Ala
50 55 60

Leu Ser His Gly Gly Gly Gly Gly Gly Gly Gly Gly Gly Gly Gly Gly
65 70 75 80

Gly Gly Gly Gly Gly Gly Gly Gly Asp Gly Ser Pro Trp Ser Thr Ser
85 90 95

Pro Leu Gly Gln Pro Asp Ile Lys Pro Ser Val Val Val Gln Gln Gly
100 105 110

Gly Arg Gly Asp Glu Leu His Gly Pro Gly Ala Leu Gln Gln Gln His
115 120 125

Gln Gln Gln Gln Gln Gln Gln Gln Gln Gln Gln Gln Gln Gln Gln Gln
130 135 140

Gln Gln Gln Gln Gln Gln Gln Arg Pro Pro His Leu Val His His Ala
145 150 155 160

Ala Asn His His Pro Gly Pro Gly Ala Trp Arg Ser Ala Ala Ala Ala
165 170 175

Ala His Leu Pro Pro Ser Met Gly Ala Ser Asn Gly Gly Leu Leu Tyr
180 185 190

Ser Gln Pro Ser Phe Thr Val Asn Gly Met Leu Gly Ala Gly Gly Gln
195 200 205

Pro Ala Gly Leu His His His Gly Leu Arg Asp Ala His Asp Glu Pro
210 215 220

His His Ala Asp His His Pro His Pro His Ser His Pro His Gln Gln
225 230 235 240

Pro Pro Pro Pro Pro Pro Pro Gln Gly Pro Pro Gly His Pro Gly Ala
245 250 255

His His Asp Pro His Ser Asp Glu Asp Thr Pro Thr Ser Asp Asp Leu
260 265 270

Glu Gln Phe Ala Lys Gln Phe Lys Gln Arg Arg Ile Lys Leu Gly Phe
275 280 285

Thr Gln Ala Asp Val Gly Leu Ala Leu Gly Thr Leu Tyr Gly Asn Val
290 295 300

Phe Ser Gln Thr Thr Ile Cys Arg Phe Glu Ala Leu Gln Leu Ser Phe
305 310 315 320

Lys Asn Met Cys Lys Leu Lys Pro Leu Leu Asn Lys Trp Leu Glu Glu
325 330 335

Ala Asp Ser Ser Ser Gly Ser Pro Thr Ser Ile Asp Lys Ile Ala Ala
340 345 350

-continued

```
Gln Gly Arg Lys Arg Lys Lys Arg Thr Ser Ile Glu Val Ser Val Lys
        355                 360                 365

Gly Ala Leu Glu Ser His Phe Leu Lys Cys Pro Lys Pro Ser Ala Gln
    370                 375                 380

Glu Ile Thr Ser Leu Ala Asp Ser Leu Gln Leu Glu Lys Glu Val Val
385                 390                 395                 400

Arg Val Trp Phe Cys Asn Arg Arg Gln Lys Glu Lys Arg Met Thr Pro
                405                 410                 415

Pro Gly Gly Thr Leu Pro Gly Ala Glu Asp Val Tyr Gly Gly Ser Arg
            420                 425                 430

Asp Thr Pro Pro His His Gly Val Gln Thr Pro Val Gln
        435                 440                 445


<210> SEQ ID NO 7
<211> LENGTH: 1184
<212> TYPE: PRT
<213> ORGANISM: Homo sapiens

<400> SEQUENCE: 7

Met Glu Val Asp Thr Glu Glu Lys Arg His Arg Thr Arg Ser Lys Gly
1               5                   10                  15

Val Arg Val Pro Val Glu Pro Ala Ile Gln Glu Leu Phe Ser Cys Pro
            20                  25                  30

Thr Pro Gly Cys Asp Gly Ser Gly His Val Ser Gly Lys Tyr Ala Arg
        35                  40                  45

His Arg Ser Val Tyr Gly Cys Pro Leu Ala Lys Lys Arg Lys Thr Gln
    50                  55                  60

Asp Lys Gln Pro Gln Glu Pro Ala Pro Lys Arg Lys Pro Phe Ala Val
65                  70                  75                  80

Lys Ala Asp Ser Ser Ser Val Asp Glu Cys Asp Asp Ser Asp Gly Thr
                85                  90                  95

Glu Asp Met Asp Glu Lys Glu Glu Asp Glu Gly Glu Glu Tyr Ser Glu
            100                 105                 110

Asp Asn Asp Glu Pro Gly Asp Glu Asp Glu Glu Asp Glu Glu Gly Asp
        115                 120                 125

Arg Glu Glu Glu Glu Glu Ile Glu Glu Glu Asp Glu Asp Asp Asp Glu
    130                 135                 140

Asp Gly Glu Asp Val Glu Asp Glu Glu Glu Glu Glu Glu Glu Glu Glu
145                 150                 155                 160

Glu Glu Glu Glu Glu Glu Glu Asn Glu Asp His Gln Met Asn Cys His
                165                 170                 175

Asn Thr Arg Ile Met Gln Asp Thr Glu Lys Asp Asp Asn Asn Asn Asp
            180                 185                 190

Glu Tyr Asp Asn Tyr Asp Glu Leu Val Ala Lys Ser Leu Leu Asn Leu
        195                 200                 205

Gly Lys Ile Ala Glu Asp Ala Ala Tyr Arg Ala Arg Thr Glu Ser Glu
    210                 215                 220

Met Asn Ser Asn Thr Ser Asn Ser Leu Glu Asp Asp Ser Asp Lys Asn
225                 230                 235                 240

Glu Asn Leu Gly Arg Lys Ser Glu Leu Ser Leu Asp Leu Asp Ser Asp
                245                 250                 255

Val Val Arg Glu Thr Val Asp Ser Leu Lys Leu Leu Ala Gln Gly His
            260                 265                 270

Gly Val Val Leu Ser Glu Asn Met Asn Asp Arg Asn Tyr Ala Asp Ser
        275                 280                 285
```

```
Met Ser Gln Gln Asp Ser Arg Asn Met Asn Tyr Val Met Leu Gly Lys
    290                 295                 300

Pro Met Asn Asn Gly Leu Met Glu Lys Met Val Glu Glu Ser Asp Glu
305                 310                 315                 320

Glu Val Cys Leu Ser Ser Leu Glu Cys Leu Arg Asn Gln Cys Phe Asp
                325                 330                 335

Leu Ala Arg Lys Leu Ser Glu Thr Asn Pro Gln Glu Arg Asn Pro Gln
            340                 345                 350

Gln Asn Met Asn Ile Arg Gln His Val Arg Pro Glu Glu Asp Phe Pro
        355                 360                 365

Gly Arg Thr Pro Asp Arg Asn Tyr Ser Asp Met Leu Asn Leu Met Arg
    370                 375                 380

Leu Glu Glu Gln Leu Ser Pro Arg Ser Arg Val Phe Ala Ser Cys Ala
385                 390                 395                 400

Lys Glu Asp Gly Cys His Glu Arg Asp Asp Asp Thr Thr Ser Val Asn
                405                 410                 415

Ser Asp Arg Ser Glu Glu Val Phe Asp Met Thr Lys Gly Asn Leu Thr
            420                 425                 430

Leu Leu Glu Lys Ala Ile Ala Leu Glu Thr Glu Arg Ala Lys Ala Met
        435                 440                 445

Arg Glu Lys Met Ala Met Glu Ala Gly Arg Arg Asp Asn Met Arg Ser
    450                 455                 460

Tyr Glu Asp Gln Ser Pro Arg Gln Leu Pro Gly Glu Asp Arg Lys Pro
465                 470                 475                 480

Lys Ser Ser Asp Ser His Val Lys Lys Pro Tyr Tyr Asp Pro Ser Arg
                485                 490                 495

Thr Glu Lys Lys Glu Ser Lys Cys Pro Thr Pro Gly Cys Asp Gly Thr
            500                 505                 510

Gly His Val Thr Gly Leu Tyr Pro His His Arg Ser Leu Ser Gly Cys
        515                 520                 525

Pro His Lys Asp Arg Val Pro Pro Glu Ile Leu Ala Met His Glu Ser
    530                 535                 540

Val Leu Lys Cys Pro Thr Pro Gly Cys Thr Gly Arg Gly His Val Asn
545                 550                 555                 560

Ser Asn Arg Asn Ser His Arg Ser Leu Ser Gly Cys Pro Ile Ala Ala
                565                 570                 575

Ala Glu Lys Leu Ala Lys Ala Gln Glu Lys His Gln Ser Cys Asp Val
            580                 585                 590

Ser Lys Ser Ser Gln Ala Ser Asp Arg Val Leu Arg Pro Met Cys Phe
        595                 600                 605

Val Lys Gln Leu Glu Ile Pro Gln Tyr Gly Tyr Arg Asn Asn Val Pro
    610                 615                 620

Thr Thr Thr Pro Arg Ser Asn Leu Ala Lys Glu Leu Glu Lys Tyr Ser
625                 630                 635                 640

Lys Thr Ser Phe Glu Tyr Asn Ser Tyr Asp Asn His Thr Tyr Gly Lys
                645                 650                 655

Arg Ala Ile Ala Pro Lys Val Gln Thr Arg Asp Ile Ser Pro Lys Gly
            660                 665                 670

Tyr Asp Asp Ala Lys Arg Tyr Cys Lys Asp Pro Ser Pro Ser Ser Ser
        675                 680                 685

Ser Thr Ser Ser Tyr Ala Pro Ser Ser Ser Ser Asn Leu Ser Cys Gly
    690                 695                 700
```

-continued

```
Gly Gly Ser Ser Ala Ser Ser Thr Cys Ser Lys Ser Ser Phe Asp Tyr
705                 710                 715                 720

Thr His Asp Met Glu Ala Ala His Met Ala Ala Thr Ala Ile Leu Asn
                725                 730                 735

Leu Ser Thr Arg Cys Arg Glu Met Pro Gln Asn Leu Ser Thr Lys Pro
            740                 745                 750

Gln Asp Leu Cys Ala Thr Arg Asn Pro Asp Met Glu Val Asp Glu Asn
        755                 760                 765

Gly Thr Leu Asp Leu Ser Met Asn Lys Gln Arg Pro Arg Asp Ser Cys
    770                 775                 780

Cys Pro Ile Leu Thr Pro Leu Glu Pro Met Ser Pro Gln Gln Gln Ala
785                 790                 795                 800

Val Met Asn Asn Arg Cys Phe Gln Leu Gly Glu Gly Asp Cys Trp Asp
                805                 810                 815

Leu Pro Val Asp Tyr Thr Lys Met Lys Pro Arg Arg Ile Asp Glu Asp
            820                 825                 830

Glu Ser Lys Asp Ile Thr Pro Glu Asp Leu Asp Pro Phe Gln Glu Ala
        835                 840                 845

Leu Glu Glu Arg Arg Tyr Pro Gly Glu Val Thr Ile Pro Ser Pro Lys
    850                 855                 860

Pro Lys Tyr Pro Gln Cys Lys Glu Ser Lys Lys Asp Leu Ile Thr Leu
865                 870                 875                 880

Ser Gly Cys Pro Leu Ala Asp Lys Ser Ile Arg Ser Met Leu Ala Thr
                885                 890                 895

Ser Ser Gln Glu Leu Lys Cys Pro Thr Pro Gly Cys Asp Gly Ser Gly
            900                 905                 910

His Ile Thr Gly Asn Tyr Ala Ser His Arg Ser Leu Ser Gly Cys Pro
        915                 920                 925

Arg Ala Lys Lys Ser Gly Ile Arg Ile Ala Gln Ser Lys Glu Asp Lys
    930                 935                 940

Glu Asp Gln Glu Pro Ile Arg Cys Pro Val Pro Gly Cys Asp Gly Gln
945                 950                 955                 960

Gly His Ile Thr Gly Lys Tyr Ala Ser His Arg Ser Ala Ser Gly Cys
                965                 970                 975

Pro Leu Ala Ala Lys Arg Gln Lys Asp Gly Tyr Leu Asn Gly Ser Gln
            980                 985                 990

Phe Ser Trp Lys Ser Val Lys Thr  Glu Gly Met Ser Cys  Pro Thr Pro
        995                 1000                1005

Gly Cys  Asp Gly Ser Gly His  Val Ser Gly Ser Phe  Leu Thr His
    1010                1015                1020

Arg Ser  Leu Ser Gly Cys Pro  Arg Ala Thr Ser Ala  Met Lys Lys
    1025                1030                1035

Ala Lys  Leu Ser Gly Glu Gln  Met Leu Thr Ile Lys  Gln Arg Ala
    1040                1045                1050

Ser Asn  Gly Ile Glu Asn Asp  Glu Glu Ile Lys Gln  Leu Asp Glu
    1055                1060                1065

Glu Ile  Lys Glu Leu Asn Glu  Ser Asn Ser Gln Met  Glu Ala Asp
    1070                1075                1080

Met Ile  Lys Leu Arg Thr Gln  Ile Thr Thr Met Glu  Ser Asn Leu
    1085                1090                1095

Lys Thr  Ile Glu Glu Glu Asn  Lys Val Ile Glu Gln  Gln Asn Glu
    1100                1105                1110

Ser Leu  Leu His Glu Leu Ala  Asn Leu Ser Gln Ser  Leu Ile His
```

```
    1115                1120                1125

Ser Leu  Ala Asn Ile Gln Leu  Pro His Met Asp Pro  Ile Asn Glu
    1130                1135                1140

Gln Asn  Phe Asp Ala Tyr Val  Thr Thr Leu Thr Glu  Met Tyr Thr
    1145                1150                1155

Asn Gln  Asp Arg Tyr Gln Ser  Pro Glu Asn Lys Ala  Leu Leu Glu
    1160                1165                1170

Asn Ile  Lys Gln Ala Val Arg  Gly Ile Gln Val
    1175                1180
```

<210> SEQ ID NO 8
<211> LENGTH: 1187
<212> TYPE: PRT
<213> ORGANISM: Mus musculus

<400> SEQUENCE: 8

```
Met Asp Val Asp Ser Glu Glu Lys Arg His Arg Thr Arg Ser Lys Gly
1               5                   10                  15

Val Arg Val Pro Val Glu Pro Ala Ile Gln Glu Leu Phe Ser Cys Pro
            20                  25                  30

Thr Pro Gly Cys Asp Gly Ser Gly His Val Ser Gly Lys Tyr Ala Arg
        35                  40                  45

His Arg Ser Val Tyr Gly Cys Pro Leu Ala Lys Lys Arg Lys Thr Gln
    50                  55                  60

Asp Lys Gln Pro Gln Glu Pro Ala Pro Lys Arg Lys Pro Phe Ala Val
65                  70                  75                  80

Lys Ala Asp Ser Ser Ser Val Asp Glu Cys Tyr Glu Ser Asp Gly Thr
                85                  90                  95

Glu Asp Met Asp Asp Lys Glu Glu Asp Asp Asp Glu Glu Phe Ser Glu
            100                 105                 110

Asp Asn Asp Glu Gln Gly Asp Asp Asp Asp Glu Asp Glu Val Asp Arg
        115                 120                 125

Glu Asp Glu Glu Glu Ile Glu Glu Glu Asp Asp Glu Glu Asp Asp Asp
    130                 135                 140

Asp Glu Asp Gly Asp Asp Val Glu Glu Glu Glu Glu Asp Asp Asp Glu
145                 150                 155                 160

Glu Glu Glu Glu Glu Glu Glu Glu Glu Glu Asn Glu Asp His Gln Met
                165                 170                 175

Ser Cys Thr Arg Ile Met Gln Asp Thr Asp Lys Asp Asp Asn Asn Asn
            180                 185                 190

Asp Glu Tyr Asp Asn Tyr Asp Glu Leu Val Ala Lys Ser Leu Leu Asn
        195                 200                 205

Leu Gly Lys Ile Ala Glu Asp Ala Ala Tyr Arg Ala Arg Thr Glu Ser
    210                 215                 220

Glu Met Asn Ser Asn Thr Ser Asn Ser Leu Glu Asp Asp Ser Asp Lys
225                 230                 235                 240

Asn Glu Asn Leu Gly Arg Lys Ser Glu Leu Ser Leu Asp Leu Asp Ser
                245                 250                 255

Asp Val Val Arg Glu Thr Val Asp Ser Leu Lys Leu Leu Ala Gln Gly
            260                 265                 270

His Gly Val Val Leu Ser Glu Asn Ile Ser Asp Arg Ser Tyr Ala Glu
        275                 280                 285

Gly Met Ser Gln Gln Asp Ser Arg Asn Met Asn Tyr Val Met Leu Gly
    290                 295                 300
```

```
Lys Pro Met Asn Asn Gly Leu Met Glu Lys Met Val Glu Glu Ser Asp
305                 310                 315                 320

Glu Glu Val Cys Leu Ser Ser Leu Glu Cys Leu Arg Asn Gln Cys Phe
                325                 330                 335

Asp Leu Ala Arg Lys Leu Ser Glu Thr Asn Pro Gln Asp Arg Ser Gln
            340                 345                 350

Pro Pro Asn Met Ser Val Arg Gln His Val Arg Gln Glu Asp Asp Phe
        355                 360                 365

Pro Gly Arg Thr Pro Asp Arg Ser Tyr Ser Asp Met Met Asn Leu Met
    370                 375                 380

Arg Leu Glu Glu Gln Leu Ser Pro Arg Ser Arg Thr Phe Ser Ser Cys
385                 390                 395                 400

Ala Lys Glu Asp Gly Cys His Glu Arg Asp Asp Asp Thr Thr Ser Val
                405                 410                 415

Asn Ser Asp Arg Ser Glu Glu Val Phe Asp Met Thr Lys Gly Asn Leu
            420                 425                 430

Thr Leu Leu Glu Lys Ala Ile Ala Leu Glu Thr Glu Arg Ala Lys Ala
        435                 440                 445

Met Arg Glu Lys Met Ala Met Asp Ala Gly Arg Arg Asp Asn Leu Arg
    450                 455                 460

Ser Tyr Glu Asp Gln Ser Pro Arg Gln Leu Ala Gly Glu Asp Arg Lys
465                 470                 475                 480

Ser Lys Ser Ser Asp Ser His Val Lys Lys Pro Tyr Tyr Gly Lys Asp
                485                 490                 495

Pro Ser Arg Thr Glu Lys Arg Glu Ser Lys Cys Pro Thr Pro Gly Cys
            500                 505                 510

Asp Gly Thr Gly His Val Thr Gly Leu Tyr Pro His His Arg Ser Leu
        515                 520                 525

Ser Gly Cys Pro His Lys Asp Arg Val Pro Pro Glu Ile Leu Ala Met
    530                 535                 540

His Glu Asn Val Leu Lys Cys Pro Thr Pro Gly Cys Thr Gly Arg Gly
545                 550                 555                 560

His Val Asn Ser Asn Arg Asn Ser His Arg Ser Leu Ser Gly Cys Pro
                565                 570                 575

Ile Ala Ala Ala Glu Lys Leu Ala Lys Ala Gln Glu Lys His Gln Ser
            580                 585                 590

Cys Asp Val Ser Lys Ser Asn Gln Ala Ser Asp Arg Val Leu Arg Pro
        595                 600                 605

Met Cys Phe Val Lys Gln Leu Glu Ile Pro Gln Tyr Gly Tyr Arg Asn
    610                 615                 620

Asn Val Pro Thr Thr Thr Pro Arg Ser Asn Leu Ala Lys Glu Leu Glu
625                 630                 635                 640

Lys Tyr Ser Lys Thr Ser Phe Glu Tyr Asn Ser Tyr Asp Asn His Thr
                645                 650                 655

Tyr Gly Lys Arg Ala Ile Ala Pro Lys Val Gln Thr Arg Asp Ile Ser
            660                 665                 670

Pro Lys Gly Tyr Asp Asp Ala Lys Arg Tyr Cys Lys Asn Ala Ser Pro
        675                 680                 685

Ser Ser Ser Thr Thr Ser Ser Tyr Ala Pro Ser Ser Ser Ser Asn Leu
    690                 695                 700

Ser Cys Gly Gly Gly Ser Ser Ala Ser Ser Thr Cys Ser Lys Ser Ser
705                 710                 715                 720

Phe Asp Tyr Thr His Asp Met Glu Ala Ala His Met Ala Ala Thr Ala
```

```
                725                 730                 735

Ile Leu Asn Leu Ser Thr Arg Cys Arg Glu Met Pro Gln Asn Leu Ser
            740                 745                 750

Thr Lys Pro Gln Asp Leu Cys Thr Ala Arg Asn Pro Asp Met Glu Val
        755                 760                 765

Asp Glu Asn Gly Thr Leu Asp Leu Ser Met Asn Lys Gln Arg Pro Arg
    770                 775                 780

Asp Ser Cys Cys Pro Val Leu Thr Pro Leu Glu Pro Met Ser Pro Gln
785                 790                 795                 800

Gln Gln Ala Val Met Ser Ser Arg Cys Phe Gln Leu Ser Glu Gly Asp
                805                 810                 815

Cys Trp Asp Leu Pro Val Asp Tyr Thr Lys Met Lys Pro Arg Arg Val
            820                 825                 830

Asp Glu Asp Glu Pro Lys Glu Ile Thr Pro Glu Asp Leu Asp Pro Phe
        835                 840                 845

Gln Glu Ala Leu Glu Glu Arg Arg Tyr Pro Gly Glu Val Thr Ile Pro
    850                 855                 860

Ser Pro Lys Pro Lys Tyr Pro Gln Cys Lys Glu Ser Lys Lys Asp Leu
865                 870                 875                 880

Ile Thr Leu Ser Gly Cys Pro Leu Ala Asp Lys Ser Ile Arg Ser Met
                885                 890                 895

Leu Ala Thr Ser Ser Gln Glu Leu Lys Cys Pro Thr Pro Gly Cys Asp
            900                 905                 910

Gly Ser Gly His Ile Thr Gly Asn Tyr Ala Ser His Arg Ser Leu Ser
        915                 920                 925

Gly Cys Pro Arg Ala Lys Lys Ser Gly Ile Arg Ile Ala Gln Ser Lys
    930                 935                 940

Glu Asp Lys Glu Asp Gln Glu Pro Ile Arg Cys Pro Val Pro Gly Cys
945                 950                 955                 960

Asp Gly Gln Gly His Ile Thr Gly Lys Tyr Ala Ser His Arg Ser Ala
                965                 970                 975

Ser Gly Cys Pro Leu Ala Ala Lys Arg Gln Lys Asp Gly Tyr Leu Asn
            980                 985                 990

Gly Ser Gln Phe Ser Trp Lys Ser  Val Lys Thr Glu Gly  Met Ser Cys
        995                 1000                1005

Pro Thr  Pro Gly Cys Asp Gly  Ser Gly His Val Ser  Gly Ser Phe
    1010                 1015                 1020

Leu Thr  His Arg Ser Leu Ser  Gly Cys Pro Arg Ala  Thr Ser Ala
    1025                 1030                 1035

Met Lys  Lys Ala Lys Leu Ser  Gly Glu Gln Met Leu  Thr Ile Lys
    1040                 1045                 1050

Gln Arg  Ala Ser Asn Gly Ile  Glu Asn Asp Glu Glu  Ile Lys Gln
    1055                 1060                 1065

Leu Asp  Glu Glu Ile Lys Glu  Leu Asn Glu Ser Asn  Ser Gln Met
    1070                 1075                 1080

Glu Ala  Asp Met Ile Lys Leu  Arg Thr Gln Ile Thr  Thr Met Glu
    1085                 1090                 1095

Ser Asn  Leu Lys Thr Ile Glu  Glu Glu Asn Lys Val  Ile Glu Gln
    1100                 1105                 1110

Gln Asn  Glu Ser Leu Leu His  Glu Leu Ala Asn Leu  Ser Gln Ser
    1115                 1120                 1125

Leu Ile  His Ser Leu Ala Asn  Ile Gln Leu Pro His  Met Asp Pro
    1130                 1135                 1140
```

```
Ile Asn  Glu Gln Asn Phe Asp  Ala Tyr Val Thr Thr  Leu Thr Glu
    1145                 1150                 1155

Met Tyr  Thr Asn Gln Asp Arg  Tyr Gln Ser Pro Glu  Asn Lys Ala
    1160                 1165                 1170

Leu Leu  Glu Asn Ile Lys Gln  Ala Val Arg Gly Ile  Gln Val
    1175                 1180                 1185


<210> SEQ ID NO 9
<211> LENGTH: 349
<212> TYPE: PRT
<213> ORGANISM: Homo sapiens

<400> SEQUENCE: 9

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45

Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
    290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
```

```
                325                 330                 335

Asp Thr Pro Asn Ser Met Val Ala Ser Pro Ile Glu Ala
            340                 345


<210> SEQ ID NO 10
<211> LENGTH: 349
<212> TYPE: PRT
<213> ORGANISM: Mus musculus

<400> SEQUENCE: 10

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
        35                  40                  45

Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
    290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
                325                 330                 335

Asp Thr Pro Asn Ser Met Val Ala Ser Pro Ile Glu Ala
            340                 345
```

<210> SEQ ID NO 11
<211> LENGTH: 189
<212> TYPE: PRT
<213> ORGANISM: Homo sapiens

<400> SEQUENCE: 11

```
Met Gly Gly Leu Ser Thr Val Gly Ala Cys Pro Gly Ile Leu Gly Ala
1               5                   10                  15

Gln Gln Ala Gln Ala Gln Ser Asn Leu Leu Gly Lys Cys Arg Arg Pro
            20                  25                  30

Arg Thr Ala Phe Thr Ser Gln Gln Leu Leu Glu Leu Glu His Gln Phe
        35                  40                  45

Lys Leu Asn Lys Tyr Leu Ser Arg Pro Lys Arg Phe Glu Val Ala Thr
    50                  55                  60

Ser Leu Met Leu Thr Glu Thr Gln Val Lys Ile Trp Phe Gln Asn Arg
65                  70                  75                  80

Arg Met Lys Trp Lys Arg Ser Lys Lys Ala Lys Glu Gln Ala Ala Gln
                85                  90                  95

Glu Ala Glu Lys Gln Lys Gly Gly Gly Gly Gly Ala Gly Lys Gly Gly
            100                 105                 110

Ala Glu Glu Pro Gly Ala Glu Glu Leu Leu Gly Pro Pro Ala Pro Gly
        115                 120                 125

Asp Lys Gly Ser Gly Arg Arg Leu Arg Asp Leu Arg Asp Ser Asp Pro
    130                 135                 140

Glu Glu Asp Glu Asp Glu Asp Asp Glu Asp His Phe Pro Tyr Ser Asn
145                 150                 155                 160

Gly Ala Ser Val His Ala Ala Ser Ser Asp Cys Ser Ser Glu Asp Asp
                165                 170                 175

Ser Pro Pro Pro Arg Pro Ser His Gln Pro Ala Pro Gln
            180                 185
```

<210> SEQ ID NO 12
<211> LENGTH: 404
<212> TYPE: PRT
<213> ORGANISM: Mus musculus

<400> SEQUENCE: 12

```
Met Glu Lys Ser Lys Asn Phe Arg Ile Asp Ala Leu Leu Ala Val Asp
1               5                   10                  15

Pro Pro Arg Ala Ala Ser Thr Gln Ser Ala Pro Leu Ala Leu Val Thr
            20                  25                  30

Ser Leu Ala Thr Thr Val Ser Gly Pro Gly Arg Gly Gly Ser Gly Gly
        35                  40                  45

Gly Gly Thr Ser Ser Gly Ala Ser Arg Ser Cys Ser Pro Ala Ser Ser
    50                  55                  60

Glu Ala Thr Ala Ala Pro Gly Asp Arg Leu Arg Ala Glu Ser Pro Ser
65                  70                  75                  80

Pro Pro Arg Leu Leu Ala Ala His Cys Ala Leu Leu Pro Lys Pro Gly
                85                  90                  95

Phe Leu Gly Ala Gly Gly Gly Gly Gly Ala Ala Gly Gly Pro Gly Thr
            100                 105                 110

Pro His His His Ala His Pro Gly Ala Ala Ala Ala Ala Ala Ala Ala
        115                 120                 125

Ala Ala Ala Ala Ala Ala Gly Gly Leu Ala Leu Gly Leu His Pro Gly
    130                 135                 140
```

-continued

```
Gly Ala Gln Gly Gly Ala Gly Leu Pro Ala Gln Ala Ala Leu Tyr Gly
145                 150                 155                 160

His Pro Val Tyr Ser Tyr Ser Ala Ala Ala Ala Ala Ala Ala Leu Ala
                165                 170                 175

Gly Gln His Pro Ala Leu Ser Tyr Ser Tyr Pro Gln Val Gln Gly Ala
            180                 185                 190

His Pro Ala His Pro Ala Asp Pro Ile Lys Leu Gly Ala Ser Thr Phe
        195                 200                 205

Gln Leu Asp Gln Trp Leu Arg Ala Ser Thr Ala Gly Met Ile Leu Pro
    210                 215                 220

Lys Met Pro Asp Phe Ser Ser Gln Ala Gln Ser Asn Leu Leu Gly Lys
225                 230                 235                 240

Cys Arg Arg Pro Arg Thr Ala Phe Thr Ser Gln Gln Leu Leu Glu Leu
                245                 250                 255

Glu His Gln Phe Lys Leu Asn Lys Tyr Leu Ser Arg Pro Lys Arg Phe
            260                 265                 270

Glu Val Ala Thr Ser Leu Met Leu Thr Glu Thr Gln Val Lys Ile Trp
        275                 280                 285

Phe Gln Asn Arg Arg Met Lys Trp Lys Arg Ser Lys Lys Ala Lys Glu
    290                 295                 300

Gln Ala Ala Gln Glu Ala Glu Lys Gln Lys Gly Gly Gly Gly Gly Thr
305                 310                 315                 320

Gly Lys Gly Gly Ser Glu Glu Lys Thr Glu Glu Glu Leu Met Gly Pro
                325                 330                 335

Pro Val Ser Gly Asp Lys Ala Ser Gly Arg Arg Leu Arg Asp Leu Arg
            340                 345                 350

Asp Ser Asp Pro Asp Glu Asp Glu Asp Asp Glu Glu Glu Asp Asn Phe
        355                 360                 365

Pro Tyr Ser Asn Gly Ala Gly Ala His Ala Ala Ser Ser Asp Cys Ser
    370                 375                 380

Ser Glu Asp Asp Ser Pro Pro Pro Arg Leu Gly Gly Pro Gly His Gln
385                 390                 395                 400

Pro Leu Pro Gln


<210> SEQ ID NO 13
<211> LENGTH: 272
<212> TYPE: PRT
<213> ORGANISM: Homo sapiens

<400> SEQUENCE: 13

Met Phe Val Lys Ser Glu Thr Leu Glu Leu Lys Glu Glu Glu Asp Val
1               5                   10                  15

Leu Val Leu Leu Gly Ser Ala Ser Pro Ala Leu Ala Ala Leu Thr Pro
            20                  25                  30

Leu Ser Ser Ser Ala Asp Glu Glu Glu Glu Glu Glu Pro Gly Ala Ser
        35                  40                  45

Gly Gly Ala Arg Arg Gln Arg Gly Ala Glu Ala Gly Gln Gly Ala Arg
    50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Glu Thr Val Gln Arg Ile Lys Lys Thr
            100                 105                 110
```

```
Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Gly Gly
                165                 170                 175

Gly Gly Gly Gly Leu Pro Gly Ala Leu Phe Ser Glu Ala Val Leu Leu
            180                 185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
    210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro Pro
                245                 250                 255

Asp Lys His Arg Tyr Ala Pro His Leu Pro Ile Ala Arg Asp Cys Ile
            260                 265                 270


<210> SEQ ID NO 14
<211> LENGTH: 263
<212> TYPE: PRT
<213> ORGANISM: Mus musculus

<400> SEQUENCE: 14

Met Phe Val Lys Ser Glu Thr Leu Glu Leu Lys Glu Glu Glu Glu Val
1               5                   10                  15

Leu Met Leu Leu Gly Ser Ala Ser Pro Ala Ser Ala Thr Leu Thr Pro
            20                  25                  30

Met Ser Ser Ser Ala Asp Glu Glu Glu Asp Glu Glu Leu Arg Arg Pro
        35                  40                  45

Gly Ser Ala Arg Gly Gln Arg Gly Ala Glu Ala Gly Gln Gly Val Gln
    50                  55                  60

Gly Ser Pro Ala Ser Gly Ala Gly Gly Cys Arg Pro Gly Arg Leu Leu
65                  70                  75                  80

Gly Leu Met His Glu Cys Lys Arg Arg Pro Ser Arg Ser Arg Ala Val
                85                  90                  95

Ser Arg Gly Ala Lys Thr Ala Glu Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Ala Gly
                165                 170                 175

Ala Gly Gly Leu Gln Gly Ala Leu Phe Thr Glu Ala Val Leu Leu Ser
            180                 185                 190

Pro Gly Ala Ala Leu Gly Ala Ser Gly Asp Ser Pro Ser Pro Pro Ser
        195                 200                 205

Ser Trp Ser Cys Thr Asn Ser Pro Ala Ser Ser Ser Asn Ser Thr Ser
    210                 215                 220
```

```
Pro Tyr Ser Cys Thr Leu Ser Pro Ala Ser Pro Gly Ser Asp Val Asp
225                 230                 235                 240

Tyr Trp Gln Pro Pro Pro Pro Glu Lys His Arg Tyr Ala Pro His Leu
                245                 250                 255

Pro Leu Ala Arg Asp Cys Ile
            260


<210> SEQ ID NO 15
<211> LENGTH: 356
<212> TYPE: PRT
<213> ORGANISM: Homo sapiens

<400> SEQUENCE: 15

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
```

-continued

```
                325                 330                 335

Asp Ser His Ser His His Glu Arg Val Met Ser Ala Gln Leu Asn Ala
            340                 345                 350

Ile Phe His Asp
        355


<210> SEQ ID NO 16
<211> LENGTH: 357
<212> TYPE: PRT
<213> ORGANISM: Mus musculus

<400> SEQUENCE: 16

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Glu Asp Glu
    50                  55                  60

Asp Leu Glu Glu Glu Glu Glu Glu Glu Glu Glu Glu Glu Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335
```

```
Phe Asp Ser His Ser His His Glu Arg Val Met Ser Ala Gln Leu Asn
            340                 345                 350

Ala Ile Phe His Asp
        355


<210> SEQ ID NO 17
<211> LENGTH: 2419
<212> TYPE: DNA
<213> ORGANISM: Homo sapiens

<400> SEQUENCE: 17

cgcagcgccc agcagcaccc ggagtcgctt ggacgccggt tcggggctat tgcggggtgg     60

cgtcgctggg cccgggaaag ttcgggactg gagagtggcg acgccgggcg gcgggaccca    120

tggaggcgcg cggggagctg ggcccggccc gggagtcggc gggaggcgac ctgctgctag    180

cactgctggc gcggagggcg gacctgcgcc gagagatccc gctgtgcgct ggctgtgacc    240

agcacatcct ggaccgcttc atcctcaagg ctctggaccg ccactggcac agcaagtgtc    300

tcaagtgcag cgactgccac acgccactgg ccgagcgctg cttcagccga ggggagagcg    360

tttactgcaa ggacgacttt ttcaagcgct tcgggaccaa gtgcgccgcg tgccagctgg    420

gcatcccgcc cacgcaggtg gtgcgccgcg cccaggactt cgtgtaccac ctgcactgct    480

ttgcctgcgt cgtgtgcaag cggcagctgg ccacgggcga cgagttctac ctcatggagg    540

acagccggct cgtgtgcaag gcggactacg aaaccgccaa gcagcgagag gccgaggcca    600

cggccaagcg gccgcgcacg accatcaccg ccaagcagct ggagacgctg aagagcgctt    660

acaacacctc gcccaagccg gcgcgccacg tgcgcgagca gctctcgtcc gagacgggcc    720

tggacatgcg cgtggtgcag gtttggttcc agaaccgccg ggccaaggag aagaggctga    780

agaaggacgc cggccggcag cgctgggggc agtatttccg caacatgaag cgctcccgcg    840

gcggctccaa gtcggacaag gacagcgttc aggaggggca ggacagcgac gctgaggtct    900

ccttccccga tgagccttcc ttggcggaaa tgggcccggc caatggcctc tacgggagct    960

tgggggaacc cacccaggcc ttgggccggc cctcgggagc cctgggcaac ttctccctgg   1020

agcatggagg cctggcaggc ccagagcagt accgagagct gcgtcccggc agcccctacg   1080

gtgtcccccc atcccccgcc gccccgcaga gcctccctgg cccccagccc ctcctctcca   1140

gcctggtgta cccagacacc agcttgggcc ttgtgccctc gggagccccc ggcgggcccc   1200

cacccatgag ggtgctggca gggaacggac ccagttctga cctatccacg gggagcagcg   1260

ggggttaccc cgacttccct gccagccccg cctcctggct ggatgaggta gaccacgctc   1320

agttctgacc caggcccggc tccaccctgc acctcacacg agggagctgc ccctgggtgg   1380

gcggctcggg gctgctgggg tttccgagga agtggggcca gggcgtcaag ggagggctgg   1440

tgccttcgga gcctcccact gccgaccgca cagctccctc tctgggggct gagggaccca   1500

cctggcccct cctctgacac agggctggcc cgccaggtgg cctcccagca agccagcctt   1560

ttttgtaagc aaatttctcc cctttattga ccaattaact gagcacttgc tgctatttct   1620

agacatgaaa tgtcaccttg ctgaggccca gcccagccca gcatagcccg agggctggaa   1680

aaacgctttc atctctaaaa ctgagaaatc atcataattg tgctttcact tcccaggctc   1740

catgtgtctt ggagccgtca ccccgaggct ccctctttag gtcggagatt ggccttgcct   1800

gtcgaggcaa gaggctgcag aggcggggac acacctgtgt cctccgggag aggccccctc   1860

ctctccccag accacagggg gcctctctgc ctccagcccc accttccccg ggagaagctt   1920

tccccaatcc ccaggtctct agatcattct gttctcgagt atcctgtgga ggaggcaaaa   1980
```

atgcctggcg ccccttctct ccaagctcaa ttctctaagc ccctcagggt ctcctcctca 2040
ccccacccca ggcccttggt gtccaggctg cacccacaga tgtctgttgc caaacagcct 2100
gccctccctg ccggagccgg ctctgccagc cccagattgg gaagtctccc cgctggagaa 2160
gggtggggct cctctgagcc tgccctgcct cctccatcag atcctttggg aagaagtttc 2220
tgggagatgc ccgcagctgt gcgtgcccca gacacaaagg ctggcctgtg tgtaagtcaa 2280
agtcactccc gcaaacctga atctcgagct acctattggt tctgtgaatg ttctgtgtct 2340
tttatttatt ctcgggtgat cagctctttc caagacttca ataaatttgt cagttacagt 2400
caaaaaaaaa aaaaaaaaa 2419

<210> SEQ ID NO 18
<211> LENGTH: 2208
<212> TYPE: DNA
<213> ORGANISM: Mus musculus

<400> SEQUENCE: 18
agcgcccagc agcgacacga gtcgctccga cgccagctcg gagtccctgc aacggtggcc 60
tcgccagacc caggggaagt tcagggtcgg agggcggcag caccaggcac ctggccccat 120
ggaagctcgc ggggagctgg acccgtcccg ggaatccgcg ggcggagacc tgctgctggc 180
gttgttggcg cgaagggctg acctgcgccg agagatcccg atgtgtgcag gctgtgacca 240
gcacatcttg gaccgtttca tccttaaggc tctggaccga cattggcaca gcaagtgtct 300
caagtgcagt gactgccacg tccctctggc tgagcgctgc ttcagccgcg gggagagcgt 360
ctactgcaaa gacgacttct ttaagcgctt cgggaccaag tgcgccgcat gccagctggg 420
catcccgccc acgcaggtgg tgcgccgcgc ccaggacttc gtgtaccacc tgcattgctt 480
cgcctgcgtg gtctgcaagc ggcagctggc cacgggcgac gagttctacc tcatggaaga 540
cagccggctg gtgtgcaagg cggactacga aacagccaag cagcgagaag ccgaggccac 600
agccaagcgg ccgcgcacca ccatcaccgc caagcagctg gagacgctga agagcgccta 660
caacacttcg cccaagccgg cgcgccacgt gcgcgagcag ctctcctccg agaccggcct 720
ggacatgcga gtggtgcagg tgtggttcca gaatcgccgg gctaaggaaa agagactgaa 780
gaaagacgct ggccggcagc gctggggaca gtatttccgc aatatgaagc gctcccgcgg 840
cagttccaag tccgacaagg acagcatcca ggagggacaa gacagcgacg ccgaagtctc 900
cttcactgat gagccgtcca tggctgacat ggggcctgct aatggcctgt acagcagcct 960
gggagagcct gcccctgcgt tgggccggcc cgtaggaggc ctgggcagct ttaccctgga 1020
tcacggaggc ttgacgggtc cagagcagta ccgagagcta cgcccaggca gcccctatgg 1080
catcccccca tctcctgcag ccccccagag ccttcctggc ccccagcctc tcctctccag 1140
cctggtatac ccagacacca acttgagcct tgtcccttca gggcccccag gtggaccccc 1200
acccatgagg gtgctggctg gaaatgggcc cagctccgac ctgtccacag agagcagttc 1260
tggctaccca gactttcctg ctagccctgc ttcctggctg gatgaagtag accatgctca 1320
gttctgaccg aggcctctgc ttcccctggc tctaactcag gggtcttggt gctgcctctg 1380
ggtggatggc tagccccatc ccatgctgtc cattccaagg acctctgagg gaaggacagg 1440
gttcccaagt gagagaatag ggactgtccc acttccaggc tctctggcag ctccctgggg 1500
ctgagggact ccaaagtcct tccttggaca caagggtggc ctgcctggtg gctgtccaca 1560
agccagtgac catttcttgt aagcatttct ctttctttac tggccagtta acccttgctg 1620

-continued

```
ctatttccga cagggcagga ggctaggcct acctaatgtc ctggcagaaa acaacagtaa   1680

cgccttgctt catcgcttct gatggggctt ggtaggagac tgtgcttgtg tccttcctgg   1740

ccactgacaa aacctgggag cacacctctc ctccttactg ctgccagctc tccctccccg   1800

gagtctccag atcattctgt tctggaatgc cgtgtgttgg gggagtagag ctttctggag   1860

ccccttctcc aaggcgtagc ctctaaatgc gagaacaatt ccccttcgga ggcacagcct   1920

ccctcgggtg caaagcagaa ttgtgcaccg tgaacagaca cctttgccaa acagactgtg   1980

gtcccgagca gggtcggggg gtggttccac tggaggaggc tgggctgggg gtcctcccaa   2040

cccaatctgt ctcagacaca aagcttgacc acgtgaaagt taagatcatt cctgaaaaca   2100

ggatcttggc tacctgttgg ttctgtaaac accctgtaac ttttatttat tccctggtga   2160

tccgctcttt ccaagacttc aataaatttg tcagtttcag tgctagaa               2208
```

<210> SEQ ID NO 19
<211> LENGTH: 2490
<212> TYPE: DNA
<213> ORGANISM: Homo sapiens

<400> SEQUENCE: 19

```
agcactctct cacttctggc cagggaacgt ggaaggcgca ccgacaggga tccggccagg     60

gagggcgagt gaaagaagga aatcagaaag gaagggagtt aacaaaataa taaaaacagc    120

ctgagccacg gctggagaga ccgagacccg gcgcaagaga gcgcagcctt agtaggagag    180

gaacgcgaga cgcggcagag cgcgttcagc actgactttt gctgctgctt ctgctttttt    240

ttttcttaga aacaagaagg cgccagcggc agcctcacac gcgagcgcca cgcgaggctc    300

ccgaagccaa cccgcgaagg gaggagggga gggaggagga ggcggcgtgc agggaggaga    360

aaaagcattt tcactttttt tgctcccact ctaagaagtc tcccggggat tttgtatata    420

ttttttaact tccgtcaggg ctcccgcttc atatttcctt ttctttccct ctctgttcct    480

gcacccaagt tctctctgtg tccccctcgc gggccccgca cctcgcgtcc cggatcgctc    540

tgattccgcg actccttggc cgccgctgcg catggaaagc tctgccaaga tggagagcgg    600

cggcgccggc cagcagcccc agccgcagcc ccagcagccc ttcctgccgc ccgcagcctg    660

tttctttgcc acggccgcag ccgcggcggc cgcagccgcc gcagcggcag cgcagagcgc    720

gcagcagcag cagcagcagc agcagcagca gcagcaggcg ccgcagctga gaccggcggc    780

cgacggccag ccctcagggg gcggtcacaa gtcagcgccc aagcaagtca agcgacagcg    840

ctcgtcttcg cccgaactga tgcgctgcaa acgccggctc aacttcagcg gctttggcta    900

cagcctgccg cagcagcagc cggccgccgt ggcgcgccgc aacgagcgcg agcgcaaccg    960

cgtcaagttg gtcaacctgg gctttgccac ccttcgggag cacgtcccca acggcgcggc   1020

caacaagaag atgagtaagg tggagacact gcgctcggcg gtcgagtaca tccgcgcgct   1080

gcagcagctg ctggacgagc atgacgcggt gagcgccgcc ttccaggcag gcgtcctgtc   1140

gcccaccatc tcccccaact actccaacga cttgaactcc atggccggct cgccggtctc   1200

atcctactcg tcggacgagg gctcttacga cccgctcagc cccgaggagc aggagcttct   1260

cgacttcacc aactggttct gaggggctcg gcctggtcag gccctggtgc gaatggactt   1320

tggaagcagg gtgatcgcac aacctgcatc tttagtgctt tcttgtcagt ggcgttggga   1380

gggggagaaa aggaaaagaa aaaaaaaaga agaagaagaa gaaaagagaa gaagaaaaaa   1440

acgaaaacag tcaaccaacc ccatcgccaa ctaagcgagg catgcctgag agacatggct   1500

ttcagaaaac gggaagcgct cagaacagta tctttgcact ccaatcattc acggagatat   1560
```

gaagagcaac tgggacctga gtcaatgcgc aaaatgcagc ttgtgtgcaa aagcagtggg 1620
ctcctggcag aagggagcag cacacgcgtt atagtaactc ccatcacctc taacacgcac 1680
agctgaaagt tcttgctcgg gtcccttcac ctcctcgccc tttcttaaag tgcagttctt 1740
agccctctag aaacgagttg gtgtctttcg tctcagtagc ccccacccca ataagctgta 1800
gacattggtt tacagtgaaa ctatgctatt ctcagccctt tgaaactctg cttctcctcc 1860
agggcccgat tcccaaaccc catggcttcc ctcacactgt cttttctacc attttcatta 1920
tagaatgctt ccaatctttt gtgaattttt tattataaaa aatctatttg tatctatcct 1980
aaccagttcg gggatatatt aagatatttt tgtacataag agagaaagag agagaaaaat 2040
ttatagaagt tttgtacaaa tggtttaaaa tgtgtatatc ttgatacttt aacatgtaat 2100
gctattacct ctgcatattt tagatgtgta gttcacctta caactgcaat tttccctatg 2160
tggttttgta aagaactctc ctcataggtg agatcaagag gccaccagtt gtacttcagc 2220
accaatgtgt cttactttat agaaatgttg ttaatgtatt aatgatgtta ttaaatactg 2280
ttcaagaaga acaaagttta tgcagctact gtccaaactc aaagtggcag ccagttggtt 2340
ttgataggtt gccttttgga gatttctatt actgcctttt tttttcttac tgttttatta 2400
caaacttaca aaaatatgta taaccctgtt ttatacaaac tagtttcgta ataaaacttt 2460
ttcctttttt taaaatgaaa ataaaaaaaa 2490

<210> SEQ ID NO 20
<211> LENGTH: 2259
<212> TYPE: DNA
<213> ORGANISM: Mus musculus

<400> SEQUENCE: 20
agcagtctct cacttctggc cagggaacgt ggaaggcgta ccggctggga gccggttagg 60
gagggcgaat tggggggaac gagagagcaa ttagaaagaa agggggttca accaaataat 120
cccagaagca ggctcaagcc caggctggag caagggagag cgggcgcaag aaagcgcagc 180
cccggagcag ctccacctgg cagagtgcgc tcggcactga cttttgcggc tgctttcctt 240
ttccctttcc tcttttaaaa ccgagaaggc gccggcggcg gccgcacacg cgagcgccac 300
gcgaggctcc cgaagccaac cgcggcggga ggaggggagg gaggaggcgg cgcagaggga 360
agacgatcgc ccaggcacct tcctccgctg cagcctgaca actctgcctc cttctgcgcg 420
tttcttcccc tttaactttc ctccggggct cgtttctccc ctctcctttt tcttcgtccc 480
cctttgatcg tgcttcgcag ccccgcttcc ttcaagggct ctgcgcaccc tgcgtcccca 540
actcgttctc ccccgcgaca gtttggcccg gcatggagag ctctggcaag atggagagtg 600
gagccggcca gcagccgcag ccccccgcagc ccttcctgcc tcccgcagcc tgcttctttg 660
cgaccgcggc ggcggcggca gcggcggcgg ccgcggcagc tcagagcgcg cagcagcaac 720
agccgcaggc gccgccgcag caggcgccgc agctgagccc ggtggccgac agccagccct 780 caggggggcgg tcacaagtca gcggccaagc aggtcaagcg ccagcgctcg tcctctccgg 840
aactgatgcg ctgcaaacgc cggctcaact tcagcggctt cggctacagc ctgccacagc 900
agcagccggc cgccgtggcg cgccgcaacg agcgcgagcg caaccgggtc aagttggtca 960
acctgggttt tgccaccctc cgggagcatg tccccaacgg cgcggccaac aagaagatga 1020
gcaaggtgga gacgctgcgc tcggcggtcg agtacatccg cgcgctgcag cagctgctgg 1080
acgagcacga cgcggtgagc gctgcctttc aggcgggcgt cctgtcgccc accatctccc 1140

-continued ccaactactc caacgacttg aactctatgg cgggttctcc ggtctcgtcc tactcctccg 1200
acgagggatc ctacgaccct cttagcccag aggaacaaga gctgctggac tttaccaact 1260
ggttctgagg acctgccagg ctctcctggg aatggacttt ggaagcagga tggcagcaga 1320
tcctgcatct ttagtgtttc tcgccaacga cgtcaaatgg ggaggcagaa aaacaagggg 1380
aaaaaagaag aagaaatgaa acaaacaaac cagacagcca acctacaggg gcaccttcac 1440
taagatgcaa tgttctcagc aaacaggggt gggctccaac agtgtctctg cattccaaca 1500
tcatttccag acacgagaag agtgactggt gtctgaacct aagcccgaat cacagatggg 1560
ttcctttcct ggagcaagag cgtcacacac acacacacac acacagacag acactatatt 1620
aactcccaac cactaacagg cagggctgga agcgcgcatg tgcaagtgcc ttcacctccc 1680
actctctgtc agagctgtct tagcccccctg aaactgggtt gatgtctttc ctcagtcacc 1740
cccattccag cgatctatgg acatttgcct ccattgaagc aacgtcagtt ctcggacagc 1800
ctttccctct cctggtggcc tcctccccaa accccacatc gccctcccac ggtctttgct 1860
tctgttttct tcatagaatg cttccaatct ttgtgaattt ttttattata agaaaaaaat 1920
ctatttgtat ctatcctaac cagtttgggg atatattaag atatttttgt acataagaaa 1980
aagagagaga aaaaatttat agaagttttg tacaaatggt ttaaaaatgt gtatatcttg 2040
atactttaac atgtaatgag attacctctg cgtactttag atatgtagtt catcttacaa 2100
ctgccatccc cacccccatc cccagtgtgg ttttggaaag aactctcctc ataggtgaga 2160
tctaaatgcc accagaatga cttcagcacc aatgtgtctt acttcacaga aacgtggtta 2220
atgtattaat gatgttatta aaaaaaactg ttcaagaag 2259

<210> SEQ ID NO 21
<211> LENGTH: 4172
<212> TYPE: DNA
<213> ORGANISM: Homo sapiens

<400> SEQUENCE: 21
agtaatagca ggagcagcaa cagaaggcgt cggagcgggc gtcggagctg cccgctgtgg 60
gagagagagg agacagaaag agcgagcgag gagagggagc ccgaggcgaa aaagtaactg 120
tcaaatgcgc ggctccttta accggagcgc tcagtccggc tccgagagtc atggcgaccg 180
cagcgtctaa ccactacagc ctgctcacct ccagcgcctc catcgtgcac gccgagccgc 240
ccggcggcat gcagcagggc gcgggggggct accgcgaagc gcagagcctg gtgcagggcg 300
actacggcgc tctgcagagc aacggacacc cgctcagcca cgctcaccag tggatcaccg 360
cgctgtccca cggcggcggc ggcgggggcg gtggcggcgg cgggggggggc gggggcggcg 420 gcgggggcgg cggcgacggc tccccgtggt ccaccagccc cctgggccag ccggacatca 480
agccctcggt ggtggtgcag cagggcggcc gcggagacga gctgcacggg ccaggcgccc 540
tgcagcagca gcatcagcag cagcaacagc aacagcagca gcaacagcag caacagcagc 600
agcagcagca gcaacagcgg ccgccgcatc tggtgcacca cgccgctaac caccacccgg 660
gacccggggc atggcggagc gcggcggctg cagcgcacct cccaccctcc atgggagcgt 720
ccaacggcgg cttgctctac tcgcagccca gcttcacggt gaacggcatg ctgggcgccg 780
gcgggcagcc ggccgggctg caccaccacg gcctgcggga cgcgcacgac gagccacacc 840
atgccgacca ccacccgcac ccgcactcgc acccacacca gcagccgccg cccccgccgc 900
ccccgcaggg tccgcctggc cacccaggcg cgcaccacga cccgcactcg gacgaggaca 960
cgccgacctc ggacgacctg gagcagttcg ccaagcagtt caagcagcgg cggatcaaac 1020

-continued

```
tgggatttac ccaagcggac gtggggctgg ctctgggcac cctgtatggc aacgtgttct   1080
cgcagaccac catctgcagg tttgaggccc tgcagctgag cttcaagaac atgtgcaagc   1140
tgaagccttt gttgaacaag tggttggagg aggcggactc gtcctcgggc agccccacga   1200
gcatagacaa gatcgcagcg caagggcgca agcggaaaaa gcggacctcc atcgaggtga   1260
gcgtcaaggg ggctctggag agccatttcc tcaaatgccc caagccctcg gcccaggaga   1320
tcacctccct cgcggacagc ttacagctgg agaaggaggt ggtgagagtt tggttttgta   1380
acaggagaca gaaagagaaa aggatgaccc ctcccggagg gactctgccg ggcgccgagg   1440
atgtgtacgg ggggagtagg gacactccac cacaccacgg ggtgcagacg cccgtccagt   1500
gaactcgagc tgggggaggg gcagagcgcg gggctccccc tccccttcgg tccttggccc   1560
tttcccggcc ctcttgttcc ctctctaact tctgattgtt cttttatttt taattattat   1620
ttccccgtcc cttaaaaaga caaaaaaaat aaggcaaaag gaaagcaact aagacactgg   1680
actatccttt aaaggtagca ggtgtaatga tgtgttttga cctttgcagg cgagtaacca   1740
ggcaatggag tggagtgtct cctggagaga gtgaggagag tgtgtgatag ctagaaagag   1800
agagagacag agagatggca agcactgaga taaatacctg gcaaaactaa ataaattacc   1860
aaaaaggaaa aaaaatccac caaaccatga taaacacaaa atgcagcttc ctgatgctta   1920
gagttggcac atgctgctgt gtttatttat tgtggattcc catcaggaaa gaggaaaaaa   1980
tacacatgtt ctttcatata ggcaaaattt aaccacataa atttgcactg caagaaaatt   2040
gaagtttacg tgaacaaatt catgagcata ttttctcttt ctccccaccg ttaatttggg   2100
agttgccgtt ttgggggatt ttgttttgct ttgctttatt catcggagag agttgaagcc   2160
agctcttggc cactctccat ttctaatgtt cttgtgttgc cccttcttcg tactgtttgt   2220
gaactttggt taccttcaca ttccccttac gagggtgtaa catctatttg ttcctcttac   2280
caaagcaaaa ggattggctt catacaaaat agacaattct ctgatttcag gaaatgtgca   2340
tggtctaccc gctttatcga aggcaagaat ccggtttgga atataaaaat aagcattggt   2400
tgttcttacc agccacaaag taaacttcat tttcaggcag tgtttctggg ggaggttatg   2460
gagggaagaa aaaagaaaaa tcgatagtga gtgactgatt gcttcatttt atcaggcggg   2520
cccattgtga aagagctcag gggaaatgtg gaggttaaat atatttccag agttgtccag   2580
cagaaagaaa gtggcacttt gaagagaact agggaagtac atatcttcag atatccctat   2640
atagttctct accttcagtt ttagtaacaa ttatgaagaa ttatttgtgc tgacagcagc   2700
agttaaactt tgtttctcta atagcttttt ttttacataa aaaaagaccc aggaacttaa   2760
tagtgtatgc ataagactgt gttttttagc acacagatac ccacagcata cactgacgat   2820
ctccacgcag tagacaggtt ttgtcttcac tagctcattt gtttatcaag tcatatttag   2880
ggtcccacac cctcttttcc tgtaatttat tgcagaatac accactttga cttggacagc   2940
tttctgcccc ctctttcact aaggaaggca aatgaagtga aaaaaaaaaa tgccattttc   3000
aatccttcct ttctcccctt tgttaatagt tttaagtgaa tttttgacct tatcttaatg   3060
gaaaacggtt aactccaaac acaaaagact ctactggaaa gtgtaggtga aaaaacttgt   3120
aactgtattg aaaataaata ccattaaact gtgatcagtt aaaatttaaa agaaaaatca   3180
gcacaaaagg gcgctaaaag ggaaaacact ttttattaat cttaaaagtt tgggggtttt   3240
tttccagtta ggtattagat aaatttttat tttaaaaaat gaaagtctca ctaccataaa   3300
attatggttc agcatcagat tagcattgca ctcagtagtc tttaaggttt taggaaatat   3360
```

-continued gctttatatt gtcttttcaa acacctgtga ttgtttcatt ttccatgttt ttgcaagata 3420
aatggtgact tataatgggc atatttattt gcctgtattt catttccccc aatgaatgtc 3480
acaaggagat gggcacggag ctgcttcggg tgcatcacgc tgctcgttcc tgaggtatgg 3540
gaactggcct ttagtgaagc tatccagagc agggcaaata gccactggta aagggaggaa 3600
atgaatttcc agatacttat taccaagtag gtaaggtcag aagctggagt tcagagaatg 3660
tgtctacagc ttctctgact cttataggtt tactaagatg aaagttacca ctgaacctta 3720
ccactatgta tatatgttta atatctgtct tttgaaatgc agaaatagtt taaatgtttc 3780
tttgtctatt tttctttttt tttaatgcta cccagggaaa tattttcata tcatttttaa 3840
gtggcctgcc tcaatgtata tttatttctt ttgaaacaaa aaggttctgg aaactgtttt 3900
tctgtagctt taaatgaata ggtgagcaaa atctatatgg gatgtaattt ttttgttcag 3960
tctcttaaaa aatactttgt tttggtacat ttggttgtgc ttgtggggaa aataaaaacg 4020
cagagatcct tatatattta tgttaaagta atattttatt atctacataa aacagaaatg 4080
cacaataaaa aaaaaaaaaa aaaaaaaaaa aaaaaaaaaa aaaaaaaaaa aaaaaaaaaa 4140
aaaaaaaaaa aaaaaaaaaa aaaaaaaaaa aa 4172

<210> SEQ ID NO 22
<211> LENGTH: 1338
<212> TYPE: DNA
<213> ORGANISM: Mus musculus

<400> SEQUENCE: 22
atggcgaccg cagcgtctaa ccactacagc ctgctcacct ccagcgcctc catcgtacat 60
gccgagccgc ctggcggcat gcagcagggc gcagggggct accgcgaggc gcagagcctg 120
gtgcagggcg actacggcgc gctgcagagc aacgggcacc cgctcagcca cgctcaccag 180
tggatcaccg cgctgtccca cggcggcggc ggcgggggcg gcggcggcgg tggaggaggc 240
gggggaggcg gcgggggagg cggcgacggc tccccgtggt ccaccagccc cctaggccag 300
ccggacatca agccctcggt ggtggtacag cagggtggcc gaggcgacga gctgcacggg 360
ccaggagcgc tgcagcaaca gcatcaacag caacagcaac agcagcagca gcagcagcag 420
cagcagcagc agcaacagca gcagcaacaa cagcgaccgc cacatctggt gcaccacgct 480
gccaaccacc atcccgggcc cggggcatgg cggagtgcgg cggctgcagc tcacctccct 540
ccctccatgg gagcttccaa cggcggtttg ctctattcgc agccgagctt cacggtgaac 600
ggcatgctgg gcgcaggagg gcagccggct gggctgcacc accacggcct gagggacgcc 660
cacgatgagc cacaccatgc agaccaccac ccgcatccgc actctcaccc acaccagcaa 720
ccgcccccgc cacctccccc acaaggccca ccgggccacc caggcgcgca ccacgacccg 780
cactcggacg aggacacgcc gacctcagac gacctggagc agttcgccaa gcaattcaag 840
cagaggcgga tcaaactcgg atttactcaa gcagacgtgg ggctggcgct tggcaccctg 900
tacggcaacg tgttctcgca gaccaccatc tgcaggtttg aggccctgca gctgagcttc 960
aagaacatgt gcaagctgaa gcctttgttg aacaagtggt tggaagaggc agactcatcc 1020
tcgggcagcc ccaccagcat agacaagatc gcagcgcaag ggcgcaaacg gaaaaagcgg 1080
acctccatcg aggtgagcgt caagggggct ctggagagcc atttcctcaa atgccctaag 1140
ccctcggccc aggagatcac ctccctcgcg gacagcttac agctggagaa ggaggtggtg 1200
agagtttggt tttgtaacag gagacagaaa gagaaaagga tgacccctcc cggagggact 1260
ctgccgggcg ccgaggatgt gtatgggggt agtagggaca cgccaccaca ccacggggtg 1320
cagacgcccg tccagtga 1338

<210> SEQ ID NO 23
<211> LENGTH: 7152
<212> TYPE: DNA
<213> ORGANISM: Homo sapiens

<400> SEQUENCE: 23
taagctactg cacactaaac agtgagagag cttttccctg cagtcttgtt gaagcacccc 60 gggtttttg ctcattgttg gtgggtgcat tttaattttt tcattccctg gactatgggt 120
tatgatatcc atactcactg aagacaaaaa gccacctttt ctgcgtcttg gtggcatgca 180
tgtgtctcat catcctttca aacttgtggt ggaacagggt tttcttccct gtctgtgtat 240
tttgagccag cacagttacc aaaattgaac ttgtctttcg cttgtgagcg gttgtggtca 300
ttgtgagggc gggtcatgag gaggctgtag ccaaggacga ggtgtgtgcg gctgttgcct 360
ggacgtttgt ccaatccacg ttgacatttg agggatcaca gcgtgtgaaa atgaactcag 420
aggagaattg gtgaattcct atccagtggg catcttcaaa ccctggtcga cggcggaaga 480
atatcaggtc ctgagatcac ccacccggcg cggcaacagt gcagagtggc cacatctggt 540
ggaagaagaa aaaaatgtag ttattgaatt caatcaagtg tttgcatctt tcaagctatc 600
aacaaaattc catcaagaaa ggttccagtt ggtctcacag acgtatggat atccgaggag 660
ccacctaaag atggagaaat caaggcatag agagattaag tgactttgcc acagtcacaa 720
gctggagagg accaggagta gagcttagag cgagcccctg actctgggcc tgcgtcctgc 780
caggagtcac gctgcctccg ttcctaggag agaagacttc ctgtaagatg gaggtggaca 840
ccgaggagaa gcggcatcgc acgcggtcca aaggggttcg agttcccgtg gaaccagcca 900
tacaagagct gttcagctgt cccaccccctg gctgtgacgg cagtggtcat gtcagtggca 960
aatatgcaag acacagaagt gtatatggtt gtcccttggc gaaaaaaaga aaaacacaag 1020
ataaacagcc ccaggaacct gctcctaaac gaaagccatt tgccgtgaaa gcagacagct 1080
cctcagtgga tgagtgtgac gacagtgatg ggactgagga catggatgag aaggaggagg 1140
atgaggggga ggagtactcc gaggacaatg acgagccagg ggatgaggac gaggaggacg 1200
aggaggggga ccgggaggag gaggaggaga tcgaggagga ggatgaggac gatgacgagg 1260
atggagaaga tgtggaggat gaagaagagg aagaggagga ggaggaggag gaggaagagg 1320
aagaagaaaa cgaagaccat caaatgaatt gtcacaatac tcgaataatg caagacacag 1380
aaaaggatga taacaataat gacgaatatg acaattacga tgaactggtg gccaagtcat 1440
tgttaaacct cggcaaaatc gctgaggatg cagcctaccg ggccaggact gagtcagaaa 1500
tgaacagcaa tacctccaat agtctggaag acgatagtga caaaaacgaa aacctgggtc 1560
ggaaaagtga gttgagttta gacttagaca gtgatgttgt tagagaaaca gtggactccc 1620
ttaaactatt agcccaagga cacggtgttg tgctctcaga aaacatgaat gacagaaatt 1680
atgcagacag catgtcgcag caagacagta gaaatatgaa ttacgtcatg ttggggaagc 1740
ccatgaacaa cggactcatg gaaaagatgg tggaggagag cgatgaggag gtgtgtctga 1800
gcagtctgga gtgtttgagg aatcagtgct tcgacctggc caggaagctc agtgagacca 1860
acccgcagga gaggaatccg cagcagaaca tgaacatccg tcagcatgtc cggccagaag 1920
aggacttccc cggaaggacg ccggacagaa actactcgga catgctgaac ctcatgcggc 1980
tggaggagca gttgagcccc cggtcgagag tgtttgccag ctgtgcgaag gaggatgggt 2040

-continued

```
gtcatgagcg ggacgacgat accacctctg tgaactcgga caggtctgaa gaggtgttcg   2100
acatgaccaa ggggaacctg accctgctgg agaaagccat cgctttggaa acggaaagag   2160
caaaggccat gagggagaag atggccatgg aagctgggag gagggacaat atgaggtcat   2220
atgaggacca gtctccgaga caacttcccg gggaggacag aaagcctaaa tccagtgaca   2280
gccatgtcaa aaagccatac tatgatccct caagaacaga aaagaaagag agcaagtgtc   2340
caacccccgg gtgtgatgga accggccacg taactgggct gtacccacat caccgcagcc   2400
tgtccggatg cccgcacaaa gatagggtcc ctccagaaat ccttgccatg catgaaagtg   2460
tcctcaagtg ccccactccg ggctgcacgg ggcgcgggca tgtcaacagc aacaggaact   2520
cccaccgaag cctctccgga tgcccgatcg ctgcagcaga gaaactggcc aaggcacagg   2580
aaaagcacca gagctgcgac gtgtccaagt ccagccaggc ctcggaccgc gtgctcaggc   2640
caatgtgctt tgtgaagcag ctggagattc ctcagtatgg ctacagaaac aatgtcccca   2700
caactacgcc gcgttccaac ctggccaagg agctcgagaa atattccaag acctcgtttg   2760
aatacaacag ttacgacaac catacttatg gcaagcgagc catagctccc aaggtgcaaa   2820
ccagggatat atcccccaaa ggatatgatg atgcgaagcg gtactgcaag gaccccagcc   2880
ccagcagcag cagcaccagc agctacgcgc ccagcagcag cagcaacctg agctgcggcg   2940
ggggcagcag cgccagcagc acgtgcagca agagcagctt cgactacacg cacgacatgg   3000
aggcggccca catggcggcc accgccatcc tcaacctgtc cacgcgctgc cgcgagatgc   3060
cgcagaacct gagcaccaag ccgcaggacc tgtgcgccac gcggaaccct gacatggagg   3120
tggatgagaa cgggaccctg gacctcagca tgaacaagca gaggccgcgg gacagctgct   3180
gccccatcct gacccctctg gagcccatgt ccccccagca gcaggcagtg atgaacaacc   3240
ggtgtttcca gctgggcgag ggcgactgct gggacttgcc cgtagactac accaaaatga   3300
aaccccggag gatagacgag gacgagtcca aagacattac tccagaagac ttggacccat   3360
tccaggaggc tctagaagaa agacggtatc ccggggaggt gaccatccca agtcccaaac   3420
ccaagtaccc tcagtgcaag gagagcaaaa aggacttaat aactctgtct ggctgccccc   3480
tggcggacaa aagcattcga agtatgctgg ccaccagctc ccaagaactc aagtgcccca   3540
cgcctggctg tgatggttct ggacatatca ccggcaatta tgcttctcat cggagccttt   3600
caggttgccc aagagcaaag aaaagtggta tcaggatagc acagagcaaa gaagataaag   3660
aagatcaaga acccatcagg tgtccggtcc ccgggtgcga cggccagggc cacatcactg   3720
ggaagtacgc gtcccatcgc agcgcctccg ggtgcccctt ggcggccaag aggcagaaag   3780
acgggtacct gaatggctcc cagttctcct ggaagtcggt caagacggaa ggcatgtcct   3840
gccccacgcc aggatgcgac ggctcaggcc acgtcagcgg cagcttcctc acacaccgca   3900
gcttgtcagg atgcccgaga gccacgtcag cgatgaagaa ggcaaagctt tctggagagc   3960
agatgctgac catcaaacag cgggccagca acggtataga aaatgatgaa gaaatcaaac   4020
agttagatga agaaatcaag gagctaaatg aatccaattc ccagatggaa gccgatatga   4080
ttaaactcag aactcagatt accacgatgg agagcaacct gaagaccatc gaagaggaga   4140
acaaagtgat tgagcagcag aacgagtctc tcctccacga gctggcgaac ctgagccagt   4200
ctctgatcca cagcctggct aacatccagc tgccgcacat ggatccaatc aatgaacaaa   4260
attttgatgc ttacgtgact actttgacgg aaatgtatac aaatcaagat cgttatcaga   4320
gtccagaaaa taaagcccta ctggaaaata taaagcaggc tgtgagagga attcaggtct   4380
gaacagctgc tgtagtgatg aaactcttgc ttaaaaagga tgcctcttgt tttttgctgc   4440
```

-continued tgtaacttac cagaaagtgt tctatattta tttctgtttg aatttgaaac agtgttatgc 4500
ttacaagact tcataatgat tttatgtctt gctttaaaga tagtacctgc agaatagttt 4560
ttgaatacac ccacattttg tacgtttcca tgtaagctga catagtgttc tgccatgtaa 4620
tgtttatagc tgctgatgta tgcacatttg gggtatatc tatttctgaa gaggtaagct 4680
gatcaaaata aatagagtgt aaattctttt taatgcttta gtgattaaat gttttagtat 4740
tttgaactga aatggacaca caaacacaca cacgcacaca cagacccaca gctttgaatg 4800
atcatgttgt ggctgagcag ccgcttttta gacgttatca ttttgcctca tgttggagga 4860
ctttatggaa tttaagaaat acattttgtg tgcatattgt ttcatagcaa gaattcgttg 4920
caaaaatgct ttatttttga acaatgcttg gaaatattat gtgacttttt tgtttgtttg 4980
ttttaggagg atggtgtatg gtgggggcaa taaatgaggt tttttgcatt ccaaggaaat 5040
ggcatatgga ttaactgtaa gaaatgaaat aagtaattta ttgtaagaca acatcaagcc 5100
atggaaactt ggcagaagat tcaaagcagc ttaaacagca cttttaaatt aactcctaag 5160
cgttacatgg ttgtgactat ggaaactcca gttaagacag gatcttatca gaggtggaca 5220
acgtgaagat ttcctttcc attttcaata aactttggaa caaccttctc gtatctcccc 5280
tagagtttcg tgcccctctg aactgtctgt tattgcaatg tagtttatca acagaatttg 5340
tgtgttttcg atttaagcta aaagataatt taagaacatt tatttcccct tttcacttta 5400
aaaaattatg attattccta ttattgttat gaaccttctt attttacatt tgagggataa 5460
aggcaaatga tttgtgagtc ttctagttac tggaccgagt tttctgctgg atctggtggg 5520
aaggcagctc ggtaaagttt ccctcctgct ccccccgccc gactttgact ctgaatcagc 5580
atttggtcct attcagagga ctcttaccac gacgtttctg ttctacactt gggtggagac 5640
cagttgacca tagagcattt gcagagcctc attgtttgat ttcttgtgac tattctaaga 5700
atgaatgcaa tcagatttta aaagtaacta aatatacttc agcacttttt tgctttaaac 5760
tagatcatct tagacttgtt tataccttcc agatttgatt gttttactcc caatgactgc 5820
actatatgta tgcataagac cacttttgag cgctgtgttc ccccttctga gtagtccttt 5880
gacgacgtgt tgtgttttct gatgttgact tgagttccat ttagtagcat ctcttccttc 5940
catgtcttga tgttatgcag gaagtacaga cgtactttaa atttttgtta tgaaataaaa 6000
aaaagatggg ttttgtaaaa ataaaaaaaa aatattttta gcagaacagg acttacaggg 6060
tcattgtccc cacaatgtgc cagtcgacta tttgcactta ccttgtccta tatatccgta 6120
cggaggtgtg caattcctcg tgtcagtagc cttgtgacac tgaacctgga tggattatag 6180
aggagccctc acggctgatc aataatgttg caaagggaga ctacagggat ctcacgacga 6240
atattctgat acaatactca acctcggtat atatatatgt gtataaatat atgtatatcc 6300
cagcggcact ttatactgtt cactgtacaa aagcttacag ttttccacaa ggactttaat 6360
aactagctgg gaaaagacga tgtaattatt tcggggctct gcggaacctt ctctgtacag 6420 cgccccccttt ctgttgtgct attggttgca gctgccatgc tcagaatgcg ttttgagagc 6480
tgaagcaagg tgcttgcagt cacctgaggc cgtccgtgtg gcccagggcc ccagctgcct 6540
ttagggcccc cattgttcat aacagcatat gcatttcccc accgcgttgt gtctgcagct 6600
tctttgccaa tatagtaatg cttttagtag agtactagat agtatcagtt ttggattctt 6660
attgttatca cctatgtaca atggaaaggg attttaagca caaacctgct gctcatctaa 6720
cgttggtaca taatctcaaa tcaaaagtta tctgtgacta ttatataggg atcacaaaag 6780

```
tgtcacatat tagaatgctg acctttcata tggattattg tgagtcatca gagtttatta   6840

taacttattg ttcatattca tttctaagtt aatttaagta atcatttatt aagacagaat   6900

tttgtataaa ctatttattg tgctctctgt ggaactgaag tttgatttat ttttgtacta   6960

cacggcatgg gtttgttgac actttaattt tgctataaat gtgtggaatc acaagttgct   7020

gtgatacttc atttttaaat tgtgaacttt gtacaaattt tgtcatgctg gatgttaaca   7080

catcttactc taaataaaca aggtgttgcc acatttgtag cacgaaggat ctctaaaaaa   7140

aaaaaaaaaa aa                                                        7152


<210> SEQ ID NO 24
<211> LENGTH: 7198
<212> TYPE: DNA
<213> ORGANISM: Mus musculus

<400> SEQUENCE: 24

gtggagctgc gtgcattagg ggctggctgt ggaggtaaag cagatctctt aggcccgcta     60

gcctctcctg ctgcatgtgt cattcctgcc cgcgcgacat tttcccccta agctactgca    120

cacaaaacag agcgagaaag cttctccctg cagtcttctt ggaggcctcc tggtttctca    180

cccattgttg gtgggtgtat ttcaattttt tgattccctg gactgtgggt tatgaaatca    240

atgctgctga agacaaaagc aaccttccct gcctctcggt gctatgcgtg gtcctcctcg    300

gcctccccact tgtgggggaa agggttttct ctttctttct gtgtgttttg agccagcaca   360

gttaccaaaa ttgaacttgc cgtcacttgt gagcggtgtg gtcatggtgt gaggggtccc    420

acagaggctg cagctgaggt ctgggtgtgt gcaattctca gctgggcttt gccctaccca    480

ggttgacgac tgaagaatca cagagtgtgg aaaagaacac aaggagaaat tggtgagaac    540

atctgcctag catctccaag tcctgtggag ggagccagca gtgctggtcc aaagaggacc    600

cagagagtga actcagagtg accacatctg atagaagagg ggaagatgta gtttctgagt    660

ccagtccagt gtttgtgtct ctcacattgt caacaaaaga aaggctccag ctgtccccac    720

agacatatgg atattccagg agccacgtaa agatggagaa atggaggcac agagaaatta    780

agtgacttgg ccacagtcac aagctgggga ggaccaggga aagcctagag agagctggct    840

ctgggcctgc atcctgccca cggagtcacc ctgcctccgt cctcaggaga gaaggcttcc    900

tacaagatgg acgtggactc tgaggagaag cgccatcgca cacggtccaa aggggttcga    960

gttcctgtgg agccagccat acaagagctg ttcagctgtc ccactccagg ctgcgacggc   1020

agtggtcacg tcagtggcaa atatgcacga cacagaagtg tatatggttg tcccttggct   1080

aaaaaaagaa aaacgcaaga taaacagccc caagaacctg ctcccaagcg aaaaccattt   1140

gcagtaaaag cagatagttc ctcagtagac gaatgttatg agagtgatgg tactgaagac   1200

atggatgata aggaggaaga tgatgatgag gagttctctg aagacaatga tgagcaaggg   1260

gatgatgacg acgaagatga ggtggatcgg gaagacgagg aggagatcga ggaggaagat   1320

gatgaagaag atgatgatga tgaagatggt gacgatgtag aagaggaaga agaggatgat   1380

gatgaagagg aggaagaaga ggaagaggaa gaagaaaatg aagaccatca aatgagttgt   1440

actcgaataa tgcaggacac agacaaggat gataacaaca atgatgagta tgataactat   1500

gatgaactgg tagctaagtc gctattaaat cttggcaaaa ttgctgagga tgcagcatac   1560

cgagccagga ctgaatcaga gatgaacagc aatacctcca atagtctgga ggacgatagt   1620

gacaaaaacg aaaacctcgg tcggaaaagc gaactgagtc tagacttaga cagtgatgtt   1680

gttagagaaa cagtggactc ccttaagctg ttagcacaag gacatggtgt tgtgctatca   1740
```

-continued

```
gagaatatca gtgacagaag ttatgctgag ggatgtcac agcaggacag tagaaatatg   1800
aactatgtca tgctagggaa gcccatgaac aatggactca tggagaagat ggtggaggag   1860
agtgatgagg aagtgtgtct aagtagtcta gagtgcctga ggaaccagtg ctttgacctg   1920
gccaggaaac tcagcgagac caacccacag gacaggagtc agccacccaa catgagtgtg   1980
cgccaacatg tccggcaaga ggacgacttc cctgggagga cgccagacag gagctactcg   2040
gatatgatga accttatgcg gctggaggag cagctcagtc ccaggtctag aacgttctcc   2100
agctgtgcca aggaggatgg gtgtcatgag agggatgatg acaccacctc agtgaactca   2160
gacaggtctg aggaagtgtt tgacatgacc aagggcaacc tgactctgct agagaaagcc   2220
attgccttgg agacagagag agccaaggcc atgcgggaga agatggccat ggatgctggg   2280
agaagggata acctgagatc ctatgaggac cagtctccaa gacagctggc tggggaagac   2340
agaaaatcca aatccagtga cagccatgtc aaaaagccat actatggtaa agatccctca   2400
agaacagaaa agagagagag caagtgtcca acccccgggt gtgatggaac cggccacgta   2460
actgggcttt acccgcatca ccgcagtctg tctggatgcc cgcacaaaga tagggtccct   2520
ccagaaattc ttgccatgca tgaaaatgtt ctcaagtgtc ccactccagg ctgcacaggg   2580
cgagggcatg tgaatagcaa caggaactcg cacagaagcc tctctggatg ccccattgct   2640
gctgcagaaa aactggcaaa ggcccaagag aaacaccaga gctgtgatgt gtccaaatcc   2700
aaccaggcct cagaccgagt cctcaggcca atgtgctttg tcaaacagct tgagattcct   2760
cagtatggct acagaaacaa tgttcccaca accacaccac gctccaacct ggccaaggag   2820
cttgagaaat actccaagac ttcgtttgag tacaacagtt acgacaacca tacttatggc   2880
aaaagagcca tagctcccaa ggtgcaaacc agggacatat cccccaaagg atatgacgat   2940
gccaagcggt actgcaagaa tgccagcccc agcagcagca ccaccagcag ctatgcacct   3000
agcagcagca gcaacctcag ctgtggtggt ggcagcagcg ccagtagcac gtgtagcaag   3060
agcagctttg actacacaca tgacatggag gccgcacaca tggcagccac agccattctc   3120
aacctgtcca cacgttgtcg tgaaatgcca cagaacctgt ccaccaagcc acaggacctg   3180
tgtactgccc ggaacccaga catggaggtg gatgagaatg gcaccctgga cctgagcatg   3240
aacaagcaga ggcctcgaga cagctgctgc ccagtcctga cacccctgga acccatgtct   3300
ccgcagcagc aggccgtgat gagcagccga tgcttccagc tgagcgaggg ggattgctgg   3360
gacttgcctg tagactacac caaaatgaag cctcggaggg tagatgagga tgagcccaaa   3420
gagattaccc cagaagactt ggacccattc caggaggctc tggaagaaag acggtatcca   3480
ggggaggtga ccatcccaag ccccaaaccc aagtaccctc agtgcaagga aagcaaaaag   3540
gacttaataa ctctgtctgg ctgcccccctg gcggacaaaa gcattcgaag tatgctggcc   3600
accagttccc aagagctcaa gtgccccacc cctggctgtg acggttctgg acacatcact   3660
ggcaattacg cttctcatcg aagcctttct gggtgcccga gagcaaagaa gagtggcatc   3720
cggatagcac agagcaaaga ggacaaggaa gaccaggagc caatcaggtg tccggtacct   3780
ggctgtgacg gtcagggaca catcactggg aagtatgcat cccaccgcag cgcctccggg   3840
tgtcccttgg cagccaagag gcagaaagat gggtacctta atggctccca gttctcctgg   3900
aagtcggtca agacggaggg catgtcctgc cctacccccg ggtgtgatgg gtcaggacac   3960
gtcagtggca gcttcctcac acaccgcagc ttgtcaggat gtccaagagc cacatcagca   4020
atgaagaaag caaagctgtc tggagaacag atgttgacta tcaagcagcg agccagcaac   4080
```

-continued

```
ggtatagaaa atgatgaaga aatcaagcag ttagatgaag agatcaagga gcttaatgag   4140
tccaattccc agatggaggc tgacatgatc aaactcagaa ctcagatcac cacaatggag   4200
agcaacctga agacgattga ggaggagaac aaagtcattg aacagcagaa tgagtcgctc   4260
ttgcacgagt tggccaacct gagccagtcc ctgatccaca gcctcgccaa catccagctg   4320
cctcacatgg atccaatcaa tgaacaaaat tttgatgctt acgtgactac tttgacggaa   4380
atgtatacaa atcaagatcg ttatcagagt ccagaaaata aagccctact ggaaaatata   4440
aagcaggctg tgagaggaat tcaggtctga acagctgctc tagtggtgac tcatgcttaa   4500
aaaggatgcc tcttgtttct tgctgctgta acttaccaga aagtgttata tatttatttc   4560
tgtcggaaca gtgttatgct acaagacttc ataatggttt tgtgtgctct cgagagagta   4620
cctgcagact agttttggat acattcacat tttgtacgtt ttcatataag ctgacatagt   4680
gtgatttgcc atgtaatgtt tatagctgct gctgtctgca catttggggg tctctatatt   4740
tctgaagagg taagctgatg aaaataaata gagtgtaaat tctttttaat gctttagtga   4800
ttaaatgttt tagtattttg aactgaaatg gacaaaaaaa gaaaaaggaa aaaaaaagca   4860
ggtttgaacg atcactttgt ggcctcctgg ccacttttag acattatcat tttgcctcag   4920
gttggaggac tttgtggaat ttaagaaata cattttgtgt gcatattgtt tcatagcaag   4980
aattggttgc aaaaaaatgc tttatttttg aacaatgctt ggaaatatta tgtgactttt   5040
ttgtttgttt gttttaggag gatggtgtat ggtgggggca ataaatgagg tttttttgcat   5100
tccaaggaaa tggcatatgg attaactata agaaatgaaa taagtaattt attgtaagac   5160
aacatcaagc catggaaact tggcagaaga ttcaaagcag cttaaacagc acttttaatt   5220
aactcctaaa cattacatgg tgggactgtg gagactccgt taagacagga gcttgtcaga   5280
ggtggacaac acgaagattt cctttgcatt ttcagtaacc tttggagcac acttctctta   5340
tttctcctag agccccgtgc cctctgaag tgttaccaca atctagctta cctagcagcc    5400
gttgattgtt tttttccat ctgagcaaac aggtaattta agcatttatc tccccctttca   5460
ctttcaaaaa gaatcatcat tgattattct tgtttcacat ctgaggatga aggctaacgg   5520
ctgtgcttgc cctggttact ggatgggatt ctctgctggg cgggtgggga agcagctcta   5580
cccttcccta cccctccctg ccccaactct gacttcgaat aagccttggt cctatccaga   5640
atacactgga caccaaggcc aaggacgttc acgttctgcc ctcgctgggt ccagctgact   5700
ctagcgtctg cacagccttg tgtgactcgt ggtgacctaa cctgagaaag agtgcaatca   5760
gatgttaaag taactaaata gactgcggca ctttttttgct ttaaactaga tcatcttaga   5820
tttgtcgata ccttcgaaat ttgatggttt catcccaaat gactgcacta tatgtatgca   5880
tacggccact tttgattgct gcgcccttc tgagtagtct ttgacaatgt gttgtgttcc    5940
ccgatgtcga cttgatttcc ttttagtagc atctctctct tccatgtctt gatgttatgc   6000
aggaagtaca aaagtacttt aaaattttgt tatgaaataa aaaaaaaaag gatgggtttt   6060
gtaaaaataa taaaaaaaat atttttagca gaacaggact tacagggtca ttgtccccac   6120
aatgtgccag tcggctcttt gcactcgcct tgtcctatat atccgtacgg aggtgtgcaa   6180
tcctgtgtca gtcgccttgt gacactgaag tggatgagtt atagaggagg ccctcgaggc   6240
tgacccaata cggttactaa gggagactac agggatctca cgacaaacat tctgatacaa   6300
tactcaacct cggtatatat atatatatat atatatatat acatatatat atatgtataa   6360
atataagaat atcccagcgg cactttatac tgttcactgt acaaaagctt acagttttcc   6420
acaaggactt taataactag ctggggaaaa gattatgtaa ttacttgggg ctctgcagga   6480
```

```
ccttctctgt ccagcgcccc ctttctgttg tgcgattagt tgtagctgcc atgctcagaa   6540

ttgccttttg agagctgaag caaggtgctt actgtcacct gatgccatac acatggtccc   6600

aggcccacac ccggggggcc tctgttcata gcggcacatg catttcccca ccgcgtcttg   6660

tctgcagctt cttggccaat gtagtaatgc ttttagtaga gtaataggta gtatcagttt   6720

ggattcttat tgttatcacc tatgtacaat ggagaggggt tctaagcaca aatctgctgc   6780

tcatgtaacg gtggtacata atatcaaatc aaaagttatc tgtgactata tatagggatc   6840

acaaagtgtc acatgttaga atgctgacct tccacatggg gttattgtga gtcatcagag   6900

catatttatt ataacttatt gttcatattc atttctaagt taatttaagt aatcatttat   6960

taagacagaa ttttgtataa actatttatt gtgctctctg tggaactgaa gtttgattta   7020

tttttgtact acacggcatg ggtttgttga cactttaatt ttgctataaa tgtgtggaat   7080

cacaagttgc tgtgatactt catttttaaa ttgtgaactt tgtacaaact ttgtcatgct   7140

gatgtgaaca catcttactc tgaataaaaa ggtgttgcca cgtttgtagc acgaagga     7198
```

<210> SEQ ID NO 25
<211> LENGTH: 2729
<212> TYPE: DNA
<213> ORGANISM: Homo sapiens

<400> SEQUENCE: 25

```
gaaggaagag gaagaggagg agagggaggc cagagccaga acagcccggc agcccgagct     60

tcgggggaga acggcctgag ccccgagcaa gttgcctcgg gagccctaat cctctcccgc    120

tggctcgccg agcggtcagt ggcgctcagc ggcggcgagg ctgaaatatg ataatcagaa    180

cagctgcgcc gcgcgccctg cagccaatgg gcgcggcgct cgcctgacgt ccccgcgcgc    240

tgcgtcagac caatggcgat ggagctgagt tggagcagag aagtttgagt aagagataag    300

gaagagaggt gcccgagccg cgccgagtct gccgccgccg cagcgcctcc gctccgccaa    360

ctccgccggc ttaaattgga ctcctagatc cgcgagggcg cggcgcagcc gagcagcggc    420

tctttcagca ttggcaaccc caggggccaa tatttcccac ttagccacag ctccagcatc    480

ctctctgtgg gctgttcacc aactgtacaa ccaccatttc actgtggaca ttactccctc    540

ttacagatat gggagacatg ggagatccac caaaaaaaaa acgtctgatt tccctatgtg    600

ttggttgcgg caatcagatt cacgatcagt atattctgag ggtttctccg gatttggaat    660

ggcatgcggc atgtttgaaa tgtgcggagt gtaatcagta tttggacgag agctgtacat    720

gctttgttag ggatgggaaa acctactgta aaagagatta tatcaggttg tacgggatca    780

aatgcgccaa gtgcagcatc ggcttcagca agaacgactt cgtgatgcgt gcccgctcca    840

aggtgtatca catcgagtgt ttccgctgtg tggcctgcag ccgccagctc atccctgggg    900

acgaatttgc gcttcgggag gacggtctct tctgccgagc agaccacgat gtggtggaga    960

gggccagtct aggcgctggc gacccgctca gtcccctgca tccagcgcgg ccactgcaaa   1020

tggcagcgga gcccatctcc gccaggcagc cagccctgcg gccccacgtc cacaagcagc   1080

cggagaagac cacccgcgtg cggactgtgc tgaacgagaa gcagctgcac accttgcgga   1140

cctgctacgc cgcaaacccg cggccagatg cgctcatgaa ggagcaactg gtagagatga   1200

cgggcctcag tccccgtgtg atccgggtct ggtttcaaaa caagcggtgc aaggacaaga   1260

agcgaagcat catgatgaag caactccagc agcagcagcc caatgacaaa actaatatcc   1320

aggggatgac aggaactccc atggtggctg ccagtccaga gagacacgac ggtggcttac   1380
```

aggctaaccc agtggaagta caaagttacc agccaccttg gaaagtactg agcgacttcg 1440
ccttgcagag tgacatagat cagcctgctt ttcagcaact ggtcaatttt tcagaaggag 1500
gaccgggctc taattccact ggcagtgaag tagcatcaat gtcctctcaa cttccagata 1560
cacctaacag catggtagcc agtcctattg aggcatgagg aacattcatt ctgtattttt 1620
tttccctgtt ggagaaagtg ggaaattata atgtcgaact ctgaaacaaa agtatttaac 1680
gacccagtca atgaaaactg aatcaagaaa tgaatgctcc atgaaatgca cgaagtctgt 1740
tttaatgaca aggtgatatg gtagcaacac tgtgaagaca atcatgggat tttactagaa 1800
ttaaacaaca aacaaaacgc aaaacccagt atatgctatt caatgatctt agaagtactg 1860
aaaaaaaaag acgtttttaa aacgtagagg atttatattc aaggatctca aagaaagcat 1920
tttcatttca ctgcacatct agagaaaaac aaaaatagaa aattttctag tccatcctaa 1980
tctgaatggt gctgtttcta tattggtcat tgccttgcca aacaggagct ccagcaaaag 2040
cgcaggaaga gagactggcc tccttggctg aaagagtcct ttcaggaagg tggagctgca 2100
ttggtttgat atgtttaaag ttgactttaa caaggggtta attgaaatcc tgggtctctt 2160
ggcctgtcct gtagctggtt tattttttac tttgccccct ccccactttt tttgagatcc 2220
atcctttatc aagaagtctg aagcgactat aaaggttttt gaattcagat ttaaaaacca 2280
acttataaag cattgcaaca aggttacctc tattttgcca caagcgtctc gggattgtgt 2340
ttgacttgtg tctgtccaag aacttttccc ccaaagatgt gtatagttat tggttaaaat 2400
gactgttttc tctctctatg gaaataaaaa ggaaaaaaaa aaaggaaact ttttttgttt 2460
gctcttgcat tgcaaaaatt ataaagtaat ttattattta ttgtcggaag acttgccact 2520
tttcatgtca tttgacattt tttgtttgct gaagtgaaaa aaaaagataa aggttgtacg 2580
gtggtctttg aattatatgt ctaattctat gtgttttgtc tttttcttaa atattatgtg 2640
aaatcaaagc gccatatgta gaattatatc ttcaggacta tttcactaat aaacatttgg 2700
catagataaa taaataaaaa aaaaaaaaa 2729

<210> SEQ ID NO 26
<211> LENGTH: 2526
<212> TYPE: DNA
<213> ORGANISM: Mus musculus

<400> SEQUENCE: 26
tttgagtaag agataaggaa gagaggtgcc ccgagccgtg cgagtccgcc gctgctgctg 60
cgcctccgct ctgccaactc cgccggctta aatcggactc ccagatctgc gagggcgcgg 120
cgcagccggg cagctgtttc ccccagtttt ggcaaccccg ggggccacta tttgccacct 180
agccacagca ccagcatcct ctctgtgggc tattcaccaa ttgtccaacc accatttcac 240
tgtggacatt actccctctt acagatatgg gagacatggg cgatccacca aaaaaaaaac 300
gtctgatttc cctgtgtgtt ggttgcggca atcaaattca cgaccagtat attctgaggg 360
tttctccgga tttggagtgg catgcagcat gtttgaaatg tgcggagtgt aatcagtatt 420
tggacgaaag ctgtacgtgc tttgttaggg atgggaaaac ctactgtaaa agagattata 480
tcaggttgta cgggatcaaa tgcgccaagt gcagcatagg cttcagcaag aacgacttcg 540
tgatgcgtgc ccgctctaag gtgtaccaca tcgagtgttt ccgctgtgta gcctgcagcc 600
gacagctcat cccgggagac gaattcgccc tgcgggagga tgggcttttc tgccgtgcag 660
accacgatgt ggtggagaga gccagcctgg gagctggaga ccctctcagt cccttgcatc 720
cagcgcggcc tctgcaaatg gcagccgaac ccatctcggc taggcagcca gctctgcggc 780
cgcacgtcca caagcagccg gagaagacca cccgagtgcg gactgtgctc aacgagaagc 840
agctgcacac cttgcggacc tgctatgccg ccaaccctcg gccagatgcg ctcatgaagg 900
agcaactagt ggagatgacg ggcctcagtc ccagagtcat ccgagtgtgg tttcaaaaca 960
agcggtgcaa ggacaagaaa cgcagcatca tgatgaagca gctccagcag cagcaaccca 1020
acgacaaaac taatatccag gggatgacag gaactcccat ggtggctgct agtccggaga 1080
gacatgatgg tggtttacag gctaacccag tagaggtgca aagttaccag ccgccctgga 1140
aagtactgag tgacttcgcc ttgcaaagcg acatagatca gcctgctttt cagcaactgg 1200
tcaatttttc agaaggagga ccaggctcta attctactgg cagtgaagta gcatcgatgt 1260
cctcgcagct cccagataca cccaacagca tggtagccag tcctattgag gcatgaggaa 1320
cattcattca gatgttttgt tttgttttgt tttgtttttt tcccctgttg gagaaagtgg 1380
gaaatgacgt tgaactccga aataaaaagt atttaacgac ccagtcaatg gaaactgaat 1440
caagaaatga acgctccagg aagcgcatga agtctgttct aatgacaaag tgatatggta 1500
gcaacactgt gaagacaatc atgggatttt actagaataa aaacaaacaa acaaacaaaa 1560
ccctaagccc aacatatgct attcaatgac cttaggagta cttaaaaaag aaaaagaaaa 1620
aaaaaagaga gagagaccgt ttttaaaacg tagaggattt atattcaagg atctcaaaaa 1680
atgcgcgttt tcatttcact gcacatctag aggaagagca gaaacagaga atttcctagt 1740
ccatcctatt ctgaatggtg ctgtttctat attggtcact gccttgccaa acaggagctc 1800
cggcacagag cggaagaaac cagcctcagt gacttgaaag tgtcctttca ggaaggcgga 1860
gctgcgttgg tttgcaatgt ttttagttga ctttgacaag gggttacgtg aaattctggg 1920
tctcttaagc atgccctgta gctggtttct cttttacgtt tgcctctcct cccatccttt 1980
tctttccttt tctttatttc tctttacaat ttttttgaga tccatcctct atcaagaagt 2040
ctgaagcgac tttaaaggtt tttaaatttg tatttaaaaa ccaacttata aagcattgca 2100
acaaggttac ctctattttg ccacaagcgt ctcgggattg tgtttgactc ctgtctgtcc 2160
aagaactttt cccccaaaga tgtgtatagt tattggttaa aatgactgtt ttcgctcttt 2220
ctggaaataa agaggaaaaa ggaaactttt tttgtttgct cttgcattgc aaaaattata 2280
aaagtaattt attatttatt gtcaggagac ttgccacttt tcatgtcatt tgactttttt 2340
tttgtttgct gaagtaaaaa gaagataaag gttgtaccgt ggtctttgaa ttatatgtct 2400
aagtttatgt gttttgtctt tttttttct ttaaatatta tgtgaaatca aagcgccata 2460
tgtagaatta tatcttcagg actatttcac taataaacgt ttggcataga taattaaata 2520
aacgca 2526

<210> SEQ ID NO 27
<211> LENGTH: 1620
<212> TYPE: DNA
<213> ORGANISM: Homo sapiens

<400> SEQUENCE: 27
tctcttaacg ggaaggggca gttggaggtg tgagactgag atctaatgat taacccgaag 60
gctgcaggag aaggaagtcg ccgggggaag gcgagccgag agcgccctga attaggcagg 120
cccgggaatg ggggtcaggg cttatcaccg gggaaaggaa cttgggccag gtcccccact 180
ggggcgttag agagacccgc ggcccctcca gggagaggga gtgcttcagg agcagcaaac 240
aagagaaatg ggcttcggag gcccggggag gcaaggccaa ggcccaggga acccccggct 300

```
cttaccaggg cgctgccctc ctctggaagg gcgttggatc cggggtgcga tggccgaggc    360

aggtggcctg gcttgaacca gctatggggg gactctcaac agtaggtgcc tgccctggaa    420

tcctgggcgc ccaacaagcc caggcgcagt cgaacctcct ggggaagtgc cgccggccgc    480

gcaccgcctt caccagccag cagctgctgg agctggagca ccagttcaag ctcaacaagt    540

acctgtcgcg gcccaagcgc ttcgaggtgg ccacctcgct catgctcacc gagacccagg    600

tgaagatttg gttccagaac cggcggatga aatggaaacg cagcaaaaag gccaaagagc    660

aggcggcgca ggaagcggag aaacagaagg gcggcggcgg gggcgcgggg aagggcggcg    720

cggaggagcc gggagccgag gagctgctgg ggccgccagc gcccggagac aagggcagcg    780

gacgccgcct gcgggacttg agggacagtg accccgagga ggacgaggac gaggacgacg    840

aggaccattt cccctacagc aacggcgcca gcgtccacgc cgcctcctcc gactgctcct    900

cggaggacga ctcgccgccc ccgcggccca gccaccagcc cgcgccccag taggagcccc    960

gcggcccagc aggtgcggcg cgcacggagc gccccggccg gcggcttctc ccggaggccc   1020

cggcgcccgc acccacccgg cccggccccg agagcaggct cgaccgccgc cccatggacc   1080

cctcgcccag gccggggctg gagggattcg gccgcggctc cggtcctggg cgcttccctt   1140

ttaagcaagg gcgcctcacc tgctcttcaa gaaacagcga gagggagacc caggggggctg  1200

aaacttgaac tctggttctt ttaaaattaa ttttggttgg tgttggggga ggcgcgagtg   1260

cgtgtgagaa gaaccgaccc accccgcgca aggggaagcc tcctgtctcc cctttccccg   1320

cgtccgagaa ggcggaaacc cacagtgtta cctgacttat gaaacttgaa accgcctctg   1380

gagccgccat tctgcagagt atttggaaaa agaaaaaagg gtttatgctt acgtctctgg   1440

ggtcgggggg attatgtcac gagcgttcaa actgctggaa atctcaaaac tgtactgtct   1500

ttatttttgt atattgtatt tatatataaa aagaaacgtc tacgtatgca tgctaaatta   1560

ttatttagct tctcccatcg cccacgatgg aatgtaaaat aaattggttt tgtactggat   1620
```

<210> SEQ ID NO 28
<211> LENGTH: 1456
<212> TYPE: DNA
<213> ORGANISM: Mus musculus

<400> SEQUENCE: 28

```
ccacgaggac cgcaaagagg aggcgcctgg acgatggtcg ctctcagctg agtttccggc     60

tgcgacttta ttggcaaaaa atcgcagtaa caataccggc cccaaggctg gccaccgcca    120

cgctcagtct ccgtaagccc gcacacgact gcatcgccca cccttggacc ctgattgtca    180

gctccaatcg agccgatgga aaaatccaaa aatttccgca tcgacgccct gctggccgtg    240

gatcccccgc gagccgcctc cacgcagagc gcgcctctgg ccttggtcac ttccctcgcg    300

actacagtat ctggtcccgg ccgcggcggc agcggcggcg gggggaccag tagcggggcg    360

agccgtagct gcagtcccgc atcctcggag gccactgcag cgcccggtga ccggctgaga    420

gctgagagcc cgtcgccccc acgcttgctg gctgcacact gcgcgctgct gcccaagccc    480

ggattcctgg gcgccggagg aggcggcggc gcggcgggtg ggccgggcac tccccaccac    540

cacgcgcacc ctggtgcagc agccgccgcg gctgccgctg ccgctgccgc ggctgccggt    600

ggcctggcac tggggctgca cccgggggc gcacagggcg gcgcgggcct ccctgcacag     660

gcggctctct atggacaccc ggtctacagt tattcggcag cagctgcagc ggccgcgcta    720

gctggccagc acccggcgct ttcctactca taccctcagg tgcagggcgc gcaccctgcg    780

caccctgccg accccatcaa gctgggtgcc agcaccttcc aactggacca gtggctgcgc    840
```

```
gcgtctactg cgggcatgat cctgcccaag atgccggact tcagctccca ggcgcagtcg    900

aacctcttgg ggaagtgccg aaggcctcgc acggccttca ccagccagca gctgttggag    960

ctggaacacc agttcaagct caacaagtac ctgtctcgac ccaagcgttt tgaggtggct   1020

acctcgctca tgctcaccga gactcaggtg aagatttggt tccagaaccg ccgaatgaaa   1080

tggaaacgca gcaaaaaggc caaagagcag gctgcgcagg aggcggagaa gcagaagggc   1140

ggcggcgggg gcaccggcaa aggcggcagt gaggagaaga cggaagagga gctgatgggg   1200

cctccggttt cgggggacaa ggcaagcggc cgtcgcctgc gggacttgcg ggacagtgac   1260

cctgatgagg acgaggatga tgaagaagag gacaacttcc cgtacagcaa tggtgccggt   1320

gcccatgctg cctcatccga ctgctcatct gaggacgact cgcctcctcc aagactaggc   1380

gggcctggac accaacctct gccccagtag ttgcctccag ggcggaagca gggatgcgaa   1440

agatggctac ctgggg                                                   1456
```

<210> SEQ ID NO 29
<211> LENGTH: 2370
<212> TYPE: DNA
<213> ORGANISM: Homo sapiens

<400> SEQUENCE: 29

```
cgcagccact gaaccacaag cagcttcgcg ttaactggag tgcctgggag tcgcgtgcca     60

ggagccgcac ggccagggac tgactgacag acagacacgc accaccacca caacacacga    120

gacccgggcg ggccgccgcc gccgccgccg gggctcttgg caaactcgcc ggtcgcagag    180

gtcccccgcg gagctgcgcc acagtagcgc cgggcttgca gctttcacgc cgggcgaagg    240

acccggcgct gcgctcgcag ctgcgcggag attcccggca caggccaaag tcacagcaac    300

gctgaggcac agttagagcc aactaagatg ttcgtcaaat ccgagacctt ggagttgaag    360

gaggaagagg acgtgttagt gctgctcgga tcggcctccc ccgccttggc ggccctgacc    420

ccgctgtcat ccagcgccga cgaagaagag gaggaggagc cgggcgcgtc aggcggggcg    480

cgtcggcagc gcggggctga ggccgggcag ggggcgcggg gcggcgtggc tgcgggtgcg    540

gagggctgcc ggcccgcacg gctgctgggt ctggtacacg attgcaaacg gcgcccttcc    600

cgggcgcggg ccgtctcccg aggcgccaag acggccgaga cggtgcagcg catcaagaag    660

acccgtagac tgaaggccaa caaccgcgag cgaaaccgca tgcacaacct caacgcggca    720

ctggacgcgc tgcgcgaggt gctccccacg ttccccgagg acgccaagct caccaagatc    780

gagaccctgc gcttcgccca caactacatc tgggcactca ccgagaccct gcgcctggcg    840

gatcactgcg gggcggcgg cgggggcctg ccgggggcgc tcttctccga ggcagtgttg    900

ctgagcccgg gaggcgccag cgccgccctg agcagcagcg gagacagccc ctcgcccgcc    960

tccacgtgga gttgcaccaa cagccccgcg ccgtcctcct ccgtgtcctc caattccacc   1020

tccccctaca gctgcacttt atcgcccgcc agcccggccg ggtcagacat ggactattgg   1080

cagcccccac ctcccgacaa gcaccgctat gcacctcacc tccccatagc cagggattgt   1140

atctagagct gccatttctg ctacccacgc caggccttag tgggttccct ttcctgtccc   1200

cagtcgagcc ctcctccctt cccctgcccc tcctttccac gccctggaaa ccatctcact   1260

tcacagggca ggtgtagcct ttctgattcc tcggttgttt cttgcatttc ttggctttgg   1320

gtatccttca ttcagacggg ctctgattta ctgaaggtgt gatggagctt attgtcaaag   1380

ccaagggtgg cgttttgggg gcgcttcttg agacgaaaaa gaccctggga agagatgatg   1440
```

-continued gtggcatatc taaagagttt gcagagcgga ctgacgctcc tcccctttct ctttaacgcc 1500
gaaggacttg gtgcagttcg tgtgaatctc acagggggaa tgcaactggt tcctgtgatc 1560
tcttcacctt tgcttctaca tagagatgtt aatgtcgagt agaaagaaat gtatcttagc 1620
atctgaatga ttttgctggt aataatatta tccacagatt tgcaatggct ggcatctgct 1680
ttattcccat tgctgtctgc aggctgtggg aatttcacct gtcaaaccaa acttccctct 1740
ctgatgtgca ctttgttctg tttcccagat tcgtcacaat gcctattgtc ctgtccttct 1800
ctttcctttt tcttccccat tttgccatct gtctcttatg atttataagg ggaaaaaaac 1860
ttgttttgtt agaggggcag gttagaagtc attgtataat ttgtaggctt tgtaatgatt 1920
gaatgcaagc gtggaaattt aggctgaact ctctatcaaa aggaaaaatg tggaggaaaa 1980
gggaaaaatc aggagggagg attgcctcat gtattattta tttcgacctt ttaggggaga 2040
aggaactccc ccattctttc aagagattaa aaataaatca acagtctgaa aacctaagca 2100
gacacggagc attatccgga tcagccacac acgtgttccc ttctatttat tataaagaaa 2160
tttttcatgg gaaaatatgt attttttgta tattctacag agtttattct agtatgtatt 2220
tacatcttga agaacaagaa agttgttctt gtgattaaac tataaataaa ctatctaatt 2280
ttcataaaaa aaaaaaaaaa aaaaaaaaaa aaaaaaaaaa aaaaaaaaaa aaaaaaaaaa 2340
aaaaaaaaaa aaaaaaaaaa aaaaaaaaaa 2370

<210> SEQ ID NO 30
<211> LENGTH: 2244
<212> TYPE: DNA
<213> ORGANISM: Mus musculus

<400> SEQUENCE: 30
gcagccactg aaccacaagc agctcggctt taactggagt gccttggagt cgcgtgccag 60
cagccacacg gccagggact gactgacaga caaccacgca cgagaacgac aacacacgag 120
actcgggcga gctgccgcgg tcgtccgggc tcttggcaaa gtcgcccagc cgagaggccc 180
ccccgcggag gtgcgcctag gaagcgccaa gcccgcggcg cggaggacac cgtgctcggt 240
tccgggctgc ggggacattc ccggacacac accggagcag cagctgcgcc gcgacacatc 300
tggagccgcg taggatgttc gtcaaatctg agactctgga gttgaaggag gaagaggagg 360
tactgatgct gctgggctcg gcttccccgg cctcggcgac cctgaccccg atgtcctcca 420
gcgcggacga ggaggaggac gaggagctgc gccggccggg ctccgcgcgt gggcagcgtg 480
gagcggaagc cgggcagggg gtgcagggca gtccggcgtc gggtgccggg ggttgccggc 540
cagggcggct gctgggcctg atgcacgagt gcaagcgtcg cccgtcgcgc tcacgggccg 600
tctcccgagg tgccaagacg gcggagacgg tgcagcgcat caagaagacc cgcaggctca 660
aggccaacaa ccgcgagcgc aaccgcatgc acaacctaaa cgccgcgctg gacgcgctgc 720
gcgaggtgct gcccaccttc cccgaggatg ccaagctcac gaagatcgag acgctgcgct 780
tcgcccacaa ttacatctgg gcgctcaccg agactctgcg cctggcggac cactgcgccg 840
gcgccggtgg cctccagggg gcgctcttca cggaggcggt gctcctgagc ccgggagctg 900
cgctcggcgc cagcggggac agcccttctc caccttcctc ctggagctgc accaacagcc 960
cggcgtcatc ctccaactcc acgtccccat acagctgcac tttatcgccc gctagccccg 1020
ggtcagacgt ggactactgg cagcccccac ctccggagaa gcatcgttat gcgcctcacc 1080
tgcccctcgc cagggactgt atctagagct gcgggtctcc ctctctcgtc ctctacccgg 1140
ccctcttccc atccttctcc cgcccctcac cctccacgcc ccggactcca cttcacagag 1200

-continued

```
cagaggtggc ccttgcaatc ccctcggcgg ctggtgcatt cgggggtgga gaccagctct   1260
ggtttattga agatgtgagg atttatggtc aaagaggact atggcgtgtg ggagtggggg   1320
ctggcgtggg gaacctcgta agactgtaaa agacactgag aaaaagtacc ataactaacg   1380
agtgtgcaga gcagactgac gctcctcccc tctctcagag ctgctggagg agaactccgg   1440
gcaggcagtt cgtgtgaatc tctcagaggg aatgcaactg gtccctgtga tcttttcacc   1500
ttcgtttcta catagagatg ttaatgtcag tcgaaagaaa tgtattttag catctgaatg   1560
aatttactgg taataatatt atccacacat ttgcaatggc tggcatctgc tctattccca   1620
ttgctgtctg caggctgtgg gaatttcacc tgtcaaacca aactttccct ctctgatgtg   1680
cactttgttt ttttcccaga ttcgtcacaa tgcctattgt cccgcccttc tttttgcttt   1740
ttttctccat tttgccatct gtctcttatg atttataagg gggaaaaact tgttttgtta   1800
gagggccagg ttagaagtca ttgtataatt tgtaggcttt tgtaagggtt gaatgcaagc   1860
gtggaaattt aggctgaatt ctctatcaaa agaaaaaatg tgaaggaaaa aggaaaaatc   1920
aggagggagg attgcttcat gcattattta tctcgacctt ttaggggaga aggaactccc   1980
ccatcctttc aagagattaa aaataaatca acagtctgaa aacctaagca gacacggggc   2040
attgccagga tcagccacac acgtgtttcc ttctatttat tttgaagaaa aatttcatgg   2100
gaaagtatgt attttttgt atattctaca gagtttattc tagtatgtat ttacatcccg   2160
aagaataaga aaattgtttt gtgattaagc tataaataaa gtatctaatt ttcataaaaa   2220
aaaaaaaaaa aaaaaaaaaa aaaa                                           2244
```

<210> SEQ ID NO 31
<211> LENGTH: 2945
<212> TYPE: DNA
<213> ORGANISM: Homo sapiens

<400> SEQUENCE: 31

```
ggggaggagg ggagaacggg gagcgcacag cctggacgcg tgcgcaggcg tcaggcgcat     60
agacctgcta gcccctcagc tagcggcccc gcccgcgctt agcatcacta actgggctat    120
ataacctgag cgcccgcgcg gccacgacac gaggaattcg cccacgcagg aggcgcggcg    180
aaatcgaaac atgaccaaat cgtacagcga gagtgggctg atgggcgagc ctcagcccca    240
aggtcctcca agctggacag acgagtgtct cagttctcag gacgaggagc acgaggcaga    300
caagaaggag gacgacctcg aagccatgaa cgcagaggag gactcactga ggaacggggg    360
agaggaggag gacgaagatg aggacctgga agaggaggaa gaagaggaag aggaggatga    420
cgatcaaaag cccaagagac gcggccccaa aaagaagaag atgactaagg ctcgcctgga    480
gcgttttaaa ttgagacgca tgaaggctaa cgcccgggag cggaaccgca tgcacggact    540
gaacgcggcg ctagacaacc tgcgcaaggt ggtgccttgc tattctaaga cgcagaagct    600
gtccaaaatc gagactctgc gcttggccaa gaactacatc tgggctctgt cggagatcct    660
gcgctcaggc aaaagcccag acctggtctc cttcgttcag acgctttgca agggcttatc    720
ccaacccacc accaacctgg ttgcgggctg cctgcaactc aatcctcgga cttttctgcc    780
tgagcagaac caggacatgc ccccccacct gccgacggcc agcgcttcct tccctgtaca    840
cccctactcc taccagtcgc ctgggctgcc cagtccgcct tacggtacca tggacagctc    900
ccatgtcttc cacgttaagc ctccgccgca cgcctacagc gcagcgctgg agcccttctt    960
tgaaagccct ctgactgatt gcaccagccc ttcctttgat ggacccctca gcccgccgct   1020
```

cagcatcaat ggcaacttct ctttcaaaca cgaaccgtcc gccgagtttg agaaaaatta 1080
tgcctttacc atgcactatc ctgcagcgac actggcaggg gcccaaagcc acggatcaat 1140
cttctcaggc accgctgccc ctcgctgcga gatccccata gacaatatta tgtccttcga 1200
tagccattca catcatgagc gagtcatgag tgcccagctc aatgccatat ttcatgatta 1260
gaggcacgcc agtttcacca tttccgggaa acgaacccac tgtgcttaca gtgactgtcg 1320
tgtttacaaa aggcagccct ttgggtacta ctgctgcaaa gtgcaaatac tccaagcttc 1380
aagtgatata tgtatttatt gtcattactg cctttggaag aaacagggga tcaaagttcc 1440
tgttcacctt atgtattatt ttctatagct cttctattta aaaaataaaa aaatacagta 1500
aagtttaaaa aatacaccac gaatttggtg tggctgtatt cagatcgtat taattatctg 1560
atcgggataa caaaatcaca agcaataatt aggatctatg caatttttaa actagtaatg 1620
ggccaattaa aatatatata aatatatatt tttcaaccag cattttacta cttgttacct 1680
ttcccatgct gaattatttt gttgtgattt tgtacagaat ttttaatgac tttttataat 1740
gtggatttcc tattttaaaa ccatgcagct tcatcaattt ttatacatat cagaaaagta 1800
gaattatatc taatttatac aaaataattt aactaattta aaccagcaga aaagtgctta 1860
gaaagttatt gtgttgcctt agcacttctt tcctctccaa ttgtaaaaaa aaaaaaaaaa 1920
aaaaaaaaaa aaaaaaaatt gcacaatttg agcaattcat ttcactttaa agtctttccg 1980
tctccctaaa ataaaaacca gaatcataat tttcaagaga agaaaaaatt aagagataca 2040
ttccctatca aaacatatca attcaacaca ttacttgcac aagcttgtat atacatatta 2100
taaataaatg ccaacatacc cttctttaaa tcaaaagctg cttgactatc acatacaatt 2160
tgcactgtta ctttttagtc ttttactcct ttgcattcca tgattttaca gagaatctga 2220
agctattgat gtttccagaa aatataaatg catgatttta tacatagtca caaaaatggt 2280
ggtttgtcat atattcatgt aataaatctg agcctaaatc taatcaggtt gttaatgttg 2340
ggatttatat ctatagtagt caattagtac agtagcttaa ataaattcaa accatttaat 2400
tcataattag aacaatagct attgcatgta aaatgcagtc cagaataagt gctgtttgag 2460
atgtgatgct ggtaccactg gaatcgatct gtactgtaat tttgtttgta atcctgtata 2520
ttatggtgta atgcacaatt tagaaaacat tcatccagtt gcaataaaat agtattgaaa 2580
gtgagagcaa ttgttgcatt tcttcttaaa gggattctgt ttttattttt ggggaaagta 2640
gttgcttttt tgctgagtta aaaaatacta aacactatat gtagaataaa agaaaagaaa 2700
aaagtttacc ttggcatatg ctcttgtctg tttatcttgc acagggagtc accagttcta 2760
tgtagataat gaaaagacct aactgatatt tcattatttg gaatatggga ctggacggca 2820
gtacaaacag tgtgtttttt tctttgtttt aagtggctta gcctttaggt tttttatttc 2880
catttttaaa aatgattgtt acatgttttc ttctatttct ttttttaaaa ggtggatttt 2940
aataa 2945

<210> SEQ ID NO 32
<211> LENGTH: 2494
<212> TYPE: DNA
<213> ORGANISM: Mus musculus

<400> SEQUENCE: 32
acgaggaatt cgcccacgca gaaggcaagg tgtcccgagg ctccagggtt atgagatcgt 60
cactattcag aaccttttaa caacaggaag tggaaacatg accaaatcat acagcgagag 120
cgggctgatg ggcgagcctc agccccaagg tcccccaagc tggacagatg agtgtctcag 180

-continued

```
ttctcaggac gaggaacacg aggcagacaa gaaagaggac gagcttgaag ccatgaatgc    240
agaggaggac tctctgagaa acgggggaga ggaggaggag gaagatgagg atctagagga    300
agaggaggaa gaagaagagg aggaggagga tcaaaagccc aagagacggg gtcccaaaaa    360
gaaaaagatg accaaggcgc gcctagaacg ttttaaatta aggcgcatga aggccaacgc    420
ccgcgagcgg aaccgcatgc acgggctgaa cgcggcgctg gacaacctgc gcaaggtggt    480
accttgctac tccaagaccc agaaactgtc taaaatagag acactgcgct tggccaagaa    540
ctacatctgg gctctgtcag agatcctgcg ctcaggcaaa agccctgatc tggtctcctt    600
cgtacagacg ctctgcaaag gtttgtccca gcccactacc aatttggtcg ccggctgcct    660
gcagctcaac cctcggactt tcttgcctga gcagaacccg gacatgcccc cgcatctgcc    720
aaccgccagc gcttccttcc cggtgcatcc ctactcctac cagtcccctg gactgcccag    780
cccgccctac ggcaccatgg acagctccca cgtcttccac gtcaagccgc cgccacacgc    840
ctacagcgca gctctggagc ccttctttga aagcccccta actgactgca ccagcccttc    900
ctttgacgga cccctcagcc cgccgctcag catcaatggc aacttctctt tcaaacacga    960
accatccgcc gagtttgaaa aaaattatgc ctttaccatg cactaccctg cagcgacgct   1020
ggcagggccc caaagccacg gatcaatctt ctcttccggt gccgctgccc ctcgctgcga   1080
gatccccata gacaacatta tgtctttcga tagccattcg catcatgagc gagtcatgag   1140
tgcccagctt aatgccatct ttcacgatta gaggcacgtc agtttcacta ttcccgggaa   1200
acgaatccac tgtgcgtaca gtgactgtcc tgtttacaga aggcagccct tttgctaaga   1260
ttgctgcaaa gtgcaaatac tcaaagcttc aagtgatata tgtatttatt gtcgttactg   1320
cctttggaag aaacagggga tcaaagttcc tgttcacctt atgtattgtt ttctatagct   1380
cttctatttt aaaaataata atacagtaaa gtaaaaaaga aaatgtgtac cacgaatttc   1440
gtgtagctgt attcagatcg tattaattat ctgatcggga taaaaaaaat cacaagcaat   1500
aattaggatc tatgcaattt ttaaactagt aatgggccaa ttaaaatata tataaatata   1560
tatttttcaa ccagcatttt actacctgtg acctttccca tgctgaatta ttttgttgtg   1620
attttgtaca gaatttttaa tgacttttta taacgtggat ttcctatttt aaaaccatgc   1680
agcttcatca atttttatac atatcagaaa agtagaatta tatctaattt atacaaaata   1740
atttaactaa tttaaaccag cagaaaagtg cttagaaagt tattgcgttg ccttagcact   1800
tctttcttct ctaattgtaa aaaagaaaag aaaagaaaaa aaaccaacaa attgcacaat   1860
ttgagcaatt catctcactt taaagttttt cctgctcgct ccctaaaata gaaaccagac   1920
ccataacact caagaggatg aaaaccgaaa tgcattcctt atcaaaacac atcaattcat   1980
tacttgcaca agcttgtaaa tacatattat aaataaatgc caacacacac tcctttaaat   2040
caaaagctgc ttgactatca catacaattt gcactctttc tttttagtct tttacttctt   2100
tgaattccat gattttacgg agtgtttgaa gatattgatg tttccagaaa atataaatgc   2160
atgattttat acatagtcaa acaaatggtg gtttgtcatc tattcatgta ataaatttga   2220
gcctaaattt attcaggttg ttaatgttgg gtttttatac ctgtgtagtc agttagtaca   2280
gtagtttaaa taaaattcaa accatcgaat tcataattag aacaatagct gttgcatgta   2340
aaatgcagtc cagaataagt gctgtttgag atgtgatgct ggtactactg gaattgacat   2400
gtactgtaat cttgtttgta atcctgtgta ttatggtgta atgcacaatt tagaaaactc   2460
ccatgcagtt gcaataaaaa tagtatggaa aatc                                2494
```

-continued

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
ccaactactc caacgact 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
ggagagcctg gcaggtcc 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
gcgccgagga tgtgtatg 18

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
aggaaagact gtggacc 17

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
acaacttccc gtacagcaat 20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
cttccgccct ggaggcaa 18

-continued

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
gcgacataga tcagcctgc 19

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
catctgaatg aatgttcc 18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
cccccaccca tgagggtgct 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
gagccagggg aagcagaggc 20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
cgtgactact ttgacgga 18

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
tcaccactag agcagctgt 19

<210> SEQ ID NO 45

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

gcgtcatcct ccaactcc                                                18


<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

agagggagac ccgcagct                                                18


<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

tttgtacaag aaagctgggt                                              20
```

CONVERSION OF SOMATIC CELLS INTO FUNCTIONAL SPINAL MOTOR NEURONS, AND METHODS AND USES THEREOF

This application is a 35 U.S.C. §371 National Phase Entry Application of International Application No. PCT/US2012/051264 filed Aug. 17, 2012, which designates the U.S., and which claims benefit under 35 U.S.C. §119(e) of the U.S. Provisional Application Ser. No. 61/524,599 filed on Aug. 17, 2011, the contents of each of which is incorporated herein in their entirety by reference.

CROSS REFERENCE TO RELATED APPLICATION

This application claims benefit under 35 U.S.C. §119(e) of the U.S. Provisional Application Ser. No. 61/524,599 filed on Aug. 17, 2011, the contents of which is incorporated herein in its entirety by reference.

GOVERNMENT SUPPORT

This invention was made with made with Government Support under Contract Nos: NS069395, HD045732, and GM007592 awarded by the National Institutes of Health. The Government has certain rights in the invention.

FIELD OF INVENTION

The invention relates to methods for transdifferentiation of a somatic cell, e.g., a fibroblast to a cell having motor neuron characteristics. The present invention also relates to an isolated population comprising induced motor neurons, compositions and their use in the treatment of motor neuron diseases and disorders (MNDs).

SEQUENCE LISTING

The instant application contains a Sequence Listing which has been submitted in ASCII format via EFS-Web and is hereby incorporated by reference in its entirety. Said ASCII copy was created on Aug. 15, 2012, is named 071451PCT.txt and is 128,713 bytes in size.

BACKGROUND OF THE INVENTION

The mammalian nervous system is composed of a multitude of distinct neuronal subtypes, each with its own phenotype and differential sensitivity to degenerative disease. Although specific neuronal types can be isolated from rodent embryos or engineered from stem cells for translational studies, transcription factor mediated reprogramming might provide a more direct route to their generation.

The mammalian central nervous system (CNS) is assembled from a diverse collection of neurons, each with its own unique properties. These discrete characteristics underlie the proper integration and function of each neuron within the circuitry of the brain and spinal cord. However, their individual qualities also render particular neurons either resistant or sensitive to particular degenerative stimuli. Thus, for each neurodegenerative disease, a stereotyped set of neuronal subtypes is destroyed, causing the hallmark presentation of that condition. Therefore, if one is to comprehend the mechanisms that underlie the development, function and degeneration of the CNS, it is important to first deeply understand the properties of individual neuronal subtypes.

Physiological and biochemical studies of individual neuronal types have been greatly facilitated by the ability to isolate distinct classes of neurons and interrogate them in vitro. Most studies have focused on neurons isolated from the developing rodent CNS. However, it is not routinely possible to isolate analogous populations of human neurons or to isolate and fully study differentiated central neurons. Pluripotent stem cells, such as embryonic stem cells (ESCs), may provide an inexhaustible reservoir of diverse neural subtypes, offering an attractive approach for in vitro studies (Wichterle et al., 2002). Although stem cells have shown great promise, to date, only a handful of neural subtypes have been produced in this way. Furthermore, in many cases the neuronal populations produced from stem cells have not been shown to possess refined subtype specific properties and may only superficially resemble their counterparts from the CNS (Peljto and Wichterle, 2011).

Experiments using the reprogramming of one set of differentiated cells directly into another suggest an alternative approach for the generation of precisely defined neural subtypes. Using distinct sets of transcription factors, it is possible to reprogram fibroblasts into pluripotent stem cells (Takahashi and Yamanaka, 2006), blood progenitors (Szabo et al., 2010), cardiomyocytes (Ieda et al., 2010) as well as functional, post-mitotic neurons (Caiazzo et al.; Pfisterer et al., 2011; Vierbuchen et al., 2010). Thus, it may be possible to use factors which act on cells intrinsically, rather than relying on morphogens that act extrinsically to more precisely specify the exact properties of a wide array of neuronal types. Most reprogramming studies have so far only produced induced neurons (iNs) with an unknown developmental ontogeny and a generic phenotype (Pang et al., 2011; Pfisterer et al., 2011; Vierbuchen et al., 2010). Recently, two studies have generated cells that resemble dopaminergic neurons based on the production of tyrosine hydroxylase (Caiazzo et al.; Pfisterer et al., 2011). However, it is unclear whether these cells are molecularly and functionally equivalent to embryo- or ESC-derived dopaminergic neurons. In particular, it has yet to be determined whether any type of neuron made by reprogramming can survive and properly integrate into the CNS. If neuronal reprogramming is to be successfully applied to the study of CNS function or degeneration, then it must be capable of producing specific neuronal types that possess the correct phenotypic properties both in vitro and in vivo.

Motor neurons control the contraction of muscle fibers actuating movement. Damage to motor neurons caused by either injury or disease can result in paralysis or death; consequently, there is significant interest in understanding how motor neurons regenerate after nerve injury and why they are selective targets of degeneration in diseases such as spinal muscular atrophy (SMA) and amyotrophic lateral sclerosis (ALS). There is a need to produce functional motor neurons for the treatment of motor neuron degenerative diseases and disorders.

SUMMARY OF THE INVENTION

The present invention relates to compositions and a method for direct reprogramming (i.e. transdifferentiation, or cellular reprogramming) of a fibroblast cell to a cell having characteristics of a functional motor neuron. In particular, the present invention relates to a method for direct conversion of a fibroblast cell by increasing the protein expression of at least three motor neuron inducing (MN-inducing factors), selected from any of Lhx3, Ascl1, Brn2, Myt1l, Isl1, Hb9, Ngn2 or NeuroD1, in the somatic cell.

Accordingly, the present invention relates to methods, compositions and kits for producing a functional motor neuron (iMN) from a fibroblast. Other embodiments of the present invention relate to an isolated population of functional motor neurons (iMNs) produced by the methods as disclosed herein, and an isolated population of functional iMNs by increasing the protein expression of at least three motor neuron inducing (MN-inducing factors), selected from any of Lhx3, Ascl1, Brn2, Myt1l, Isl1, Hb9, Ngn2 or NeuroD1 in a fibroblast cell, and methods of their use.

Herein, the inventors have demonstrated that the forced expression of a group of select transcription factors is sufficient to convert mouse and human fibroblasts into induced motor neurons (iMNs). iMNs displayed a morphology, gene expression signature, electrophysiology, synaptic functionality, in vivo engraftment capacity and sensitivity to degenerative stimuli, similar to embryo-derived motor neurons. In particular, the inventors demonstrate that the converting fibroblasts do not transit through a proliferative neural progenitor state, and thus form bona fide motor neurons via a route distinct from embryonic development. The inventors have successfully demonstrated that fibroblasts can be converted directly into a specific differentiated and functional spinal motor neuron subtype, referred to herein as "iMN" or "induced motor neuron". Importantly, the inventors demonstrate that iMNs are a distinct neuronal subtype with different functional characteristics to other neuronal subtypes derived from fibroblasts, which are commonly referred to as iNs (induced neurons).

In some embodiments, iMNs exhibit characteristic of normal motor neurons (e.g., motor neurons differentiated from embryonic stem cells (ESCs)) and can express at least two motor neuron specific genes selected from the group consisting of: β2-tubulins (e.g, Tubb2a and Tubb2b), Map2, synapsins (e.g., Syn1 and Syn2), synaptophysin, synaptotagmins (e.g., Syt1, Syt4, Syt13, Syt16), NeuroD, Isl1, cholineacetyltransferase (ChAT), e.g., vescular ChAT. In some embodiments, the iMNs have decreased level of expression of fibroblast genes from which they are derived, e.g., have decreased expression of any of the following genes selected from the group of: Snail1, thy1 and Fsp1.

In some embodiments, the iMNs generated by the methods as disclosed herein exhibit typical motor neuron morphology, e.g., comprising a cell body with axonal projections which form functional synaptic junctions with muscle cells.

In some embodiments, iMNs generated by the methods as disclosed herein have an average resting potential of lower than about −50 mV, e.g., between −48 to −51 mV, or about −49.5 mV, which is similar to motor neurons differentiated from embryonic stem cells. In some embodiments, the iMN can have a resting potential of about −50 mV to about −65 mV and any integer between, e.g., about −50 mV, or about −50 to −55 mV or about −55 mV to about −60 mV or about −60 mV to about −65 mV. In some embodiments, the iMNs generated by the methods as disclosed herein exhibit the ability to fire action potentials, are responsive to inhibitor neurotransmitters, e.g., produce an outward current in response to glycine and GABA, and are responsive to excitatory neurotransmitters, e.g., produce an inward current in response to glutamate or kainate.

In some embodiments, iMNs and compositions comprising iMNs are produced by the methods comprising contacting a somatic cell, or a population of somatic cells with an agent, such as a nucleic acid agent, or nucleic acid analogue, peptide, polypeptide aptamer, antibody, antibody fragment, ribosomes, small molecule and the like, which increases the protein expression of at least three transcription factors selected from any combination of Lhx3, Ascl1, Brn2, Myt1l, Isl1, Hb9, Ngn2 or NeuroD1 in a somatic cell, e.g., a fibroblast. In some embodiments, iMNs can be produced by introducing a nucleic acid sequence or nucleic acid analogue encoding at least three MN-inducing factors Lhx3, Ascl1, Brn2, Myt1l, Isl1, Hb9, Ngn2 or NeuroD1 or functional fragments thereof into a somatic cell, e.g., a fibroblast. In some embodiments, a nucleic acid sequence which encodes at least three MN-inducing factors Lhx3, Ascl1, Brn2, Myt1l, Isl1, Hb9, Ngn2 or NeuroD1 or functional fragments thereof is expressed transiently for a transient increase the protein expression of the polypeptides MN-inducing factors Lhx3, Ascl1, Brn2, Myt1l, Isl1, Hb9, Ngn2 or NeuroD1 in the somatic cell, e.g., fibroblast.

One aspect of the present invention provides a method for transdifferentiation of a somatic cell, e.g., a fibroblast, the method comprising increasing the protein expression of at least three MN-inducing factors selected from any of: Lhx3, Ascl1, Brn2, Myt1l, Isl1, Hb9, Ngn2 or NeuroD1 in the somatic cell, e.g, fibroblast cell, wherein the somatic cell is converted to an induced motor neuron (iMN) and exhibits at least two characteristics of a motor neuron, for example, but not limited to, motor neuron morphology, firing action potentials, responsive to inhibitory neurotransmitters, glycine, GABA or kainate, responsive to excitatory neurotransmitters, e.g., glutamate, and express motor-neuron specific markers, selected from, but not limited to: β2-tubilins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vescular ChAT. In some embodiments, the protein expression of Lhx3, Ascl1, Brn2, Myt1l, Isl1, Hb9, Ngn2 or NeuroD1 are increased in a somatic cell, e.g., fibroblast.

In some embodiments, in increase in the protein expression of least three MN-inducing factors selected from any of: Lhx3, Ascl1, Brn2, Myt1l, Isl1, Hb9, Ngn2 or NeuroD1 can be achieved by contacting a somatic cell, e.g., a fibroblast with an agent which increases the expression of the MN-inducing factor, where an agent can be selected from the group consisting of: a nucleotide sequence, a nucleic acid analogue (e.g., Locked nucleic acid (LNA), modified RNA (modRNA)), a protein, an aptamer and small molecule, ribosome, RNAi agent and peptide-nucleic acid (PNA) and analogues or variants thereof. In some embodiments, protein expression is increased by introducing at least three nucleic acid sequences encoding at least three MN-inducing factors selected from any of: Lhx3, Ascl1, Brn2, Myt1l, Isl1, Hb9, Ngn2 or NeuroD1, or encoding a functional fragment thereof, in the somatic cell, e.g., fibroblast.

In some embodiments, protein expression of Lhx3 is increased by introducing a nucleic acid sequence encoding a Lhx3 polypeptide comprising SEQ ID NO: 1 or SEQ ID NO: 2 or a functional fragment of SEQ ID NO: 1 or SEQ ID NO: 2 into the somatic cell, e.g., fibroblast.

In some embodiments, protein expression of Ascl1 is increased by introducing a nucleic acid sequence encoding a Ascl1 polypeptide comprising SEQ ID NO: 3 or SEQ ID NO: 4 or a functional fragment of SEQ ID NO: 3 or SEQ ID NO: 4 into the somatic cell, e.g., fibroblast.

In some embodiments, protein expression of Brn2 is increased by introducing a nucleic acid sequence encoding a Brn2 polypeptide comprising SEQ ID NO: 5 or SEQ ID NO: 6 or a functional fragment of SEQ ID NO: 5 or SEQ ID NO: 6 into the somatic cell, e.g., fibroblast.

In some embodiments, protein expression of Myt1l is increased by introducing a nucleic acid sequence encoding a Myt1l polypeptide comprising SEQ ID NO: 7 or SEQ ID NO: 8 or a functional fragment of SEQ ID NO: 7 or SEQ ID NO: 8 into the somatic cell, e.g., fibroblast.

In some embodiments, protein expression of Isl1 is increased by introducing a nucleic acid sequence encoding a Isl1 polypeptide comprising SEQ ID NO: 9 or SEQ ID NO: 10 or a functional fragment of SEQ ID NO: 9 or SEQ ID NO: 10 into the somatic cell, e.g., fibroblast.

In some embodiments, protein expression of Hb9 is increased by introducing a nucleic acid sequence encoding a Hb9 polypeptide comprising SEQ ID NO: 11 or SEQ ID NO: 12 or a functional fragment of SEQ ID NO: 11 or SEQ ID NO: 12 into the somatic cell, e.g., fibroblast.

In some embodiments, protein expression of Ngn2 is increased by introducing a nucleic acid sequence encoding a Ngn2 polypeptide comprising SEQ ID NO: 13 or SEQ ID NO: 14 or a functional fragment of SEQ ID NO: 13 or SEQ ID NO: 14 into the somatic cell, e.g., fibroblast.

In some embodiments, protein expression of NeuroD1 is increased by introducing a nucleic acid sequence encoding a NeuroD1 polypeptide comprising SEQ ID NO: 15 or SEQ ID NO: 16 or a functional fragment of SEQ ID NO: 15 or SEQ ID NO: 16 into the somatic cell, e.g., fibroblast.

In some embodiments, a nucleic acid sequence is in a vector, such as a viral vector or a non-viral vector. In some embodiments, the vector is a viral vector comprising a genome that does not integrate into the host cell genome.

In some embodiments, somatic cell, e.g., fibroblast is in vitro. In some embodiments, somatic cell, e.g., fibroblast is ex vivo.

In some embodiments, a subject is a human subject. In some embodiments, the subject has, or is at risk of developing a motor neuron disease or disorder, e.g., ALS or spinal muscular atrophy (SMA). In some embodiments, a somatic cell, e.g., fibroblast is a mammalian cell, such as a human cell.

In some embodiments, the vector comprises a nucleic acid sequence encoding a Lhx3 polypeptide or a functional fragment thereof, and/or comprises a nucleic acid sequence encoding a Ascl1 polypeptide or a functional fragment thereof and/or comprises a nucleic acid sequence encoding a Brn2 polypeptide or a functional fragment thereof, and/or comprises a nucleic acid sequence encoding a Myt1l polypeptide or a functional fragment thereof, and/or comprises a nucleic acid sequence encoding a Isl1 polypeptide or a functional fragment thereof, and/or comprises a nucleic acid sequence encoding a Hb9 polypeptide or a functional fragment thereof, and/or comprises a nucleic acid sequence encoding a Ngn2 polypeptide or a functional fragment thereof, and/or comprises a nucleic acid sequence encoding a NeuroD1 polypeptide or a functional fragment thereof.

Another aspect of the present invention relates to a method for the treatment of a subject with a motor neuron disease or disorder, the method comprising administering a composition comprising an isolated population of iMNs according to the methods as disclosed herein.

Another aspect of the present invention relates to the use of the isolated population of iMNs produced by the methods as disclosed herein for administering to a subject in need thereof.

In some embodiments, iMNs can be produced from somatic cells, e.g., fibroblasts obtained from the same subject as the composition is administered to (e.g., autologous iMNs). In alternative embodiments, the iMNs are produced from a donor subject (e.g., allogenic iMNs). In some embodiments, the subject has, or has an increased risk of developing a motor neuron disease or disorder, e.g., ALS, SMA, or PLS or other motor neuron diseases as disclosed herein.

Another aspect of the present invention relates to kits for producing iMNs as disclosed herein. In some embodiments, a kit comprises (i) a nucleic acid sequence encoding a Lhx3 polypeptide or a functional fragment thereof; and/or (ii) a nucleic acid sequence encoding a Ascl1 polypeptide or a functional fragment thereof; and/or (iii) a nucleic acid sequence encoding a Brn2 polypeptide or a functional fragment thereof, and/or (iv) a nucleic acid sequence encoding a Myt1l polypeptide or a functional fragment thereof, and/or (v) a nucleic acid sequence encoding a Isl1 polypeptide or a functional fragment thereof, and/or (vi) a nucleic acid sequence encoding a Hb9 polypeptide or a functional fragment thereof, and/or (vii) a nucleic acid sequence encoding a Ngn2 polypeptide or a functional fragment thereof, and/or (viii) a nucleic acid sequence encoding a NeuroD1 polypeptide or a functional fragment thereof. In some embodiments, the kit further comprises instructions for direct conversion of a somatic cell, e.g., fibroblast to an iMN cell with at least two characteristics of a motor neuron which is differentiated from a embryonic stem cell.

Another aspect of the present invention relates to methods of identifying agents that alone or in combination with other agents directly convert somatic cell, e.g., fibroblast to a iMN. In some embodiments, the method includes contacting one or more somatic cell, e.g., fibroblast with one or more test agents (simultaneously or at separate times) and determining the presence of a iMN comprising at least two characteristics of a motor neuron which is differentiated from an embryonic stem cell. The test agents may include, but are not limited to, small molecules, nucleic acids, peptides, polypeptides, immunoglobulins, and oligosaccharides. In some embodiments, the method includes determining the level of expression of one or more of the MN-inducing factors selected from the group consisting of: Lhx3, Ascl1, Brn2, MOB, Isl1, Hb9, Ngn2 or NeuroD1. Expression levels can be determined by any means known by one of ordinary skill in the art, for example, by RT-PCR or immunological methods.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A shows a schematic of the experimental outline. 11 candidate transcription factors include eight developmental genes in addition to the three iN factors. FIG. 1B shows immunostaining of Hb9::GFP+ neurons express Tuj1. Scale bars represent 40 m. FIG. 1C shows iMNs generated with 10 factors (without Isl1) express endogenous Islet. Scale bars represent 40 μm. FIG. 1D shows Isl1 is dispensable for generating iMNs. Scale bar represents 200 μm. FIG. 1E shows the reprogramming efficiency is greater with Hb9 or Isl1 on top of 4 factors (Lhx3, Ascl1, Brn2 and Myt1l) at day 21 post-transduction. Error bars indicate +s.d. *$P<0.05$ (Student's t-test, two tailed). FIG. 1F shows the addition of Ngn2 to the 6-factor pool (Hb9, Isl1, Lhx3, Ascl1, Brn2 and Myt1l) greatly enhances reprogramming efficiency as seen 10 days after transduction. Error bars indicate +s.d.***$P<0.001$;

**P<0.01 (Student's t-test, two-tailed). FIG. 1G shows the 7 iMN factors convert adult tail tip fibroblasts into motor neurons. Scale bar represents 100 μm.

FIG. 2A shows the global transcriptional analysis of FACS-purified Hb9::GFP+ motor neurons. iMNs cluster with control motor neurons and away from MEFs. FIGS. 2B-2D show pairwise gene expression comparisons show that iMNs are highly similar to embryo derived motor neurons and dissimilar from the starting MEFs; labeled genes denotes genes that are expressed in motor neurons, genes labeled with an asterix (*) denotes genes expressed in fibroblasts, and the lines indicate the diagonal and 2-fold changes between the sample pairs. FIG. 2E is results of qRT-PCR data showing expression of endogenous transcripts of the 7 iMN factors relative to their levels in ES-MNs. Error bars indicate +s.d.

FIG. 3A shows iMNs express the pan-neuronal marker Map2. Scale bars represent 100 μm. FIG. 3B shows iMNs express synapsin. Scale bars represent 20 μm. FIG. 3C shows iMNs express vesicular cholineacetyltransferase (vChAT). Scale bars represent 40 μm. FIG. 3D shows iMNs express the motor neuron-selective transcription factor Hb9. Scale bars represent 80 μm.

FIG. 4A shows iMNs express functional sodium channels. FIG. 4B shows iMNs express functional sodium and potassium channels. FIG. 4C shows iMN sodium channel activity is appropriately blocked by tetrodotoxin (TTX). FIG. 4D shows iMNs fire a single action potential upon depolarization. FIG. 4E shows iMNs fire multiple action potentials upon depolarization. FIG. 4F shows 100 μM GABA induces inward currents in iMNs. FIG. 4G shows 100 μM glycine induces inward currents in iMNs. FIG. 4H shows 100 μM kainate induces inward currents in iMNs. FIG. 4I shows iMN-induced contractions of C2C12 myotubes are blocked by 50 μM curare. The arrow indicates the timing of curare addition. FIG. 4J shows iMNs cultured with chick myotubes form NMJs with characteristic α-bungarotoxin (α-BTX, red) staining. The dotted line outlines the boundaries of a myotube. Scale bar represents 5 μm.

FIG. 5A is a schematic diagram showing the injection of iMNs into the neural tube of the stage 17 chick embryo. FIG. 5B shows transverse sections of iMN-injected chick neural tube 5 day after transplantation. Arrows in both panels indicate the same axon of an iMN exiting the spinal cord through the ventral root. D: dorsal, V: ventral, VR: ventral root. FIG. 5C shows FACS-purified Hb9::GFP+ iMNs co-cultured with wild-type or the mutant SOD1G93A overexpressing glia for 10 days. Scale bars represent 5 μm. FIG. 5D shows the quantification of FIG. 5C. Error bars indicate +s.d. P<0.01 (Student's t-test, two-tailed). FIG. 5E shows SOD1G93A iMNs exhibit reduced survival in culture with wild-type glia. Error bars indicate +s.d. P<0.01 (Student's t-test, two-tailed). FIG. 5F shows the changes in iMN number after 9 days of culture in the presence or absence of neurotrophic factors (GDNF, BDNF and CNTF). Error bars indicate +s.d. **P<0.01 (Student's t-test, two tailed).

FIG. 6A shows the percentage of iMNs that have incorporated BrdU. FIG. 6B shows an outline of the lineage tracing experiment using Nestin::CreER; LOX-STOP-LOX-H2BmCherry; Hb9::GFP iPSCs or MEFs. To detect Nestin+ intermediates, cultures were treated with 1-2 μM 4-OHT during directed diffentiation of iPSCs (positive control) or during transdifferentiation of fibroblasts by the 7 factors. FIG. 6C shows FACS-purified, mCherry+ Hb9::GFP+ motor neurons derived from the triple transgenic iPSCs in the presence of 1 μM 4-OHT. Expression of mCherry was observed in 3% of Hb9::GFP+ cells (n>10,000) and indicates the activation of Nestin::CreER during directed differentiation. Scale bars represent 40 μm. FIG. 6D shows mCherry− Hb9::GFP+ iMNs generated from the triple transgenic MEFs by transdifferentiation in the presence of 2 μM 4-OHT. mCherry+ iMNs were never observed (n>5,000), suggesting a Nestin+ state is not accessed during reprogramming. Scale bars represent 40 μm.

FIG. 7A shows an Hb9::GFP+ neuron generated from a HEF culture by 8 transcription factors. Scale bars represent 80 μm. FIG. 7B shows quantification of human iMN reprogramming efficiency at day 30 post-transduction. FIG. 7C shows human iMNs express vesicular choline acetyltransferase (vChAT). Scale bars represent 80 μm. FIG. 7D shows human iMNs express functional sodium and potassium channels. FIG. 7E shows human iMNs fire action potentials upon depolarization. FIG. 7F shows 100 μM kainate induces inward currents in human iMNs. FIG. 7G shows 100 μM GABA induces inward currents in human iMNs.

FIG. 8A shows Hb9::GFP+ cells are generated from MEFs by transduction with 8 or 11 factors by day 35 post-transduction, but more efficiently by 11 factors. Scale bars represent 50 μm. FIG. 8B shows the eficiency of reprogramming 35 days post-transduction when each factor is omitted from the 11-factor pool individually. Error bars indicate +s.d. FIG. 8C shows Lhx3 and Ascl1 are not sufficient to convert fibroblasts into motor neurons. Error bars indicate +s.d. * p<0.001 (Student's t-test, two-tailed). FIG. 8D shows that adding each of the neural progenitor factors to 7 factors (Ngn2+6 factors) inhibits iMN formation as seen 10 days after transduction. Error bars indicate +s.d. *P<0.001; **P<0.01 (Student's t-test, two-tailed). FIG. 8E shows N3 medium promotes iMN accumulation. Efficiency of fibroblast-to-iMN reprogramming in two different media conditions. Error bars indicate +s.d.

FIG. 9A shows iMN morphology is similar to that of embryonic and ESC-derived motor neurons. Scale bars represent 100 μm. FIGS. 9B-9F show microarray analysis reveals that iMNs have a motor neuron-like gene expression signature. FIG. 9B shows iMNs express the pan-neuronal genes Map2 and b2-tubulin. FIG. 9C shows iMNs express genes required for synapse formation. FIG. 9D shows iMNs endogenously express transcription factors expressed in motor neurons. FIG. 9E shows iMNs endogenously express choline acetyltransferase. FIG. 9F shows fibroblast-specific genes are down-regulated in iMNs. mRNA expression levels are shown relative to an embryonic motor neuron control (9B-9E) or relative to a MEF control (9F). All motor neuron samples were FACS-purified by Hb9::GFP expression prior to mRNA extraction. FIG. 9G shows immunostaining of 7 factor iMNs for tyrosine hydroxylase (TH). A rare TH+ iMN with a low level of Hb9::GFP reporter expression is shown on the right. Scale bars represent 200 μm. FIG. 9H shows iMNs have not silenced viral transgenes. qRT-PCR using primers for the viral transcripts of 7 iMN factors. Expression levels shown relative to ESC-derived motor neurons.

FIG. 10A-10D show tail tip fibroblast-derived iMNs exhibit electrophysiology characteristic of motor neurons. FIG. 10A shows sodium and potassium currents. FIG. 10B shows single and multiple action potentials. FIG. 10C shows inward current in response to 100 μM GABA. FIG. 10D shows inward current in response to 100 μM kainate. FIGS. 10E-10G show iMNs express genes required for ion channel function and neurotransmitter response. FIG. 10 E shows sodium channel mRNA expression levels relative to an embryo-derived motor neuron control genes. FIG. 10F shows potassium channel mRNA expression levels relative to an embryo-derived motor neuron control genes. FIG. 10G shows glutamate receptor mRNA expression levels relative to an embryo-derived motor neuron control genes. All motor neuron samples were FACS-purified by Hb9::GFP expression prior to mRNA extraction. FIG. 10H shows iMNs co-cultured with a monolayer of C2C12 myotubes. Scale bar represents 200 μm. FIGS. 10I-10L show iMNs induce acetylcholine receptor clustering and form anatomical endplates on cultured myotubes. FIG. 10I shows fluorescence image of GFP+ iMNs after 7 weeks of coculture with chick myotubes. FIG. 10*j* shows rhodamine-conjugated a-BTX staining showed Ach clustering occurred on the chick myotubes. FIG. 10K shows merged image of FIG. 10I and FIG. 10J) showed Ach receptors clustering preferentially occurred near the GFP+ axons (open arrowhead) and at the end of the neurites at putative endplates regions (arrows). ACh clusters were less pronounced on myotubes not associated with axons (arrowhead). FIG. 10L shows confocal image depicting a GFP+ axon co-localized with acetylcholine receptors at a putative endplate in a 3-week co-culture. Imaging in both the x-z and y-z orthogonal planes confirms the close proximity of the receptors to the axon terminal. Scale bars represent 50 μm (FIG. 10K) and 5 μm (FIG. 10L).

DETAILED DESCRIPTION OF THE INVENTION

Figure 1A:
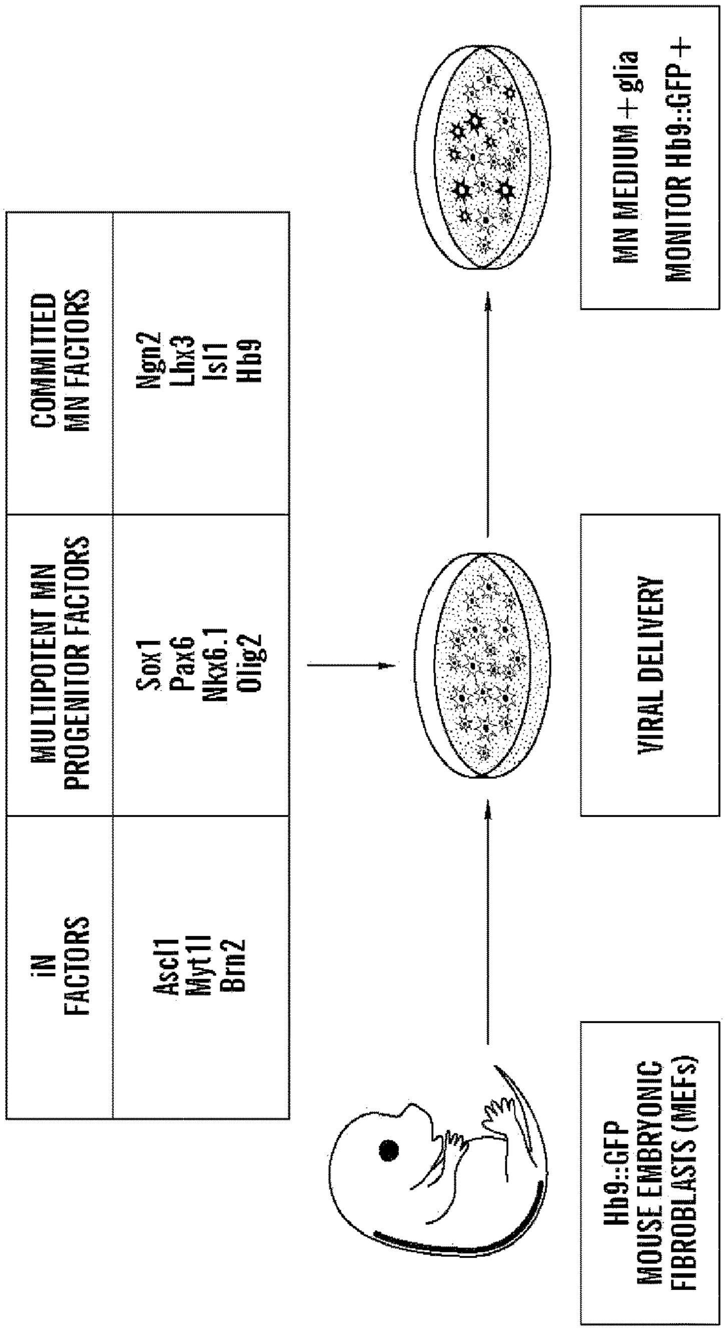
FIGS. 1A-1G show the generation of Hb9::GFP+ Induced Motor Neurons by 7 Factors.

The present invention provides compositions and methods for producing functional motor neurons from fibroblast cells. In some embodiments, the present invention provides compositions and methods for direct conversion of fibroblast cells to functional motor neurons (iMNs), without the somatic cell, e.g., fibroblast becoming an induced pluripotent stem cell (iPS) intermediate prior to being transdifferentated into a functional motor neuron.

The present invention relates to a population of induced motor neurons (iMNs) from a somatic cell, e.g., fibroblast, and methods and compositions for the direct reprogramming cells, such as a somatic cell, e.g., fibroblast to an iMN. In particular, the present invention relates to a method for transdifferentiation of a somatic cell, e.g., fibroblast by increasing the protein expression of at least three MN-inducing factors selected from any of: Lhx3, Ascl1, Brn2, Myt1l, Isl1, Hb9, Ngn2 or NeuroD1 in the somatic cell, e.g., fibroblast. In some embodiments, the method comprises increasing the expression of least three MN-inducing factors selected from any of: Lhx3, Ascl1, Brn2, Myt1l, Isl1, Hb9, Ngn2 or NeuroD1. In some embodiments, the method comprises increasing the protein expression of a functional fragment of least three MN-inducing factors selected from any of: Lhx3, Ascl1, Brn2, Myt1l, Isl1, Hb9, Ngn2 or NeuroD1 in a somatic cell, e.g., fibroblast. In some embodiments, the method further comprises increasing the protein expression of additional MN-inducing factors in addition to at least 8 factors disclosed herein.

Accordingly, the present invention relates to methods, compositions and kits for producing an induced motor neuron (iMN) from a somatic cell, e.g., fibroblast. Other embodiments of the present invention relate to an isolated population of induced motor neurons (iMNs) by increasing the protein expression of least three MN-inducing factors selected from any of: Lhx3, Ascl1, Brn2, Myt1l, Isl1, Hb9, Ngn2 or NeuroD1 in the somatic cell, e.g., fibroblast.

In some embodiments, an isolated population of iMNs produced by the methods and compositions as disclosed herein is a mammalian iMN, for example, a human iMN.

In some embodiments, an isolated population of iMNs and compositions are produced by a method comprising contacting a cell or a population of a somatic cell, e.g., fibroblast with an agent, such as a nucleic acid agent, peptide, polypeptide aptamer, antibody, antibody fragment, ribosomes, small molecules, RNAi agents, ribosomes and the like, which increase the protein expression of least three MN-inducing factors selected from any of: Lhx3, Ascl1, Brn2, Myt1l, Isl1, Hb9, Ngn2 or NeuroD1 in the somatic cell, e.g., fibroblast. In some embodiments, the method to produce an isolated population of iMNs comprises introducing a nucleic acid sequence encoding of least three MN-inducing factors selected from any of: Lhx3, Ascl1, Brn2, Myt1l, Isl1, Hb9, Ngn2 or NeuroD1 or functional fragments thereof into the somatic cell, e.g., fibroblast. In some embodiments, the nucleic acid sequence encoding of least three MN-inducing factors selected from any of: Lhx3, Ascl1, Brn2, Myt1l, Isl1, Hb9, Ngn2 or NeuroD1, or functional fragments thereof is expressed transiently for a transient increase the protein expression of the polypeptides of least three MN-inducing factors selected from any of: Lhx3, Ascl1, Brn2, Myt1l, Isl1, Hb9, Ngn2 or NeuroD1 in the somatic cell, e.g., fibroblast.

In some embodiments, the method comprises increasing the protein expression of at least three MN-inducing factors selected from any of: Lhx3, Ascl1, Brn2, Myt1l, Isl1, Hb9, Ngn2 or NeuroD1 of SEQ ID NOs 1-8, or functional fragments of proteins of SEQ ID NO: 1-8 respectively for human polypeptide sequences. In some embodiments, the method comprises increasing the protein expression of at least three MN-inducing factors selected from any of: Lhx3, Ascl1, Brn2, Myt1l, Isl1, Hb9, Ngn2 or NeuroD1 of SEQ ID NOs 1-16, or functional fragments of proteins of SEQ ID NO: 1-16 respectively for human and mouse polypeptides.

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

The term "transdifferentiation" is used interchangeably herein with the phrase "direct conversion" or "direct reprogramming" and refers to the conversion of one differentiated somatic cell type into a different differentiated somatic cell type without undergoing complete reprogramming to an induced pluripotent stem cell (iPSC) intermediate.

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. A partial reversal of differentiation produces a partially induced pluripotent (PiPS) cell. Reprogramming also encompasses partial reversion of the differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The term "differentiated cell" is meant any primary cell that is not, in its native form, pluripotent as that term is defined herein. It should be noted that placing many primary cells in culture can lead to some loss of fully differentiated characteristics. However, simply culturing such cells does not, on its own, render them pluripotent. The transition to pluripotency requires a reprogramming stimulus beyond the stimuli that lead to partial loss of differentiated character in culture. Reprogrammed pluripotent cells also have the characteristic of the capacity of extended passaging without loss of growth potential, relative to primary cell parents, which generally have capacity for only a limited number of divisions in culture. Stated another way, the term "differentiated cell" refers to a cell of a more specialized cell type derived from a cell of a less specialized cell type (e.g., a stem cell such as an induced pluripotent stem cell) in a cellular differentiation process.

As used herein, the term "somatic cell" refers to are any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for direct conversion of a somatic cell, e.g., fibroblast to a iMN can be performed both in vivo and in vitro (where in vivo is practiced when somatic a somatic cell, e.g., fibroblast are present within a subject, and where in vitro is practiced using isolated somatic a somatic cell, e.g., fibroblast maintained in culture).

As used herein, the term "adult cell" refers to a cell found throughout the body after embryonic development.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "motor neuron" also referred to as a "motoneuron" refers to a neuron that sends electrical output signals to a muscle, gland, or other effector tissue.

The term "induced motor neuron" or "iMN" as used herein refers to a functional motor neuron produced by direct conversion from a somatic cell, e.g., a fibroblast.

The term "functional" as used in relation to a functional motor neuron refers to a motor neuron which can fire action potentials and can signal a muscle to contract. A functional motor neuron expresses ChAT, an enzyme necessary for synthesizing the motor neuron transmitter acetylcholine, and expresses VAChAT, which is necessary for the storage and uptake of the transmitter acetylcholine, and expresses synapsin for formation of synapses, and can transmit action potentials and synapse with muscle cells to result in muscle contraction.

As used herein, the term "endogenous motor neuron" refers to a motor neuron in vivo or a motor neuron produced by differentiation of an embryonic stem cell into a motor neuron, and exhibiting an adult motor neuron phenotype. The phenotype of a motor neuron is well known by persons of ordinary skill in the art, and include, for example, formation of synaptic junctions with muscle cells, expression of ChAT, immunostaining with αBTX, responsive to inhibitory and excitatory neurotransmitters, as well as distinct morphological characteristics such long axonal projections and synaptic connections with muscle cells.

The term "progenitor cell" is used herein to refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

The term a "MN-inducing factor", as used herein, refers to a gene whose expression, contributes to the direct conversion of a somatic cell, e.g., fibroblast, to a MN which exhibits at least two characteristics of an endogenous motor neuron. A MN-inducing factor be, for example, genes encoding transcription factors Lhx3 (SEQ ID NO: 1-2 encoded by SEQ ID NO: 17-18), Ascl1 (SEQ ID NO: 3-4 encoded by SEQ ID NO: 19-20), Brn2 (SEQ ID NO: 5-6 encoded by SEQ ID NO: 21-22), Myt1l (SEQ ID NO: 7-8 encoded by SEQ ID NO: 23-24), Isl1 (SEQ ID NO: 9-10 encoded by SEQ ID NO: 25-26), Hb9 (SEQ ID NO: 11-12 encoded by SEQ ID NO: 27-28), Ngn2 (SEQ ID NO: 13-14 encoded by SEQ ID NO: 29-30) or NeuroD1 (SEQ ID NO: 15-16 encoded by SEQ ID NO: 31-32).

The term "MN-inducing agent" refers to any agent which increases the protein expression of a MN-inducing factor, as that term is described herein. Preferably, a MN-inducing agent increases the expression of a MN-inducing factor selected from Lhx3, Ascl1, Brn2, Myt1l, Isl1, Hb9, Ngn2 or NeuroD1.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. Sci. USA 87:22264-2268, 1990) modified as in Karlin and Altschul, Proc. Natl. Acad. Sci. USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of iMNs, refers to a population of cells that contain fewer than about 20%, more preferably fewer than about 15%, 10%, 8%, 7%, most preferably fewer than about 5%, 4%, 3%, 2%, 1%, or less than 1%, of cells that are not iMNs or their progeny as defined by the terms herein. In some embodiments, the present invention encompasses methods to expand a population of iMNs, wherein the expanded population of iMNs is a substantially pure population of iMNs.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

As used herein, the term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated. The terms "nucleic acid" can also refer to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH-group can be replaced by a group selected from H. OR, R. halo, SH, SR, $NH_2$, NHR, $NR_2$ or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The terms "polypeptide variant" refers to any polypeptide differing from a naturally occurring polypeptide by amino acid insertion(s), deletion(s), and/or substitution(s). Variants may be naturally occurring or created using, e.g., recombinant DNA techniques or chemical synthesis. In some embodiments amino acid "substitutions" are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments not more than 1%, 5%, 10%, 15% or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

By "amino acid sequences substantially homologous" to a particular amino acid sequence (e.g. Lhx3, Ascl1, Brn2, Myt1l, Isl1, Hb9, Ngn2 or NeuroD1) is meant polypeptides that include one or more additional amino acids, deletions of amino acids, or substitutions in the amino acid sequence of Lhx3, Ascl1, Brn2, Myt1l, Isl1, Hb9, Ngn2 or NeuroD1 without appreciable loss of functional activity as compared to wild-type Lhx3, Ascl1, Brn2, Myt1l, Isl1, Hb9, Ngn2 or NeuroD1 polypeptides in terms of the ability to produce iMNs from a somatic cell, e.g., fibroblast. For example, the deletion can consist of amino acids that are not essential to the presently defined differentiating activity and the substitution(s) can be conservative (i.e., basic, hydrophilic, or hydrophobic amino acids substituted for the same). Thus, it is understood that, where desired, modifications and changes may be made in the amino acid sequence of Lhx3, Ascl1, Brn2, Myt1l, Isl1, Hb9, Ngn2 or NeuroD1, and a protein having like characteristics still obtained. It is thus contemplated that various changes may be made in the amino acid sequence of the Lhx3, Ascl1, Brn2, Myt1l, Isl1, Hb9, Ngn2 or NeuroD1 amino acid sequence (or underlying nucleic acid sequence) without appreciable loss of biological utility or activity and possibly with an increase in such utility or activity. In some embodiments, the amino acid sequences substantially homologous to a particular amino acid sequence are at least 70%, e.g., 75%, 80%85%, 90%, 95% or another percent from 70% to 100%, in intergers thereof, identical to the particular amino acid sequence.

As used herein, "Lhx3" is refers to the Lhx3 protein of Genebank accession No: NP_055379.1 (SEQ ID NO: 1); (human) NP_001034742.1 (SEQ ID NO: 2) (mouse) encoded by genes NM_014564 (SEQ ID NO: 17) (human) NM_001039653.1 (SEQ ID NO: 18) (mouse). The term Lhx3 also encompasses species variants, homologues, allelic forms, mutant forms, and equivalents thereof, including conservative substitutions, additions, deletions therein not adversely affecting the structure of function. Lhx3 is referred in the art as aliases; *Homo sapiens* LIM homeobox 3 (LHX3), transcript variant 2, mRNA, CPHD3; LIM3; M2-LHX3. In addition to naturally-occurring allelic variants of the Lhx3 sequences that may exist in the population, it will be appreciated that, as is the case for virtually all proteins, a variety of changes can be introduced into the sequences of SEQ ID NO: 1 or SEQ ID NO: 2 (referred to as "wild type" sequences) without substantially altering the functional (biological) activity of the polypeptides. Such variants are included within the scope of the terms "Lhx3", "Lhx3 protein", etc.

As used herein, "Ascl1" is refers to the Ascl1 protein of Genebank accession No: NP_004307.2 (SEQ ID NO: 3) (human), or NP_032579.2 (SEQ ID NO: 4) (mouse) and is encoded by genes NM_004316.3 (SEQ ID NO: 19) (human) or NM_008553.4 (SEQ ID NO:20) (mouse), respectively. The term Ascl1 also encompasses species variants, homologues, allelic forms, mutant forms, and equivalents thereof, including conservative substitutions, additions, deletions therein not adversely affecting the structure of function. Ascl1 is referred in the art as aliases; *Homo sapiens* achaete-scute complex homolog 1 (Drosophila) (ASCL1), ASH1; bHLHa46; HASH1; MASH1. In addition to naturally-occurring allelic variants of the Ascl1 sequences that may exist in the population, it will be appreciated that, as is the case for virtually all proteins, a variety of changes can be introduced into the sequences of SEQ ID NO: 3 or SEQ ID NO: 4 (referred to as "wild type" sequences) without substantially altering the functional (biological) activity of the polypeptides. Such variants are included within the scope of the terms "Ascl1", "Ascl1 protein", etc.

As used herein, "Brn2" is refers to the Brn2 protein of Genebank accession No: NP_005595.2 (SEQ ID NO: 5) (human) or NP_032925.1 (SEQ ID NO: 6) (mouse) and encoded by genes NM_005604.2 (SEQ ID NO: 21) (human) or NM_008899.1 (SEQ ID NO: 22) (mouse), respectively. The term Brn2 also encompasses species variants, homologues, allelic forms, mutant forms, and equivalents thereof, including conservative substitutions, additions, deletions therein not adversely affecting the structure of function. Brn2 is referred in the art as aliases; POU3F2, POU class 3 homeobox 2, BRN2, OCT7, POUF3. In addition to naturally-occurring allelic variants of the Brn2 sequences that may exist in the population, it will be appreciated that, as is the case for virtually all proteins, a variety of changes can be introduced into the sequences of SEQ ID NO: 5 or SEQ ID NO: 6 (referred to as "wild type" sequences) without substantially altering the functional (biological) activity of the polypeptides. Such variants are included within the scope of the terms "Brn2", "Brn2 protein", etc.

As used herein, "Myt1l" is refers to the Myt1l protein of Genebank accession No: NP_055840.2 (SEQ ID NO: 7) (human) or NP_001087244.1 (SEQ ID NO: 8) (mouse) and encoded by genes NM_015025.2 (SEQ ID NO: 23) (human) or NM_001093775.1 (SEQ ID NO: 24) (mouse), respectively. The term Myt1l also encompasses species variants, homologues, allelic forms, mutant forms, and equivalents thereof, including conservative substitutions, additions, deletions therein not adversely affecting the structure of function. Myt1l is referred in the art as aliases; myelin transcription factor 1-like (MYT1L), KIAA1106, "neural zinc finger transcription factor 1", NZF1. In addition to naturally-occurring allelic variants of the Myt1l sequences that may exist in the population, it will be appreciated that, as is the case for virtually all proteins, a variety of changes can be introduced into the sequences of SEQ ID NO: 7 or SEQ ID NO: 8 (referred to as "wild type" sequences) without substantially altering the functional (biological) activity of the polypeptides. Such variants are included within the scope of the terms "Myt1l ", " Myt1l protein", etc.

As used herein, "Isl1" is refers to the Isl1 protein of Genebank accession No: NP_002193.2 (SEQ ID NO: 9) (human) or NP_067434.3 (SEQ ID NO: 10) (mouse) and is encoded by genes NM_002202.2 (SEQ ID NO: 25) (human) or NM_021459.4 (SEQ ID NO: 26) (mouse) respectively.

The term Isl1 also encompasses species variants, homologues, allelic forms, mutant forms, and equivalents thereof, including conservative substitutions, additions, deletions therein not adversely affecting the structure of function. Isl1 is referred in the art as aliases; ISL LIM homeobox 1, Isl-1, ISLET1. In addition to naturally-occurring allelic variants of the Isl1 sequences that may exist in the population, it will be appreciated that, as is the case for virtually all proteins, a variety of changes can be introduced into the sequences of SEQ ID NO: 9 or SEQ ID NO: 10 (referred to as "wild type" sequences) without substantially altering the functional (biological) activity of the polypeptides. Such variants are included within the scope of the terms "Isl1", "Isl1 protein", etc.

As used herein, "Hb9" is refers to the Hb9 protein of Genebank accession No: NP_001158727.1 (SEQ ID NO: 11) (human) or NP_064328.2 (SEQ ID NO: 12) (mouse) and encoded by genes NM_001165255.1 (SEQ ID NO: 27) (human) or NM_019944.2 (SEQ ID NO: 28) (mouse) respectively. The term Hb9 also encompasses species variants, homologues, allelic forms, mutant forms, and equivalents thereof, including conservative substitutions, additions, deletions therein not adversely affecting the structure of function. Hb9 is referred in the art as aliases; motor neuron and pancreas homeobox 1, MNX1, HB9, HOXHB9, SCRA1. In addition to naturally-occurring allelic variants of the Hb9 sequences that may exist in the population, it will be appreciated that, as is the case for virtually all proteins, a variety of changes can be introduced into the sequences of SEQ ID NO: 11 or SEQ ID NO: 12 (referred to as "wild type" sequences) without substantially altering the functional (biological) activity of the polypeptides. Such variants are included within the scope of the terms "Hb9", "Hb9 protein", etc.

As used herein, "Ngn2" is refers to the Ngn2 protein of Genebank accession No: NP_076924.1 (SEQ ID NO: 13) (human) or NP_033848.1 (SEQ ID NO: 14) (mouse) and are encoded by NM_024019.2 (SEQ ID NO: 29) (human) or NM_009718.2 (SEQ ID NO: 30) (mouse), respectively. The term Ngn2 also encompasses species variants, homologues, allelic forms, mutant forms, and equivalents thereof, including conservative substitutions, additions, deletions therein not adversely affecting the structure of function. Ngn2 is referred in the art as aliases; Neurogenin 2 (NEUROG2), Atoh4, bHLHa8, Math4A, ngn-2. In addition to naturally-occurring allelic variants of the Ngn2 sequences that may exist in the population, it will be appreciated that, as is the case for virtually all proteins, a variety of changes can be introduced into the sequences of SEQ ID NO: 13 or SEQ ID NO: 14 (referred to as "wild type" sequences) without substantially altering the functional (biological) activity of the polypeptides. Such variants are included within the scope of the terms "Ngn2", "Ngn2 protein", etc.

As used herein, "NeuroD1" is refers to the NeuroD/ protein of Genebank accession No: NP_002491.2 (SEQ ID NO: 15) (human) or NP_035024.1 (SEQ ID NO: 16) (mouse) and encoded by genes NM_002500.3 (SEQ ID NO: 31) (human) or NM_010894.2 (SEQ ID NO: 32) (mouse), respectively. The term NeuroD1 also encompasses species variants, homologues, allelic forms, mutant forms, and equivalents thereof, including conservative substitutions, additions, deletions therein not adversely affecting the structure of function. NeuroD1 is referred in the art as aliases; neurogenic differentiation 1, beta-cell E-box transactivator 2", BETA2, BHF-1, bHLHa3, MODY6, NeuroD, "neurogenic helix-loop-helix protein NEUROD". In addition to naturally-occurring allelic variants of the NeuroD1 sequences that may exist in the population, it will be appreciated that, as is the case for virtually all proteins, a variety of changes can be introduced into the sequences of SEQ ID NO: 15 or SEQ ID NO: 16 (referred to as "wild type" sequences) without substantially altering the functional (biological) activity of the polypeptides. Such variants are included within the scope of the terms "NeuroD1", "NeuroD1 protein", etc.

The term a "variant" in referring to a polypeptide could be, e.g., a polypeptide at least 80%, 85%, 90%, 95%, 98%, or 99% identical to full length polypeptide. The variant could be a fragment of full length polypeptide, e.g., a fragment of at least 10 or at least 20 contagious amino acids of the wild type version of the polypeptide. In some embodiments, a variant is a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest such as the ability to directly convert fibroblasts to iMNs. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

One of skill in the art will be aware of, or will readily be able to ascertain, whether a particular polypeptide variant, fragment, or derivative is functional using assays known in the art. For example, the ability of a variant of a Lhx3, Ascl1, Brn2, Myt1l, Isl1, Hb9, Ngn2 or NeuroD1 polypeptides of SEQ ID NOs: 1-16 to convert a somatic cell, e.g., fibroblast to a iMN can be assessed using the assays as disclose herein in the Examples. Other convenient assays include measuring the ability to activate transcription of a reporter construct containing a Lhx3, Ascl1, Brn2, Myt1l, Isl1, Hb9, Ngn2 or NeuroD1 binding site operably linked to a nucleic acid sequence encoding a detectable marker such as luciferase. One assay involves determining whether the Lhx3, Ascl1, Brn2, Myt1l, Isl1, Hb9, Ngn2 or NeuroD1 variant induces a somatic cell, e.g., fibroblast to become a iMN or express markers of a motor neuron or exhibit functional characteristics of a motor neuron as disclosed herein. Determination of such expression of MN markers can be determined using any suitable method, e.g., immunoblotting. Such assays may readily be adapted to identify or confirm activity of agents that directly convert a somatic cell, e.g., fibroblast to a iMN. In certain embodiments of the invention a functional variant or fragment has at least 50%, 60%, 70%, 80%, 90%, 95% or more of the activity of the full length wild type polypeptide.

The term "functional fragments" as used herein regarding Lhx3, Ascl1, Brn2, Myt1l, Isl1, Hb9, Ngn2 or NeuroD1 polypeptides having amino acid sequences substantially homologous thereto means a polypeptide sequence of at least 5 contiguous amino acids of Lhx3, Ascl1, Brn2, Myt1l, Isl1, Hb9, Ngn2 or NeuroD1 sequences of SEQ ID NO: 1-16 having amino acid sequences substantially homologous thereto, wherein the functional fragment polypeptide sequence is about at least 50%, or 60% or 70% or at 80% or 90% or 100% or greater, for example 1.5-fold, 2-fold, 3-fold, 4-fold or greater than 4-fold as effective at direct conversion of a somatic cell, e.g., fibroblast to a iMN as the corresponding wild type Lhx3, Ascl1, Brn2, Myt1l, Isl1, Hb9, Ngn2 or NeuroD1 polypeptides of SEQ ID NO: 1-16, respectively as described herein. The functional fragment polypeptide may have additional functions that can include decreased antigenicity, increased DNA binding (as in transcription factors), or altered RNA binding (as in regulating RNA stability or degradation).

The term "vector" refers to a carrier DNA molecule into which a DNA sequence can be inserted for introduction into a host cell. Preferred vectors are those capable of autonomous replication and/or expression of nucleic acids to which they are linked Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g. EPV and EBV vectors.

As used herein, the term "adenovirus" refers to a virus of the family Adenovirida. Adenoviruses are medium-sized (90-100 nm), nonenveloped (naked) icosahedral viruses composed of a nucleocapsid and a double-stranded linear DNA genome.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome. It goes without saying that an iPS cell generated by a non-integrating viral vector will not be administered to a subject unless it and its progeny are free from viral remnants.

As used herein, the term "viral remnants" refers to any viral protein or nucleic acid sequence introduced using a viral vector. Generally, integrating viral vectors will incorporate their sequence into the genome; such sequences are referred to herein as a "viral integration remnant". However, the temporary nature of a non-integrating virus means that the expression, and presence of, the virus is temporary and is not passed to daughter cells. Thus, upon passaging of a re-programmed cell the viral remnants of the non-integrating virus are essentially removed.

As used herein, the term "free of viral integration remnants" and "substantially free of viral integration remnants" refers to iPS cells that do not have detectable levels of an integrated adenoviral genome or an adenoviral specific protein product (i.e., a product other than the gene of interest), as assayed by PCR or immunoassay. Thus, the iPS cells that are free (or substantially free) of viral remnants have been cultured for a sufficient period of time that transient expression of the adenoviral vector leaves the cells substantially free of viral remnants.

The terms "regulatory sequence" and "promoter" are used interchangeably herein, and refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause lesser expression in other tissues as well.

The term "phenotype" refers to one or a number of total biological characteristics that define the cell or organism under a particular set of environmental conditions and factors, regardless of the actual genotype.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, "the presence of lower amounts of a marker in the iMN as compared to the somatic cell, e.g., fibroblast from which the iMN was derived" refers to an amount of a marker protein or gene product (e.g. mRNA) that is significantly decreased in the iMN as compared to the amount of the same marker present in the somatic cell, e.g., fibroblast from which is was derived. The term "significantly decreased" means that the differences between the compared levels is statistically significant. The levels of the marker level can be represented by arbitrary units, for example as units obtained from a densitometer, luminometer, or an Elisa plate reader. As a non-limiting example, a iMN has significantly decreased levels of Snail1, thy1, Fsp1 expression as compared to a fibroblast from which it was derived.

As used herein, "the presence of higher amounts of a marker in the iMN as compared to the somatic cell, e.g., fibroblast from which is was derived" refers to an amount of a marker protein or gene product (e.g. mRNA) that is significantly increased in the iMN as compared to the amount of the same marker present in the somatic cell, e.g., fibroblast from which is was derived. The phrase "significantly increased" means that the differences between the compared levels is statistically significant. The levels of the marker level can be represented by arbitrary units, for example as units obtained from a densitometer, luminometer, or an Elisa plate reader. As a non-limiting example, a iMN has significantly increased levels of β2-tubilins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vascular ChAT (VChAT) as compared to a fibroblast from which it was derived.

As used herein, the term "transcription factor" refers to a protein that binds to specific parts of DNA using DNA binding domains and is part of the system that controls the transfer (or transcription) of genetic information from DNA to RNA.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. In the context of a cell that is of "neuronal linage" this means the cell can differentiate along the neuronal lineage restricted pathways.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "xenogeneic" refers to cells that are derived from different species.

The term "iMN inducing factor" refers to a gene, RNA, or protein that promotes or contributes to direct conversion or transdifferentiation of a somatic cell to a iMN. In aspects of the invention relating to reprogramming factor(s), the invention provides embodiments in which the iMN-inducing factors of interest for transdifferentiation of somatic cells to iMN in vitro.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

A "reporter gene" as used herein encompasses any gene that is genetically introduced into a cell that adds to the phenotype of the stem cell. Reporter genes as disclosed in this invention are intended to encompass fluorescent, luminescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny. A reporter gene is generally operatively linked to sequences that regulate its expression in a manner dependent upon one or more conditions which are monitored by measuring expression of the reporter gene. In some cases, expression of the reporter gene may be determined in live cells. Where live cell reporter gene assays are used, reporter gene expression may be monitored at multiple timepoints, e.g., 2, 3, 4, 5, 6, 8, or 10 or more timepoints. In some cases, where a live cell reporter assay is used, reporter gene expression is monitored with a frequency of at least about 10 minutes to about 24 hours, e.g., 20 minutes, 1 hour, 2 hours, 3 hours, 4 hours, 5 hours, 6 hours, 7 hours, 8 hours, 9 hours, 10 hours, 12 hours, 18 hours, or another frequency from any integer between about 10 minutes to about 24 hours.

The terms "subject" and "individual" are used interchangeably herein, and refer to an animal, for example, a human from whom cells can be obtained and/or to whom treatment, including prophylactic treatment, with the cells as described herein, is provided. For treatment of those conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "treat", "treating", "treatment", etc., as applied to an isolated cell, include subjecting the cell to any kind of process or condition or performing any kind of manipulation or procedure on the cell. As applied to a subject, the term "treating" refer to providing medical or surgical attention, care, or management to an individual. The individual is usually ill or injured, or at increased risk of becoming ill relative to an average member of the population and in need of such attention, care, or management.

In some embodiments, the term "treating" and "treatment" refers to administering to a subject an effective amount of a composition, e.g., a composition comprising iMN or their differentiated progeny so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. In some embodiments, treatment can be "prophylaxic treatment, where the subject is administered a composition as disclosed herein (e.g., a population of iMN or their progeny) to a subject at risk of developing a motor neuron disease as disclosed herein. In some embodiments, treatment is "effective" if the progression of a disease is reduced or halted. Those in need of treatment include those already diagnosed with a motor neuron disease or disorder, e.g., ALS or SMA, as well as those likely to develop a motor neuron disease or disorder due to genetic susceptibility or other factors such as family history of motor neuron disease, exposure to susceptibility factors, weight, diet and health.

As used herein, the terms "administering," "introducing" and "transplanting" are used interchangeably in the context of the placement of iMNs of the invention into a subject, by a method or route which results in at least partial localization of the iMN at a desired site. In some embodiments, the iMNs can be placed directly in the spinal cord or in the cerebellum, or alternatively be administered by any appropriate route which results in delivery to a desired location in the subject where at least a portion of the cells or components of the cells remain viable. The period of viability of the cells after administration to a subject can be as short as a few hours, e.g. twenty-four hours, to a few days, to as long as several or more years.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The term "tissue" refers to a group or layer of specialized cells which together perform certain special functions. The term "tissue-specific" refers to a source of cells from a specific tissue.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Direct Reprogramming (Transdifferentiation):

The process of altering the cell phenotype of a differentiated cell (i.e. a first cell), e.g., altering the phenotype of a somatic cell to a differentiated cell of a different phenotype (i.e. a second cell) without the first differentiated cell being completely reprogrammed to a less differentiated phenotype intermediate is referred to as "direct reprogramming" or "transdifferentiation". Stated another way, cells of one type can be converted to another type in a process by what is commonly referred to in the art as transdifferentiation, cellular reprogramming or lineage reprogramming.

Transdifferentiation encompasses a process of switching the phenotype of a first differentiated cell to the phenotype of a second different differentiated cell, without the complete reversal of the differentiation state of the somatic cell, and is different from "reprogramming a cell to a pluripotent state" which typically refers to a process which partially or completely reverses the differentiation state of a somatic cell to a cell with a stem cell-like phenotype, e.g., to an induced pluripotent stem cell (iPSC).

As disclosed herein, the present invention relates to compositions and methods for the direct conversion of a somatic cell, e.g., a fibroblast to a functional motor neuron, referred to herein as an "induced motor neuron (iMN)". In certain embodiments of the invention, the transdifferentiation of a somatic cell, e.g., fibroblast causes the somatic cell to assume a MN like state, without being completely reprogrammed to a pluripotent state prior to becoming an iMN.

In some embodiments, the methods and compositions of the present invention can be practiced on somatic cells that are fully differentiated and/or restricted to giving rise only to cells of that particular type. The somatic cells can be either partially or terminally differentiated prior to direct conversion to iMNs. In some embodiments, somatic cells which are trandifferentiated into iMNs are fibroblast cells.

The present invention relates to compositions and methods for direct conversion of a somatic cell, e.g., a fibroblast to a functional motor neuron. In some embodiments, the present invention provides methods for direct conversion of fibroblasts to a different phenotype, such as an iMN.

Direct Conversion of Fibroblasts to iMNs

The present invention relates to a method of trandifferentiating somatic cells, e.g., fibroblasts to motor neurons, referred to herein as iMNs (induced motor neurons). In some embodiments, a somatic cell, e.g., fibroblast are the preferred starting material. In some embodiments, a population of iMNs are produced by increasing the protein expression of at least three transcription factors selected from Lhx3, Ascl1, Brn2, Myt1l, Isl1, Hb9, Ngn2 or NeuroD1 in a somatic cell, e.g., fibroblast. In alternative embodiments, the population of a somatic cell, e.g., fibroblast can comprise a mixture or combination of different a somatic cells, e.g., fibroblast, for example a mixture of cells such as a fibroblasts and other somatic cells.

In some embodiments, the population of a somatic cell, e.g., fibroblast is a substantially pure population of fibroblasts. In some embodiments, a population of a somatic cell, e.g., fibroblast is a population of somatic cells or differentiated cells. In some embodiments, the population of a somatic cell, e.g., fibroblast are substantially free or devoid of embryonic stem cells or pluripotent cells or iPS cells.

In some embodiments, a somatic cell, e.g., fibroblast is genetically modified. In some embodiments, the somatic cell, e.g., fibroblast comprises one or more nucleic acid sequences encoding at the proteins of least three MN-inducing factors selected from Lhx3, Ascl1, Brn2, Myt1l, Isl1, Hb9, Ngn2 or NeuroD1 (encoded by genes of SEQ ID NO: 17-32 respectively) or functional variants or functional fragments thereof, as shown in Table 1.

TABLE 1

MN-inducing factors

| MN inducing factor | Gene synonyms | Human Protein | Mouse protein | Human Nucleic Acid | Mouse Nucleic acid |
|---|---|---|---|---|---|
| Lhx3 | *Homo sapiens* LIM homeobox 3 (LHX3), transcript variant 2, mRNA, CPHD3; LIM3; M2-LHX3 | NP_055379.1 (SEQ ID NO: 1); | NP_001034742.1 (SEQ ID NO: 2) | NM_014564 (SEQ ID NO: 17); | NM_001039653.1 (SEQ ID NO: 18) |
| Ascl1 | *Homo sapiens* achaete-scute complex homolog 1 (*Drosophila*) (ASCL1), ASH1; bHLHa46; HASH1; MASH1 | NP_004307.2 (SEQ ID NO: 3) | NP_032579.2 (SEQ ID NO: 4) | NM_004316.3 (SEQ ID NO: 19); | NM_008553.4 (SEQ ID NO:20) |
| Brn2 | POU3F2, POU class 3 homeobox 2, BRN2, OCT7, POUF3 | NP_005595.2 (SEQ ID NO: 5) | NP_032925.1 (SEQ ID NO: 6) | NM_005604.2 (SEQ ID NO: 21) | NM_008899.1 (SEQ ID NO: 22) |
| Myt1l | myelin transcription factor 1-like (MYT1L), KIAA1106, “neural zinc finger transcription factor 1”, NZF1 | NP_055840.2 (SEQ ID NO: 7) | NP_001087244.1 (SEQ ID NO: 8) | NM_015025.2 (SEQ ID NO: 23) | NM_001093775.1 (SEQ ID NO: 24) |
| Isl1 | ISL LIM homeobox 1, Isl-1, ISLET1 | NP_002193.2 (SEQ ID NO: 9) | NP_067434.3 (SEQ ID NO: 10) | NM_002202.2 (SEQ ID NO: 25) | NM_021459.4 (SEQ ID NO: 26) |
| Hb9 | motor neuron and pancreas homeobox 1, MNX1, HB9, HOXHB9, SCRA1 | NP_001158727.1 (SEQ ID NO: 11) | NP_064328.2 (SEQ ID NO: 12) | NM_001165255.1 (SEQ ID NO: 27) | NM_019944.2 (SEQ ID NO: 28) |
| Ngn2 | Neurogenin 2 (NEUROG2), Atoh4, bHLHa8, Math4A, ngn-2. | NP_076924.1 (SEQ ID NO: 13) | NP_033848.1 (SEQ ID NO: 14) | NM_024019.2 (SEQ ID NO: 29) | NM_009718.2 (SEQ ID NO: 30) |
| NeuroD1 | neurogenic differentiation 1, beta-cell E-box transactivator 2", BETA2, BHF-1, bHLHa3, MODY6, NeuroD, | NP_002491.2 (SEQ ID NO: 15) | NP_035024.1 (SEQ ID NO: 16) | NM_002500.3 (SEQ ID NO: 31) | NM_010894.2 (SEQ ID NO: 32) |

TABLE 1-continued

| MN-inducing factors | | | | | |
|---|---|---|---|---|---|
| MN inducing factor | Gene synonyms | Human Protein | Mouse protein | Human Nucleic Acid | Mouse Nucleic acid |
| | "neurogenic helix-loop-helix protein NEUROD". | | | | |

In some embodiments, a somatic cell, e.g., fibroblast can be isolated from a subject, for example as a tissue biopsy, such as, for example, a skin biopsy. In some embodiments, the a somatic cell, e.g., fibroblast are maintained in culture by methods known by one of ordinary skill in the art, and in some embodiments, propagated prior to being directly converted into iMNs by the methods as disclosed herein.

Further, a somatic cell, e.g., fibroblast can be from any mammalian species, with non-limiting examples including a murine, bovine, simian, porcine, equine, ovine, or human cell. For clarity and simplicity, the description of the methods herein refers to a mammalian somatic cell, e.g., fibroblast, but it should be understood that all of the methods described herein can be readily applied to other cell types of somatic cells. In one embodiment, the somatic cell, e.g., fibroblast is derived from a human individual, wherein the suitable MN-inducing factors are human (e.g., proteins of SEQ ID NO: 1, 3, 5, 7, 9, 11, 13 and 15 corresponding to human Lhx3, Ascl1, Brn2, Myt1l, Isl1, Hb9, Ngn2 or NeuroD1 polypeptides respectively). In alternative embodiments, the fibroblast is derived from a mouse subject, and wherein the suitable MN-inducing factors are mouse (e.g., proteins of SEQ ID NO: 2, 4, 6, 8, 10, 12, 14 and 16 corresponding to mouse Lhx3, Ascl1, Brn2, Myt1l, Isl1, Hb9, Ngn2 or NeuroD1 polypeptides respectively). In some embodiments, mouse MN-inducing factors can be used to directly convert human fibroblasts to iMNs and vice versa, human MN-inducing factors can be used for transdifferentiation of mouse fibroblasts into iMNs. In some embodiments, any combination of mouse or human MN-inducing factors can be used for transdifferentiation of mouse or human fibroblasts into iMNs.

In some embodiments, at least three MN-inducing factors are used in the method for transdifferentiation of a somatic cell, e.g., a fibroblast to a iMN according to the methods as disclosed herein. In some embodiments, at least 3, or a least 4, or a least 5, or a least 6, or a least 7, or a least 8, or a least 9, or a least 10, or a least 11 MN-inducing factors selected from any of the group consisting of Lhx3, Ascl1, Brn2, Myt1l, Isl1, Hb9, Ngn2 or NeuroD1 are used in the methods of transdifferentiation of a somatic cell, e.g., a fibroblast to a iMN according to the methods as disclosed herein.

In some embodiments, Lhx3 and Ascl1 are used with any combination of other MN-inducing factor selected from the group of Brn2, Myt1l, Isl1, Hb9, Ngn2 or NeuroD1. In some embodiments, Ascl1, Lhx3 MN-inducing agents are used with Brn2, and Myt1l in the methods to transdifferentiate a somatic cell, e.g., a fibroblast to a iMN. In some embodiments to increase efficiency of transdifferentiation, any one or more of a combination of the MN-inducing factors selected from isl1, Hb9 and Ngn2 can also be used with Ascl1, Lhx3, Brn2, and Myt1l MN-inducing factors. In some embodiments, Myt1l and/or Brn2 and/or isl1 are not used as MN-inducing factors in the methods as disclosed herein. Additionally, in some embodiments, miR-124 is not used as a MN-inducing agent. In some embodiments, for transdifferentiation of human somatic cells, e.g., human fibroblasts, NeuroD1 is used as one of the MN-inducing agents.

In some embodiments, a subject from which a somatic cell, e.g., fibroblast are obtained is a mammalian subject, such a human subject, and in some embodiments, the subject is suffering from a motor neuron disease, e.g., a amylotrophic lateral sclerosis (ALS), spinal muscular atrophy (SMA), primary lateral sclerosis (PLS), progressive bulbar palsy, pseudobulbar palsy, progressive muscular atrophy, post-polio syndrome (PPS) and the like. In such embodiments, the a somatic cell, e.g., fibroblast can be transdifferentiated into a iMNs ex vivo by the methods as described herein and then administered to the subject from which the cells were harvested in a method to treat the subject for the motor neuron disease or disorder.

In some embodiments, a somatic cell, e.g., fibroblast are located within a subject (in vivo) and are directly converted to become an iMN by the methods as disclosed herein in vivo. In some embodiments, direct conversion of a somatic cell, e.g., a fibroblast to a iMN in vivo can be achieved transducing the fibroblast with a viral vector, such as adenovirus which has the ability to express three or more MN-inducing agents selected from any combination of Lhx3, Ascl1, Brn2, Myt1l, Isl1, Hb9, Ngn2 or NeuroD1 in the somatic cell.

In some embodiments, such contacting may be performed by maintaining the somatic cell, e.g., fibroblast in culture medium comprising the agent(s). In some embodiments a somatic cell, e.g., fibroblast can be genetically engineered. In some embodiments, a somatic cell, e.g., fibroblast can be genetically engineered to express one or more MN-inducing factors as disclosed herein, for example express at least one a polypeptide selected from Lhx3, Ascl1, Brn2, Myt1l, Isl1, Hb9, Ngn2 or NeuroD1, or an amino acid sequences substantially homologous thereof, or functional fragments or functional variants thereof.

Where the somatic cell, e.g., fibroblast is maintained under in vitro conditions, conventional tissue culture conditions and methods can be used, and are known to those of skill in the art. Isolation and culture methods for various cells are well within the abilities of one skilled in the art.

In the methods of the present invention a somatic cell, e.g., fibroblast can, in general, be cultured under standard conditions of temperature, pH, and other environmental conditions, e.g., as adherent cells in tissue culture plates at 37° C. in an atmosphere containing 5-10% $CO_2$. The cells and/or the culture medium are appropriately modified to achieve direct conversion to iMNs as described herein. In certain embodiments, a somatic cell, e.g., fibroblast can be cultured on or in the presence of a material that mimics one or more features of the extracellular matrix or comprises one or more extracellular matrix or basement membrane components. In some embodiments Matrigel™ is used. Other materials include proteins or mixtures thereof such as gelatin, collagen, fibronectin, etc. In certain embodiments of the invention, a somatic cell, e.g., fibroblast can be cultured in the presence of a feeder layer of cells. Such cells may, for example, be of murine or human origin. They can also be irradiated, chemically inactivated by treatment with a chemical inactivator such as mitomycin c, or otherwise treated to inhibit their proliferation if desired. In other embodiments a somatic cell, e.g., fibroblast are cultured without feeder cells.

Methods of Transdifferentiation of Somatic Cells to iMNs

Generating iMN by direct conversion of a somatic cell, e.g., fibroblast using the methods of the present invention has a number of advantages. First, the methods of the present invention allow one to generate autologous iMNs, which are cells specific to and genetically matched with an individual. The cells are derived from a somatic cell, e.g., fibroblast obtained from the individual. In general, autologous cells are less likely than non-autologous cells to be subject to immunological rejection.

Second, the methods of the present invention allow the artisan to generate iMNs without using embryos, oocytes, and/or nuclear transfer technology. Herein, the applicants' results demonstrate that a somatic cell, e.g., fibroblast can be directly converted to become a motor neuron (iMN), without the need to be fully reprogrammed to a pluripotent state, therefore minimizing the risk of differentiation into unwanted cell types or risk of teratomas formation.

Also encompassed in the methods of the present invention is a method of transdifferentiation of a somatic cell, e.g., fibroblast by means other than engineering the cells to express MN-inducing factors, i.e., by contacting the a somatic cell, e.g., fibroblast with a MN-inducing factors other than a nucleic acid or viral vector capable of being taken up and causing a stable genetic modification to the cells. In particular, the invention encompasses the recognition that extracellular signaling molecules, e.g., molecules that when present extracellularly bind to cell surface receptors and activate intracellular signal transduction cascades, are of use to reprogram somatic cells. The invention further encompasses the recognition that activation of such signaling pathways by means other than the application of extracellular signaling molecules is also of use to directly convert a somatic cell, e.g., fibroblast into a iMN. In addition, the methods of the present invention relate to methods of identification of the iMNs that are detectable based on morphological criteria, without the need to employ a selectable marker, as well as functional characteristics, such as ability to generate action potentials, resting membrane potential of less than −50 mV, responsive to inhibitory neurotransmitters such as glycine and GABA, and responsiveness to excitatory neurotransmitters such as glutamate. The present disclosure thus reflects several fundamentally important advances in the area of somatic cell transdifferentiation technology, in particular direct conversion of somatic cells to a subtype of neurons, in particular, motor neurons.

While certain aspects of the invention are exemplified herein using at least three of eleven different MN-inducing factors, e.g., Lhx3 (SEQ ID NO: 1-2), Ascl1 (SEQ ID NO: 3-4), Brn2 (SEQ ID NO: 5-6), Myt1l (SEQ ID NO: 7-8), Isl1 (SEQ ID NO: 9-10), Hb9 (SEQ ID NO: 11-12), Ngn2 (SEQ ID NO: 13-14) NeuroD1 (SEQ ID NO: 15-16), the methods of the invention encompass use of any other MN-inducing factors in replace of any one of Lhx3, Ascl1, Brn2, Myt1l, Isl1, Hb9, Ngn2 or NeuroD1, where the other MN-inducing factors includes, for example, but is not limited to, Oligo2, Pax6, Sox1, NRx6.1 or functional variants, homologues or functional fragments thereof for the purposes of converting a somatic cell, e.g., fibroblast to iMN.

Another aspect of the present invention relates to methods to produce a population of isolated iMN by increasing the protein expression of at least three MN-inducing factors in a population of a somatic cell, e.g., fibroblast. In some embodiments, a somatic cell, e.g., fibroblast can be treated in any of a variety of ways to cause direct conversion of the fibroblast to an iMN according to the methods of the present invention. For example, in some embodiments, the treatment can comprise contacting the cells with one or more agent(s), herein referred to as a "MN-inducing factor" which increases the protein expression of at least three of the transcription factors selected from Lhx3, Ascl1, Brn2, Myt1l, Isl1, Hb9, Ngn2 or NeuroD1, or increases the protein expression of a functional homologue or a functional fragment of at least three of any combination of Lhx3, Ascl1, Brn2, Myt1l, Isl1, Hb9, Ngn2 or NeuroD1, polypeptides in the somatic cell, e.g., fibroblast.

In some embodiments, the method comprises converting a somatic cell, e.g., fibroblast by increasing the protein expression of at least three in any combination of the following MN-inducing factors Lhx3, Ascl1, Brn2, Myt1l, Isl1, Hb9, Ngn2 or NeuroD1, in the somatic cell, e.g., fibroblast, wherein the expression is for sufficient amount of time, typically transient increase in expression, to allow the conversion of the cell to become a cell which exhibits at least two characteristics of a endogenous motor neuron (e.g., a motor neuron differentiated from an embryonic stem cell), for example at least two of the following characteristics; (i) expression of motor neuron markers, for example, but not limited to β2-tubulins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vescular ChAT, (ii) significantly decreased level of expression of fibroblast genes from which they are derived, selected from the group of: Snail1, thy1 and Fsp1, (iii) exhibit typical motor neuron morphology, e.g., comprising a cell body with axonal projections which form functional synaptic junctions with muscle cells and (iv) an average resting potential of lower than about −50 mV, e.g., a resting potential of about −50 mV to about −65 mV and any interger between, e.g., about −50 mV, or about −50 to −55 mV or about −55 mV to about −60 mV or about −60 mV to about −65 mV, or alternatively a resting potential substantially the same as the resting membrane potential of motor neurons differentiated from embryonic stem cells (v) functional motor neuron characteristics selected from (a) the ability to fire action potentials, (b) responsiveness to inhibitory neurotransmitters glycine and GABA, and (c) responsiveness to excitatory neurotransmitters, e.g., glutamate or kainate.

In some embodiments, the method comprises reprogramming a somatic cell, e.g., fibroblast by increasing the protein expression of three or more of following MN-inducing transcription factors Lhx3, Ascl1, Brn2, Myt1l, Isl1, Hb9, Ngn2 or NeuroD1 in the somatic cell, e.g., fibroblast. The increase in expression of the transcription factors can be done all at the same time (e.g. concurrently), or alternatively, subsequently in any order.

In some embodiments, the method comprises reprogramming a somatic cell, e.g., fibroblast by expressing at least 2, or at least 3, or at least 4 or at least 5, or at least 6, or at least 7 or at least 8, or at least 9 or at least 10 or 11 of any combination of MN-inducing factors selected from, for example, but is not limited to, Lhx3 (SEQ ID NO: 1-2), Ascl1 (SEQ ID NO: 3-4), Brn2 (SEQ ID NO: 5-6), Myt1l (SEQ ID NO: 7-8), Isl1 (SEQ ID NO: 9-10), Hb9 (SEQ ID NO: 11-12), Ngn2 (SEQ ID NO: 13-14) NeuroD1 (SEQ ID NO: 15-16) or functional variants, polypeptides with amino acids substantially homologues or functional fragments thereof in a somatic cell, e.g., fibroblast to reprogram to an iMN.

In some embodiments, increasing the protein expression can be by any means known by one of ordinary art, for example can include introduction of nucleic acid, or nucleic acid analogue encoding one or more of the MN-inducing factors, or contacting the somatic cell, e.g., fibroblast with an agent which converts the somatic cell, e.g., fibroblast to a cell with a motor neuron phenotype. In some embodiments, a nucleic acid analogue is a locked nucleic acid (LNA), or a modified synthetic RNA (modRNA) encoding one or more of the MN-inducing factors. ModRNA are well known by one of ordinary skill in the art, and are described in U.S. Provisional Application 61/387,220, filed Sep. 28, 2010, and U.S. Provisional Application 61/325,003, filed: Apr. 16, 2010, both of which are incorporated herein in their entirety by reference.

In some embodiments, a MN-inducing agent is a vector comprising a nucleotide sequence encoding the polypeptide one or more of Lhx3 (SEQ ID NO: 1-2), Ascl1 (SEQ ID NO: 3-4), Brn2 (SEQ ID NO: 5-6), Myt1l (SEQ ID NO: 7-8), Isl1 (SEQ ID NO: 9-10), Hb9 (SEQ ID NO: 11-12), Ngn2 (SEQ ID NO: 13-14) NeuroD (SEQ ID NO: 15-16) or encoding a polypeptide substantially homologous to SEQ ID NO:1-16 or a functional variant or functional fragment of polypeptides of sequences SEQ ID NO:1-16. In such embodiments, the nucleotide sequence can comprise any nucleic acid sequence selected from SEQ ID NO: 17-32 respectively, or a fragment or variant thereof.

In some embodiments, the vector is a viral vector. In some embodiments, the viral vector is a non-integrating viral vector. While retroviral vectors incorporate into the host cell genome and can potentially disrupt normal gene function, non-integrating vectors have the advantage of controlling expression of a gene product by extra-chromosomal transcription. It follows that since non-integrating vectors do not become part of the host genome, non-integrating vectors tend to express a nucleic acid transiently in a cell population. This is due in part to the fact that the non-integrating vectors as used herein are rendered replication deficient. Thus, non-integrating vectors have several advantages over retroviral vectors including but not limited to: (1) no disruption of the host genome, and (2) transient expression, and (3) no remaining viral integration products.

Some non-limiting examples of non-integrating vectors include adenovirus, baculovirus, alphavirus, picornavirus, and vaccinia virus. In one embodiment, the non-integrating viral vector is an adenovirus. The advantages of non-integrating viral vectors further include the ability to produce them in high titers, their stability in vivo, and their efficient infection of host cells.

While it is known that some non-integrating vectors integrate into the host genome at extremely low frequencies (i.e., $10^{-4}$ to $10^{-5}$), a non-integrating vector, as the term is used herein, refers to vectors having a frequency of integration of less than 0.1% of the total number of infected cells; preferably the frequency of integration is less than 0.01%, less than 0.001%, less than 0.0001%, or less than 0.000001% (or lower) of the total number of infected cells. In one embodiment, the vector does not integrate at all. In another embodiment, the viral integration remnants of the virus are below the detection threshold as assayed by PCR (for nucleic acid detection) or immunoassay (for protein detection). In general, iMNs produced by the methods described herein should be assayed for an integration event by the viral vector using, for example, PCR-mediated detection of the viral genome prior to administering a population of iMNs to a subject. Any iMN with detectable integration products should not be administered to a subject.

The viral titer necessary to achieve a desired (i.e., effective) level of gene expression in a host cell is dependent on many factors, including, for example, the cell type, gene product, culture conditions, co-infection with other viral vectors, and co-treatment with other agents, among others. It is well within the abilities of one skilled in the art to test a range of titers for each virus or combination of viruses by detecting the expression levels of either (a) a marker expression product, or (b) a test gene product. Detection of protein expression in cells can be achieved by several techniques including Western blot analysis, immuno-cytochemistry, and fluorescence-mediated detection, among others. It is contemplated that experiments are first optimized by testing a variety of titer ranges for each cell type under the desired culture conditions. Once an optimal titer of a virus or a cocktail of viruses is determined, then that protocol will be used to induce the reprogramming of somatic cells.

In addition to viral titers, it is also important that the infection and induction times are appropriate with respect to different cells. For example, as discussed in the Examples section herein, initial attempts with an adenoviral vector were deemed unsuccessful due to an inadequate induction time. Upon recognition of this important consideration and considerable lengthening of induction time, induced pluripotent stem cells were produced using an adenoviral vector. With the knowledge provided herein that length of time is an important variable in induced pluripotent stem cell induction, one of skill in the art can test a variety of time points for infection or induction using a non-integrating vector and recover induced pluripotent stem cells from a given somatic cell type.

In some embodiments, the vector is a non-viral polycystronic vector as disclosed in Gonzalez et al., Proc. Natl. Acad. Sci. USA 2009 106:8918-8922; Carey et al., PNAS, 2009; 106; 157-162, WO/2009/065618 and WO/2000/071096 and Okita et al., Science 7, 2008: 322; 949-953, which are all incorporated herein in their entirety by reference.

In some embodiments, the nucleic acid is a modified synthetic RNA (modRNA) encoding one or more of the MN-inducing factors. ModRNA are well known by one of ordinary skill in the art, and are are described in U.S. Provisional Application 61/387,220, filed Sep. 28, 2010, and U.S. Provisional Application 61/325,003, filed: Apr. 16, 2010, both of which are incorporated herein in their entirety by reference.

In other embodiments, the methods or the present invention encompass non-viral means to increase the expression of iMN inducing factors (e.g. Lhx3 (SEQ ID NO: 1-2), Ascl1 (SEQ ID NO: 3-4), Brn2 (SEQ ID NO: 5-6), Myt1l (SEQ ID NO: 7-8), Isl1 (SEQ ID NO: 9-10), Hb9 (SEQ ID NO: 11-12), Ngn2 (SEQ ID NO: 13-14) NeuroD1 (SEQ ID NO: 15-16) in a somatic cell, e.g., fibroblast for the purposes for converting to an iMN as disclosed herein. For example, in one embodiment, naked DNA technology can be used, for example nucleic acid encoding the polypeptides of least three transcription factors selected from Lhx3, Ascl1, Brn2, Myt1l, Isl1, Hb9, Ngn2 or NeuroD1 (encoded by SEQ ID NO: 17-32 respectively) can be introduced into a somatic cell, e.g., fibroblast for the purposes of converting the cell to an iMN. Methods of naked DNA technology are well known in the art, and are disclosed in U.S. Pat. No. 6,265,387 (which is incorporated herein in its entirety by reference) which describes a method of delivering naked DNA into a hepatocyte in vivo the via bile duct. U.S. Pat. No. 6,372,722 (which is incorporated herein in its entirety by reference) describes a method of naked DNA delivery to a secretory gland cell, for example, a pancreatic cell, a mammary gland cell, a thyroid cell, a thymus cell, a pituitary gland cell, and a liver cell.

In some embodiments, another non-viral means to increase the expression of the transcription factors (e.g. Lhx3, Ascl1, Brn2, Myt1l, Isl1, Hb9, Ngn2 or NeuroD1,) in a somatic cell, e.g., fibroblast include use of piggyBac transposon vectors, as disclosed in U.S. Pat. Nos. 7,129,083, and 6,5518,25; U.S. Patent Application 2009/0042297 and International Patent Application WO/2007/100821 which are incorporated herein in their entirety by reference.

Other non-viral means to increase the expression of the transcription factors (e.g. Lhx3, Ascl1, Brn2, Myt1l, Isl1, Hb9, Ngn2 or NeuroD1,) in a somatic cell, e.g., fibroblast for the purposes for transdifferentiation to a iMN are also encompassed for use in the methods as disclosed herein.

In one embodiment, one can contact the a somatic cell, e.g., fibroblast with polypeptides or peptides of Lhx3 (SEQ ID NO: 1-2), Ascl1 (SEQ ID NO: 3-4), Brn2 (SEQ ID NO: 5-6), Myt1l (SEQ ID NO: 7-8), Isl1 (SEQ ID NO: 9-10), Hb9 (SEQ ID NO: 11-12), Ngn2 (SEQ ID NO: 13-14) NeuroD1 (SEQ ID NO: 15-16) or functional variants, polypeptides with amino acids substantially homologues or functional fragments thereof in a somatic cell, e.g., fibroblast to convert to an iMN. Alternatively, one can use aptamers or antibodies or any other agent which activates and increases the expression of the transcription factors (e.g. Lhx3, Ascl1, Brn2, Myt1l, Isl1, Hb9, Ngn2 or NeuroD1) in a somatic cell, e.g., fibroblast.

In alternative embodiments, one can contact the somatic cell, e.g., fibroblast with a small molecule or combination of small molecules (e.g. chemical complementation) to increase the expression of at least two transcription factors in the somatic cell, e.g., fibroblast.

Thus, in some embodiments, the contacting step will typically be for at least twenty-four hours. By "at least twenty-four hours," is meant twenty-four hours or greater. In some embodiments, fibroblast cells can be contacted with MN-inducing factor (e.g. small molecule, polypeptide, nucleic acid, nucleic acid analogues, etc) for about 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 hours up to 3, 4, 5, 6, 7, or more days or any particular intervening time in hours or minutes within the above range. Preferably, somatic cells, e.g., fibroblasts can be contacted with a MN-inducing agent for seven days.

In another embodiment, the present invention provides a method of direct conversion of somatic cells, e.g., fibroblasts by contacting the somatic cell with at least 3 or more polypeptides selected from any combination from the group of Lhx3, Ascl1, Brn2, Myt1l, Isl1, Hb9, Ngn2 or NeuroD1, or having amino acid sequences substantially homologous thereto, and functional fragments or functional variants thereof. In some embodiments, the present invention provides a method of reprogramming a somatic cell, e.g., fibroblast comprising contacting the somatic cell, e.g., fibroblast with at least 3 polypeptides selected from the group of polypeptides of SEQ ID NO: 1-16, or having amino acid sequences substantially homologous thereto, and functional fragments or functional variants thereof.

Where the MN-inducing factor is a polypeptide, e.g. a polypeptide of Lhx3, Ascl1, Brn2, Myt1l, Isl1, Hb9, Ngn2 or NeuroD1, the dosages of Lhx3, Ascl1, Brn2, Myt1l, Isl1, Hb9, Ngn2 or NeuroD1 polypeptides, their active fragments or related growth factors to be used in the in vivo or in vitro methods and processes of the invention preferably range from about 1 pmoles/kg/minute to about 100 nmoles/kg/minute for continuous administration and from about 1 nmoles/kg to about 40 mmoles/kg for bolus injection. Preferably, the dosage of Lhx3, Ascl1, Brn2, Myt1l, Isl1, Hb9, Ngn2 or NeuroD polypeptides in in vitro methods will be 10 pmoles/kg/min to about 100 nmoles/kg/min, and in in vivo methods from about 0.003 nmoles/kg/min to about 48 nmoles/kg/min. More preferably, the dosage of Lhx3, Ascl1, Brn2, Myt1l, Isl1, Hb9, Ngn2 or NeuroD1 polypeptides in in vitro methods ranges from about 100 picomoles/kg/minute to about 10 nanomoles/kg/minute, and in in vivo methods from about 0.03 nanomoles/kg/minute to about 4.8 nanomoles/kg/minute. In some embodiments, the preferred dosage of Lhx3, Ascl1, Brn2, Myt1l, Isl1, Hb9, Ngn2 or NeuroD1 polypeptides, or other polypeptides of sequences SEQ ID NO: 1-16 in in vitro methods is 1 pmoles/kg/min to about 10 nmoles/kg/mine, and in in vivo from about 1 pmole/kg to about 400 pmoles/kg for a bolus injection. The more preferred dosage of the preferred dosage of Lhx3, Ascl1, Brn2, Myt1l, Isl1, Hb9, Ngn2 or NeuroD1 polypeptides, or other polypeptides of sequences SEQ ID NO: 1-16 in in vitro methods ranges from about 10 pmole/kg/minute to about 1 nmole/kg/minute, and in in vivo from about 10 pmoles/kg to about 40 pmoles/kg for a bolus injection.

Confirming Presence of a iMN

An iMN as disclosed herein, produced by the methods as disclosed herein is a cell with the phenotypic characteristics of an endogenous motor neurons. An iMN can have all the phenotypic and functional characteristics of an endogenous motor neuron or may have less than all the phenotypic and functional characteristics of an endogenous motor neuron.

In some embodiments, the iMN can exhibit a motor neuron morphology but otherwise maintain at least one phenotypic characteristic of the somatic cell from which it as converted from. For example, in some embodiments, a somatic cell, e.g., fibroblast that is subjected to an increase in at least three MN-inducing factors as disclosed herein can continue to express Snail and other fibroblast markers, but, unlike the typical fibroblast, the iMN cell also conducts action potentials and exhibits one or more functional characteristics of a motor neuron. Thus, a continuum between complete phenotypic change and a single phenotypic change is possible. An increase in proliferation of a somatic cell, e.g., fibroblast may precede the direct conversion to iMNs, and "transdifferentiation" is not meant to exclude any proliferation that accompanies the change of the cell to a iMN phenotype.

To confirm the transdifferentiation of a somatic cell, e.g., fibroblast to an iMN, isolated clones can be tested for the expression of a marker of motor neurons. Such expression identifies the cells as motor neuron. Markers for motor neurons (iMNs) can be selected from the non-limiting group including β2-tubulins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vescular ChAT (VChAT), immunostaining of α-BTX, where expression is by a statistically significant amount as compared to the somatic cell, e.g., fibroblast from which the iMN was converted from.

Methods for detecting the expression of such markers are well known in the art, and include, for example, RT-PCR and immunological methods that detect the presence of the encoded polypeptides, such as ELISA.

In some embodiments, an iMNs produced by the methods as disclosed herein can be identified based on unique morphological characteristics. In some embodiments, the iMN have a large cell body and axonal projections which form synaptic connections with muscle. As disclosed herein, iMN can be co-cultured with muscle cells, e.g., myotubules or C2C12 muscle co-culture according to the methods disclosed in the Examples section and form axonal projections alonh the length of the myotubules, which undergo regular and rhythmic contractions due to the synaptic connections with the iMNs (see FIG. 4I). Thus, in some embodiments, the iMN have a unique functional characteristics with muscle as compared to other non-motor neuron neuronal subtypes.

In some embodiments, the iMN can be identified based on an average resting potential of lower than about −50 mV, e.g., a resting potential of about −50 mV to about −65 mV and any integer between, e.g., about −50 mV, or about −50 to −55 mV or about −55 mV to about −60 mV or about −60 mV to about −65 mV, or alternatively a resting potential substantially the same as the resting membrane potential of motor neurons differentiated from embryonic stem cells. In some embodiments, a iMN can be identified based on functional motor neuron characteristics, such as, but not limited to (a) the ability to fire action potentials, (b) responsiveness to inhibitory neurotransmitters glycine and GABA, and (c) responsiveness to excitatory neurotransmitters, e.g., glutamate or kainate.

In some embodiments, the iMN has a cell body size between about 30-80 μm in diameter, for example, in some embodiments, the iMN are gamma MN and are about at least about 40 μm, or at least about 50 μm, or about at least 60 μm, or at least about 70 μm, or at least about 80 μm, or any integer between about 40-80 μm, and in some embodiments, the iMN is an alpha motor neuron, and has a cell body size of at least about 19 μm, or at least about 20 μm, or at least about 21 μm, or at least about 22 μm, or at least about 23 μm, or at least about 24 μm, or at least about 25 μm, or at least about 26 μm, or at least about 27 μm, or greater than about 30 μm in diameter, or any integer between about 15-35 m in diameter.

In some embodiments, the present invention relates to an isolated population of iMN produced by the methods as disclosed herein. In some embodiments, iMN can be isolated by methods known in the art, for example FACs sorting, as disclosed in Liu et al., Journal Sichuan University, medical science edition, 209; 40(1); 153-6 or Liu et al., J Biol Chem, 1998; 273, 22201-22208, which are incorporated herein by reference).

Monitoring the Production of iMNs from a Somatic Cell, e.g., Fibroblast

The progression of a somatic cell, e.g., fibroblast to an iMN can be monitored by determining the expression of markers characteristic of motor neurons. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of motor neurons as well as the lack of significant expression of markers characteristic of the somatic cell, e.g., fibroblast from which it was derived can readily be determined.

As described in connection with monitoring the production of an iMN, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that many of the markers of iMNs are secreted compounds such as acetylycholine. As such, techniques for measuring extracellular motor neuron marker content include HPLC or ELISA or other methods commonly known by persons of ordinary skill in the art.

As set forth in the Examples below, markers of motor neurons include the expression of markers, but are not limited to, β2-tubulins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vascular ChAT (VChAT), immunostaining of α-BTX.

The iMNs produced by the processes described herein express one or more of the above-listed markers, thereby producing the corresponding gene products. However, it will be appreciated that iMNs need not express all of the above-described markers. For example, iMNs converted from a somatic cell, e.g., fibroblast do not always express Isl1.

In some embodiments, the transition of a somatic cell, e.g., fibroblast to an iMN can be validated by monitoring the decrease in expression of fibroblast markers, e.g., Snail, Thy1 and Fsp1 while monitoring the increase in expression of one or more of motor neuron markers. In addition to monitor the increase and/or decrease in expression of one or more the above-described markers, in some processes, the expression of genes indicative motor neurons or other neuronal markers can also be monitored.

It will be appreciated that β2-tubulins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vescular ChAT (VChAT) marker expression is induced over a range of different levels in iMN depending on the differentiation conditions. As such, in some embodiments described herein, the expression of these markers are similar to the levels of expression in motor neurons differentiated from embryonic stem cells, e.g., at least about 70%, or at least about 80% or at least about 90% or at least about 100% or more than 100% the level of the expression of these markers by ES-derived motor neurons (see FIG. 9B-9F in the Examples section).

Methods of Identifying Agents for Transdifferentiation of Somatic Cells to iMNs.

Another aspect of the present invention relates to methods of identifying agents that alone or in combination with other agents convert a somatic cell, e.g., fibroblast to an iMN. In some embodiments, the method includes contacting one or more a somatic cell, e.g., fibroblast with one or more test agents (simultaneously or at separate times) and determining the level of expression of one or more MN-inducing factors as defined herein. In some embodiments, the MN-inducing factors include any one of Lhx3, Ascl1, Brn2, Myt1l, Isl1, Hb9, Ngn2 or NeuroD1. Where one or more test agents increase the level of expression of one or more of the foregoing genes above the level of expression normally found in the somatic cell, in the absence of one or more test agents, are considered candidate agents to be used as an MN-inducing agents for transdifferentiation of a somatic cell, e.g., fibroblast to an iMN. The test agents may include, but are not limited to, small molecules, nucleic acids, peptides, polypeptides, immunoglobulins, and oligosaccarides. In some embodiments, the just-mentioned method includes determining the level of expression of one or more of Lhx3, Ascl1, Brn2, Myt1l, Isl1, Hb9, Ngn2 or NeuroD1, and preferably, in some embodiments, a single agent which increase one or more (e.g., 2, 3, 4, or 5 or more than 5) of the genes selected from Lhx3, Ascl1, Brn2, Myt1l, Isl1, Hb9, Ngn2 or NeuroD1. In some embodiments, the method includes determining the level of expression of one or more of Lhx3, Ascl1, Brn2, Myt1l, Isl1, Hb9, Ngn2 or NeuroD1. Expression levels can be determined by any means known by one of ordinary skill in the art, for example, by RT-PCR or immunological methods.

Of particular interest are screening assays for agents that are active transdifferentiation human a somatic cell, e.g., fibroblast to a iMN. A wide variety of assays may be used for this purpose, including immunoassays for protein binding; determination of cell growth, differentiation and functional activity; production of factors; and the like.

In the screening method of the invention for agents, the a somatic cell, e.g., fibroblast are contacted with the agent of interest, and the effect of the agent assessed by monitoring output parameters, such as expression of MN-inducing factors such as, but not limited to Lhx3, Ascl1, Brn2, Myt1l, Isl1, Hb9, Ngn2 or NeuroD1, cell viability, motor neuron functional characteristics, and the like. The cells may be freshly isolated, cultured, genetically engineered as described above, or the like. The somatic cell, e.g., fibroblast may be environmentally induced variants of clonal cultures: e.g. split into independent cultures and grown under distinct conditions, for example with or without virus; in the presence or absence of other cytokines or combinations thereof. Alternatively, a somatic cell, e.g., fibroblast may be variants with a desired pathological characteristic. For example, the desired pathological characteristic includes a mutation and/or polymorphism which contribute to disease pathology.

In alternative embodiments, the methods of the invention can be used to screen for agents in which a somatic cell, e.g., fibroblast comprising a particular mutation and/or polymorphism respond differently compared with a somatic cell, e.g., fibroblast without the mutation and/or polymorphism, therefore the methods can be used for example, to asses an effect of a particular drug and/or agent on iMNs from a defined subpopulation of people and/or cells, therefore acting as a high-throughput screen for personalized medicine and/or pharmogenetics. The manner in which cells respond to an agent, particularly a pharmacologic agent, including the timing of responses, is an important reflection of the physiologic state of the cell. Accordingly, the iMNs generated from human fibroblasts can be useful to study disease mechanisms due to different mutations for ALS and SMA, as well as to identify agents or therapeutic treatment to treat motor neuron diseases of different genetic ALS and SMA phenotypes, as well iMNs from subjects where the complex genetic variation resulting in the motor neuron disease is not yet known.

The agent used in the screening method can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. The agent may be applied to the media, where it contacts the cell (such as a somatic cell, e.g., fibroblast) and induces its effects. Alternatively, the agent may be intracellular within the cell (e.g. a somatic cell, e.g., fibroblast) as a result of introduction of the nucleic acid sequence into the cell and its transcription resulting in the production of the nucleic acid and/or protein agent within the cell. An agent also encompasses any action and/or event the cells (e.g. a somatic cell, e.g., fibroblast) are subjected to. As a non-limiting examples, an action can comprise any action that triggers a physiological change in the cell, for example but not limited to; heat-shock, ionizing irradiation, cold-shock, electrical impulse, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below. The exposure to agent may be continuous or non-continuous.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

Parameters are quantifiable components of a somatic cell, e.g., fibroblast, particularly the expression of genes (e.g., protein expression or mRNA expression) such as, one or more in any combination of Lhx3, Ascl1, Brn2, Myt1l, Isl1, Hb9, Ngn2 or NeuroD1. In some embodiments, expression of one or more, in any combination of Lhx3, Ascl1, Brn2, Myt1l, Isl1, Hb9, Ngn2 or NeuroD1 that can be accurately measured, desirably in a high throughput system. In some embodiments, a high throughput screen for resting membrane potential and responsiveness to inhibitory neurotransmitters, such as GABA and glycine, and excitatory neurotransmitters, such as glutamate can be used to identify an agent which induces transdifferentiation of a fibroblast into a functional iMN. In some embodiments, a secondary screen can be used to assess the functional characteristics if the iMN, e.g., ability to form synaptic junctions with muscle cells, as well as expression of motor neuron markers, for example, but not limited to, expression of β2-tubulins (e.g, Tubb2a and Tubb2b), Map2, synapsins (e.g., Syn1 and Syn2), synaptophysin, synaptotagmins (e.g., Syt1, Syt4, Syt13, Syt 16), NeuroD, Isl1, cholineacetyltransferase (ChAT), e.g., vescular ChAT (VChAT), immunostaining of α-BTX. In some embodiments, the iMNs may express transcription factors specifically expressed in motor neurons, including Lim3, and HoxB1, HoxB6, HoxC5 and HoxC8, but not other neuronal markers of non-motor neuron subtypes. For instance, iMNs can be identified by lack of expression of forebrain neuronal markers, Otx2 and Bf-1, or mid-brain markers, En-1.

In some embodiments, an output parameter from the screen can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. In some embodiments, the assay is a computerized assay or a robotic high-throughput system operated through a computer interface.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for effect on a somatic cell, e.g., fibroblast by adding the agent to at least one and usually a plurality of a somatic cell, e.g., a population of fibroblasts, and can be performed concurrently with a test well with a somatic cell, e.g., fibroblast lacking the agent (e.g., reference culture). The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, a somatic cell, e.g., fibroblast used in the screen can be manipulated to express desired gene products. Gene therapy can be used to either modify a cell to replace a gene product or add or knockdown a gene product. In some embodiments the genetic engineering is done to facilitate regeneration of tissue, to treat disease, or to improve survival of the iMN following implantation into a subject (i.e. prevent rejection). Techniques for transfecting cells are known in the art.

A skilled artisan could envision a multitude of genes which would convey beneficial properties to a iMN cell or, more indirectly, to a somatic cell, e.g., fibroblast used for transdifferentiation. The added gene may ultimately remain in the recipient cell and all its progeny, or may only remain transiently, depending on the embodiment. For example, genes encoding wild-type SOD1 could be transfected into a somatic cell, e.g., fibroblast. Such genes would be useful for producing iMNs with functional SOD1 protein where the fibroblast was obtained from a subject with an ALS-causing SOD1 mutation. In some situations, it may be desirable to transfect the cell with more than one gene.

In some instances, it is desirable to have the gene product secreted. In such cases, the gene product preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene can be transfected into the cell using a variety of techniques. Preferably, the gene is transfected into the cell using an expression vector. Suitable expression vectors include plasmid vectors (such as those available from Stratagene, Madison Wis.), viral vectors (such as replication defective retroviral vectors, herpes virus, adenovirus, adeno-virus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in a somatic cell, e.g., fibroblast, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Enrichment, Isolation and/or Purification of a Population of iMNs.

Another aspect of the present invention relates to the isolation of a population of iMN from a heterogeneous population of cells, such a comprising a mixed population of iMN and somatic cells from which the iMNs were derived. A population of iMN produced by any of the above-described processes can be enriched, isolated and/or purified by using an affinity tag that is specific for such cells. Examples of affinity tags specific for iMN are antibodies, ligands or other binding agents that are specific to a marker molecule, such as a polypeptide, that is present on the cell surface of iMN but which is not substantially present on other cell types (i.e. on the a somatic cell, e.g., fibroblast) that would be found in the heterogeneous population of cells produced by the methods described herein. In some processes, an antibody which binds to a cell surface antigen on human iMN is used as an affinity tag for the enrichment, isolation or purification of iMN produced by in vitro methods, such as the methods described herein. Such antibodies are known and commercially available.

The skilled artisan will readily appreciate that the processes for making and using antibodies for the enrichment, isolation and/or purification of iMN are also readily adaptable for the enrichment, isolation and/or purification of iMN. For example, analyzing and sorting for iMNs using a fluorescence activated cell sorter (FACS). Antibody-bound, fluorescent cells are collected separately from non-bound, non-fluorescent, thereby resulting in the isolation of such cell types.

In preferred embodiments of the processes described herein, the isolated cell composition comprising iMN can be further purified by using an alternate affinity-based method or by additional rounds of sorting using the same or different markers that are specific for iMN.

In some embodiments of the processes described herein, iMN are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label iMN using the methods described above, and as disclose in the Examples, where GFP is expressed in HB9 expressing cell. For example, in some embodiments, at least one copy of a nucleic acid encoding GFP or a biologically active fragment thereof is introduced into a somatic cell, e.g., fibroblast, preferably a human somatic cell, e.g., fibroblast, downstream of the HB9 promoter such that the expression of the GFP gene product or biologically active fragment thereof is under control of the HB9 promoter. In some embodiments, the entire coding region of the nucleic acid, which encodes HB9, is replaced by a nucleic acid encoding GFP or a biologically active fragment thereof. In other embodiments, the nucleic acid encoding GFP or a biologically active fragment thereof is fused in frame with at least a portion of the nucleic acid encoding HB9, thereby generating a fusion protein. In such embodiments, the fusion protein retains a fluorescent activity similar to GFP.

It will be appreciated that promoters other than the HB9 promoter can be used provided that the promoter corresponds to a marker that is expressed in motor neurons.

Fluorescently marked cells, such as the above-described a somatic cell, e.g., fibroblast, are differentiated to motor neurons as described previously above. Because iMN express the fluorescent marker gene, whereas other cell types do not, iMN can be separated from the other cell types. In some embodiments, cell suspensions comprising a population of a mixture of fluorescently-labeled iMN and unlabeled non-iMNs (i.e. somatic cells, e.g., fibroblast from which the iMNs were derived) are sorted using a FACS. iMNs can be collected separately from non-fluorescing cells, thereby resulting in the isolation of iMNs. If desired, the isolated cell compositions comprising iMNs can be further purified by additional rounds of sorting using the same or different markers that are specific for motor neurons.

In preferred processes, iMNs are enriched, isolated and/or purified from other non-iMNs (i.e. from a somatic cell, e.g., fibroblast which have not been reprogrammed to become iMNs) after the cell population is induced to reprogram towards motor neurons using the methods and compositions as disclosed herein.

In addition to the procedures just described, iMNs may also be isolated by other techniques for cell isolation. Additionally, iMNs may also be enriched or isolated by methods of serial subculture in growth conditions which promote the selective survival or selective expansion of iMNs.

Using the methods described herein, enriched, isolated and/or purified populations of iMNs cells can be produced in vitro from a somatic cell, e.g., fibroblast, which has undergone sufficient transdifferentiation to produce at least some iMNs. In a preferred method, a population of somatic cells, e.g., fibroblasts can be trandifferentiated primarily into a population of iMNs, where only a portion of the somatic cell population, e.g., about 5-10% has converted to iMNs. Some preferred enrichment, isolation and/or purification methods relate to the in vitro production of iMNs from human a somatic cell, e.g., fibroblast.

Using the methods described herein, isolated cell populations of iMNs are enriched in p iMNs content by at least about 2- to about 1000-fold as compared to a population before transdifferentiation of the a somatic cell, e.g., fibroblast. In some embodiments, iMNs can be enriched by at least about 5- to about 500-fold as compared to a population before transdifferentiation of the a somatic cell, e.g., fibroblast. In other embodiments, iMNs can be enriched from at least about 10- to about 200-fold as compared to a population before transdifferentiation of the a somatic cell, e.g., fibroblast. In still other embodiments, iMNs can be enriched from at least about 20- to about 100-fold as compared to a population before transdifferentiation of the a somatic cell, e.g., fibroblast. In yet other embodiments, iMNs can be enriched from at least about 40- to about 80-fold as compared to a population before transdifferentiation of the a somatic cell, e.g., fibroblast. In certain embodiments, iMNs can be enriched from at least about 2- to about 20-fold as compared to a population before transdifferentiation of the a somatic cell, e.g., fibroblast.

Compositions Comprising iMNs

Some embodiments of the present invention relate to cell compositions, such as cell cultures or cell populations, comprising iMNs, wherein the iMNs are motor neurons which have been derived from cells e.g. human a somatic cell, e.g., fibroblast, which express or exhibit one or more characteristics of an endogenous motor neuron. In accordance with certain embodiments, the iMNs are mammalian cells, and in a preferred embodiment, such cells are human iMNs.

Other embodiments of the present invention relate to compositions, such as cell cultures or cell populations, comprising iMNs. In such embodiments, somatic cells, e.g., fibroblasts comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the cell population.

Certain other embodiments of the present invention relate to compositions, such as cell cultures or cell populations, comprising iMNs. In some embodiments, a somatic cell, e.g., fibroblast from which the iMNs are derived comprise less than about 25%, less than about 20%, less than about 15%, less than about 10%, less than about 5%, less than about 4%, less than about 3%, less than about 2% or less than about 1% of the total cells in the culture. In certain embodiments, iMNs comprise less than about 25%, less than about 20%, less than about 15%, less than about 10%, less than about 5%, less than about 4%, less than about 3%, less than about 2% or less than about 1% of the total cells in the culture.

Additional embodiments of the present invention relate to compositions, such as cell cultures or cell populations, produced by the processes described herein and which comprise iMNs as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% iMNs. In preferred embodiments, the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about IT %, at least about 10%, at least about 9%, at least about 8%, at least about 7%, at least about 6%, at least about 5%, at least about 4%, at least about 3%, at least about 2% or at least about 1% iMNs. In preferred embodiments, the cells of the cell cultures or cell populations comprise human cells. In some embodiments, the percentage of iMNs in the cell cultures or populations is calculated without regard to the feeder cells remaining in the culture.

Still other embodiments of the present invention relate to compositions, such as cell cultures or cell populations, comprising mixtures of iMNs and a somatic cell, e.g., fibroblast. For example, cell cultures or cell populations comprising at least about 5 iMNs for about every 95 somatic cell, e.g., fibroblast can be produced. In other embodiments, cell cultures or cell populations comprising at least about 95 iMNs for about every 5 somatic cell, e.g., fibroblast can be produced. Additionally, cell cultures or cell populations comprising other ratios of iMNs to somatic cell, e.g., fibroblast are contemplated. For example, compositions comprising at least about 1 iMNs for about every 1,000,000, or at least 100,000 cells, or a least 10,000 cells, or at least 1000 cells or 500, or at least 250 or at least 100 or at least 10 somatic cell, e.g., fibroblast. Further embodiments of the present invention relate to compositions, such as cell cultures or cell populations, comprising human cells, including human iMNs.

In preferred embodiments of the present invention, cell cultures and/or cell populations of iMNs comprise human iMNs that are non-recombinant cells. In such embodiments, the cell cultures and/or cell populations are devoid of or substantially free of recombinant human iMNs.

Using the processes described herein, compositions comprising iMNs are substantially free of other cell types can be produced. In some embodiments of the present invention, the iMNs populations or cell cultures produced by the methods described herein are substantially free of cells that significantly express the fibroblast markers, or non-motor neuron markers.

Use of the iMNs

Another aspect of the present invention further provides a method of treating a subject with a motor neuron disease or disorder, or treating a subject at risk of developing a motor neuron disease or disorder, comprising administering to the subject a composition comprising a population of iMNs. In some embodiments the motor neuron disease or disorder is amyotrophic lateral sclerosis (ALS) or spinal muscular atrophy (SMA).

In some embodiments, the present invention also provides a method of treating a motor neuron disease or disorder in a subject, comprising obtaining a population of a somatic cell, e.g., fibroblast from a subject, e.g. from the subject being treated, or from a donor subject; increasing the protein expression of at least three, or all three transcription factors selected Lhx3, Ascl1, Brn2, Myt1l, Isl1, Hb9, Ngn2 or NeuroD1 in the population of a somatic cell, e.g., fibroblast in vitro, for example by the methods as described herein, thereby promoting conversion of the population of a somatic cell, e.g., fibroblast into iMNs; and administering a substantially pure population of iMNs to the subject.

In the method of treating a motor neuron disease, wherein a somatic cell, e.g., fibroblast can be from a donor, the donor can be a cadaver. As a further embodiment of the present invention, the a somatic cell, e.g., fibroblast can be allowed to proliferate in vitro prior to increasing the protein expression of at least three or more MN-inducing factors selected from any combination of Lhx3, Ascl1, Brn2, Myt1l, Isl1, Hb9, Ngn2 or NeuroD1. Preferably, promoting conversion of a somatic cell, e.g., fibroblast into iMN as disclosed herein will result in greater than about 5% or about 10% of conversion of a somatic cell, e.g., fibroblast into iMN. Even more preferably, greater than about 25%, 30%, 35%, 40%, 45%, 50%, 55%, 60%, 65%, 70%, 75%, 80%, 85%, or 90% of the a somatic cell, e.g., fibroblast will be converted into iMNs.

In some embodiments, the iMNs as disclosed herein can be used in cellular models of human motor neuron disease, where such models could be used for basic research and drug discovery, e.g., to find treatments for motor neuron diseases or disorders including but not limited to: amyotrophic lateral sclerosis (ALS), also called Lou Gehrig's disease or classical motor neuron disease; progressive bulbar palsy, also called progressive bulbar atrophy; pseudobulbar palsy; primary lateral sclerosis (PLS); progressive muscular atrophy; spinal muscular atrophy (SMA, including SMA type I, also called Werdnig-Hoffmann disease, SMA type II, and SMA type III, also called Kugelberg-Welander disease); Fazio-Londe disease; Kennedy disease, also known as progressive spinobulbar muscular atrophy; congenital SMA with arthrogryposis or post-polio syndrome (PPS).

In an exemplary embodiment, gene therapy can be used to insert DNA into a fibroblast which is transdifferentiated into a iMN, where the fibroblast is from a patient or subject with a genetic defect or a defect of unknown origin in their motor neurons, followed by the transdifferentiation of the fibroblast into a iMN. The thus formed iMN population may then be used as a cellular model for the disorder associated with the genetic defect or any other abnormality carried by these cells. In some embodiments, the cellular model may be used for the development of drugs. In addition, a population of iMNs transdifferentiated from fibroblasts obtained from a subject with a motor neuron disease may serve for drug development and testing for the specific patient from which they were developed in the course of personalized medicine.

In an other exemplary embodiment stem cell, neural precursors or neural progenitors may be developed from any source of somatic cells, e.g., the gonads, bone marrow, brain biopsy or any transdifferentiation of somatic cells obtained from a patient with motor neuron disorder of any etiology, and directed to convert by transdifferentiation method as disclosed herein into a population of motor neurons. Such a iMN population may then be used as a cellular model for the motor neuron disorder of the patient. The cellular model may be used for the development of drugs. In addition, the thus formed population may serve for drug development and testing for the specific patient from which they were developed in the course of personalized medicine.

In some embodiments, an iMN population as disclosed herein may serve for testing and high throughput screening of molecules for neurotoxic, teratogenic, neurotrophic, neuroprotective and neuroregenerative effects. In accordance with another embodiment, the iMNs can be used for studying exogenous diseases and disorders of motor neurons. In one exemplary embodiment, the iMNs can be used to study viral infections of motor neurons such as polio.

In some embodiments, altering the surface antigens of the iMNs produced by the methods as disclosed herein can reduce the likelihood that iMNs will cause an immune response. The iMNs with altered surface antigens can then be administered to the subject. The cell surface antigens can be altered prior to, during, or after the fibroblasts are trandifferentiated into iMNs.

The subject of the invention can include individual humans, domesticated animals, livestock (e.g., cattle, horses, pigs, etc.), pets (like cats and dogs).

Accordingly, the methods for treatment as described herein can be combined with other methods of treating motor neuron diseases which are known by a skilled physician in the art of neurological treatment of motor neuron diseases.

Kits

The cells and components such as one or more MN-inducing factors can be provided in a kit. The kit includes (a) the cells and components described herein, e.g., a composition(s) that includes a cell and component(s) described herein, and, optionally (b) informational material. The informational material can be descriptive, instructional, marketing or other material that relates to the methods described herein and/or the use of a compound(s) described herein for the methods described herein.

The informational material of the kits is not limited in its form. In one embodiment, the informational material can include information about production of a cell, the nature of the components such as the transcription factor, concentration of components, date of expiration, batch or production site information, and so forth. In one embodiment, the informational material relates to methods for administering the cells or other components.

In one embodiment, the informational material can include instructions to administer a compound(s) component such as a transcription factor described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a component(s) described herein to a suitable subject, e.g., a human, e.g., a human having or at risk for a disorder described herein or to a cell in vitro.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound(s) described herein, the composition of the kit can include other ingredients, such as a solvent or buffer, a stabilizer, a preservative, and/or an additional agent, e.g., for reprogramming a somatic cell, e.g., fibroblast, such as a somatic cell (e.g., in vitro or in vivo) or for treating a condition or disorder described herein. Alternatively, the other ingredients can be included in the kit, but in different compositions or containers than a component described herein. In such embodiments, the kit can include instructions for admixing a component(s) described herein and the other ingredients, or for using a component(s) described herein together with the other ingredients, e.g., instructions on combining the two agents prior to administration.

The kit can include one or more containers for the composition containing a component(s) described herein. In some embodiments, the kit contains separate containers (e.g., two separate containers for the two agents), dividers or compartments for the component(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a component described herein. The containers of the kits can be air tight, waterproof (e.g., impermeable to changes in moisture or evaporation), and/or light-tight.

The kit optionally includes a device suitable for administration of the component, e.g., a syringe, inhalant, pipette, forceps, measured spoon, dropper (e.g., eye dropper), swab (e.g., a cotton swab or wooden swab), or any such delivery device.

Pharmaceutical Compositions Comprising a Population of iMNs.

In another aspect of the invention, the methods provide use of an isolated population of iMNs as disclosed herein. In one embodiment of the invention, an isolated population of iMNs as disclosed herein may be used for the production of a pharmaceutical composition, for the use in transplantation into subjects in need of treatment, e.g. a subject that has, or is at risk of developing a motor neuron disease or disorder, for example but not limited to subjects with congenital and acquired ALS or SMA. In one embodiment, an isolated population of iMNs may be genetically modified. In another aspect, the subject may have or be at risk of a motor neuron disease, e.g., carry a particular mutation for susceptibility for ALS by has not yet observed or detected ALS symptoms. In some embodiments, an isolated population of iMNs as disclosed herein may be autologous and/or allogenic. In some embodiments, the subject is a mammal, and in other embodiments the mammal is a human.

The use of an isolated population of iMNs as disclosed herein provides advantages over existing methods because the iMNs can be reprogrammed from a somatic cell, e.g., fibroblast obtained or harvested from the subject administered an isolated population of iMNs. This is highly advantageous as it provides a renewable source of functional motor neurons for transplantation into a subject, in particular a substantially pure population of iMNs that do not have the risks and limitations of iMNs derived from other systems, such as from iPS cells which have risks of formation of teratomas (Lafamme and Murry, 2005, Murry et al, 2005; Rubart and Field, 2006).

In another embodiment, an isolated population of p iMNs can be used as models for studying properties of motor neurons, or pathways of development of a somatic cell, e.g., fibroblast into motor neuron cells. In some embodiments, the iMNs cells may be genetically engineered to comprise markers operatively linked to promoters that are expressed when a marker is expressed or secreted, for example, a marker can be operatively linked to Hb9 promoter, so that the marker is expressed when the cell becomes a functional motor neuron. In some embodiments, a population of iMNs can be used as a model for studying the differentiation pathway of cells which differentiate into motor neurons. In other embodiments, the iMNs may be used as models for studying the role of motor neurons in development and in the development of motor neuron disease or disorders. In some embodiments, the iMNs can be from a normal subject, or from a subject which carries a mutation and/or polymorphism (e.g. a mutation in the SOD1 gene is one form of the inherited form of ALS), as well as effect of mutations on late onset ALS, which can be use to identify small molecules and other therapeutic agents that can be used to treat subjects with ALS with such mutations or polymorphism in ALS associated genes. In some embodiments, the iMNs may be genetically engineered to correct the polymorphism in the SOD1 gene, or other ALS susceptibility genes, including but not limited to, heavy neurofilament chain (NFH), dynactin, vescicular binding protein 1 gene and the ALSIN (ALS2) gene, prior to being administered to a subject in the therapeutic treatment of a subject with ALS. In some embodiments, the iMNs may be genetically engineered to carry a mutation and/or polymorphism for studying the effects of the mutation and/or polymorphism on the development and contribution to the motor neuron disease.

In one embodiment of the invention relates to a method of treating a motor neuron disease, e.g., ALS or SMA in a subject comprising administering an effective amount of a composition comprising a population of iMNs as disclosed herein to a subject with a motor neuron disease, e.g., ALS or SMA. In a further embodiment, the invention provides a method for treating a motor neuron disease, e.g., ALS or SMA, comprising administering a composition comprising a population of iMNs as disclosed herein to a subject that has, or has increased risk of developing a motor neuron disease, e.g., ALS or SMA, in an effective amount sufficient to produce motor neurons which can support degenerating or dying motor neurons in the subject.

In some embodiments, a population of iMNs can be administered to a subject in combination with other treatment for motor neuron diseases, such as, for example, administration on combination with riluzole, RNA interference (RNAi) for ALS susceptibility or mutated genes (e.g., RNAi of mutant SOD1 genes, or RNAi for any of the mutant NFH, dynactin, vesicular binding protein or ALSIN genes), neurotrophic factors (e.g., IGF-1, EPO, CTNF, BDNF, VEGF), anti-oxidative agents such as HIF-1a, amino acids, e.g., creatine, as well as small molecules drugs such as ceftriaxone, lithium, xaliproden, pioglitazone, pyridostigmine and seligiline and other agents or stem cells, e.g, embryonic stem cells used for the treatment of motor neuron diseases.

In one embodiment of the above methods, the subject is a human and a population of iMNs as disclosed herein are human cells. In some embodiments, the invention contemplates that a population of iMNs as disclosed herein are administered directly to the spinal cord of a subject, or is administered systemically. In some embodiments, a population of iMNs as disclosed herein can be administered to any suitable location in the subject, for example in a capsule in the blood vessel or any suitable site where administered population of iMNs can integrate into the spinal cord and send axonal projections which make synaptic contact with the muscle tissues in the subject.

The present invention is also directed to a method of treating a subject with a motor neuron disease, e.g., ALS or SMA which occurs as a consequence of genetic defect, physical injury, environmental insult or conditioning, bad health, obesity and other a motor neuron disease risk factors commonly known by a person of ordinary skill in the art. Efficacy of treatment can be monitored by clinically accepted criteria and tests, which include for example, using Electromyography (EMG), which is used to diagnose muscle and nerve dysfunction and spinal cord disease, and measure the speed at which impulses travel along a particular nerve. EMG records the electrical activity from the brain and/or spinal cord to a peripheral nerve root (found in the arms and legs) that controls muscles during contraction and at rest. One can also monitor efficacy of treatment using a nerve conduction velocity study to measure electrical energy to test the nerve's ability to send a signal, as well as laboratory screening tests of blood, urine, as well as magnetic resonance imaging (MRI), which uses computer-generated radio waves and a powerful magnetic field to produce detailed images of body structures including tissues, organs, bones, and nerves to detect and monitor degenerative disorders. In some embodiments, efficacy of treatment can also be assessed by a muscle or nerve biopsy can help confirm nerve disease and nerve regeneration. A small sample of the muscle or nerve is removed under local anesthetic and studied under a microscope. The sample may be removed either surgically, through a slit made in the skin, or by needle biopsy, in which a thin hollow needle is inserted through the skin and into the muscle. A small piece of muscle remains in the hollow needle when it is removed from the body. In some embodiments, efficacy of treatment can also be monitored by a transcranial magnetic stimulation to study areas of the brain related to motor activity.

Other motor neuron diseases which can be treated by the methods as disclosed herein include, but are not limited to: Amyotrophic lateral sclerosis (ALS), Progressive bulbar palsy, Pseudobulbar palsy, Primary lateral sclerosis (PLS), Progressive muscular atrophy, Spinal muscular atrophy (SMA), including Type I (also called Werdnig-Hoffmann disease), Type II, Type III (Kugelberg-Welander disease), Fazio-Londe disease, Kennedy's disease also known as progressive spinobulbar muscular atrophy; congenital SMA with arthrogryposis, Post-polio syndrome (PPS) and traumatic spinal cord injury.

ALS, also called Lou Gehrig's disease or classical motor neuron disease, is a progressive, ultimately fatal disorder that eventually disrupts signals to all voluntary muscles. In the United States, doctors use the terms motor neuron disease and ALS interchangeably. Both upper and lower motor neurons are affected. Approximately 75 percent of people with classic ALS will also develop weakness and wasting of the bulbar muscles (muscles that control speech, swallowing, and chewing). Symptoms are usually noticed first in the arms and hands, legs, or swallowing muscles. Muscle weakness and atrophy occur disproportionately on both sides of the body. Affected individuals lose strength and the ability to move their arms, legs, and body. Other symptoms include spasticity, exaggerated reflexes, muscle cramps, fasciculations, and increased problems with swallowing and forming words. Speech can become slurred or nasal. When muscles of the diaphragm and chest wall fail to function properly, individuals lose the ability to breathe without mechanical support. Although the disease does not usually impair a person's mind or personality, several recent studies suggest that some people with ALS may have alterations in cognitive functions such as problems with decision-making and memory. ALS most commonly strikes people between 40 and 60 years of age, but younger and older people also can develop the disease. Men are affected more often than women. Most cases of ALS occur sporadically, and family members of those individuals are not considered to be at increased risk for developing the disease. (There is a familial form of ALS in adults, which often results from mutation of the superoxide dismutase gene, or SOD1, located on chromosome 21.) A rare juvenile-onset form of ALS is genetic. Most individuals with ALS die from respiratory failure, usually within 3 to 5 years from the onset of symptoms. However, about 10 percent of affected individuals survive for 10 or more years.

Progressive bulbar palsy, also called progressive bulbar atrophy, involves the bulb-shaped brain stem—the region that controls lower motor neurons needed for swallowing, speaking, chewing, and other functions. Symptoms include pharyngeal muscle weakness (involved with swallowing), weak jaw and facial muscles, progressive loss of speech, and tongue muscle atrophy. Limb weakness with both lower and upper motor neuron signs is almost always evident but less prominent. Affected persons have outbursts of laughing or crying (called emotional lability). Individuals eventually become unable to eat or speak and are at increased risk of choking and aspiration pneumonia, which is caused by the passage of liquids and food through the vocal folds and into the lower airways and lungs. Stroke and myasthenia gravis each have certain symptoms that are similar to those of progressive bulbar palsy and must be ruled out prior to diagnosing this disorder. In about 25 percent of ALS cases early symptoms begin with bulbar involvement. Some 75 percent of individuals with classic ALS eventually show some bulbar involvement. Many clinicians believe that progressive bulbar palsy by itself, without evidence of abnormalities in the arms or legs, is extremely rare.

Pseudobulbar palsy, which shares many symptoms of progressive bulbar palsy, is characterized by upper motor neuron degeneration and progressive loss of the ability to speak, chew, and swallow. Progressive weakness in facial muscles leads to an expressionless face. Individuals may develop a gravelly voice and an increased gag reflex. The tongue may become immobile and unable to protrude from the mouth. Individuals may also experience emotional lability.

Primary lateral sclerosis (PLS) affects only upper motor neurons and is nearly twice as common in men as in women. Onset generally occurs after age 50. The cause of PLS is unknown. It occurs when specific nerve cells in the cerebral cortex (the thin layer of cells covering the brain which is responsible for most higher level mental functions) that control voluntary movement gradually degenerate, causing the muscles under their control to weaken. The syndrome—which scientists believe is only rarely hereditary—progresses gradually over years or decades, leading to stiffness and clumsiness of the affected muscles. The disorder usually affects the legs first, followed by the body trunk, arms and hands, and, finally, the bulbar muscles. Symptoms may include difficulty with balance, weakness and stiffness in the legs, clumsiness, spasticity in the legs which produces slowness and stiffness of movement, dragging of the feet (leading to an inability to walk), and facial involvement resulting in dysarthria (poorly articulated speech). Major differences between ALS and PLS (considered a variant of ALS) are the motor neurons involved and the rate of disease progression. PLS may be mistaken for spastic paraplegia, a hereditary disorder of the upper motor neurons that causes spasticity in the legs and usually starts in adolescence. Most neurologists follow the affected individual's clinical course for at least 3 years before making a diagnosis of PLS. The disorder is not fatal but may affect quality of life. PLS often develops into ALS.

Progressive muscular atrophy is marked by slow but progressive degeneration of only the lower motor neurons. It largely affects men, with onset earlier than in other MNDs. Weakness is typically seen first in the hands and then spreads into the lower body, where it can be severe. Other symptoms may include muscle wasting, clumsy hand movements, fasciculations, and muscle cramps. The trunk muscles and respiration may become affected. Exposure to cold can worsen symptoms. The disease develops into ALS in many instances.

Spinal muscular atrophy (SMA) is a hereditary disease affecting the lower motor neurons. Weakness and wasting of the skeletal muscles is caused by progressive degeneration of the anterior horn cells of the spinal cord. This weakness is often more severe in the legs than in the arms. SMA has various forms, with different ages of onset, patterns of inheritance, and severity and progression of symptoms. Some of the more common SMAs are described below.

SMA type I, also called Werdnig-Hoffmann disease, is evident by the time a child is 6 months old. Symptoms may include hypotonia (severely reduced muscle tone), diminished limb movements, lack of tendon reflexes, fasciculations, tremors, swallowing and feeding difficulties, and impaired breathing. Some children also develop scoliosis (curvature of the spine) or other skeletal abnormalities. Affected children never sit or stand and the vast majority usually die of respiratory failure before the age of 2. Symptoms of SMA type II usually begin after the child is 6 months of age. Features may include inability to stand or walk, respiratory problems, hypotonia, decreased or absent tendon reflexes, and fasciculations. These children may learn to sit but do not stand. Life expectancy varies, and some individuals live into adolescence or later. Symptoms of SMA type III (Kugelberg-Welander disease) appear between 2 and 17 years of age and include abnormal gait; difficulty running, climbing steps, or rising from a chair; and a fine tremor of the fingers. The lower extremities are most often affected. Complications include scoliosis and joint contractures—chronic shortening of muscles or tendons around joints, caused by abnormal muscle tone and weakness, which prevents the joints from moving freely.

Symptoms of Fazio-Londe disease appear between 1 and 12 years of age and may include facial weakness, dysphagia (difficulty swallowing), stridor (a high-pitched respiratory sound often associated with acute blockage of the larynx), difficulty speaking (dysarthria), and paralysis of the eye muscles. Most individuals with SMA type III die from breathing complications.

Kennedy disease, also known as progressive spinobulbar muscular atrophy, is an X-linked recessive disease. Daughters of individuals with Kennedy disease are carriers and have a 50 percent chance of having a son affected with the disease. Onset occurs between 15 and 60 years of age. Symptoms include weakness of the facial and tongue muscles, hand tremor, muscle cramps, dysphagia, dysarthria, and excessive development of male breasts and mammary glands. Weakness usually begins in the pelvis before spreading to the limbs. Some individuals develop noninsulin-dependent diabetes mellitus. The course of the disorder varies but is generally slowly progressive. Individuals tend to remain ambulatory until late in the disease. The life expectancy for individuals with Kennedy disease is usually normal. Congenital SMA with arthrogryposis (persistent contracture of joints with fixed abnormal posture of the limb) is a rare disorder. Manifestations include severe contractures, scoliosis, chest deformity, respiratory problems, unusually small jaws, and drooping of the upper eyelids.

Post-polio syndrome (PPS) is a condition that can strike polio survivors decades after their recovery from poliomyelitis. PPS is believed to occur when injury, illness (such as degenerative joint disease), weight gain, or the aging process damages or kills spinal cord motor neurons that remained functional after the initial polio attack. Many scientists believe PPS is latent weakness among muscles previously affected by poliomyelitis and not a new MND. Symptoms include fatigue, slowly progressive muscle weakness, muscle atrophy, fasciculations, cold intolerance, and muscle and joint pain. These symptoms appear most often among muscle groups affected by the initial disease. Other symptoms include skeletal deformities such as scoliosis and difficulty breathing, swallowing, or sleeping. Symptoms are more frequent among older people and those individuals most severely affected by the earlier disease. Some individuals experience only minor symptoms, while others develop SMA and, rarely, what appears to be, but is not, a form of ALS. PPS is not usually life threatening. Doctors estimate the incidence of PPS at about 25 to 50 percent of survivors of paralytic poliomyelitis.

In some embodiments, the effects of administration of a population of iMNs as disclosed herein to a subject in need thereof is associated with improved exercise tolerance or other quality of life measures, and decreased mortality. The effects of cellular therapy can be evident over the course of days to weeks after the procedure. However, beneficial effects may be observed as early as several hours after the procedure, and may persist for several years.

In some embodiments, the iMNs can be used for transplantation into any tissue of interest, where such tissues could be neural tissues (central nervous system or peripheral nervous system, e.g. spinal cord, nerve bundles, motor nerves, nerve ganglia) or non-neural tissues (muscle, liver, lungs). The iMNs can be transplanted into the spinal cord at any position from the cervical to lumbar regions. One of skill in the art can determine what procedures would be necessary for transplanting the cells into a particular position in the spinal cord, e.g., in some embodiments, a laminectomy may be appropriate to facility entry to the spinal cord, while in other embodiments the cells could be administered by directly accessing the spinal cord, as may be possible for neonatal applications, or administration to adult subjects by inserted the injection apparatus between vertebral bodies (similar to a spinal tap), to deliver the cells either into nervous tissue or intra thecal or into any other appropriate site.

In accordance with one aspect of the invention, when the iMNs are used in a therapeutic application wherein the cells are expected to exhibit functions similar or identical to motor neuron functions. In one embodiment, the iMNs are transplanted using procedures to target the cells to selected sites. In an exemplary embodiment, when iMNs are introduced into the spinal cord, the cells may be targeted to spinal cord grey matter, including the dorsal or ventral horn of the grey matter. In another exemplary embodiment, iMNs can be targeted to other sites including, but not limited to, an emerging ventral or dorsal root, a dorsal root ganglion, a spinal nerve, a peripheral nerve a motor nerve, or any other appropriate site as determined by one of skill in the art. In one embodiment, the iMNs are transplanted directly or indirectly (e.g. ex vivo) to mammals, preferably, to humans.

In some other embodiments, the iMNs can be used as carriers for gene therapy, or as carriers for protein delivery.

In some embodiments, a population of iMNs as disclosed herein may be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting a population of iMNs as disclosed herein into the spinal cord or at an alternative desired location. The cells may be administered to a recipient by injection, or administered by intramuscular injection.

To determine the suitability of cell compositions for therapeutic administration, the cells can first be tested in a suitable animal model. At one level, cells are assessed for their ability to survive and maintain their phenotype in vivo. Cell compositions can be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or beta-galactosidase); that have been prelabeled (for example, with BrdU or [3H] thymidine), or by subsequent detection of a constitutive cell marker (for example, using human-specific antibody). The presence and phenotype of the administered population of iMNs can be assessed by immunohistochemistry or ELISA using human-specific antibody, or by RT-PCR analysis using primers and hybridization conditions that cause amplification to be specific for human polynucleotides, according to published sequence data.

A number of animal models for testing in models of motor neuron diseases are available for such testing, and are commonly known in the art, for example as the SOD1 (G93A) mutant mouse and SMA (B6.129-Smn1$^{tm1Jme/J}$) mouse models from Jackson laboratories.

In some embodiments, a population of iMNs as disclosed herein may be administered in any physiologically acceptable excipient, where the cells may find an appropriate site for regeneration and differentiation. In some embodiments, a population of iMNs as disclosed herein can be introduced by injection, catheter, or the like. In some embodiments, a population of iMNs as disclosed herein can be frozen at liquid nitrogen temperatures and stored for long periods of time, being capable of use on thawing. If frozen, a population of iMNs will usually be stored in a 10% DMSO, 50% FCS, 40% RPMI 1640 medium. Once thawed, the cells may be expanded by use of growth factors and/or feeder cells associated with culturing iMNs as disclosed herein.

In some embodiments, a population of iMNs as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of iMNs as disclosed herein will be adapted in accordance with the route and device used for administration. In some embodiments, a composition comprising a population of iMNs can also comprise or be accompanied with one or more other ingredients that facilitate the engraftment or functional mobilization of the iMNs. Suitable ingredients include matrix proteins that support or promote adhesion of the iMNs, or complementary cell types, especially glial and/or muscle cells. In another embodiment, the composition may comprise resorbable or biodegradable matrix scaffolds.

In some embodiments, a population of iMNs as disclosed herein may be genetically altered in order to introduce genes useful in the iMNs, e.g. repair of a genetic defect in an individual, selectable marker, etc., or genes useful in selection against non-iMNs or for the selective suicide of implanted iMNs. In some embodiments, a population of iMNs can also be genetically modified to enhance survival, control proliferation, and the like. In some embodiments, a population of iMNs as disclosed herein can be genetically altering by transfection or transduction with a suitable vector, homologous recombination, or other appropriate technique, so that they express a gene of interest. In one embodiment, a iMNs is transfected with genes encoding a telomerase catalytic component (TERT), typically under a heterologous promoter that increases telomerase expression beyond what occurs under the endogenous promoter, (see International Patent Application WO 98/14592, which is incorporated herein by reference). In other embodiments, a selectable marker is introduced, to provide for greater purity of the population of iMNs. In some embodiments, a population of iMNs may be genetically altered using vector containing supernatants over a 8-16 h period, and then exchanged into growth medium for 1-2 days. Genetically altered iMNs can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, a population of iMNs as disclosed herein can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type.

Many vectors useful for transferring exogenous genes into target iMNs as disclosed herein are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. In some embodiments, combinations of retroviruses and an appropriate packaging cell line may also find use, where the capsid proteins will be functional for infecting the iMNs as disclosed herein. Usually, iMNs and virus will be incubated for at least about 24 hours in the culture medium. In some embodiments, iMNs are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, a population of iMNs as disclosed herein are suitable for administering systemically or to a target anatomical site. A population of iMNs can be grafted into or nearby a subject's spinal cord, for example, or may be administered systemically, such as, but not limited to, intra-arterial or intravenous administration. In alternative embodiments, a population of iMNs of the present invention can be administered in various ways as would be appropriate to implant in the central nervous system or peripheral nervous system, including but not limited to parenteral, including intravenous and intraarterial administration, intrathecal administration, intraventricular administration, intraparenchymal, intracranial, intracisternal, intrastriatal, and intranigral administration. Optionally, a population of iMNs can be administered in conjunction with an immunosuppressive agent.

In some embodiments, a population of iMNs can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of iMNs can be administered to a subject the following locations: clinic, clinical office, emergency department, hospital ward, intensive care unit, operating room, catheterization suites, and radiologic suites.

In other embodiments, a population of iMNs is stored for later implantation/infusion. A population of iMNs may be divided into more than one aliquot or unit such that part of a population of iMNs is retained for later application while part is applied immediately to the subject. Moderate to long-term storage of all or part of the cells in a cell bank is also within the scope of this invention, as disclosed in U.S. Patent Application Serial No. 20030054331 and Patent Application No. WO03024215, and is incorporated by reference in their entireties. At the end of processing, the concentrated cells may be loaded into a delivery device, such as a syringe, for placement into the recipient by any means known to one of ordinary skill in the art.

In some embodiments, a population of iMNs can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of iMNs may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of iMNs could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid' adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell co-stimulation pathways, such as agents that interfere with the coupling of T-cells and B-cells via the CTLA4 and B7 pathways, as disclosed in U.S. Patent Pub. No 2002/0182211, which is incorporated herein by reference. In one embodiment, an immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

Pharmaceutical compositions comprising effective amounts of a population of iMNs are also contemplated by the present invention. These compositions comprise an effective number iMNs, optionally, in combination with a pharmaceutically acceptable carrier, additive or excipient. In certain aspects of the present invention, a population of iMNs can be administered to the subject in need of a transplant in sterile saline. In other aspects of the present invention, a population of iMNs can be administered in Hanks Balanced Salt Solution (HBSS) or Isolyte S, pH 7.4. Other approaches may also be used, including the use of serum free cellular media. In one embodiment, a population of iMNs can be administered in plasma or fetal bovine serum, and DMSO. Systemic administration of a population of iMNs to the subject may be preferred in certain indications, whereas direct administration at the site of or in proximity to the diseased and/or damaged tissue may be preferred in other indications.

In some embodiments, a population of iMNs can optionally be packaged in a suitable container with written instructions for a desired purpose, such as the reconstitution or thawing (if frozen) of a population of iMNs prior to administration to a subject.

In one embodiment, an isolated population of iMNs as disclosed herein can be administered with a differentiation agent. In one embodiment, iMNs can be combined with the differentiation agent to administration into the subject. In another embodiment, the cells are administered separately to the subject from the differentiation agent. Optionally, if the cells are administered separately from the differentiation agent, there is a temporal separation in the administration of the iMNs and the differentiation agent. The temporal separation may range from about less than a minute in time, to about hours or days in time. The determination of the optimal timing and order of administration is readily and routinely determined by one of ordinary skill in the art.

Some embodiments of the present invention may be defined in any of the following numbered paragraphs:

1. A method for transdifferentiation of a first somatic cell into a motor neuron, the method comprising increasing the protein expression of at least three motor-neuron inducing (MN-inducing) factors selected from the group consisting of: Lhx3, Ascl1, Brn2, Myt1l, Isl1, Hb9, Ngn2 or NeuroD1, wherein the motor neuron exhibits at least two characteristics of an endogenous motor neuron.

2. The method of paragraph 1, wherein the three motor-neuron inducing factors are Lhx2, Ascl1 and one motor neuron inducing factor selected from the group consisting of: Brn2, Myt1l, Isl1, Hb9, Ngn2 or NeuroD.

3. The method of any of paragraphs 1 to 3, wherein the three motor-neuron inducing factors are Myt1l, Brn2 and one motor neuron inducing factor selected from the group consisting of: Lhx3, Ascl1, Isl1, Hb9, Ngn2 or NeuroD.

4. The method of any of paragraphs 1 to 3, wherein the three motor-neuron inducing factors do not include Myt1l or Brn2.

5. The method of any of paragraphs 1 to 4, wherein the motor neuron inducing factors does not comprise miR-124.

6. The method of any of paragraphs 1 to 5, wherein the motor neuron inducing factors does not comprise isl1.

7. The method of any of paragraphs 1 to 5, wherein the somatic cell is a fibroblast cell.

8. The method of any of paragraphs 1 to 6, wherein a characteristic of the motor neuron is expression of at least two motor neuron specific genes selected from the group consisting of: β2-tubulins, Map2, synapsins, synaptophysin, synaptotagmins, NeuroD, Isl1, cholineacetyltransferase (ChAT).

9. The method of paragraph 8, wherein the β2-tubulin is selected from Tubb2a and Tubb2b.

10. The method of paragraph 8, wherein the synapsins is selected from Syn1 and Syn2.

11. The method of paragraph 8, wherein the synaptotagmins are selected from: Syt1, Syt4, Syt13, Syt 16.

12. The method of paragraph 8, wherein the ChAT is vesicular ChAT.

13. The method of any of paragraphs 1 to 12, wherein a characteristic of the motor neuron is expression of a decreased level of a fibroblast gene selected from the group of: Snail1, thy1 and Fsp1, by a statistically significant level as compared to the somatic cell from which the motor neuron was derived.

14. The method of any of paragraphs 1 to 13, wherein a characteristic of the motor neuron is a motor neuron morphology, comprising a cell body with axonal projections which form functional synaptic junctions with muscle cells.

15. The method of any of paragraphs 1 to 14, wherein a characteristic of the motor neuron is an average resting potential of below −50 mV.

16. The method of paragraphs 15, wherein the motor neuron has an average resting potential of between −65 mV and −50 mV.

17. The method of any of paragraphs 1 to 16, wherein a characteristic of the motor neuron is a functional characteristic selected from the group consisting of: ability to fire action potentials, produce an outward current in response to glycine, GABA or kainate, or produce an inward current in response to glutamate.

18. The method of any of paragraphs 1 to 17, wherein the protein expression of a MN-inducing factor is increased by contacting the somatic cell with an agent which increases the expression of the MN-inducing factor.

19. The method of paragraph 18, wherein the agent is selected from the group consisting of: a nucleotide sequence, a protein, an aptamer, a small molecule, a ribosome, a RNAi agent, a peptide-nucleic acid (PNA), or analogues or variants thereof.

20. The method of any of paragraphs 1 to 19, wherein protein expression is increased by introducing at least one nucleic acid sequence encoding a MN-inducing factor protein selected from Lhx3, Ascl1, Brn2, Myt1l, Isl1, Hb9, Ngn2 or NeuroD1, or encoding a functional fragment thereof, in the somatic cell.

21. The method of any of paragraphs 1 to 20, wherein the protein expression of Lhx3 is increased by introducing a nucleic acid sequence encoding Lhx3 polypeptide comprising SEQ ID NO: 1 or SEQ ID NO: 2 a functional fragment thereof.

22. The method of any of paragraphs 1 to 20, wherein the protein expression of Ascl1 is increased by introducing a nucleic acid sequence encoding Ascl1 polypeptide comprising SEQ ID NO: 3 or SEQ ID NO: 4 or a functional fragment thereof.

23. The method of any of paragraphs 1 to 20, wherein the protein expression of Brn2 is increased by introducing a nucleic acid sequence encoding Brn2 polypeptide comprising SEQ ID NO: 5 or SEQ ID NO: 6 or a functional fragment thereof.

24. The method of any of paragraphs 1 to 20, wherein the protein expression of Myt1l is increased by introducing a nucleic acid sequence encoding Myt1l polypeptide comprising SEQ ID NO: 7 or SEQ ID NO: 8 or a functional fragment thereof.

25. The method of any of paragraphs 1 to 20, wherein the protein expression of Isl1 is increased by introducing a nucleic acid sequence encoding Isl1 polypeptide comprising SEQ ID NO: 9 or SEQ ID NO: 10 or a functional fragment thereof.

26. The method of any of paragraphs 1 to 20, wherein the protein expression of Hb9 is increased by introducing a nucleic acid sequence encoding Hb9 polypeptide comprising SEQ ID NO: 11 or SEQ ID NO: 12 or a functional fragment thereof.

27. The method of any of paragraphs 1 to 20, wherein the protein expression of Ngn2 is increased by introducing a nucleic acid sequence encoding Ngn2 polypeptide comprising SEQ ID NO: 13 or SEQ ID NO: 14 or a functional fragment thereof.

28. The method of any of paragraphs 1 to 20, wherein the protein expression of NeuroD1 is increased by introducing a nucleic acid sequence encoding NeuroD1 polypeptide comprising SEQ ID NO: 15 or SEQ ID NO: 16 or a functional fragment thereof.

29. The method of any of paragraphs 1 to 28, wherein the nucleic acid sequence is in a vector.

30. The method of any of paragraphs 1 to 29, wherein the vector is a viral vector or a non-viral vector.

31. The method of paragraph 30, wherein the viral vector comprises a genome which does not integrate into the somatic cell genome.

32. The method of any of paragraphs 1 to 31, wherein the somatic cell is in vitro.

33. The method of any of paragraphs 1 to 31, wherein the somatic cell is ex vivo.

34. The method of any of paragraphs 1 to 33, wherein the somatic cell is a mammalian somatic cell.

35. The method of paragraph 34, wherein the mammalian somatic cell is a human somatic cell.

36. The method of any of paragraphs 1 to 35, wherein the somatic cell is obtained from a subject.

37. The method of paragraph 36, wherein the subject is a human subject.

38. The method of paragraph 37, wherein the subject has, or is at risk of developing a motor neuron disease or disorder.

39. The method of paragraph 38, wherein the motor neuron disease or disorder is selected from amyotrophic lateral sclerosis (ALS) or spinal muscular atrophy (SMA) or associated diseases thereof.

40. The method of any of paragraphs 1 to 39, wherein the motor neuron is a motor neuron-like cell.

41. An isolated population of motor neurons obtained from a population of somatic cells by a process of increasing the protein expression of at least three motor-neuron inducing (MN-inducing) factors selected from the group consisting of: Lhx3, Ascl1, Brn2, Myt1l, Isl1, Hb9, Ngn2 or NeuroD1, or a functional fragment thereof, in a somatic cell.

42. The isolated population of motor neurons of paragraph 41, wherein the motor neuron exhibits at least two characteristics of an endogenous motor neuron.

43. The isolated population of motor neurons of paragraph 41, wherein the somatic cell is a fibroblast.

44. The isolated population of motor neurons of any of paragraphs 41 to 43, produced by the method of any of paragraphs 1 to 40.

45. The isolated population of motor neurons of any of paragraphs 41 to 44, wherein the somatic cell is a mammalian somatic cell.

46. The isolated population of motor neurons of any of paragraphs 41 to 45, wherein the mammalian somatic cell is a human somatic cell.

47. The isolated population of motor neurons of any of paragraphs 41 to 46, wherein the human somatic cell is obtained from a subject at risk or, or having a motor neuron disease or disorder.

48. The isolated population of motor neurons of paragraph 47, wherein the motor neuron disease or disorder is selected from amyotrophic lateral sclerosis (ALS) or spinal muscular atrophy (SMA) or associated diseases thereof.

49. A method for treating a subject with a motor neuron disease or disorder, comprising administering a composition comprising an isolated population of motor neurons according to paragraphs 41 to 48.

50. The method of paragraph 49, wherein the motor neurons are produced from a somatic cell obtained from the same subject as the composition is administered to.

51. The method of paragraph 49, wherein motor neuron disease or disorder is selected from amyotrophic lateral sclerosis (ALS) or spinal muscular atrophy (SMA) or associated diseases thereof.

52. Use of an isolated population of motor neurons according to paragraphs 41 to 48 for administering to a subject in need thereof.

53. An assay comprising an isolated population of motor neurons according to any of paragraphs 41 to 48.

54. The assay of paragraph 53 for use in identifying one or more test agents which promote or inhibit motor neuron survival.

55. The assay of paragraph 53, for use in identifying one or more test agents which promote the direct transdifferentiation of a somatic cell into a motor neuron.

56. A kit comprising at least three of the following agents:

a. a nucleic acid sequence encoding a Lhx3 polypeptide or a functional fragment thereof,
b. a nucleic acid sequence encoding a Ascl1 polypeptide or a functional fragment thereof,
c. a nucleic acid sequence encoding a Brn2 polypeptide or a functional fragment thereof,
d. a nucleic acid sequence encoding a Myt1l polypeptide or a functional fragment thereof,
e. a nucleic acid sequence encoding a Isl1 polypeptide or a functional fragment thereof, f. a nucleic acid sequence encoding a Hb9 polypeptide or a functional fragment thereof,
g. a nucleic acid sequence encoding a Ngn2 polypeptide or a functional fragment thereof, and
h. a nucleic acid sequence encoding a NeuroD1 polypeptide or a functional fragment thereof.

57. The kit of paragraph 56, further comprising instructions for direct transdifferentiation of a somatic cell into a motor neuron comprising at least two characteristics of an endogenous motor neuron.

58. A composition comprising at least one somatic cell and at least three motor-neuron inducing (MN-inducing) factors selected from the group consisting of: Lhx3, Ascl1, Brn2, Myt1l, Isl1, Hb9, Ngn2 or NeuroD1, or a functional fragment thereof.

59. The composition of paragraph 58, wherein the somatic cell is a fibroblast cell.

60. The composition of paragraph 58, further comprising a motor neuron exhibiting at least two characteristics of an endogenous motor neuron.

61. A culture comprising a motor neuron and muscle cells.

62. The culture of paragraph 61, wherein the motor neurons are human motor neurons.

63. The culture of any of paragraphs 61 to 62, wherein the motor neurons are produced according to any of paragraphs 1 to 48.

64. The culture of any of paragraphs 61 to 63, wherein the muscle cells are myotubules.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following Examples are provided to illustrate the present invention, and should not be construed as limiting thereof.

EXAMPLES

The examples presented herein relate to the methods and compositions for producing induced motor neurons (iMNs) from somatic cells, e.g., fibroblasts by increasing the expression of at least three MN-inducing factors selected from Lhx3, Ascl1, Brn2, Myt1l, Isl1, Hb9, Ngn2 or NeuroD1, for example by using nucleic acid sequences to encoding the proteins Lhx3, Ascl1, Brn2, Myt1l, Isl1, Hb9, Ngn2 or NeuroD1 of SEQ ID NO: 1-16 or functional fragments thereof. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods and Materials

Molecular Cloning, Isolating Embryonic and Adult Fibroblasts, Viral Transduction, and Cell Culture.

Complementary DNAs for the 11 candidate factors were each cloned into the pMXs retroviral expression vector using Gateway technology (Invitrogen). Hb9::GFP-transgenic mice (Jackson Laboratories) were mated with ICR mice (Taconic) and MEFs were harvested from Hb9::GFP E12.5 embryos under a dissection microscope (Leica). TTFs were isolated from Hb9::GFPtransgenic adult mice as previously described (Vierbuchen et al., 2010). The fibroblasts were passaged at least once before being used for experiments. HEFs were isolated from human ESCs by culturing them in DMEM+20% fetal bovine serum without bFGF for at least three passages.

Retroviral transduction was performed as described (Ichida et al., 2009). Glial cells isolated from P2 ICR mouse pups were added to infected fibroblasts two days after transduction. The next day, medium was switched either to mouse motor neuron medium containing F-12 (Invitrogen), 5% horse serum, N2 and B27 supplements, glutamax and penicillin/streptomycin, or to N3 medium (Vierbuchen et al., 2010). Both media were supplemented with GDNF, BDNF and CNTF, all at 10 ng/ml. Efficiency of iMN generation was estimated by counting the number of Hb9::GFP+ cells with neuronal morphologies using a fluorescence microscope (Nikon).

Obtaining ESC-Derived and Embryonic Motor Neurons, FACS, Microarray Analysis, and qPCR.

Motor neurons were derived from Hb9::GFP mouse ESCs and isolated by FACS using standard protocol (Di Giorgio et al., 2007). Embryonic motor neurons were harvested from Hb9::GFP E13.5 embryos. Briefly, whole spinal cords were washed in F-12 (Invitrogen) and incubated in 10 nil of 0.025% trypsin with DNase for 45 minutes with gentle agitation every 15 minutes. Media was added to the dissociated spinal cords and the cells were triturated, spun down at 1,000 rpm for 5 minute and resuspended in DMEM/F-12 with glutamax and penicillin/streptomycin. FACS was performed in the same way as with ESC-derived motor neurons. Total RNA isolation, RNA amplification and microarray analysis were performed as described previously (Ichida et al., 2009). qPCR was performed using iScript cDNA synthesis, SYBR green qPCR supermix (Bio-rad), and the primers in Table 2.

TABLE 2

RT-Primer sequences:

| Gene | Forward Primer | Reverse Primer |
|---|---|---|
| Ascl1 | CCAACTACTCCAACGACT (SEQ ID NO: 33) | GGAGAGCCTGGCAGGTCC (SEQ ID NO: 34) |
| Brn2 | GCGCCGAGGATGTGTATG (SEQ ID NO: 35) | AGGAAAGACTGTGGACC (SEQ ID NO: 36) |
| Hb9 | ACAACTTCCCGTACAGCAAT (SEQ ID NO: 37) | CTTCCGCCCTGGAGGCAA (SEQ ID NO: 38) |
| Isl1 | GCGACATAGATCAGCCTGC (SEQ ID NO: 39) | CATCTGAATGAATGTTCC (SEQ ID NO: 40) |

TABLE 2-continued

RT-Primer sequences:

| Gene | Forward Primer | Reverse Primer |
|---|---|---|
| Lhx3 | CCCCCACCCATGAGGGTGCT (SEQ ID NO: 41) | GAGCCAGGGGAAGCAGAGGC (SEQ ID NO: 42) |
| Myt1l | CGTGACTACTTTGACGGA (SEQ ID NO: 43) | TCACCACTAGAGCAGCTGT (SEQ ID NO: 44) |
| Ngn2 | GCGTCATCCTCCAACTCC (SEQ ID NO: 45) | AGAGGGAGACCCGCAGCT (SEQ ID NO: 46) |
| Viral LTR | N/A | TTTGTACAAGAAAGCTGGGT (SEQ ID NO: 47) |

Immunocytochemistry.

Antibody staining was performed as previously described (Ichida et al., 2009). The following primary antibodies were used: mouse anti-Hb9 (DSHB, 1:50), mouse anti-Islet (DSHB, 1:100); mouse anti-TuJ1 (Covance, 1:500); rabbit anti-vChAT (Sigma, 1:1000); rabbit anti-synapsin I (Millipore, 1:500); goat anti-Chx10 (Santa Cruz, 1:200); and rabbit anti-tyrosine hydroxylase (ThermoScientific, 1:300).

Electrophysiology.

Whole-cell voltage-clamp and current-clamp recordings were made using a Multiclamp 700B (Molecular Devices) at room temperature (21-23° C.). Data were digitized with a Digidata 1440A A/D interface and recorded using pCLAMP 10 software (Molecular Devices). Data were lowpass filtered at 2 kHz and sampled at 20 kHz (1 kHz and 2 kHz, respectively, for transmitter application). Patch pipettes were pulled from borosilicate glass capillaries on a Sutter Instruments P-97 puller and had resistances of 2-4 MΩ. The pipette capacitance was reduced by wrapping the shank with Parafilm and compensated for using the amplifier circuitry. Series resistance was typically 5-10 MΩ, always less than 15 MΩ, and compensated by at least 80%. Leak currents were typically less than 200 pA with mean input resistance 675 MΩ and mean resting potential −49 mV. For study of voltage-gated conductances, linear leakage currents were digitally subtracted using a P/4 protocol and voltage was stepped from a holding potential of −80 mV to test potentials from −80 to 30 mV in 10 mV increments. Intracellular solutions were potassium-based solution and contained KCl, 150; MgCl2, 2; HEPES, 10; pH 7.4 used for earlier experiments and KCl, 135; MgCl2, 2; HEPES, 10; MgATP, 4; NaGTP, 0.3; Na2PhosCr, 10; EGTA, 1; pH 7.4 used for later experiments with no obvious difference in sodium and potassium currents. The extracellular was sodium-based and contained NaCl, 135; KCl, 5; CaCl2, 2; MgCl2, 1; glucose, 10; HEPES, 10; pH 7.4). Based on the chloride Nernst potential of −2 mV, inward currents were expected following GABA and glycine treatment (Puia et al., 1990). Transmitters were not washed out, explaining the delayed current decay.

C2C12 Muscle Co-Culture.

C2C12 myoblasts were expanded in DMEM with 20% fetal bovine serum and penicillin/streptomycin. When the culture reached 100% confluency, the serum content was reduced to 5% to induce differentiation. Flow-purified iMNs or iNs were added to the myotubes after 7-14 days and the medium switched to either mouse motor neuron or N3 media. The cocultures were monitored for myotube contractions under the microscope with 10× or 20× objectives. To stop contractions, a solution of tubocurarine hydrochloride was added to a final concentration of between 50 nM and 50 μM. Twitching myotubes were filmed using Nikon ACT-2U Imaging Software (Excel Technologies) and contraction frequencies determined.

iMN-Chick Myotube Co-Cultures and Immunocytochemistry.

Myoblasts were isolated from the epaxial (longissimus) muscles of E10 White Leghorn chick embryos and plated in 24-well plates at a density of 100,000 cells/well. Cultures were maintained at 370 C in F10 media (Gibco) supplemented with 0.44 mg/ml calcium chloride, 10% horse serum, 5% chicken serum and 2% penicillin streptomycin. iMNs were added to the myotubes 5 days later in Neurobasal media (Gibco) supplemented with B27 (Gibco), 1% Lglutamine and 1% penicillin streptomycin. Co-cultures were supplemented with 10 ng/mL CNTF and GDNF every two days for the first week following the addition of the iMNs. Co-cultures were maintained for 3 weeks when they were prepared for immunocytochemistry. Antibody staining was performed as previously described (Soundararajan et al., 2006). A rabbit anti-GFP (Chemicon, 1:2000) primary antibody was used to visualize the iMNs and rhodamine-conjugated α-bungarotoxin (Invitrogen, 1:500) was used to visualize the AChRs. Images were acquired on a laser scanning-confocal microscope (Zeiss LSM 510). Orthogonal images were rendered and edited with LSM imaging software (Zeiss) and further contrast and brightness adjustments were performed on Photoshop version 7.0.

In Ovo Transplantation of ESC-Derived Motor Neurons and iMNs.

In ovo transplantations and immunohistochemistry were performed as previously described 12. Briefly, E2.5 chick embryos were exposed; the vitelline membrane and amnion were cut to allow surgical access to the neural tube. An incision of 1-1.5 somites in length was made along the midline of the neural tube at the rostral extent of the developing hind limb bud (T7-L1) using a flame-sterilized tungsten needle (0.077 mm wire, World Precision Instruments). For control ESC-derived motor neuron transplantations, Hb9::GFP-transgenic mouse ESCs were differentiated into motor neurons as described previously (Soundararajan et al., 2006; Wichterle et al., 2002). A single embryoid body containing approximately 150-200 differentiated Hb9::GFP+ motor neurons was transplanted into the ventral lumen of the neural tube of E2.5 chick embryos as described previously (Soundararaj an et al., 2006). For iMN transplantations, a sphere of iMNs mixed with non-transgenic, ESC-derived motor neurons containing approximately 200 cells was transplanted into the ventral lumen of the neural tube of E2.5 chick embryos. For all transplantations, the chick embryos were harvested five days later, fixed in 4% paraformaldehyde/PBS, cut on a cryostat and then processed for immunohistochemistry. The following primary antibodies were used: rabbit anti-GFP (Chemicon, 1:1000) and mouse anti-Tuj1 (Covance, 1:1000). Images were captured with a digital camera (C4742; Hamamatsu Photonics, Hamamatsu, Japan) in conjunction with digital imaging acquisition software (IPLab; Version 4.0; BD Biosciences, Rockville, Md., USA).

Glia-Neuron Co-Culture for Disease Modeling.

SOD1G93A transgenic mice (Jackson Laboratories) were mated with ICR mice. Glial preps were derived from transgenic P2 pups and their littermates. 3 weeks later, confluent flasks of glial cells were passaged 1:2 onto 6-well plates and iMNs were plated on top. The co-cultures were kept in mouse motor neuron medium with neurotrophic factors and the media changed every other day for the duration of the experiment.

Nestin:: CreER Lineage Tracing.

MEFs were isolated from E13.5 embryos that were transgenic for Nestin::CreER, LOX-STOPLOX H2B-mCherry, and Hb9::GFP. To generate iPSCs, the MEFs were transduced with retroviruses (pMXs vector) encoding Oct4, Sox2, and Klf4. Cells were cultured in mES media containing 13% Knockout Serum Replacement and colonies were picked, expanded, and verified by Nanog immunostaining. For the positive control, iPSCs were differentiated into motor neurons using retinoic acid and Sonic Hedgehog (Wichterle et al., 2002) in the presence or absence of 2 μM 4-OHT. iMNs were also created in the presence or absence of 2 μM 4-OHT.

Example 1

In order to determine whether transcription factors can bestow a precise neural subtype identity, we sought factors that could reprogram fibroblasts into spinal motor neurons. Here, the inventors demonstrate induction of motor neurons based on their significant translational utility and because the developmental origins and functional properties of this neural subtype are among the most well understood.

The inventors demonstrate that when mouse fibroblasts express factors previously found to induce reprogramming toward a generic neuronal phenotype (Vierbuchen et al., 2010), they also respond to components of the transcription factor network that act in the embryo to confer a motor neuron identity on committed neural progenitors. Thus, the inventors demonstrated that forced expression of these transcription factors converted mouse fibroblasts into induced motor neurons (iMNs).

Importantly, the inventors demonstrated that the resulting iMNs had a gene expression program, electrophysiological activity, synaptic functionality, in vivo engraftment capacity and sensitivity to disease stimuli that are all indicative of a motor neuron identity. The inventors also demonstrate that the converting fibroblasts do not transition through a proliferative neural progenitor state before becoming motor neurons, indicating they are formed in a manner that is distinct from embryonic development. Finally, the inventors demonstrate that this same approach can convert human fibroblasts into motor neurons.

Example 2

11 Factors Convert Fibroblasts into Hb9::GFP+ Cells with Neuronal Morphologies

The inventors assessed if transcription factors known to instruct motor neuron formation during development might also facilitate the conversion of other cell types into motor neurons. The inventors used the literature to select eight candidate transcription factors that participate in varied stages of motor neuron specification (Jessell, 2000). In order to potentially aid the transition toward a neuronal phenotype, the inventors supplemented the motor neuron specification factors with three factors that convert fibroblasts into induced neurons (iNs) of a generic character (Ascl1, Brn2 and Myt1l) (Vierbuchen et al., 2010) (FIG. 1A).

Figure 8A:
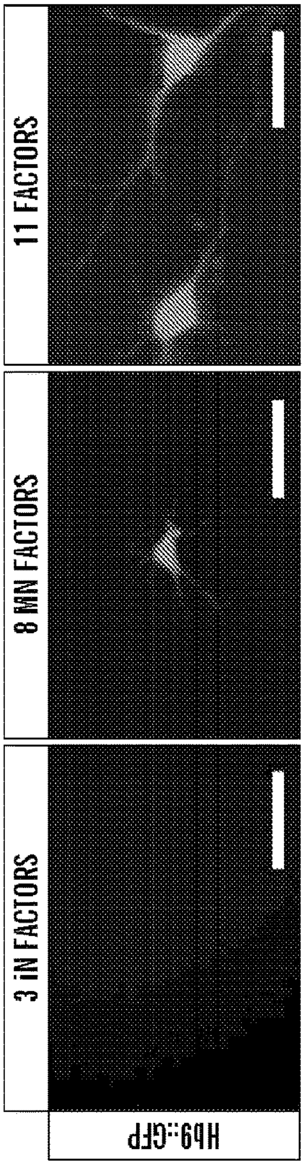
FIGS. 8A-8E are related to FIG. 1 and show the induction of Hb9::GFP+ Neurons from Fibroblast Cultures.

For reprogramming studies, mouse embryonic fibroblasts (MEFs) were harvested from Hb9::GFP mouse embryos at day E12.5, allowing spinal motor neuron conversion to be monitored. Prior to use, cultures of MEFs were carefully screened for the absence of any contaminating GFP+ cells. First, the action of the three iN factors alone was assessed to determine if they could generate Hb9::GFP+ cells by transducing MEFs with retroviral vectors encoding Ascl1, Brn2 and Myt1l (FIG. 1A). Although cells with a neuronal morphology were observed, as previously reported (Vierbuchen et al., 2010), no Hb9::GFP+ cells emerged, even after 35 days (FIG. 8A). This demonstrates that while iN factors can generate neurons, the iN factors alone do not generate motor neurons, consistent with the report that cholinergic neurons were not generated by these factors (Vierbuchen et al., 2010).

Figure 1B:
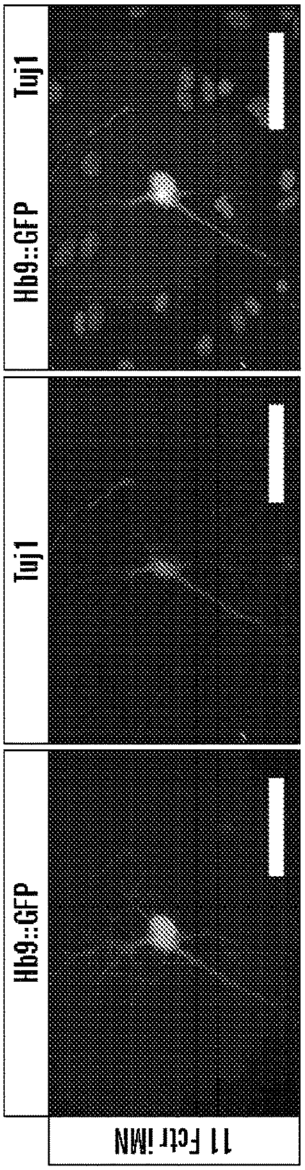

The inventors next assessed whether the selected eight motor neuron (MN) specification factors could induce motor neurons in the absence of the three iN factors. Based on titering with a control virus encoding GFP, the inventors determined that each factor was expressed in >95% of the fibroblasts. Encouragingly, a small number of Hb9::GFP+ cells were detected at 35 days post-transduction; however, they did not possess a normal neuronal morphology (FIG. 8A). The inventors therefore next asked whether the two sets of factors, iN factors and motor neuron specification factors, together could synergize to produce motor neurons. Indeed, when the aggregate set of 11 factors was transduced into fibroblasts, a significant number of Hb9::GFP+ cells emerged, which elaborated complex processes and all of which expressed a neuronal form of tubulin (n=50) (FIG. 1B). These cells were preliminarily designated these Hb9::GFP+ cells, induced motor neurons (iMNs).

Example 3 iMNs are Efficiently Induced by 7 Factors

Figure 1C:
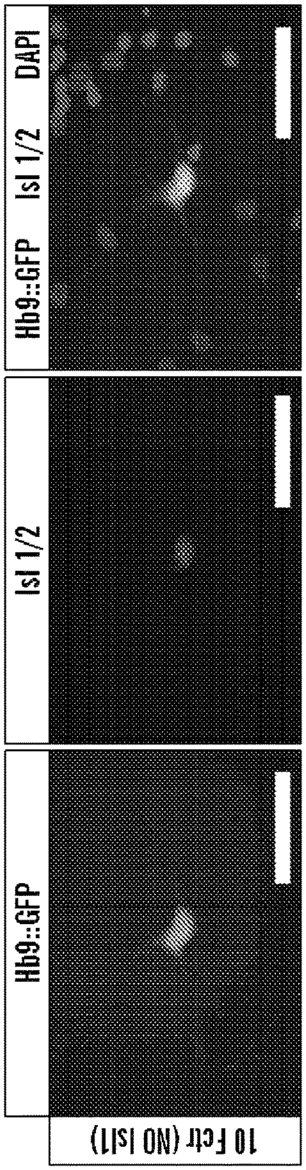
Figure 1E:
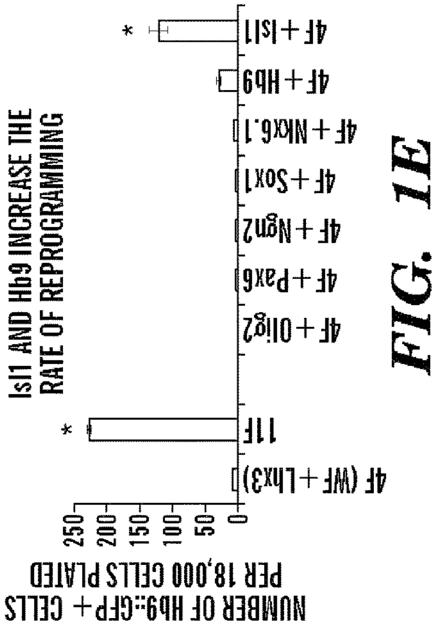
Figure 1G:
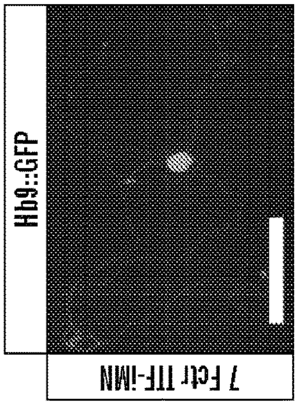
Figure 1D:
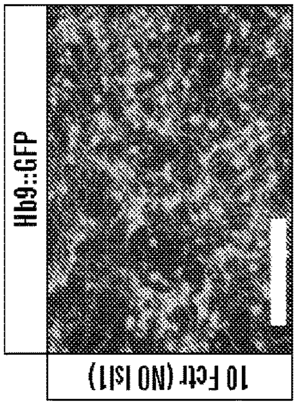
Figure 8B:
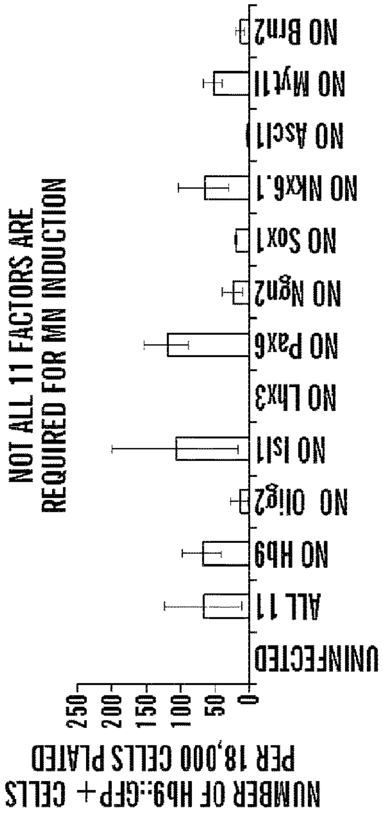

To determine which of the 11 factors were necessary for generating iMNs, each gene was omitted one at a time (FIG. 8B). Excluding either Lhx3 or Ascl1 eliminated iMN formation. However, reprogramming efficiency was either only slightly reduced or unchanged when each of the remaining factors were removed (FIG. 8B). Interestingly, ectopic expression of Hb9 was not required for iMN formation (FIG. 8B), demonstrating that, at least in that case, exogenous Hb9 was not simply transactivating its own promoter. Similarly, Isl1/2 expression was detected by immunostaining in iMNs (80.6%, n=36), even when the Isl1 retrovirus was omitted from the transduction (FIGS. 1C-D and FIG. 8B).

Figure 1F:
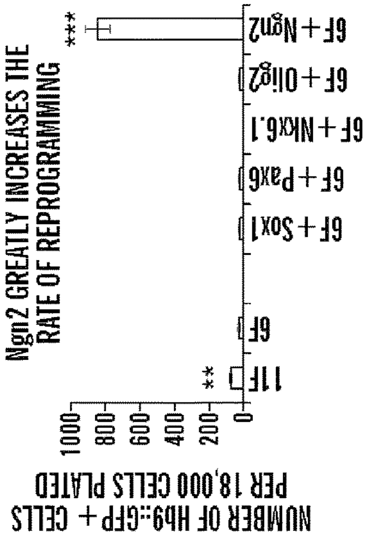
Figure 8C:
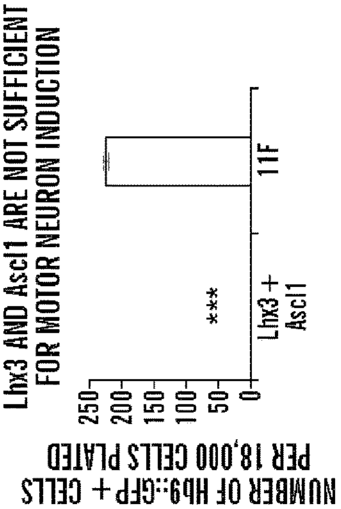
Figure 8E:
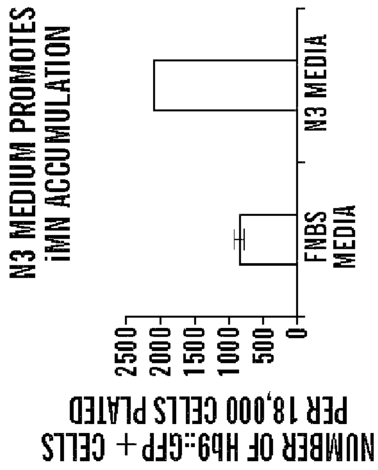
Figure 8D:
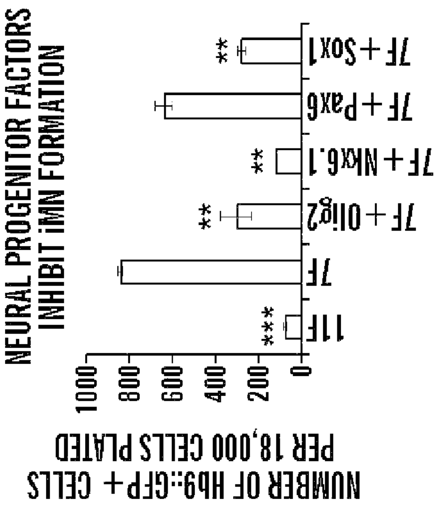

Although Lhx3 and Ascl1 seemed necessary for reprogramming, they were not sufficient to induce motor neuron formation (FIG. 8C). However, when Lhx3 was combined with the three iN factors (Ascl1, Brn2 and Myt1l), a modest number of Hb9:: GFP+ cells were detected (FIG. 1E). Because these four factors could not efficiently induce motor neuron formation, the inventors next individually added each of the other factors back to this smaller set (FIG. 1E). The inventors discovered that either Isl1 or Hb9 were capable of increasing the efficiency of iMN induction, which was further enhanced when Ngn2 was added to the other 6 factors (FIG. 1F). Indeed, the efficiency of motor neuron induction with these 7 factors (Ascl1, Brn2, Myt1l, Lhx3, Hb9, Isl1 and Ngn2) surprisingly surpassed the activity of the 11 as a whole and, depending on the culture conditions used, reached between 5% and 10% of the number of MEFs transduced (FIG. 1F and FIG. 8E). Surprisingly, adding any one of the remaining factors, which were previously all known to function in earlier stages of motor neuron specification (Lee et al., 2005), dramatically decreased the efficiency of reprogramming by the 7 factors (FIG. 8D).

The inventors next assessed if the apparently homogeneous MEF cultures which lacked Hb9::GFP+ cells, could be contaminated with rare embryonic neuronal progenitors that might be more responsive to reprogramming. To rule out the possibility that iMNs originated from such progenitors, fibroblasts from the tails of adult Hb9::GFP mice were prepared and transduced with the optimal set of 7 factors. Again, GFP+ cells with neuronal morphologies were detected (FIG. 1G), demonstrating that the ability to respond to the 7 iMN factors was not restricted to cells of an embryonic origin.

Example 4 iMNs Possess a Motor Neuron Gene Expression Signature

Figure 2A:
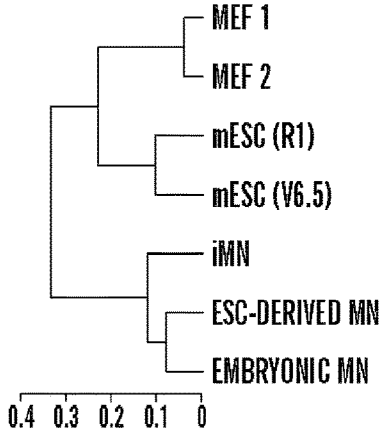
FIG. 2A-2E shows iMNs Possess Gene Expression Signatures of Motor Neurons.
Figure 2B:
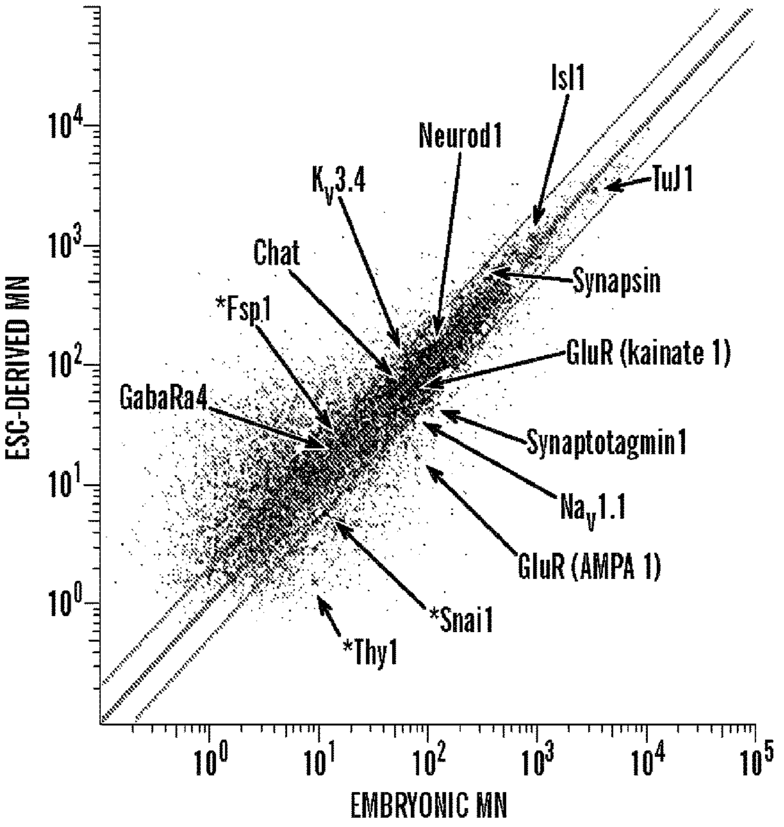
Figure 9A:
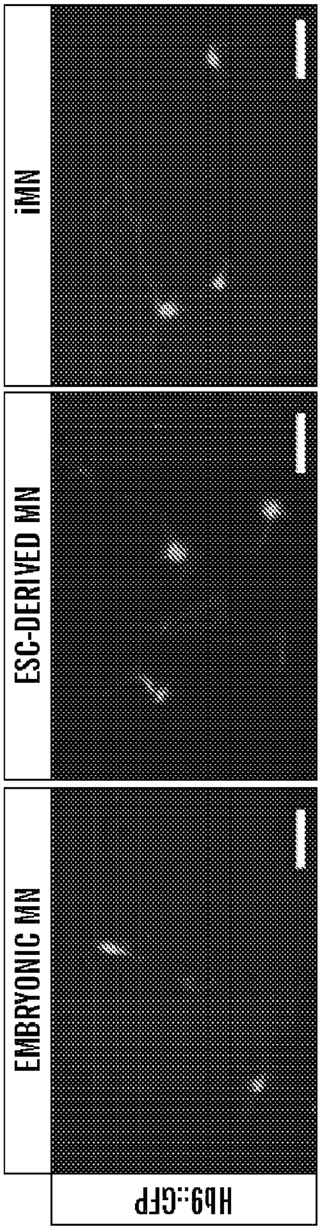
FIG. 9A-9H, is related to FIGS. 2 and 3. iMNs Possess Molecular Signatures of Motor Neurons.
Figure 9B:
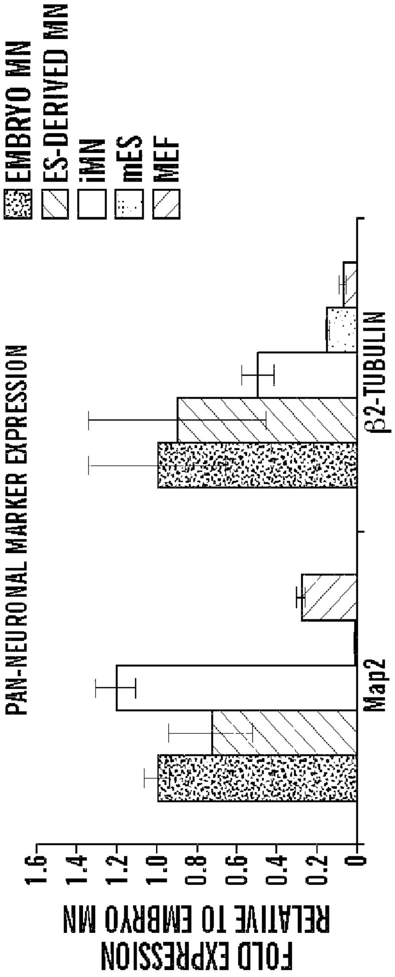
Figure 9C:
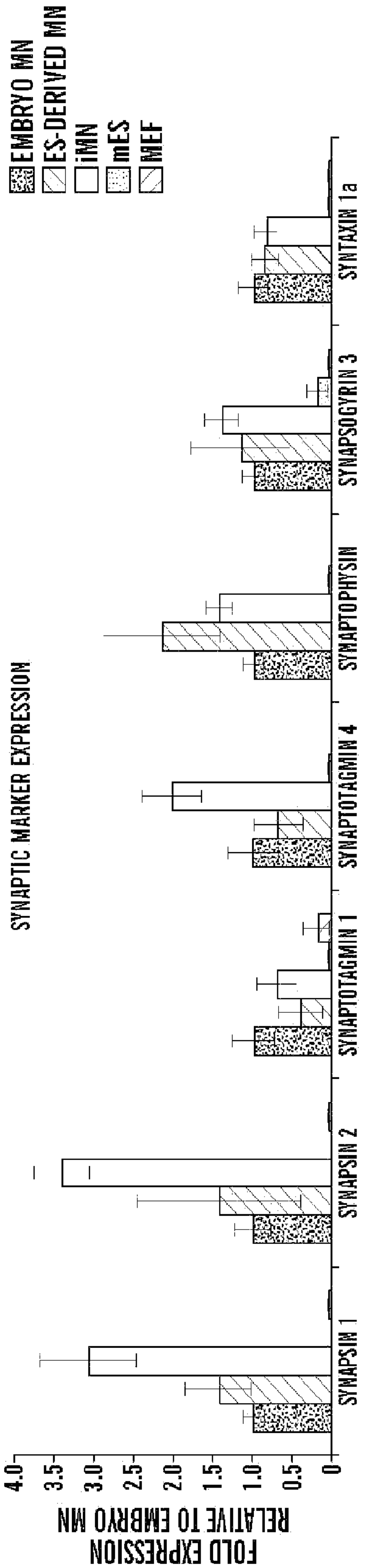
Figure 9D:
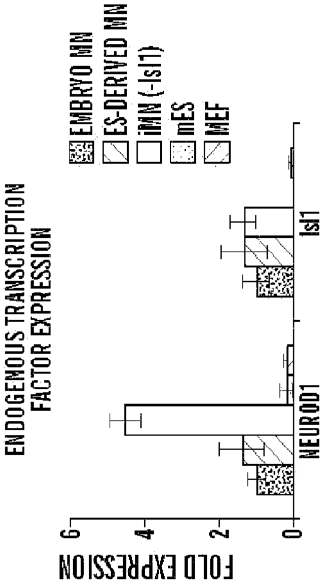

To assess whether iMNs had the known characteristics of cultured embryonic motor neurons, the inventors carefully examined the phenotype of iMNs made with 10 factors (Isl1 omitted). The inventors demonstrated that iMNs were comparable in cell body size and projection length to both E13.5 embryo and ESC-derived motor neuron controls (FIG. 9A). To determine how similar overall transcription in iMNs was to control motor neurons, the three motor neuron types were isolated by fluorescence-activated cell sorting (FACS) and assessed by transcriptional profiling (FIG. 2A-2D). For these analyses, RNAs isolated from MEFs and ESCs were used as negative controls. On hierarchical clustering of the data, iMNs grouped closely to embryonic motor neurons, as did ESC-derived motor neurons (FIG. 2A). In contrast, iMNs were very distinct from the initial MEF population. Thus, the inventors demonstrate that transduction of MEFs with these transcription factors results in a global shift towards a motor neuron transcriptional program.

Figure 2C:
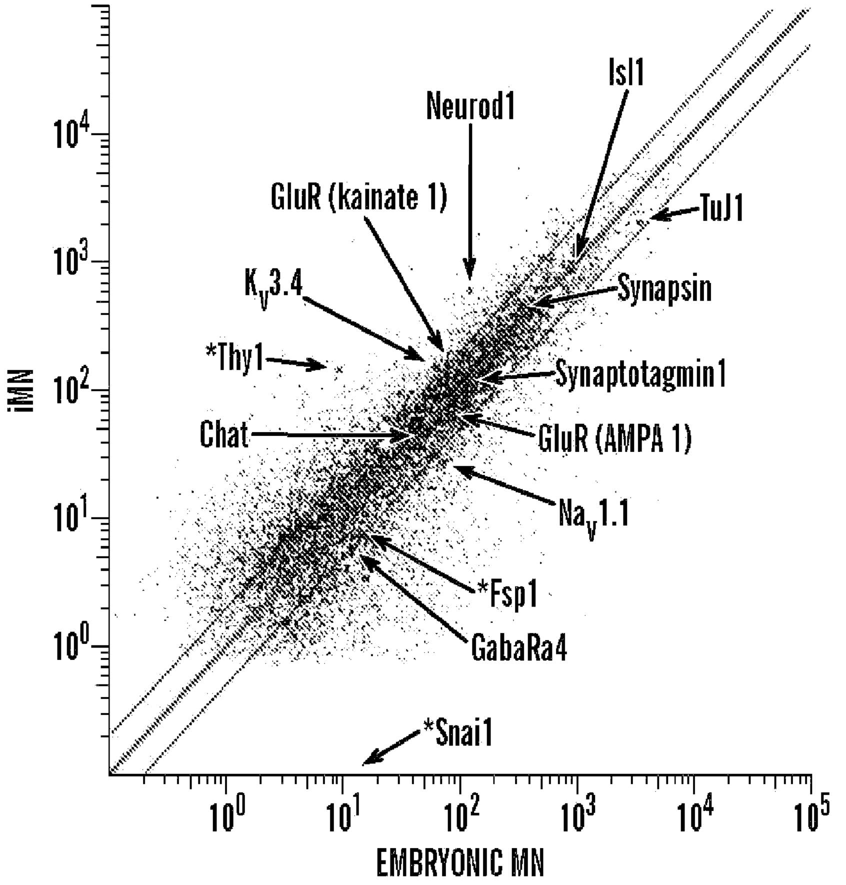
Figure 2D:
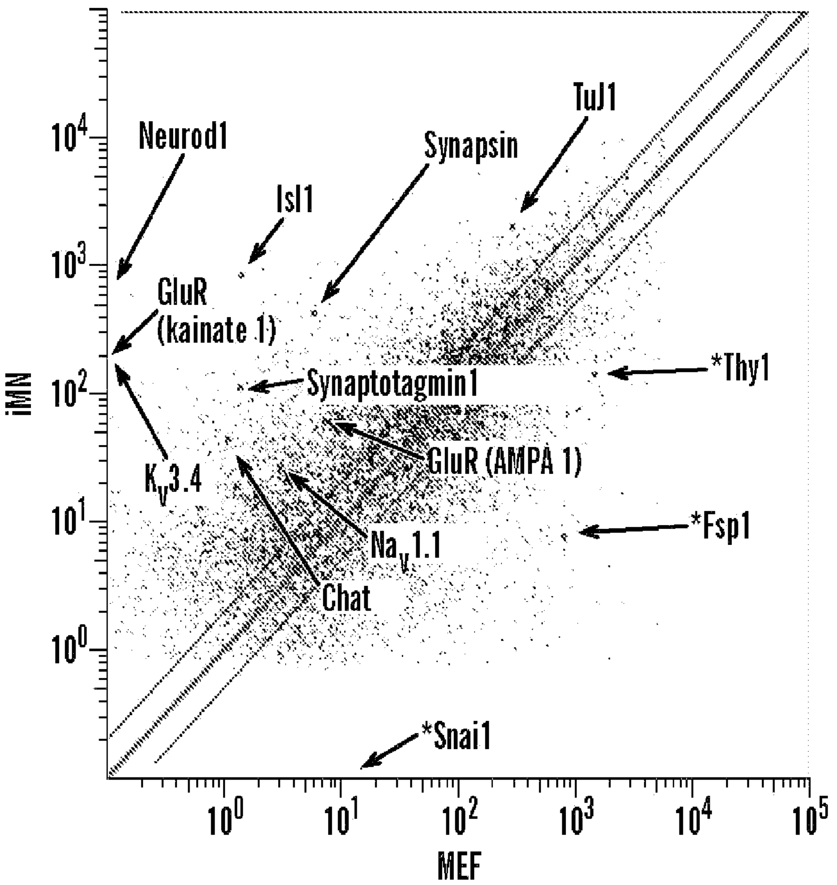
Figure 9E:
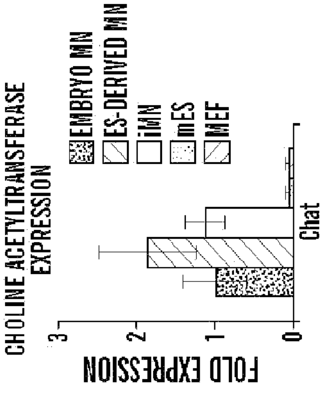
Figure 9F:
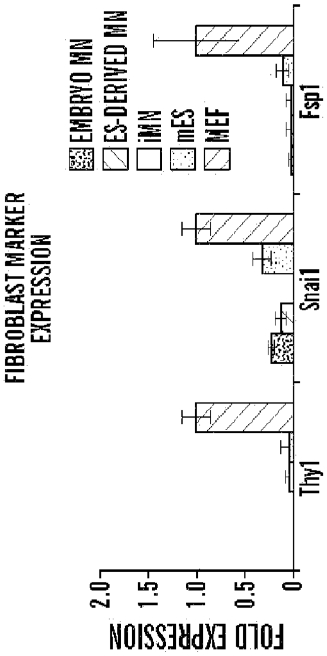

On examination of the transcription of specific neuronal genes, the inventors demonstrated that iMNs and control motor neurons were very similar. Relative to either MEFs or ESCs, iMNs and both types of control motor neurons expressed elevated levels of β2-tubulins (Tubb2a and Tubb2b) and Map2 (FIG. 2B-D and FIG. 9B), as well as synaptic components such as synapsins (Syn1 and Syn2), synaptophysin (Syp) and synaptotagmins (Syt1, Syt4, Syt13 and Syt 16) (FIG. 2B-D and FIG. 9C). iMNs also expressed known motor neuron transcription factors that were not provided exogenously (NeuroD and Isl1) (FIG. 2C-D and FIG. 9D), as well as the gene encoding the enzyme cholineacetyltransferase (ChAT) (FIG. 2C-D and FIG. 9E). In contrast, iMNs had downregulated the fibroblast program as exemplified by reduced transcription of Snai1, Thy1 and Fsp1 (FIG. 2D and FIG. 9F).

Figure 2E:
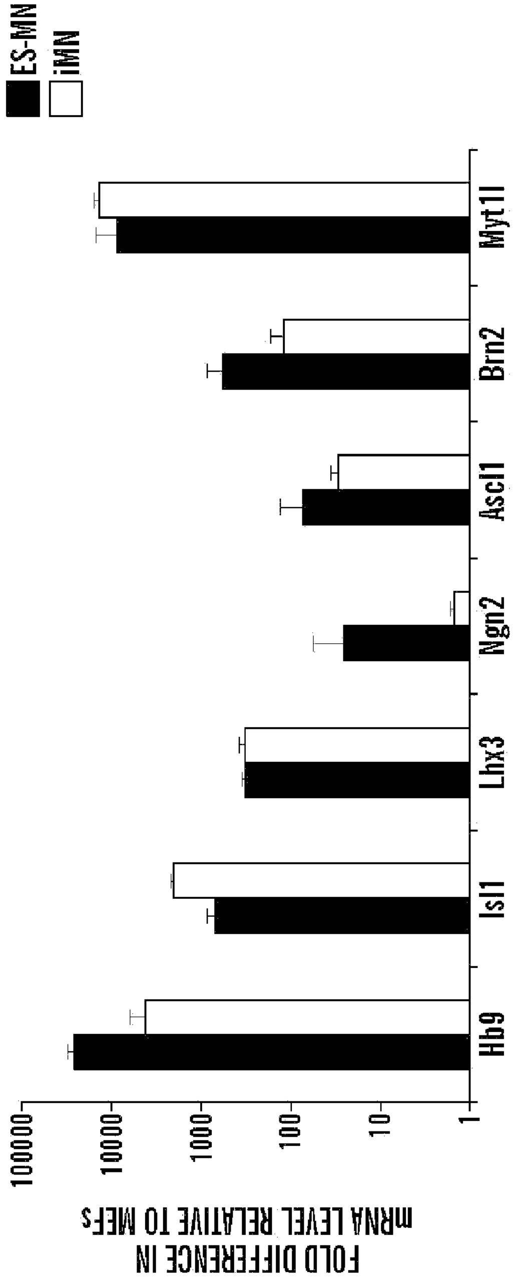
Figure 3A:
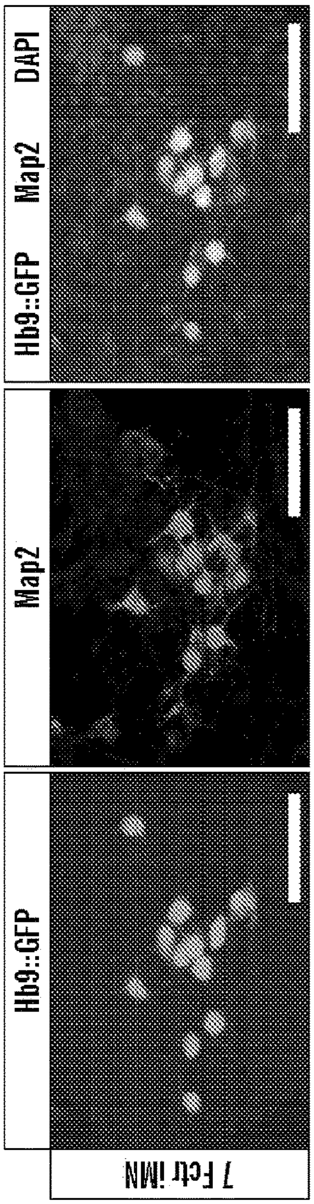
FIGS. 3A-3D show iMNs Express Neuronal and Motor Neuron Proteins.
Figure 3B:
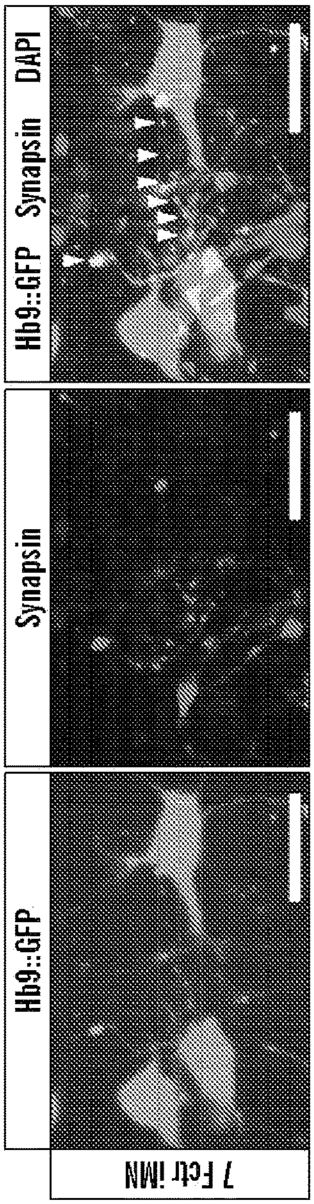
Figure 3C:
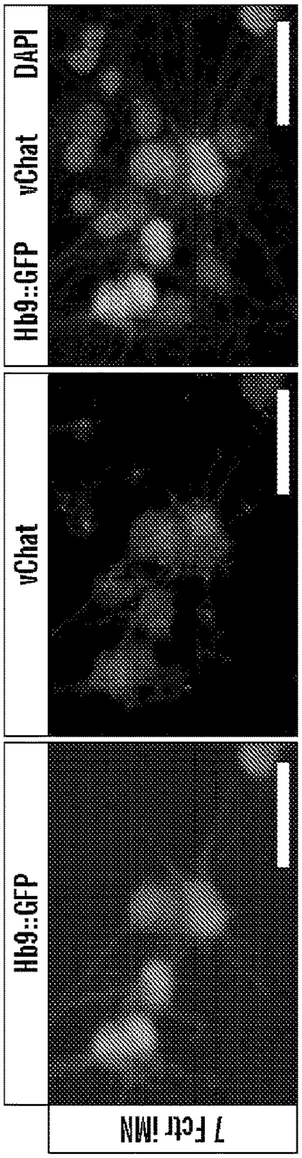
Figure 3D:
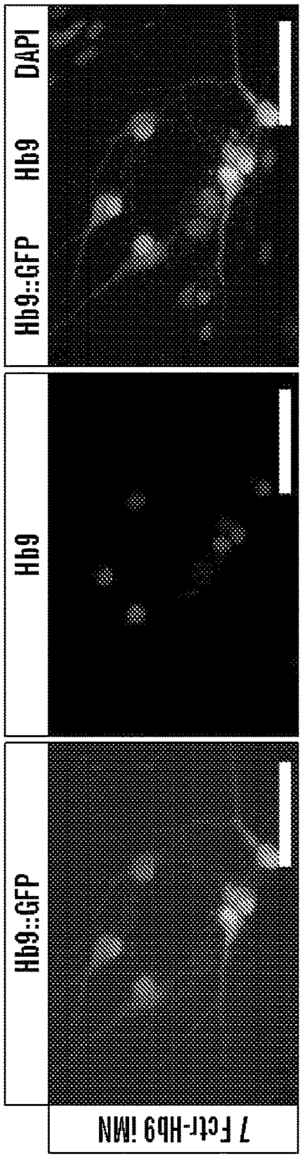
Figure 9G:
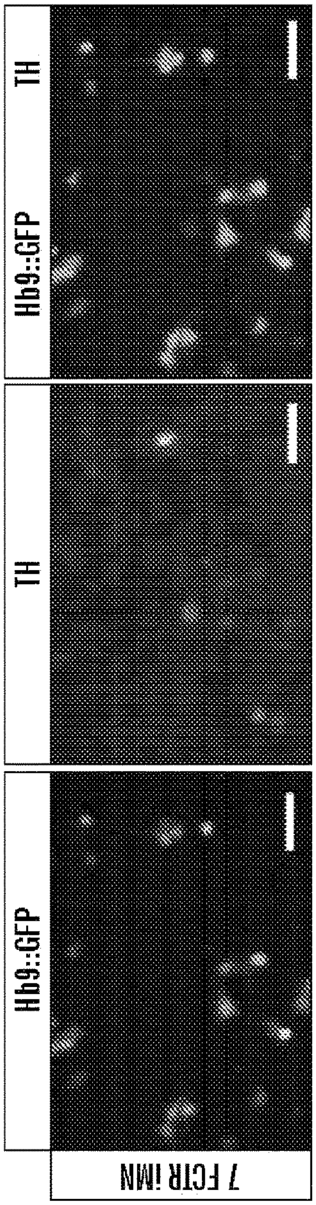
Figure 9H:
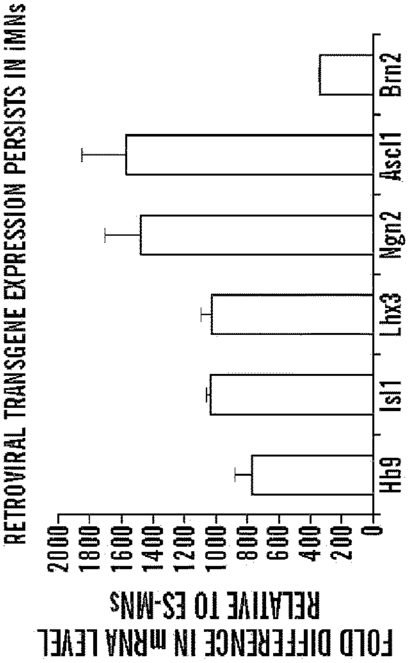

Immunostaining confirmed that the iMNs expressed Map2 (100%, n=120) (FIG. 3A), synapsin (FIG. 3B), and vesicular ChAT (97.6%, n=124) (FIG. 3C), demonstrating that they had indeed activated the enzymatic pathways for producing acetylcholine (ACh), the neurotransmitter released by motor neurons, and demonstrating that iMNs should be capable of forming functional synapses. In contrast, the vast majority of iMNs did not express tyrosine hydroxylase (3%, n=150) (FIG. 9G), demonstrating that they were not of a mixed neuronal character. In order to determine if the iMNs truly adopted a new cellular identity through transdifferentiation, qRT-PCR analysis was performed to assess if they established an endogenous program of motor neuron gene expression (Table 2). As expected for a somatic cell type such as the motor neuron, the retroviral transgenes used for reprogramming were not silenced in the iMNs (FIG. 9H), leaving it unclear as to whether the endogenous loci of these motor neuron genes had been activated. When the inventors quantified the endogenous mRNA levels of the motor neuron-specific genes used for conversion, they discovered that all 7 transcription factors were expressed at levels similar to those in ESC-derived motor neurons (FIG. 2E). Furthermore, immunostaining revealed that iMNs created without exogenous Hb9 still activated expression of this important transcription factor from the endogenous locus (87.9%, n=149) (FIG. 3D). Together, the inventors herein demonstrate that the iMNs produced had established a transcriptional program characteristic of motor neurons.

Example 5 iMNs Possess the Electrophysiological Characteristics of Motor Neurons

Figures 4A, 4B, 4C, 4D, 4E, 4F, 4G, 4H:
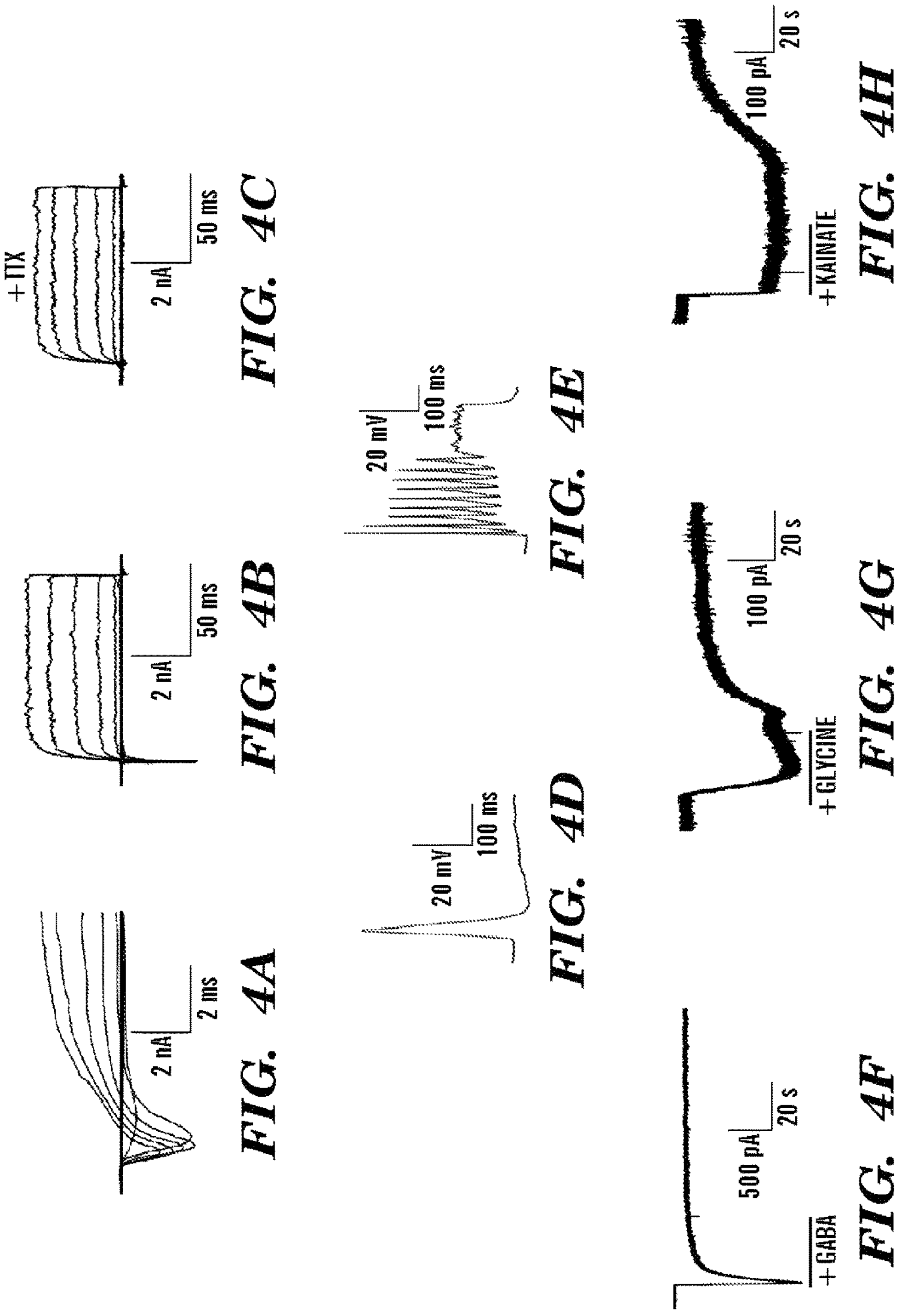
FIGS. 4A-4J show Electrophysiological Activity and In Vitro Functionality of iMNs.
Figure 10A:
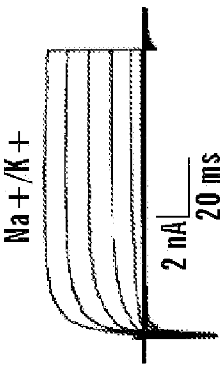
FIGS. 10A-10L is related to FIG. 4 and shows electrophysiological Activity and In Vitro Functionality of iMNs.
Figure 10B:
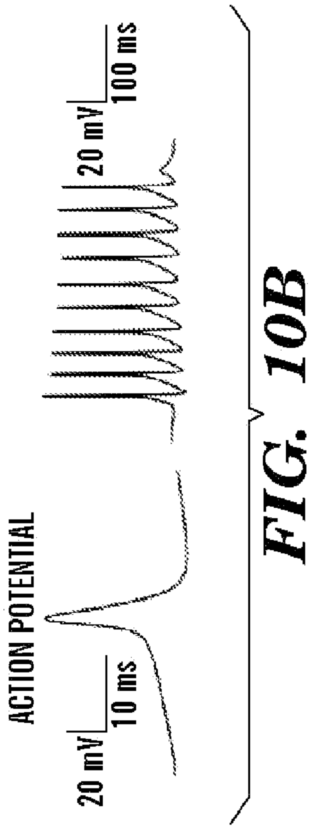

In order to determine if MEF- and tail tip fibroblast-derived iMNs possessed the electrophysiological properties of motor neurons, the inventors performed whole-cell patch clamp recordings. The average resting membrane potential for iMNs was −49.5 mV (SEM 5.6, n=6), which was similar to that for control ESC-derived motor neurons (−50.5 mV, SEM 3.5, n=13). Depolarizing voltage steps in voltage clamp elicited fast inward currents followed by slow outward currents, consistent with the opening of voltage-activated sodium and potassium channels, respectively (FIGS. 4A-B and FIG. 10A). The inward current was blocked by addition of 500 nM tetrodotoxin (TTX), a potent antagonist of TTX-sensitive voltage-activated sodium channels (FIG. 4C). A defining feature of a neuron is its ability to fire action potentials. In current clamp experiments with iMNs, depolarizing current steps produced single or multiple action potentials (90%, n=10), with overshoot, after-hyperpolarizations and a firing frequency similar to that reported for ESC-derived motor neurons and rat embryonic motor neurons (Alessandri-Haber et al., 1999) (FIGS. 4D-E and FIG. 10B).

Figure 10C:
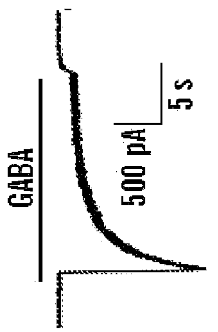
Figure 10D:

The inventors next assessed whether iMNs express functional receptors for the excitatory and inhibitory neurotransmitters that normally act on motor neurons. As might be expected given the known receptor subunit transitions associated with development of immature neurons to a fully differentiated state, certain agonists yielded responses in some but not all neurons. Glycine and GABA are the major inhibitory neurotransmitters, and their ionotropic activity is mediated by opening chloride channels. Addition of 100 μM glycine (44.4%, n=9, FIG. 4F) or GABA (72.7%, n=11, FIG. 4G, and FIG. 10C) elicited inward currents when cells were held at −80 mV. We also evaluated the response of iMNs to fast excitatory glutamatergic neurotransmitters and observed a strong response to the receptor agonist kainate (80%, n=15 cells, FIG. 4H, and FIG. 10D).

Figure 10E:
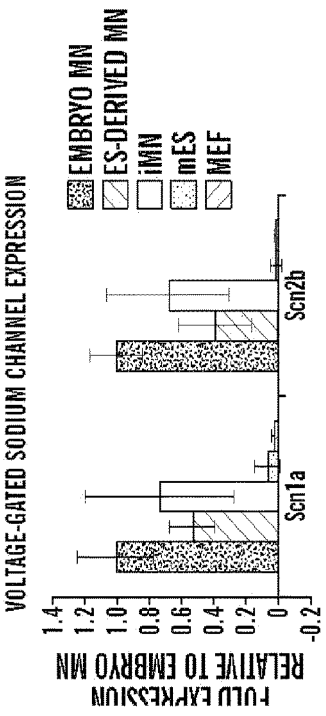
Figure 10F:
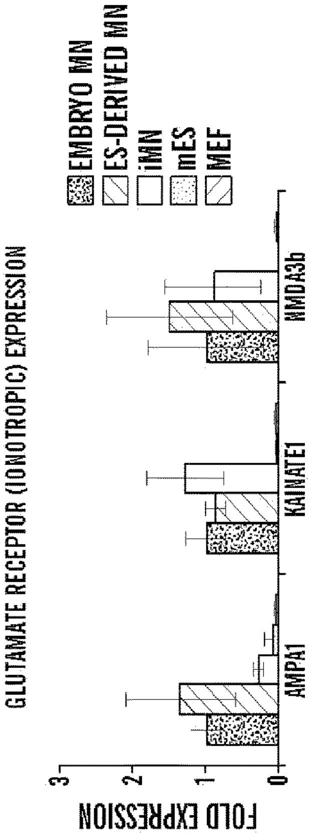
Figure 10G:
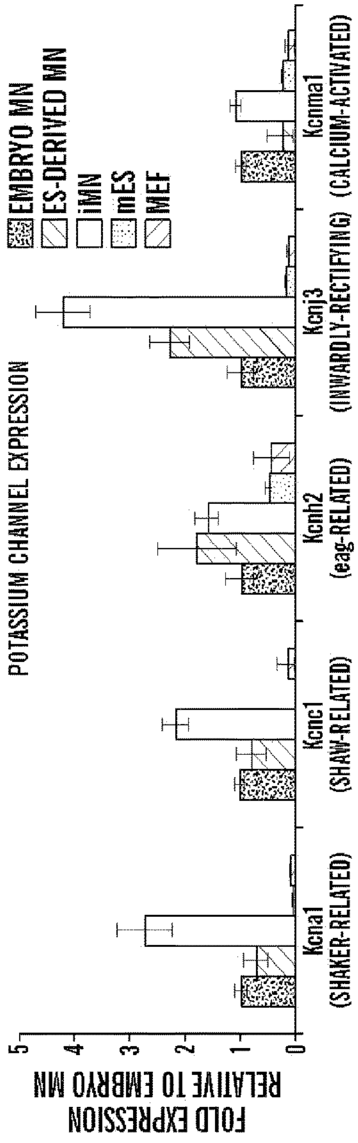

Consistent with the physiological analyses, and similar to previously reported control embryonic motor neurons and motor neuron populations (Cui et al., 2006), the iMNs transcribed the genes encoding a and (3 subunits of voltage-gated sodium channels (FIG. 2C-D and FIG. 10E), as well as members of the Shaker-, Shaw-, and Eag-related, inwardly rectifying, and calcium-activated families of potassium channels (FIG. 2C-D and FIG. 10G). In addition, iMNs transcribed genes encoding the receptor components required for responding to the neurotransmitter glutamate (FIG. 2C-D and FIG. 10F). Thus the inventors, using physiological and gene expression analyses, clearly demonstrate that iMNs are excitable, generate action potentials and respond to both inhibitory and excitatory neurotransmitters in a manner characteristic of both ESC-derived and embryonic motor neurons.

Example 6 iMNs Form Functional Synapses with Muscle

Figure 10H:
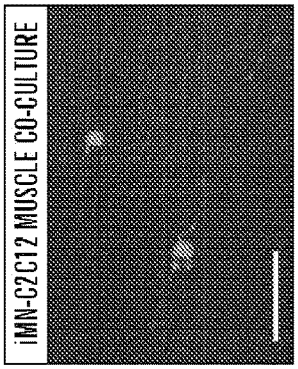
Figure 10I:
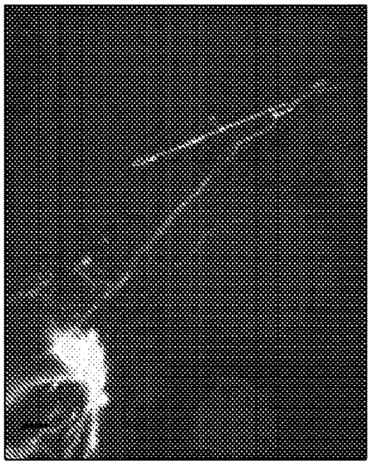
Figure 10J:
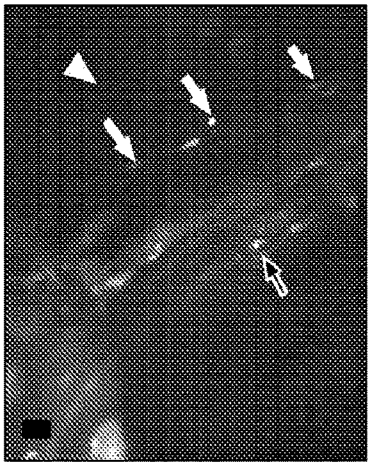
Figure 10K:
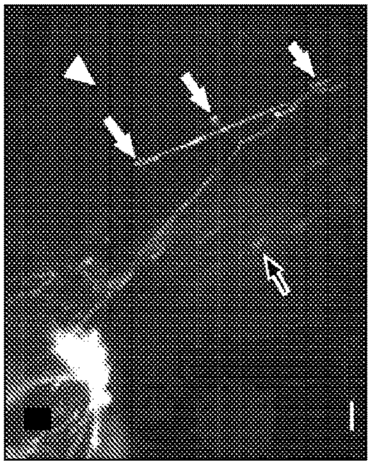

The inventors initial analysis demonstrated that iMNs have many of the phenotypic and electrophysiological properties of bona fide motor neurons. However, the defining functional characteristic of the spinal motor neuron is its ability to synapse with muscle and, through the release of acetylcholine (ACh), stimulate muscle contraction. To test whether iMNs could form functional neuromuscular junctions (NMJs), the inventors co-cultured FACS-purified iMNs with myotubes derived from the C2C12 muscle cell line. The inventors demonstrate that iMNs could establish themselves in these muscle cultures and sent projections along the length of the myotubes (FIG. 10H).

Figure 4I:
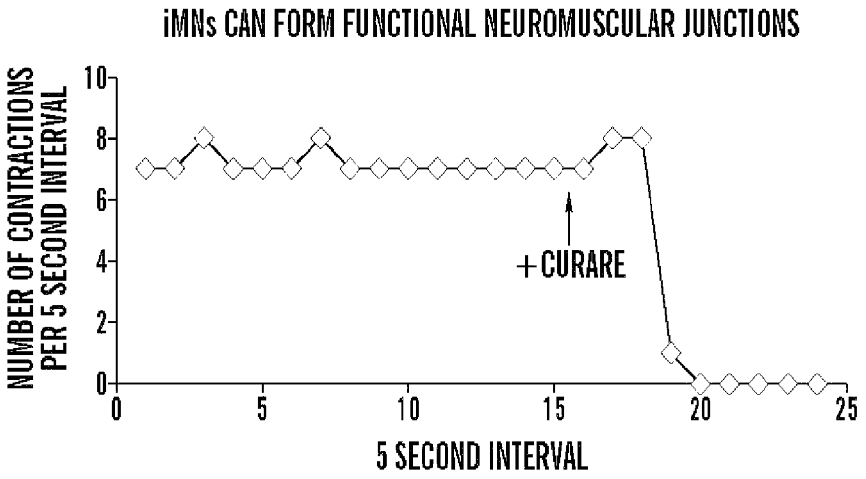
Figure 4J:
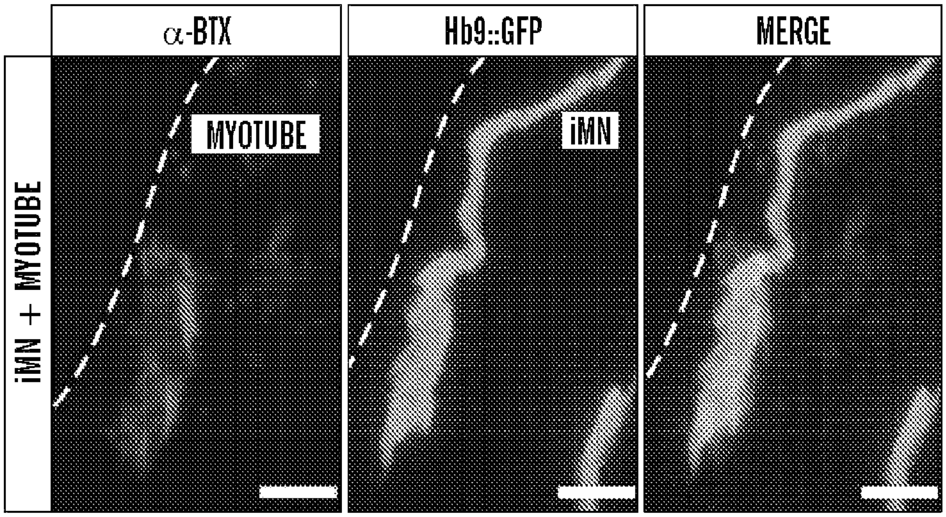

Strikingly, the inventors demonstrated that several days following the addition of purified iMNs, C2C12 myotubes began to undergo regular and rhythmic contraction (FIG. 4I). Regular contractions were not seen at this time point in myotubes that were cultured alone or with generic iNs (Table 3).

Figure 10L:
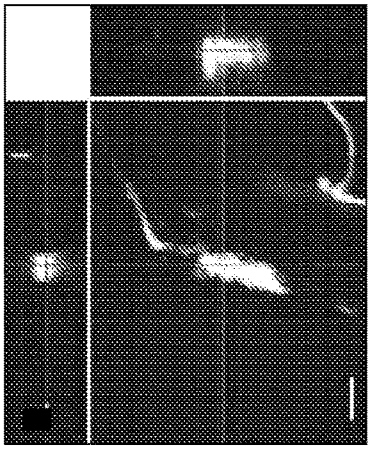

To directly test whether the regular contractions of myotubes were due to synaptic stimulation of ACh receptors, the inventors quantified the frequency of myotube contraction and then added curare to the culture medium. As curare selectively and competitively antagonizes nicotinic ACh receptors, its addition should only inhibit muscle contractions that result from stimulation of such receptors (FIG. 4I and data not shown). Shortly after the addition of curare, the inventors detected a precipitous and sustained decline in the frequency of myotube contraction, demonstrating that the contractions were indeed dependent on the stimulation of ACh receptors. In order to directly visualize NMJ formation in iMN cultures, iMNs were co-cultured with primary chick myotubes (FIG. 4J and FIGS. 10I-10L). After one week of co-culture, the inventors determined that many Hb9::GFP+ iMNs survived even following withdrawal of neurotrophic support, demonstrating that they had formed synapses with the muscle. Three weeks after co-culture had been initiated, staining with α-bungarotoxin (α-BTX) revealed ACh receptor clustering on the myofibers (FIG. 4J and FIG. 10I-K). As occurs in ESC-derived motoneuron/chick myotube cocultures (Miles et al., 2004; Soundararajan et al., 2007), ACh receptors clustered preferentially near the iMN axons, although the clustering was not always clearly opposed to Hb9::GFP+ axons. This phenomenon is similar to what occurs during chick (Dahm and Landmesser, 1988) and mouse (Lupa and Hall, 1989) neuromuscular development where receptor clustering first appears near the innervating motor axons, but not always in direct contact. Imaging in the x-z and y-z orthogonal planes verified that ACh receptors clustered near iMN axons superimposed with the Hb9::GFP+ axons (FIG. 10L). These results demonstrate that the iMNs signal to the post-synaptic muscle fiber to induce appropriate receptor clustering which is necessary for neuromuscular transmission. Together, the inventors have determined that functional iMNs can be produced from fibroblasts which make functional synaptic functions with muscle.

TABLE 3 iMNs induce contraction of C2C12 myotubules. FACS-purified iMNs and ins were plated on top of C2C12 myotubules. At day 10 after the start of co-culture, contraction was detected in myotubules cultured with iMNs. Myotubules cultured alone or with iNs did not exhibit contractions at this time point.

| | Total number of dishes | Dishes with twitching muscle | Dishes with <2 twitching areas |
|---|---|---|---|
| iMN on muscle | 5 | 4 | 3 |
| iN on muscle | 2 | 0 | n/a |
| Muscle only | 10 | 0 | n/a |

Example 7 iMNs Integrate into the Developing Chick Spinal Cord

Figure 5A:
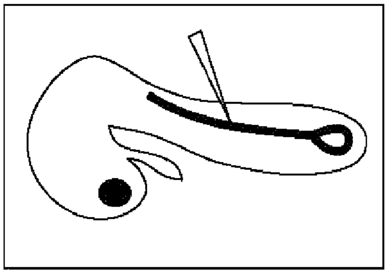
FIGS. 5A-5F show In Vivo Functionality and In Vitro Utility of iMNs.
Figure 5B:
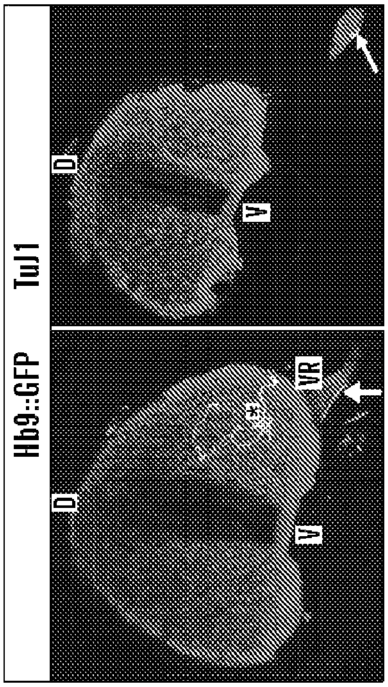
Figure 11:
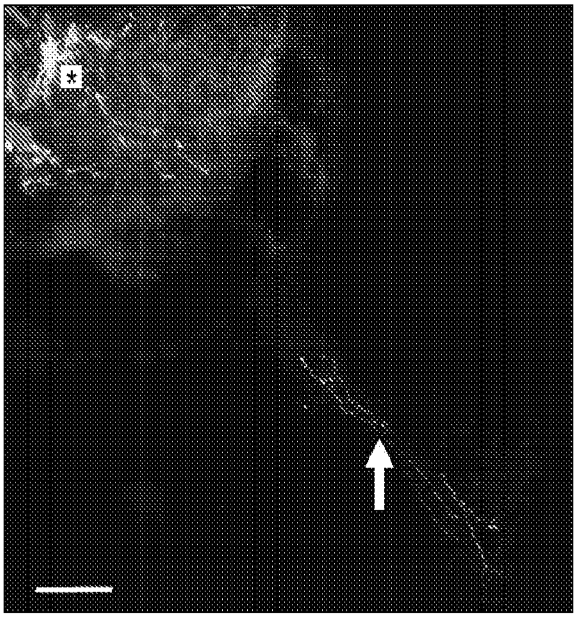
FIG. 11 is related to FIG. 5, and shows mouse ESC-Derived Motor Neurons Integrate into the Developing Chick CNS. ESC-derived motor neurons (asterisks) engrafted into the ventral horn and extended axons out of the spinal cord through the ventral root (arrow) 5 days after transplantation into an E2.5 chick embryo neural tube. Scale bar represents 100 μm.

Transplantation of motor neurons into the developing chick spinal cord provides a rigorous test of their ability to survive in vivo, migrate to appropriate engraftment sites in the ventral region of the spinal cord, and to properly respond to axon guidance cues to send their axonal projections out of the spinal cord through the ventral root (Peljto et al., 2011; Soundararajan et al., 2006; Wichterle et al., 2002). In order to test the ability of iMNs to survive and function in vivo, FACS-purified iMNs or control ESC-derived motor neurons were transplanted into the neural tube of stage 17 chick embryos at 12-16 days post-transduction (FIG. 5A). Although the injection of the iMNs along the dorsal-ventral axis was not precisely controlled, the inventors determined that Hb9::GFP+ iMNs engrafted in the ventral horn of the spinal cord in the location where endogenous motor neurons reside at stage 31 (FIG. 5B). Like transplanted ESC-derived motor neurons (Soundararajan et al., 2006; Wichterle et al., 2002), the Hb9::GFP+ cells maintained Tuj1 expression and exhibited extensive dendritic arbors (FIG. 5B). In addition, the inventors assessed whether iMNs project their axons out of the CNS. Endogenous and transplanted ESC-derived motor neurons send axonal projections out of the spinal cord through the ventral root towards musculature (FIG. 11) (Soundararajan et al., 2010; Wichterle et al., 2002). When Hb9::GFP ESCs are subjected to directed differentiation toward motor neurons, the resulting EBs contain both GFP+ motor neurons and distinct, non-motor neuronal subtypes that do not express GFP. In contrast to GFP+ motor neurons, GFP− non-motor neuron subtypes present within the same transplants extend extensive processes whose projections remain restricted to the developing spinal cord and do not exit through the ventral root (Soundararajan et al., 2010). Therefore, the chick transplantation assay can be used to measure motor neuron-specific axonal pathfinding. Indeed, after transplantation, the inventors determined Hb9::GFP+ iMNs in the ventral horn of the spinal cord, and in 80% (n=5) of these cases, axons of Hb9::GFP+ iMNs were detected to be projecting out of the spinal cord through the ventral root towards the musculature (FIG. 5B). Thus, Hb9::GFP+ iMNs in vivo engraftment capacity was similar to that for ESC-derived Hb9::GFP+ motor neurons (FIG. 11). Thus the inventors have demonstrated that iMNs are able to engraft, migrate to appropriate sites of integration, and correctly respond to guidance cues in vivo, projecting their axons out of the CNS.

Example 8 iMNs are Sensitive to Disease Stimuli

Figure 5C:
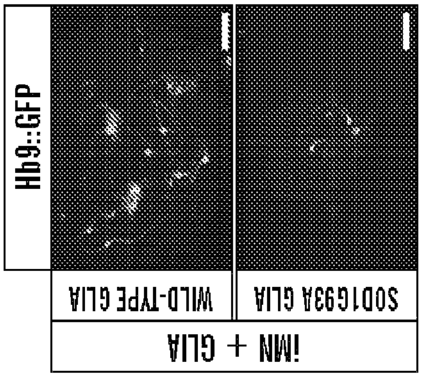
Figure 5D:

ALS is an invariably fatal neurological condition whose hallmark is the selective and relentless degeneration of motor neurons. The inventors assessed if iMNs fully phenocopied bona fide motor neurons by assessing if they are also sensitive to degenerative stimuli thought to contribute to ALS. To assess this, iMNs were co-cultured with glial cells from the SOD1G93A mouse model of ALS. The inventors demonstrate, as was previously reported, that both embryonic and ESC-derived motor neurons are selectively sensitive to the toxic effect of mutant glia, while other neural cell types, such as spinal interneurons, are relatively unaffected (Di Giorgio et al., 2007) (Nagai et al., 2007). iMNs were co-cultured with either wild-type or mutant SOD1G93A glia and the number of Hb9::GFP+ iMNs quantified 10 days later. It was determined that iMNs were indeed bona fide motor neurons, as there was a sharp reduction in the number of iMNs co-cultured with mutant glia relative to those cultured with wild-type glia (FIGS. 5C-D), and the effect was similar in magnitude to its reported effect on ESC-derived motor neurons (Di Giorgio et al., 2007) (Nagai et al., 2007).

Figure 5E:
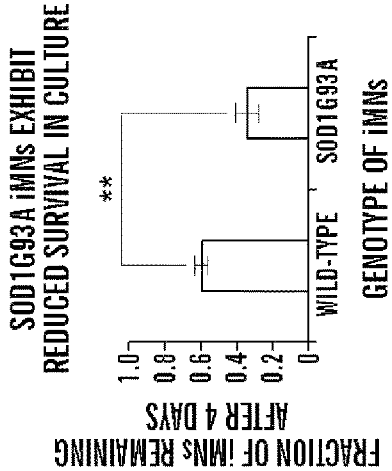

Currently, it is unclear whether there are cell-autonomous mechanisms of motor neuron degeneration induced by mutant SOD1 that can lead to overt differences in motor neuron survival in vitro. To assess whether iMNs could be used to answer this question, the inventors assessed if there is a survival difference between wild-type and SOD1G93A iMNs in culture with wild-type glia. MEFs were prepared from mouse embryos that overexpress the SOD1G93A transgene as well as harbor the Hb9::GFP reporter, and transdifferentiated them into Hb9::GFP+ iMNs alongside MEFs which only contain the Hb9::GFP reporter. FACS-purified Hb9::GFP+ iMNs of both genotypes were performed in parallel and plated the same number of cells for each on wild-type glia. After 4 days in culture, the inventors detected impaired survival of SOD1G93A iMNs relative to control iMNs (FIG. 5E), demonstrating a cell-autonomous disease phenotype. Thus, the inventors have demonstrated that iMNs are useful for studying both cell autonomous and non-autonomous contributors to motor neuron degeneration in ALS.

Figure 5F:
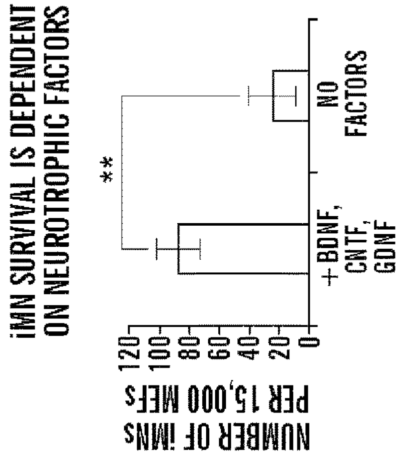

Because there is significant interest in the identity of factors and pathways that modulate neuronal survival in the context of neurodegenerative diseases, the inventors also tested whether iMNs were similar to motor neurons in their sensitivity to growth factor withdrawal. Indeed, when the neurotrophic factors GDNF, BDNF and CNTF were all withdrawn from the medium, iMNs were lost more rapidly (FIG. 5F). Thus, iMNs were determined share a neurotrophic support requirement similar to embryonic motor neurons, and the inventors demonstrate that iMNs could serve as a suitable substrate for in vitro studies of motor neuron function, disease and injury.

Example 9

Figure 6A:
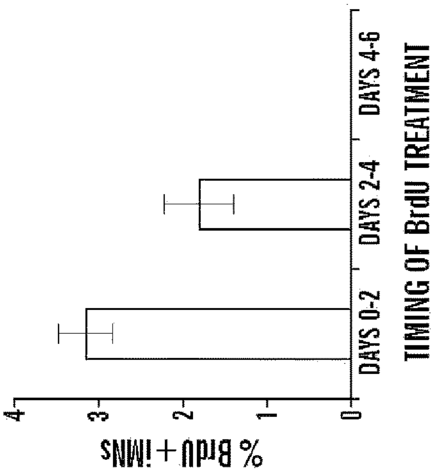
FIGS. 6A-6D show transdifferention Does Not Occur Through a Nestin+ Neural Progenitor State.

Fibroblasts Do Not Transit Through a Neural Progenitor State Before Becoming iMNs The process by which the initial fibroblasts undergo conversion into another cell type in defined factor reprogramming and transdifferentiation experiments remains poorly understood. In particular, it is currently unknown if the somatic cells reprogram through the same developmental intermediates that are found in the developing embryo, for example, by first dedifferentiating and then re-differentiating through a neural progenitor state into a neuron, or if they instead convert more “directly”. To address this question, the inventors used a lineage tracing approach to assess if during the course of reprogramming, a gene commonly used to identify neuronal progenitors ever became expressed. Motor neuron progenitor cells are highly proliferative in culture (Frederiksen and McKay, 1988; Jessell, 2000). To determine whether iMNs transited through a highly proliferative intermediate during the reprogramming process, the inventors quantified the timing of cell division in the reprogramming cultures using 48-hour pulses of BrdU. Following transduction, the inventors demonstrated that the cells incorporated decreasing amounts of BrdU at each subsequent time point and did not incorporate detectable levels of Brdu after 4 days post-transduction (FIG. 6A). Consistent with a previous report (Vierbuchen et al., 2010), these results demonstrate that the transduced cells quickly become post-mitotic. Since 10% of the fibroblasts eventually become iMNs and because GFP+ iMNs do not begin to appear in culture until day 5 and the majority arise between 7 and 14 days in culture these results demonstrate that the iMNs are not being produced from highly proliferative neuronal progrenitors.

Figure 6B:
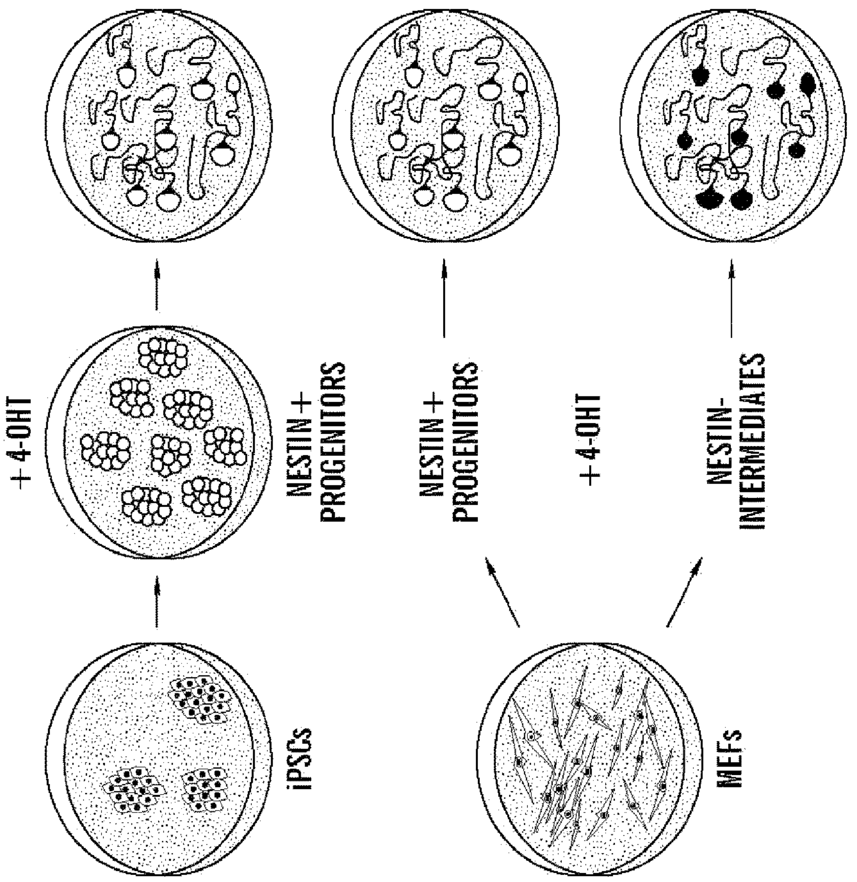

To more definitively test if the fibroblasts become motor neuron progenitors before differentiating into iMNs, the inventors repeated the induction of a motor neuron identity using transgenic fibroblasts with a Nestin::CreER (Burns et al., 2007); lox-stop-lox-H2B-mCherry (Abe et al.); Hb9::GFP genotype (FIG. 6B). Because Nestin is a well-known marker of neural progenitor cells in the mammalian CNS (Messam et al., 2002), the inventors assessed if the fibroblasts transited through a progenitor state before becoming motor neurons by assessing if the resulting iMNs activate expression of Nestin::CreER, recombine the reporter gene and thus express both mCherry and Hb9::GFP.

Figure 6C:
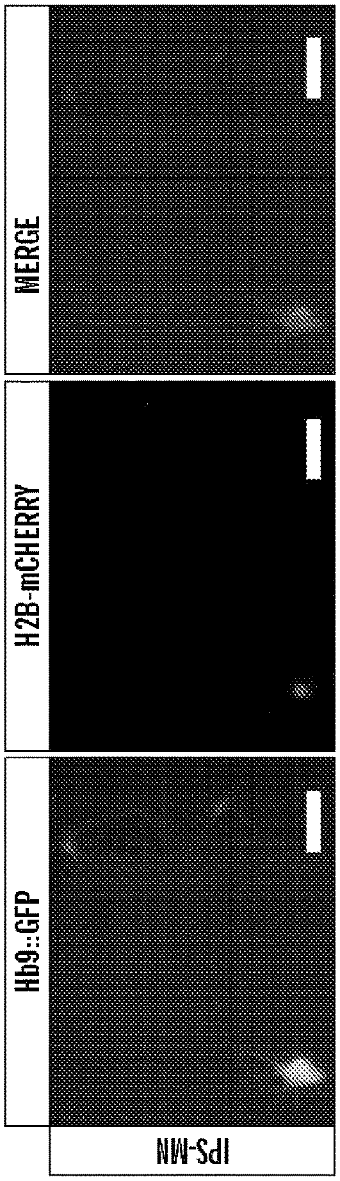
Figure 6D:
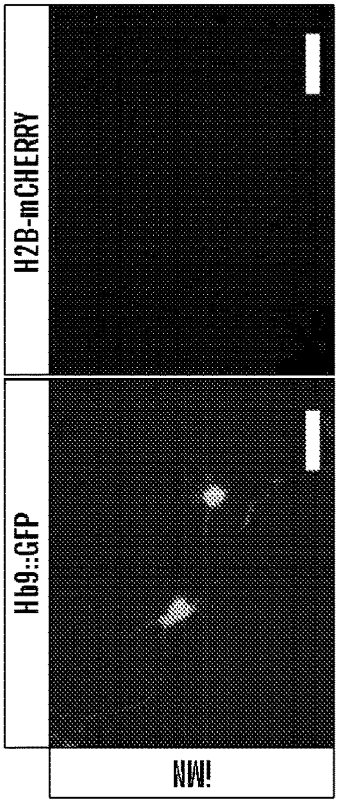

First, as a positive control for this experiment, iPSCs were generated from the fibroblasts, and differentiated into motor neurons using retinoic acid and sonic hedgehog (Wichterle et al., 2002). As this directed differentiation protocol mimics development, the inventors expected the resulting motor neurons to originate from Nestin+ precursors. When the differentiation was performed without 4-hydroxytamoxifen (4-OHT), none of the resulting Hb9::GFP+ motor neurons expressed mCherry (FIG. 6C). However, when 4-OHT was added to the differentiation, 3% of the motor neurons co-expressed mCherry (n>10,000) (FIG. 6C), verifying that the Nestin::CreER reporter successfully identified motor neurons that transited through a Nestin+ progenitor state. In contrast, when the 7 factor-transduced MEF cultures were treated with 4-OHT both before and during transdifferentiation, none of the resulting iMNs expressed mCherry (n>5,000) (FIG. 6D). These results demonstrate that fibroblasts do not become iMNs by transiting through a motor neuron progenitor cell state and further rule out the possibility that many of the iMNs are derived from contaminating neural progenitor cells in the MEF cultures.

Example 10

Human iMNs can be Generated by 8 Transcription Factors

Figure 7B:
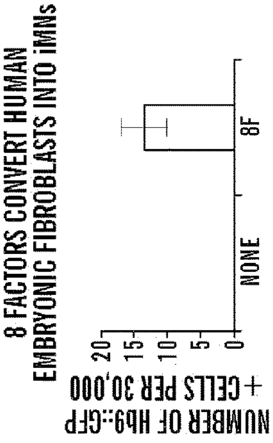
FIGS. 7A-7G shows Human iMNs Generated by 8 Transcription Factors.
Figure 7A:
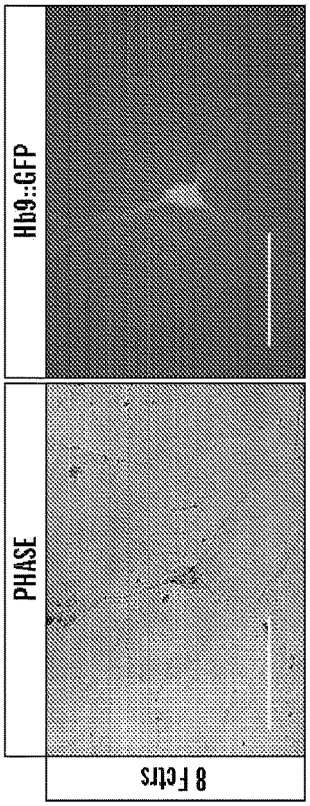
Figure 7C:
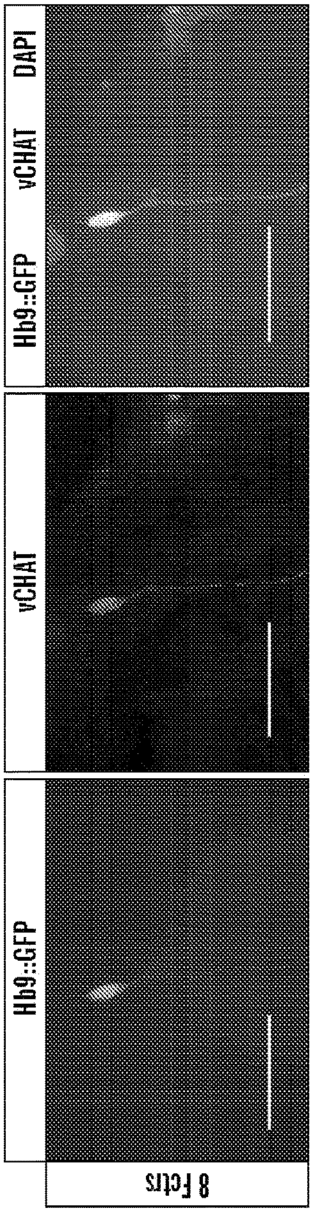
Figure 7D:
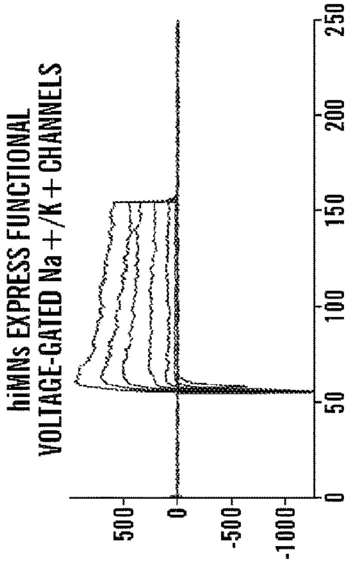
Figure 7E:
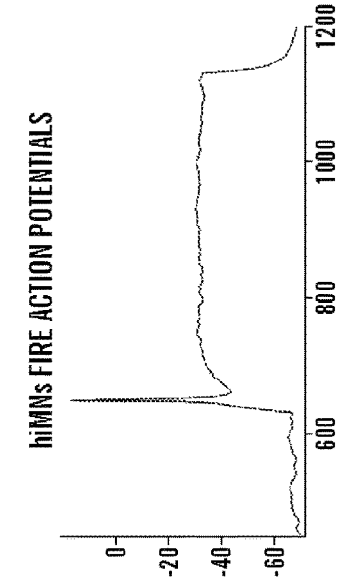
Figure 7F:
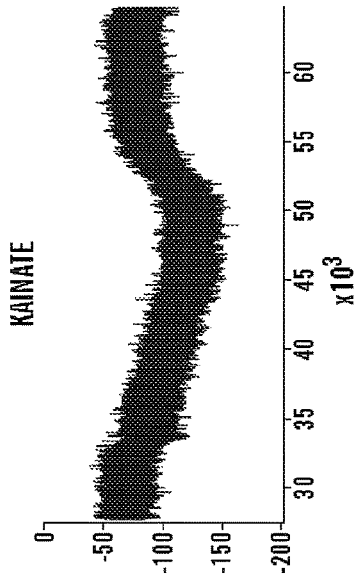
Figure 7G:
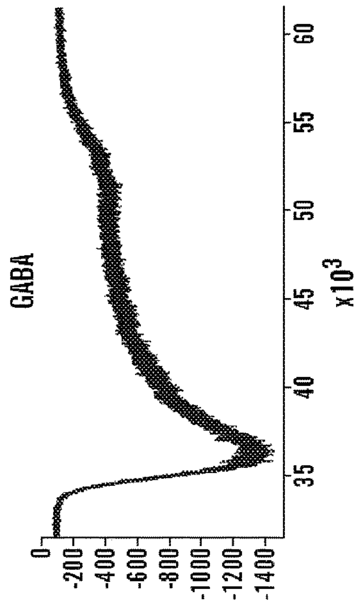

The inventors next assessed whether the same, or a similar set of factors could be used to generate human iMNs from fibroblasts. To this end, human embryonic fibroblasts (HEFs) were derived from a human ESC line harboring the Hb9::GFP transgene (Di Giorgio et al., 2008). The HEFs were then transduced with viruses containing the 7 iMN factors identified in the mouse system as well as NEUROD1, a pro-neural gene reported to enhance the conversion efficiency of human fibroblasts into iNs (Pang et al., 2011). 30 days after transduction, Hb9::GFP+ cells were detected with highly neuronal morphologies in the culture of 8 factor-transduced HEFs (FIGS. 7A-B), whereas untransduced HEFs never spontaneously expressed the transgene under the same conditions (FIG. 7B). These putative human iMNs expressed vesicular ChAT (FIG. 7C), demonstrating that they were indeed cholinergic in nature. In order to assess the functionality of human iMNs made with 8 factors, whole-cell patch clamp recording was used to look at their electrophysiological properties. Similar to their mouse counterparts, human iMNs expressed functional voltage-gated sodium and potassium channels (FIG. 7D) and were able to fire action potentials (FIG. 7E) when depolarized. Importantly, human iMNs responded appropriately to the addition of 100 μM kainate (FIG. 7F) and 100 μM GABA (FIG. 7G), demonstrating their ability to receive and respond to the major excitatory and inhibitory inputs, respectively, that govern spinal motor neuron activity. Therefore, the inventors demonstrate the generation of functional human iMNs from human fibroblasts by transdifferentiation.

Example 11

The inventors have demonstrated that a small set of transcription factors can convert embryonic and adult fibroblasts into functional motor neurons. The iMNs expressed pan-neuronal and motor neuron specific markers, as well as the receptors and channels that generate excitable membranes sensitive to transmitters, allowing them both to fire action potentials and receive synaptic input.

These cholinergic iMNs also possessed the defining hallmark of motor neurons: the ability to synapse with muscle and to induce its contraction. Most importantly, iMNs are able to contribute to the developing CNS in vivo, migrating appropriately to the ventral horn and sending out axonal projections through the ventral root. The inventors also demonstrated that the iMNs are sensitive to a degenerative ALS stimulus that selectively affects motor neurons. Thus we provide several lines of evidence that iMNs are functional motor neurons with consequent utility for the study of motor neuron physiology and disease susceptibility.

It is also possible that other motor neuron inducing (MN-inducing) factors can be used, or that varying the cocktail of genetic factors might further enhance the frequency or even accuracy of conversion, which can be determined by routine screening experiments by someone of ordinary skill in the art. Thus, a smaller number of the MN-inducing factors as identified here, or a group of similar factors, can be capable of converting adult human fibroblasts into motor neurons. Such a reprogramming approach has significant advantages of greatly facilitate the production of patient-specific motor neurons for therapeutic uses in regenerative medicine as well as for disease-related studies.

Additionally, the inventors have demonstrated a efficient conversion of fibroblasts to motor neurons via trandifferentiation, which occurs extremely efficiently given that the cells do not transit through a neural progenitor state. Surprisingly, under certain conditions, as many as one Hb9::GFP+ iMN was made from every 10 MEFs. This efficiency was substantially higher than previously reported iPSC reprogramming (Takahashi and Yamanaka, 2006). The inventors demonstrate herein that the massive changes in gene expression induced during defined-factor reprogramming can be executed efficiently even though they do not mimic embryonic development precisely.

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, $3^{rd}$ Ed., by Hogan et al., Cold Spring Contain Laboratory Press, Cold Spring Contain, New York, 2003; Gene Targeting: A Practical Approach, IRL Press at Oxford University Press, Oxford, 1993; and Gene Targeting Protocols, Human Press, Totowa, N.J., 2000. All patents, patent applications and references cited herein are incorporated in their entirety by reference.

The present invention is well adapted to carry out the objects and obtain the ends and advantages mentioned, as well as those inherent therein. The methods, systems and kits are representative of certain embodiments, are exemplary, and are not intended as limitations on the scope of the invention. Modifications therein and other uses are also contemplated herein. These modifications are encompassed within the spirit of the invention and are defined by the scope of the claims. Varying substitutions and modifications may be made to the invention disclosed herein without departing from the scope and spirit of the invention.

The articles "a" and an as used herein in the specification and in the claims, unless clearly indicated to the contrary, should be understood to include the plural referents. Claims or descriptions that include or between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention can be explicitly excluded from the claims, regardless of whether the specific exclusion is recited in the specification. For example, any somatic cell, e.g., fibroblast, any agent, any somatic cell type, any β-cell reprogramming agent, etc., may be excluded.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" is intended to encompass numbers that fall within a range of ±10% of a number, in some embodiments within ±5% of a number, in some embodiments within ±1%, in some embodiments within ±0.5% of a number, in some embodiments within ±0.1% of a number unless otherwise stated or otherwise evident from the context (except where such number would impermissibly exceed 100% of a possible value).

Certain claims are presented in dependent form for the sake of convenience, but Applicant reserves the right to rewrite any dependent claim in independent form to include the limitations of the independent claim and any other claim(s) on which such claim depends, and such rewritten claim is to be considered equivalent in all respects to the dependent claim in whatever form it is in (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited.

REFERENCES

All references cited herein are incorporated herein by reference in their entirety as if each individual publication or patent or patent application was specifically and individually indicated to be incorporated by reference in its entirety.

Many modifications and variations of this invention can be made without departing from its spirit and scope, as will be apparent to those skilled in the art. The specific embodiments described herein are offered by way of example only, and the invention is to be limited only in terms of the appended claims, along with the full scope of equivalents to which such claims are entitled.

Abe, T., Kiyonari, H., Shioi, G., Inoue, K., Nakao, K., Aizawa, S., and Fujimori, T. Establishment of conditional reporter mouse lines at ROSA26 locus for live cell imaging. Genesis 49, 579-590.

Alessandri-Haber, N., Paillart, C., Arsac, C., Gola, M., Couraud, F., and Crest, M. (1999). Specific distribution of sodium channels in axons of rat embryo spinal motoneurones. J Physiol 518 (Pt 1), 203-214.

Burns, K. A., Ayoub, A. E., Breunig, J. J., Adhami, F., Weng, W. L., Colbert, M. C., Rakic, P., and Kuan, C. Y. (2007). Nestin-CreER mice reveal DNA synthesis by nonapoptotic neurons following cerebral ischemia hypoxia. Cereb Cortex 17, 2585-2592.

Caiazzo, M., Dell'anno, M. T., Dvoretskova, E., Lazarevic, D., Taverna, S., Leo, D., Sotnikova, T. D. Menegon, A., Roncaglia, P., Colciago, G., et al. Direct generation of functional dopaminergic neurons from mouse and human fibroblasts. Nature.

Cui, D., Dougherty, K. J., Machacek, D. W., Sawchuk, M., Hochman, S., and Baro, D. J. (2006). Divergence between motoneurons: gene expression profiling provides a molecular characterization of functionally discrete somatic and autonomic motoneurons. Physiol Genomics 24, 276-289.

Dahm, L. M., and Landmesser, L. T. (1988). The regulation of intramuscular nerve branching during normal development and following activity blockade. Dev Biol 130, 621-644.

Di Giorgio, F. P., Boulting, G. L., Bobrowicz, S., and Eggan, K. C. (2008). Human embryonic stem cell derived motor neurons are sensitive to the toxic effect of glial cells carrying an ALS-causing mutation. Cell Stem Cell 3, 637-648.

Di Giorgio, F. P., Carrasco, M. A., Siao, M. C., Maniatis, T., and Eggan, K. (2007). Non-cell autonomous effect of glia on motor neurons in an embryonic stem cell-based ALS model. Nat Neurosci 10, 608-614.

Frederiksen, K., and McKay, R. D. (1988). Proliferation and differentiation of rat neuroepithelial precursor cells in vivo. J Neurosci 8, 1144-1151.

Ichida, J. K., Blanchard, J., Lam, K., Son, E. Y., Chung, J. E., Egli, D., Loh, K. M., Carter, A. C., Di Giorgio, F. P., Koszka, K., et al. (2009). A small-molecule inhibitor of tgf-Beta signaling replaces sox2 in reprogramming by inducing nanog. Cell Stem Cell 5, 491-503.

Ieda, M., Fu, J. D., Delgado-Olguin, P., Vedantham, V., Hayashi, Y., Bruneau, B. G., and Srivastava, D. (2010). Direct reprogramming of fibroblasts into functional cardiomyocytes by defined factors. Cell 142, 375-386.

Jessell, T. M. (2000). Neuronal specification in the spinal cord: inductive signals and transcriptional codes. Nat Rev Genet. 1, 20-29.

Lee, S. K., Lee, B., Ruiz, E. C., and Pfaff, S. L. (2005). Olig2 and Ngn2 function in opposition to modulate gene expression in motor neuron progenitor cells. Genes Dev 19, 282-294.

Lupa, M. T., and Hall, Z. W. (1989). Progressive restriction of synaptic vesicle protein to the nerve terminal during development of the neuromuscular junction. J Neurosci 9, 3937-3945.

Messam, C. A., Hou, J., Berman, J. W., and Major, E. O. (2002). Analysis of the temporal expression of nestin in human fetal brain derived neuronal and glial progenitor cells. Brain Res Dev Brain Res 134, 87-92.

Miles, G. B., Yohn, D. C., Wichterle, H., Jessell, T. M., Rafuse, V. F., and Brownstone, R. M. (2004). Functional properties of motoneurons derived from mouse embryonic stem cells. J Neurosci 24, 7848-7858.

Nagai, M., Re, D. B., Nagata, T., Chalazonitis, A., Jessell, T. M., Wichterle, H., and Przedborski, S. (2007). Astrocytes expressing ALS-linked mutated SOD1 release factors selectively toxic to motor neurons. Nat Neurosci 10, 615-622.

Pang, Z. P., Yang, N., Vierbuchen, T., Ostermeier, A., Fuentes, D. R., Yang, T. Q., Citri, A., Sebastiano, V., Marro, S., Sudhof, T. C., et al. (2011). Induction of human neuronal cells by defined transcription factors. Nature.

Peljto, M., Dasen, J. S., Mazzoni, E. O., Jessell, T. M., and Wichterle, H. (2011). Functional diversity of ESC derived motor neuron subtypes revealed through intraspinal transplantation. Cell Stem Cell 7, 355-366.

Peljto, M., and Wichterle, H. (2011). Programming embryonic stem cells to neuronal subtypes. Curr Opin Neurobiol 21, 43-51.

Pfisterer, U., Kirkeby, A., Torper, O., Wood, J., Nelander, J., Dufour, A., Bjorklund, A., Lindvall, O., Jakobsson, J., and Parmar, M. (2011). Direct conversion of human fibroblasts to dopaminergic neurons. Proc Natl Acad Sci USA 108, 10343-10348.

Puia, G., Santi, M. R., Vicini, S., Pritchett, D. B., Purdy, R. H., Paul, S. M., Seeburg, P. H., and Costa, E. (1990). Neurosteroids act on recombinant human GABAA receptors. Neuron 4, 759-765.

Soundararajan, P., Fawcett, J. P., and Rafuse, V. F. (2010). Guidance of postural motoneurons requires MAPK/ERK signaling downstream of fibroblast growth factor receptor 1. J Neurosci 30, 6595-6606. Soundararajan, P., Lindsey, B. W., Leopold, C., and Rafuse, V. F. (2007). Easy and rapid differentiation of embryonic stem cells into functional motoneurons using sonic hedgehog-producing cells. Stem Cells 25, 1697-1706.

Soundararaj an, P., Miles, G. B., Rubin, L. L., Brownstone, R. M., and Rafuse, V. F. (2006). Motoneurons derived from embryonic stem cells express transcription factors and develop phenotypes characteristic of medial motor column neurons. J Neurosci 26, 3256-3268.

Szabo, E., Rampalli, S., Risueno, R. M., Schnerch, A., Mitchell, R., Fiebig-Comyn, A., Levadoux-Martin, M., and Bhatia, M. (2010). Direct conversion of human fibroblasts to multilineage blood progenitors. Nature 468, 521-526.

Takahashi, K., and Yamanaka, S. (2006). Induction of pluripotent stem cells from mouse embryonic and adult fibroblast cultures by defined factors. Cell 126, 663-676.

Vierbuchen, T., Ostermeier, A., Pang, Z. P., Kokubu, Y., Sudhof, T. C., and Wernig, M. (2010). Direct conversion of fibroblasts to functional neurons by defined factors. Nature 463, 1035-1041.

Wichterle, H., Lieberam, I., Porter, J. A., and Jessell, T. M. (2002). Directed differentiation of embryonic stem cells into motor neurons. Cell 110, 385-397.

What is claimed:

1. A method for producing a motor neuron from transdifferentiation of fibroblast, the method comprising increasing the protein expression of at least four motor-neuron inducing (MN-inducing) factors in the fibroblast, wherein the four motor-neuron inducing factors are Lhx3 and Ascl1 and two motor neuron inducing factors selected from the group consisting of: Brn2, Myt1l, Isl1, Hb9, Ngn2 or NeuroD, and wherein the motor neuron exhibits at least two characteristics selected from:

(i) the expression of at least two genes selected from the group consisting of: α2-tubulins, Map2, synapsins, synaptophysin, synaptotagmins, NeuroD, Isl1, cholineacetyltransferase (ChAT), or (ii) functional characteristic of any of: ability to fire action potentials, produce an outward current in response to glycine, GABA or kainate, or produce an inward current in response to glutamate, and wherein the fibroblast does not become a motor neuron progenitor prior to transdifferentiating into a motor neuron.

2. The method of claim 1, wherein the four motor-neuron inducing factors do not include Myt1l or Brn2.

3. The method of claim 1, wherein the four motor neuron inducing factors does not comprise miR-124.

4. The method of claim 1, wherein the four motor neuron inducing factors does not comprise Isl1.

5. The method of claim 1, wherein protein expression is increased by introducing into the fibroblast at least one nucleic acid encoding a MN-inducing factor.

6. The method of claim 1, wherein the fibroblast is in vitro or ex vivo.

7. The method of claim 1, wherein the fibroblast is obtained from a subject that has been diagnosed, or suspected as having a motor neuron disease or disorder, or has been identified to have a genetic predisposition linked with an increased risk of developing a motor neuron disease or disorder.

8. The method of claim 7, wherein the motor neuron disease or disorder is amyotrophic lateral sclerosis (ALS) or spinal muscular atrophy (SMA).

* * * * *